US007572808B2

(12) United States Patent  
Sun et al.

(10) Patent No.: US 7,572,808 B2  
(45) Date of Patent: Aug. 11, 2009

(54) TRIAZOLOPYRIDINE CANNABINOID RECEPTOR 1 ANTAGONISTS

(75) Inventors: Chongqing Sun, East Windsor, NJ (US); Philip M. Sher, Plainsboro, NJ (US); Gang Wu, Princeton, NJ (US); William R. Ewing, Yardley, PA (US); Yanting Huang, Pennington, NJ (US); Taekyu Lee, Doylestown, PA (US); Natesan Murugesan, Princeton Junction, NJ (US); Richard B. Sulsky, West Trenton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/454,322

(22) Filed: Jun. 16, 2006

(65) Prior Publication Data

US 2007/0004772 A1    Jan. 4, 2007

Related U.S. Application Data

(60) Provisional application No. 60/692,043, filed on Jun. 17, 2005.

(51) Int. Cl.  
*A61K 31/44* (2006.01)  
*C07D 471/02* (2006.01)

(52) U.S. Cl. ..................... 514/303; 546/119  
(58) Field of Classification Search ............ 546/119; 514/300, 303  
See application file for complete search history.

(56) References Cited

U.S. PATENT DOCUMENTS

| 3,674,836 A | 7/1972 | Creger |
| 3,983,140 A | 9/1976 | Endo et al. |
| 4,027,009 A | 5/1977 | Grier et al. |
| 4,231,938 A | 11/1980 | Monaghan et al. |
| 4,346,227 A | 8/1982 | Terahara et al. |
| 4,379,785 A | 4/1983 | Weyer et al. |
| 4,448,784 A | 5/1984 | Glamkowski et al. |
| 4,450,171 A | 5/1984 | Hoffman et al. |
| 4,499,289 A | 2/1985 | Baran et al. |
| 4,613,610 A | 9/1986 | Wareing |
| 4,639,436 A | 1/1987 | Junge et al. |
| 4,647,576 A | 3/1987 | Hoefle et al. |
| 4,681,893 A | 7/1987 | Roth |
| 4,686,237 A | 8/1987 | Anderson |
| 4,759,923 A | 7/1988 | Buntin et al. |
| 4,871,721 A | 10/1989 | Biller |
| 4,904,769 A | 2/1990 | Rauenbusch |
| 4,924,024 A | 5/1990 | Biller |
| 5,006,530 A | 4/1991 | Angerbauer et al. |
| 5,011,930 A | 4/1991 | Fujikawa et al. |
| 5,177,080 A | 1/1993 | Angerbuer et al. |
| 5,260,440 A | 11/1993 | Hirai et al. |
| 5,273,995 A | 12/1993 | Roth |
| 5,354,772 A | 10/1994 | Kathawala |
| 5,385,929 A | 1/1995 | Bjorge et al. |
| 5,447,954 A | 9/1995 | Gribble et al. |
| 5,488,064 A | 1/1996 | Sher |
| 5,491,134 A | 2/1996 | Sher et al. |
| 5,506,219 A | 4/1996 | Robl |
| 5,541,204 A | 7/1996 | Sher et al. |
| 5,594,016 A | 1/1997 | Ueno et al. |
| 5,612,359 A | 3/1997 | Murugesan |
| 5,686,104 A | 11/1997 | Mills et al. |
| 5,691,322 A | 11/1997 | Robl |
| 5,698,527 A | 12/1997 | Kim |
| 5,712,396 A | 1/1998 | Magnin et al. |
| 5,753,675 A | 5/1998 | Wattanasin |
| 5,770,615 A | 6/1998 | Cheng et al. |
| 5,776,983 A | 7/1998 | Washburn et al. |
| 5,990,109 A | 11/1999 | Chen et al. |
| 6,043,265 A | 3/2000 | Murugesan et al. |
| 6,184,231 B1 | 2/2001 | Hewawasam et al. |
| 6,414,002 B1 | 7/2002 | Cheng et al. |
| 6,635,626 B1 | 10/2003 | Barrish et al. |

FOREIGN PATENT DOCUMENTS

| DE | 196 22 222 A1 | 12/1997 |
| EP | 0 142 146 | 5/1985 |

(Continued)

OTHER PUBLICATIONS

Yurugi et. al., "Studies on the syntheses of N-Heterocyclic compounds", Yakugaku Zasshi: Journal of the Pharmaceutical Society of Japan, May 1973;93 (5): 642-7.*

(Continued)

*Primary Examiner*—Janet L. Andres  
*Assistant Examiner*—Binta Robinson  
(74) *Attorney, Agent, or Firm*—Maureen S. Gibbons

(57) ABSTRACT

The present application describes compounds according to Formula I, pharmaceutical compositions comprising at least one compound according to Formula I and optionally one or more additional therapeutic agents, and methods of treatment using the compounds according to Formula I both alone and in combination with one or more additional therapeutic agents. The compounds have the following general formula:

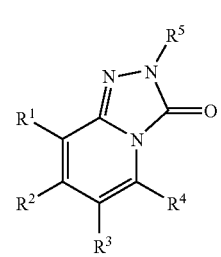

I including all prodrugs, solvates, pharmaceutically acceptable salts and stereoisomers, wherein $R^1$, $R^2$, $R^3$, $R^4$ and $R^5$ are described herein.

13 Claims, No Drawings

FOREIGN PATENT DOCUMENTS

| | | |
|---|---|---|
| EP | 0 221 025 | 5/1987 |
| EP | 0 675 714 B1 | 10/1995 |
| EP | 1 022 272 B1 | 7/1997 |
| EP | 0 818 448 B1 | 1/1998 |
| EP | 0 992 496 B1 | 8/2005 |
| FR | 2 596 393 | 10/1987 |
| GB | 2 205 837 | 12/1988 |
| GB | 2 304 106 | 3/1997 |
| WO | WO 86/03488 | 6/1986 |
| WO | WO 86/07054 | 12/1986 |
| WO | WO93/14091 | 7/1993 |
| WO | WO 94/15592 | 7/1994 |
| WO | WO 97/21993 | 6/1997 |
| WO | WO 97/35576 | 10/1997 |
| WO | WO 97/48701 | 12/1997 |
| WO | WO 99/00353 | 1/1999 |
| WO | WO 00/01389 | 1/2000 |
| WO | WO 00/15201 | 3/2000 |
| WO | WO 00/30665 | 6/2000 |
| WO | WO 00/38722 | 7/2000 |
| WO | WO 00/39077 | 7/2000 |
| WO | WO 00/50574 | 8/2000 |
| WO | WO2004/026301 | 4/2004 |
| WO | WO 2005/037197 A2 | 4/2005 |
| WO | WO 2005/041663 A1 | 5/2005 |

OTHER PUBLICATIONS

Antel et. al., "CB1 Cannabinoid Receptor Antagonists for Treatment of Obesity and Prevention of Comorbid Metabolic Disorders", Antel et al., J. Med. Chem. 2006, 49, 4008-4016.*
Hcaplus 143:243137.*
Hertzog, Donald, Recent Advances in the Cannabinoids, Expert Opin. Ther. Patetns (2004) 14(10):1435-1452.*
Hertzog, Donald, Recent Advances in the Cannabinoids, "Expert Opin. Ther. Patents" (2004) 14(10);1435-1452.*
Maldonado et. al., "Involvement of the endocannabinoid system in drug addiction", Trends in Neurosciences, vol. 29, No. 4, Apr. 2006.*
J. Lange et al., Journal of Medicinal Chemistry, vol. 27, pp. 627-643, 2004.
U. Pagotto et al., Endocrine Reviews, vol. 27, No. 1, pp. 73-100, 2008.
J. Mussinu et al., Bioorganic & Medicinal Chemistry, vol. 11, pp. 251-263, 2003.
J. Lange et al., Journal of Medicinal Chemistry, vol. 48, pp. 1823-1838, 2005.
M. Krishnamurthy et al., Bioorganic & Medicinal Chemistry, vol. 12, pp. 393-404, 2004.
J. Wiley et al., British Journal of Pharmacology, vol. 145, pp. 293-300, 2005.
R. Katoch-Rouse et al., Journal of Medicinal Chemistry, vol. 46, pp. 642-645, 2003.
Aranyos, A. et al., "Novel Electron-Rich Bulky Phosphine Ligands Facilitate the Palladium-Catalyzed Preparation of Diaryl Ethers", J. Am. Chem. Soc., vol. 121, pp. 4369-4378 (1999).
Bakke, Jan M., "Nitropyridines: Synthesis and reactions", Pure Appl. Chem., vol. 75(10), pp. 1403-1415 (2003).
Barder, T. et al., "Catalysts for Suzuki-Miyaura Coupling Processes: Scope and Studies of the Effect of Ligand Structure", J. Am. Chem. Soc., vol. 127, pp. 4685-4696 (2005).
Biller, S. et al., "Isoprenoid (Phosphinylmethyl) phosphonates as Inhibitors of Squalene Synthetase", J. of Med. Chem., vol. 31 (10), pp. 1869-1871 (1988).
Biller, S. et al., "Squalene Synthase Inhibitors", Current Pharmaceutical Design, vol. 2, pp. 1-40 (1996).
Bobbio, C. et al., "Selective Functionalization of 2-Fluoropyridine, 2,3-Difluoropyridine, and 2,5-Diflurorpyridine at Each Vacant Position", J. Org. Chem., vol. 70, pp. 3039-3045 (2005).

Buback, M. et al., "Diastereoselectivity and Kinetics of Intermolecular Hetero Diels-Alder Reactions under High Pressure. A Significant Pressure-Induced Increase in Stereoselectivity", Chem. Ber., vol. 122, pp. 1179-1186 (1989).
Canibano, V. et al., "Mild Regioselective Halogenation of Activated Pyridines with N-Bromosuccinimide", Synthesis, vol. 14, pp. 2175-2179 (2001).
Capson, T., "Synthesis and Evaluation of Ammonium Analogs of Carbocationic Intermediates in Squalene Biosynthesis", Dissertation, Dept Med Chem U of Utah, Abstract, Table of Contents, pp. 16,17,40-43,48-51, Summary (1987).
Carles, L. et al., "2-Pyridones from Cyanoacetamides and Enecarbonyl Compounds: Application to the Synthesis of Nothapodytine B", J. Org. Chem., vol. 67, pp. 4304-4308 (2002).
Coffey, D. et al., "Six-Membered Ring Systems: Pyridines and Benzo Derivatives", Progress in Heterocyclic Chemistry, vol. 14, pp. 257-278 (2002).
Coffey, D. et al., "Six-membered Ring Systems: Pyridines and Benzo Derivatives", Progress in Heterocyclic Chemistry, vol. 13, pp. 238-260 (2001).
Colombo, G. et al., "Appetite Suppression and Weight Loss after the Cannabinoid Antagonist SR 141716", Life Sciences, vol. 63(8), pp. PL 113-PL 117 (1998).
Comins, D et al., "Pyridines and their Benzo Derivatives: Reactivity at the Ring", Comprehensive Heterocyclic Chemistry II, vol. 5, pp. 37-90 (1996).
Corey, E. et al., "Application of Unreactive Analogs of Terpenoid Pyrophosphates to Studies of Multistep Biosynthesis. Demonstration that "Presqualene Pyrophosphate" is an Essential Intermediate on the Path to Squalene", J. Amer. Chem. Soc., vol. 98(5), pp. 1291-1293 (1976).
Cottet, F. et al., "Three Chloro (trifluoromethyl) pyridines as Model Substrates for Regioexhaustive Functionalization", Eur. J. Org. Chem., pp. 3793-3798 (2004).
Dennis, N., "Pyridines and their Benzo Derivatives: Reactivity of Substituents", Comprehensive Heterocyclic Chemistry II, vol. 5, pp. 91-134 (1996).
Di Marzo, V. et al., "Leptin-regulated endocannabinoids are involved in maintaining food intake", Nature, vol. 410, pp. 822-825 (2001).
Erian, A., "The Chemistry of β-Enaminonitriles as Versatile Reagents in Heterocyclic Synthesis", Chem. Rev., vol. 93, pp. 1991-2005 (1993).
Galiegue, S. et al., "Expression of central and peripheral cannabinoid receptors in human immune tissues and leukocyte subpopulations", Eur. J. Biochem., vol. 232, pp. 54-61 (1995).
Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Review, vol. 16(1), pp. 16-30 (1998).
Glass, M. et al., "Cannabinoid Receptors in the Human Brain: A detailed anatomical and quantitative autoradiographic study in the fetal, neonatal and adult human brain", Neuroscience, vol. 77(2), pp. 299-318 (1997).
Hamann, B. et al., "Sterically Hindered Chelating Alkyl Phosphines provide large rate Accelerations in Palladium-Catalyzed Amination of Aryl Iodides, Bromides, and Chlorides, and the First Amination of Aryl Tosylates", J. Am. Chem. Soc., vol. 120, pp. 7369-7370 (1998).
Hara, S., "Ileal Na+/bile acid cotransporter inhibitors", Drugs of the Future, vol. 24(4), pp. 425-430 (1999).
Henry, G., "De novo synthesis of substituted pyridines", Tetrahedron, vol. 60, pp. 6043-6061 (2004).
Hildebrandt, A. et al., "Antiobesity effects of chronic cannabinoid $CB_1$ receptor antagonist treatment in diet-induced obese mice", Eur. J. of Pharmacology, vol. 462, pp. 125-132 (2003).
Hojo, M. et al., "O-N, S-N and N-N exchange reactions at olefinic carbon atoms: Facile synthetic method for β-Trifluoroacetylvinylamines", Tetrahedron Letters, vol. 30(45), pp. 6173-6176 (1989).
Hollenbaugh, D. et al., "The human T cell antigen gp39, a member of the TNF gene family, is a ligand for the CD40 receptor: expression of a soluble form of gp39 with B cell co-stimulatory activity", The EMBO Journal, vol. 11(12), pp. 4313-4321 (1992).

Hollenbaugh, D. et al., "Cleavable CD40lg fusion proteins and the binding to sgp39", J. of Immunological Methods, vol. 188, pp. 1-7 (1995).

Jones, G., "The Chemistry of the Triazolopyridines: an Update", Advances in Heterocyclic Chemistry, vol. 83, pp. 1-70 (2002).

Jones, G., "Pyridines and their Benzo Derivatives: Synthesis", Comprehensive Heterocyclic Chemistry II, vol. 5, pp. 167-244 (1996).

Keay, J. et al., "Six-Membered Ring Systems: Pyridine and Benzo Derivatives", Progress in Heterocyclic Chemistry, vol. 4, pp. 168-185 (1992).

Keay, J. et al., "Six-Membered Ring Systems: Pyridine and Benzo Derivatives", Progess in Heterocyclic Chemistry, vol. 3, pp. 186-204 (1991).

Kobrakov, K. et al., Methods for the Synthesis of Hydrazinopyridines and some of their Characteristics.(Review) Chemistry of Heterocyclic Compounds, vol. 39(3), pp. 283-307 (2003).

Krause, B. et al., "ACAT Inhibitors: Physiologic Mechanisms for Hypolipidemic and Anti-Atherosclerotic Activities in Experimental Animals", Inflammation: Mediators and Pathways, pp. 173-198 (1995).

Larsen, R., "Six-Membered Ring Systems: Pyridine and Benzo Derivatives", Progress in Heterocyclic Chemistry, vol. 10, pp. 226-250 (1998).

Larsen, R. et al., "Six-Membered Ring Systems: Pyridines and Benzo Derivatives", Progress in Heterocyclic Chemistry, vol. 11, pp. 230-255 (1999).

Ljung, B. et al., "AZ 242, a novel PPARα/γ agonist with beneficial effects on insulin resistance and carbohydrate and lipid metabolism in ob/ob mice and obese Zucker rats", J. of Lipid Research, vol. 43, pp. 1855-1863 (2002).

Makosza, M. et al., "Hydroxylation of Nitroarenes with Alkyl Hydroperoxide Anions via Vicarious Nucleophilic Substitution of Hydrogen", J. Org. Chem., vol. 63, pp. 4199-4208 (1998).

Mallet, M. et al., "Migration du lithium en serie pyridinique: double catalyse et reformage. Acces aux derives de la bromo-2 lithio-3 pyridine et des bromo-4 halogeno-2 lithio-3 pyridines", J. of Organometallic Chemistry, vol. 382, pp. 319-332 (1990).

Marsais, F. et al., "A New Convergent Route to 1-Substituted Ellipticines", J. Org. Chem., vol. 57, pp. 565-573 (1992).

Matsuda, L. et al., "Structure of a cannabionoid receptor and functional expression of the cloned cDNA", Nature, vol. 346, pp. 561-564 (1990).

McClard, R. et al., "Novel Phosphonylphosphinyl (P-C-P-C-) Analogues of Biochemically Interesting Diphosphates. Syntheses and Properties of P-C-P-C- Analogues of Isopentenyl Diphoshpate and Dimethylallyl Diphosphate", J. Am. Chem. Soc., vol. 109, pp. 5544-5545 (1987).

Moreland, L. et al., "Treatment of Rheumatoid Arthritis with a Recombinant Human Tumor Necrosis Factor Receptor (p75)-Fc Fusion Protein", The New England J. of Medicine, vol. 337(3), pp. 141-147 (1997).

Munro, S. et al., "Molecular characterization of a peripheral receptor for cannabinoids", Nature, vol. 365, pp. 61-65 (1993).

Nlcolosi, R. et al., "The ACAT inhibitor, CI-1011 is effective in the prevention and regression of aortic fatty streak area in hamsters", Atherosclerosis, vol. 137, pp. 77-85 (1998).

Okada, E. et al. "A simple and convenient synthetic method for α-trifluoromethylpyridines", Heterocycles, vol. 46, pp. 129-132 (1997).

Ortiz de Montellano, P. et al., "Inhibition of Squalene Synthetase by Farnesyl Pyrophosphate Analogues", J. of Medicinal Chemistry, vol. 20(2), pp. 243-249 (1977).

Queguiner, G., "Efficient Synthesis of Organometallics of Pyridines, Quinolines and Diazines: New Synthetic Methodologies for Azaaromatic Biomolecules", J. Heterocyclic Chem., vol. 37, pp. 615-621 (2000).

Rocca, P. et al., "Connection between Metalation and Cross-Coupling Strategies. A New Convergent Route to Azacarbazoles". Tetrahedron, vol. 49(1), pp. 49-64 (1993).

Rocca, P. et al., "First Metalation of Aryl Iodides: Directed Ortho-Lithiation of Iodopyridines, Halogen-Dance, and Application to Synthesis", J. Org. Chem., vol. 58, pp. 7832-7838 (1993).

Rosenblum, S. et al., "Discovery of 1-(4-Fluorophenyl)-(3$R$)-[3-(4-fluorophenyl)-(3$S$)- hydroxypropyl]-(4$S$)-(4-hydroxyphenyl)-2-azetidinone (SCH 58235): A Designed, Potent, Orally Active Inhibitor of Cholesterol Absorption", J. Med. Chem., vol. 41, pp. 973-980 (1998).

Rowland, N. et al., "Effects of the cannabinoid receptor antagonist SR 141716, alone and in combination with dexfenfluramine or naloxone, on food intake in rats", Psychopharmacology, vol. 159, pp. 111-116 (2001).

Salisbury, B. et al., "Hypocholesterolemic activity of a novel inhibitor of cholesterol absorption, SCH 48461", Atherosclerosis, vol. 115, pp. 45-63 (1995).

Schlosser, M. et al., "Rerouting Nucleophilic Substitution from the 4-Position to the 2- or 6-Position of 2,4-Dehalopyridines and 2,4,6-Trihalopyridines: The Solution to a Long-Standing Problem", Organic Letters, vol. 7(1), pp. 127-129 (2005).

Schlosser, M. et al., "Regiochemically Flexible Substitutions of Di-, Tri-, and Tetrahalopyridines: The Trialkylsilyl Trick", J. Org. Chem., vol. 70, pp. 2494-2502 (2005).

Silvester, M., "Fluoroheterocyclic Compounds: Synthesis, Reactions and Commercial Applications", Aldrichimica Acta, vol. 24(2), pp. 31-38 (1991).

Sliskovic, D. et al., "ACAT Inhibitors: Potential Anti-atherosclerotic Agents", Current Medicinal Chemistry, vol. 1, pp. 204-225 (1994).

Smith, C. et al., "RP 73163: A Bioavailable Alkylsulphinyl-Diphenylimidazole ACAT Inhibitor", Bioorganic & Medicinal Chemistry Letters, vol. 6(1) pp. 47-50 (1996).

Sorbera, L. et al., "Treatment of Lipoprotein Disorders" Avasimibe, Drugs of the Future, vol. 24(1), pp. 9-15 (1999).

Stout, D., "Inhibitors of Acyl-CoA: Cholesterol $O$-Acyl Transferase (ACAT) as Hypocholesterolemic Agents. 6. The First Water-Soluble ACAT Inhibitor with Lipid-Regulating Activity. Inhibitors of Acyl-CoA: Cholesterol Acyltransferase (ACAT). 7. Development of a Series of Substituted $N$-Phenyl-$N$-[( 1-phenylcyclopentyl)-methyl] ureas with Enhanced Hypocholestrolemic Activity", Chemtracts-Organic Chemistry, vol. 8, pp. 359-362 (1995).

Toomey, J. et al., "Six-Membered Ring Systems: Pyridine and Benzo Derivatives", Progress in Heterocyclic Chemistry, vol. 7, pp. 195-225 (1995).

Toomey, J. et al., "Six-Membered Ring Systems: Pyridine and Benzo Derivatives", Progress in Heterocyclic Chemistry, vol. 6, pp. 206-230 (1994).

Toomey, Jr. J. et al., "Six-Membered Ring Systems: Pyridine and Benzo Derivatives", Progress in Heterocyclic Chemistry, vol. 8, pp. 209-230 (1996).

Trillou, C. et al., "Anti-obesity effect of SR141716, a CB1 receptor antagonist, in diet-induced obese mice", Am. J. Physiol. Regul. Integr. Comp. Physiol., vol. 284, pp. R345-R353 (2003).

Walters, M. et al., "A Practical 2,3-Pyridyne Precursor", Synthetic Communications, vol. 22(19), PP. 2829-2837 (1992).

Williams, C. et al., "Anandamide induces overeating: mediation by central cannabinoid (CB1) receptors", Psychopharmacology, vol. 143, pp. 315-317 (1999).

Yajima, K. et al., "Combination therapy with PPARγ and PPARα agonists increases glucose-stimulated insulin secretion in $db/db$ mice", Am. J. Physiol. Endocrinol. Metab., vol. 284, pp. E966-E971 (2003).

Yamamoto, K. et al., "Ring Contraction Reactions of Dihydro- and Tetrahydrothiazepines to Isothiazolone Derivatives under Pummerer Conditions", J. Org. Chem., vol. 52, pp. 5239-5243 (1987).

Yurovskaya, M. et al., "Functionalization of Pyridines. 3** Reactions forming a carbon-heteroatom bond with Group IV, V, and VI Elements", Chemistry of Heterocyclic Compounds, vol. 35(4), pp. 383-435 (1999).

Yurovskaya, M. et al., "Functionalization of Pyridines. * 2. Synthesis of Acylpyridines, Pyridinecarboxylic Acids, and their Derivatives. Review", Chemistry of Heterocyclic Compounds, vol. 34(8), pp. 871-899 (1998).

Keay, J. et al., "Six-Membered Ring Systems: Pyridine and Benzo Derivatives", Progress in Heterocyclic Chemistry, vol. 2, pp. 166-184 (1990).

Bonnemann, Von Helmut, "Cobalt-katalysierte Pyridin-Synthesen aus Alkinen und Nitrilen", Angew, Chem., vol. 90, pp. 517-516 (1978).

Giannangeli, M. et al., "Effect of Modifications of the Alkylpiperazine Moiety of Trazodone on $5HT_{2A}$ and $_{\alpha 1}$ Receptor Binding Affinity", J. Med. Chem., vol. 42, pp. 336-345 (1999).

Yurugi, S. et al., "Studies on the Syntheses on N-Heterocyclic Compounds. XIV.[1]) Syntheses of 7-Phenyl-$_s$-triazolo[4,3-α] pyridine Derivatives", Yakaguku Zasshi, vol. 93(5), pp. 642-647 (1973).

* cited by examiner

TRIAZOLOPYRIDINE CANNABINOID RECEPTOR 1 ANTAGONISTS

RELATED APPLICATION

This application claims priority benefit under Title 35 §119(e) of U.S. Provisional Application No. 60/692,043, filed Jun. 17, 2005, the contents of which are herein incorporated by reference.

BACKGROUND

Delta-9-tetrahydrocannabinol or Delta-9 THC, the principle active component of *Cannabis sativa* (marijuana), is a member of a large family of lipophilic compounds (i.e., cannabinoids) that mediate physiological and psychotropic effects including regulation of appetite, immunosuppression, analgesia, inflammation, emesis, anti-nocioception, sedation, and intraocular pressure. Other members of the cannabinoid family include the endogenous (arachidonic acid-derived) ligands, anandamide, 2-arachidonyl glycerol, and 2-arachidonyl glycerol ether. Cannabinoids work through selective binding to and activation of G-protein coupled cannabinoid receptors. Two types of cannabinoid receptors have been cloned including CB-1 (L. A. Matsuda, et al., *Nature*, 346, 561-564 (1990)), and CB-2 (S. Munro, et al., *Nature*, 365, 61-65 (1993)). The CB-1 receptor is highly expressed in the central and peripheral nervous systems (M. Glass, et al., *Neuroscience*, 77, 299-318 (1997)), while the CB-2 receptor is highly expressed in immune tissue, particularly in spleen and tonsils. The CB-2 receptor is also expressed on other immune system cells, such as lymphoid cells (S. Galiegue, et al., *Eur J Biochem*, 232, 54-61 (1995)). Agonist activation of cannabinoid receptors results in inhibition of cAMP accumulation, stimulation of MAP kinase activity, and closure of calcium channels.

There exists substantial evidence that cannabinoids regulate appetitive behavior. Stimulation of CB-1 activity by anandamide or Delta-9 THC results in increased food intake and weight gain in multiple species including humans (Williams and Kirkham, *Psychopharm.*, 143, 315-317 (1999)). Genetic knock-out of CB-1 result in mice that were hypophagic and lean relative to wild-type litter mates (DiMarzo, et al., *Nature*, 410, 822-825 (2001)). Published studies with CB-1 small molecule antagonists have demonstrated decreased food intake and body weight in rats (Trillou, et. al., *Am. J. Physiol. Regul. Integr. Comp. Physiol.*, R345-R353, (2003)). Chronic administration of the CB-1 antagonist AM-251 for two weeks resulted in substantial body weight reduction and decreased adipose tissue mass (Hildebrandt, et. al., *Eur. J. Pharm*, 462, 125-132 (2003)). There are multiple studies that have assessed the anorexic effect of the Sanofi CB-1 antagonist, SR-141716 (Rowland, et. al., *Pyschopharm.*, 159, 111-116 (2001); Colombo, et. al., *Life Sci.*, 63, 113-117 (1998)). There are at least two CB-1 antagonists in clinical trials for regulation of appetite, Sanofi's SR-141716 and Solvay's SLV-319. Published Phase IIb data reveal that SR-141716 dose-dependently reduced body weight in human subjects over a 16 week trial period. CB-1 antagonists have also been shown to promote cessation of smoking behavior. Phase II clinical data on smoking cessation were presented in September of 2002 at Sanofi-Synthelabo's Information meeting. This data showed that 30.2% of patients treated with the highest dose of SR-141716 stayed abstinent from cigarette smoke relative to 14.8% for placebo.

DETAILED DESCRIPTION

The present application describes compounds according to Formula I, pharmaceutical compositions comprising at least one compound according to Formula I and optionally one or more additional therapeutic agents, and methods of treatment using the compounds according to Formula I both alone and in combination with one or more additional therapeutic agents.

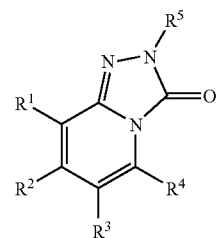

including all prodrugs, pharmaceutically acceptable salts and stereoisomers, wherein $R^1$, $R^2$, $R^3$, $R^4$, and $R^5$ are described herein.

Definitions

The following definitions apply to the terms as used throughout this specification, unless otherwise limited in specific instances.

The term "alkyl" as employed herein, alone or as part of another group, includes saturated straight chain, branched chain, cyclic and bicyclic hydrocarbons, containing 1 to 20 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, cyclopropyl, cyclohexyl, norbornyl, and the like. The term "alkyl" as employed herein therefore encompasses cycloalkyl groups.

Unless otherwise indicated, the term "alkenyl" as used herein alone or as part of another group refers to straight chain, branched chain, cyclic and bicyclic hydrocarbons of 2 to 20 carbons, that include one or more double bonds, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, and 1-cyclohexenyl. The term "alkenyl" as employed herein therefore encompasses cycloalkenyl groups.

Unless otherwise indicated, the term "aryl" or "Ar" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one additional fused heterocyclic ring, for example:

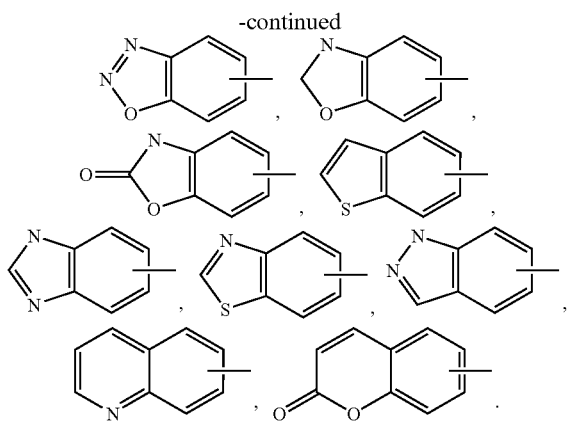

The term "arylalkyl" as used alone or as part of another group refers to an alkyl as defined herein, having an aryl substituent. Representative examples of arylalkyl include, but are not limited to, benzyl, 2-phenylethyl, 3-phenylpropyl, benzhydryl, naphthylmethyl, 4-trifluoromethylphenylpropyl and the like.

The term "halogen" or "halo" as used herein alone or as part of another group refers to chlorine, bromine, fluorine and iodine.

Unless otherwise indicated, the term "alkoxy" or "aryloxy" as employed herein alone or as part of another group refers to an alkyl or aryl group, as defined herein, linked to an oxygen atom.

Unless otherwise indicated, the term "heteroaryl" as used herein alone or as part of another group refers to a 5- or 6-membered aromatic ring which includes 1, 2, 3 or 4 heteroatoms such as nitrogen, oxygen or sulfur, and includes possible N-oxides. Heteroaryl groups may also contain a fused benzene ring. Examples of heteroaryl groups include the following:

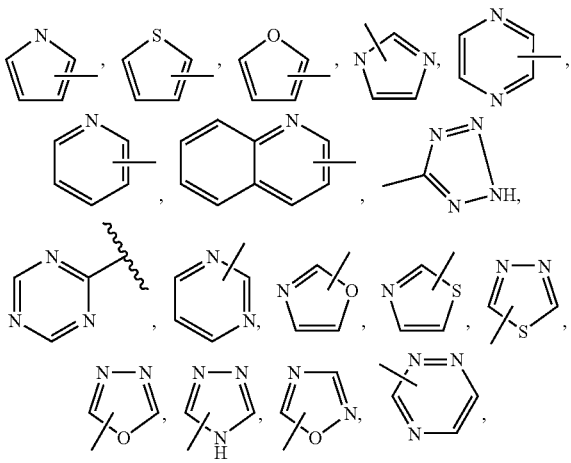

and the like.

As used herein, the term "heteroarylalkyl" means an alkyl group having a heteroaryl substituent.

Unless otherwise indicated, the term "heterocyclyl" as used herein alone or as part of another group refers to a 5- or 6-membered non-aromatic ring which includes 1, 2, 3 or 4 heteroatoms such as nitrogen, oxygen or sulfur, and includes possible N-oxides. Heterocyclyl groups may be saturated or monounsaturated. Examples of heterocyclyl groups include 4-morpholinyl, 3-piperidinyl, 2-tetrahydropyranyl, 3-tetrahydrothiophenyl, and the like.

It is understood that, where necessary, the valency of all atoms is made proper by the addition of hydrogens.

An administration of a therapeutic agent of the application includes administration of a therapeutically effective amount of the agent of the application. The term "therapeutically effective amount" as used herein refers to an amount of a therapeutic agent to treat or prevent a condition treatable by administration of a composition of the application. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

All stereoisomers of the compounds of the instant application are contemplated, either in mixture or in pure or substantially pure form. The compounds of the present application can have asymmetric centers at any of the carbon atoms including those within any of the R substituents. Consequently, compounds of Formula I can exist in enantiomeric or diastereomeric forms or in mixtures thereof. The processes for preparation can utilize racemates, enantiomers or diastereomers as starting materials. In order to prepare diastereomeric or enantiomeric products, conventional methods for isomer separation may be employed. These include, for example, chromatographic techniques, chiral HPLC, fractional crystallization, and sequences of derivatization, separation and de-derivatization.

It is anticipated that compounds of Formula I can be prepared as prodrugs by one skilled in the art, and the definition of Formula I above includes all prodrug, stereoisomers, atropisomers and pharmaceutically acceptable salts of Formula I. Various forms of prodrugs are well known in the art. A comprehensive description of prodrugs and prodrug derivatives are described in:

a) *The Practice of Medicinal Chemistry*, Camille G. Wermuth et al., Ch 31, (Academic Press, 1996);

b) *Hydrolysis in Drug and Prodrug Metabolism*, Bernard Testa and Joachim M. Mayer, (Wiley-VCH, 2003);

c) *Design of Prodrugs*, edited by H. Bundgaard, (Elsevier, 1985); and d) *A Textbook of Drug Design and Development*, P. Krogsgaard-Larson and H. Bundgaard, eds. Ch 5, pgs 113-191 (Harwood Academic Publishers, 1991). Said references are incorporated herein by reference.

Any compound that can be converted in vivo to provide the bioactive agent (i.e., the compound of Formula I) is a prodrug within the scope and spirit of the application.

The compounds of Formula I can be present as salts, which are also within the scope of this application. Pharmaceutically acceptable (i.e., non-toxic, physiologically acceptable) salts are preferred. If the compounds of Formula I have at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 8 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or such as benzoic acid, or with organic sulfonic acids, such as ($C_1$-$C_4$) alkyl or arylsulfonic acids which are unsubstituted or substituted, for example by halogen, for example methyl- or p-toluenesulfonic acid. Corresponding acid addition salts can also be formed having, if desired, an additionally present basic center. The compounds of Formula I having at least one acid group (for example COOH) can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethylpropylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula I or their pharmaceutically acceptable salts, are also included.

Preferred salts of the compounds of Formula I which contain a basic group include monohydrochloride, hydrogen sulfate, methanesulfonate, phosphate, acetate and nitrate salts.

Preferred salts of the compounds of Formula I which contain an acid group include sodium, potassium and magnesium salts and pharmaceutically acceptable organic amine salts.

The term "modulator" refers to a chemical compound with capacity to either enhance (e.g., "agonist" activity) or partially enhance (e.g., "partial agonist" activity) or inhibit (e.g., "antagonist" activity or inverse agonist activity) a functional property of biological activity or process (e.g., enzyme activity or receptor binding). Such enhancement or inhibition may be contingent on the occurrence of a specific event, such as activation of a signal transduction pathway, and/or may be manifest only in particular cell types.

The present application provides compounds of Formula I, pharmaceutical compositions employing such compounds and methods of using such compounds. In particular, the present application provides for a pharmaceutical composition comprising a therapeutically effective amount of a compound of Formula I alone or in combination with a pharmaceutically acceptable carrier.

Further, in accordance with the present application, a method is provided for preventing, inhibiting or treating the progression or onset of diseases or disorders associated with the cannabinoid receptor, such as the diseases or disorders defined above and hereinafter, wherein a therapeutically effective amount of a compound of Formula I is administered to a mammalian, i.e., human patient in need of treatment.

The compounds of the application can be used alone, in combination with other compounds of the present application, or in combination with one or more other agent(s) active in the therapeutic areas described herein.

In addition, a method is provided for preventing, inhibiting or treating the diseases as defined above and hereinafter, wherein a therapeutically effective amount of a combination of a compound of Formula I and another compound of the application and/or another type of therapeutic agent, is administered to a mammalian patient in need of treatment.

Methods of Preparation

The compounds of Formula I of the application can be prepared as shown below in the following reaction schemes, charts and descriptions thereof, as well as by using relevant published literature procedures that may be used by one skilled in the art. Exemplary reagents and procedures for these reactions appear hereinafter and in the working Examples.

The following abbreviations may be employed herein:
min=minute(s)
h=hour(s)
L=liter(s)
mL=milliliter(s)
μL=microliter(s)
g=gram(s)
mg=milligram(s)
mol=mole(s)
M=molar
mmol=millimole(s)
HPLC=high performance liquid chromatography
HPLC/MS or LC/MS=high performance liquid chromatography/mass spectrometry
MS or Mass Spec=mass spectrometry
[M+H]$^+$=parent plus a proton
[M+Na]$^+$=parent plus a sodium ion
[M−H]$^−$=parent minus a proton
Me=methyl
Et=ethyl
Ph=phenyl
TMS=trimethylsilyl
Ts=p-toluenesulfonyl
Ac=acetyl
THF=tetrahydrofuran
TFA=trifluoroacetic acid
EDC=1-[3-(dimethylamino)propyl]-3-ethylcarbodiimide hydrochloride
HOAt=1-hydroxy-7-azabenzotriazole
(BOC)$_2$O=di-tert-butyl dicarbonate
mCPBA=m-chloroperoxybenzoic acid
Ra—Ni=Raney® Nickel
LDA=lithium diisopropylethylamide
pyr=pyridine
DIBAl-H=diisobutylaluminum hydride
PXPd=bis[di-tert-butylphosphinous chloride-κP]di-μ-chlorodichloro-di-palladium
Pd$_2$(dba)$_3$=tris(dibenzylideneacetone)dipalladium
Pd(dppf)Cl$_2$.CH$_2$Cl$_2$=(1,1'-bis(diphenylphosphino)ferrocene)-palladium (II) chloride dichloromethane complex
dppf=1,1'-bis(diphenylphosphino)ferrocene
DEAD=diethyl azodicarboxylate
NBS=N-bromosuccinimide
NCS=N-chlorosuccinimide
DMF=N,N-dimethylformamide
DMSO=dimethyl sulfoxide
EtOAc=ethyl acetate
Et$_2$O=diethyl ether=ether
PG=any standard protecting group known to those skilled in the art—see Protective Groups in Organic Synthesis (2$^{nd}$ Edition, T. W. Greene and P. G. M. Wuts, John Wiley & Sons, 1991)

Possible synthetic pathways for preparing the compounds of Formula I are illustrated below through a series of retrosynthetic charts. For example, compounds of Formula I may be prepared from the immediate precursors shown in Chart 1. The compound labeling system employed in the retrosynthetic charts equates Formula I with "A". The immediate precursors of "A" in Chart 1 are "A1", "A2", "A3", "A4", "A5", and "A6". Each of the immediate precursors of "A" are themselves the subject of unnumbered charts, as are the immediate precursors of each of those immediate precursors, and so on as generated by retrosynthetic analysis, which concludes when known or commercially available precursors are reached. Each precursor is labeled with a label of the form "Annn . . . " wherein "nnn . . . " is a sequence of 1 to 8 digits. While the vast majority of the retrosynthetic charts are unnumbered, they appear in an order determined by the subject (product) compound's label. The system used to order these charts is analogous to that used in a telephone book. Therefore, chart order is determined by evaluating the digits of the subject compound's label from left to right. The relative order of two charts is determined by the first point of difference (reading from left to right) in the subject compounds' labels. The chart having the subject compound's label with the lower digit at this first point of difference appears first. If there is no digit at the first point of difference, a zero is implied, and the chart with the subject compound's label having the implied zero appears first. Thus, for example, the following labels are placed in order: A11, A111, A1111, A11321, A12, A3, A4, A411.

CHART 1

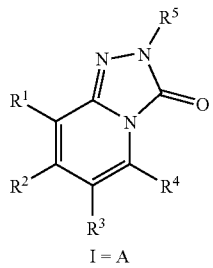

I = A

A CAN BE PREPARED FROM:

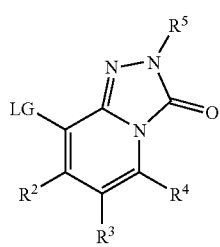

A1

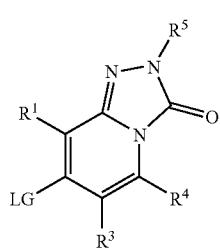

A2

-continued

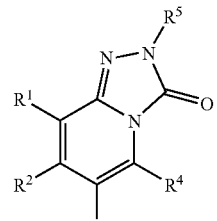

A3

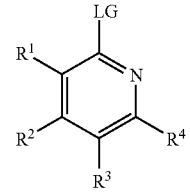

A4

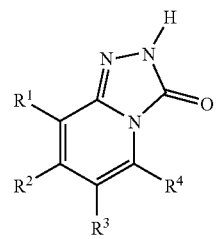

A5

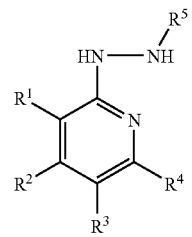

A6

Some of the synthetic pathways shown in the retrosynthetic charts are exemplified in the working Examples. For instance, Examples 1 and 2 follow the path of "A11111" to "A1111" to "A111" to "A11" to "A1" to "A", while Examples 3 and 4 follow the path of "A1111" to "A211" to "A21" to "A2" to "A".

In the retrosynthetic charts and synthetic schemes and descriptions thereof, LG represents a leaving group, especially fluoride, chloride, bromide, iodide, methanesulfonate, methanesulfinate, trifluoromethanesulfonate, p-toluenesulfonate, dinitrogen (as in a diazonium salt), phenoxide, and imidazolide, which is useful in nucleophilic displacement, electron transfer metallation, and/or palladium and other metal catalyzed coupling reactions. LG may also be trichloromethoxide or acetate or another carboxylic acid conjugate base when it is bonded to a carbonyl as, for example, in triphosgene, acetic anhydride or an organic mixed anhydride. LG may also be a hydroxyl, alkoxy, or amino group when it is bonded to a carbonyl and can be displaced by an intramolecular nucleophilic group. Where multiple LG appear in a single structure, they are independent of one another. For example, one LG may represent chloride and another may represent iodide. Furthermore, one LG may be changed into another LG prior to use in a displacement, metallation, or palladium or other metal catalyzed coupling reaction, for example replacement of chloride with iodide or replacement of dinitrogen (diazonium salt) with bromide.

In the retrosynthetic charts and synthetic schemes and descriptions thereof, Q represents a group that is a common precursor for a leaving group (LG) after one or two chemical steps. For example, Q may be a hydroxyl group because it can be converted to a chloride or a trifluoromethanesulfonate leaving group in one step. As another example, Q may be a methoxy group because it can be converted to a halogen or a sulfonate leaving group in two steps through the intermediacy of a hydroxyl group. As other examples, Q may be an amino group or a nitro group because they may be converted to a dinitrogen (diazonium salt) leaving group in one or two steps, respectively. As another example, Q may be a methylthio group because it can be converted to a methylsulfonyl group (which can leave as methanesulfinate) in one step. Where multiple Q appear in a single structure, they are independent of one another. For example, one Q may represent a hydroxyl group and another may represent an amino group.

In certain cases wherein Q represents a hydroxyl group, a tautomeric carbonyl structure is possible. It is understood that tautomeric structures are chemically equivalent and represent the same compound. In general, tautomeric possibilities exist for compounds which can be drawn with a carbon atom both double bonded to a nitrogen atom and single bonded to the oxygen atom of a hydroxyl group. In the tautomer of this depiction, the carbon atom is double bonded to the oxygen atom and single bonded to the nitrogen atom, which bears a hydrogen atom. Typically, in tautomeric compounds represented in the retrosynthetic charts, the carbon and nitrogen atoms are within a ring. For example, "A2211 wherein Q represents a hydroxyl group" and "A5" are each depicted below in both of their tautomeric forms.

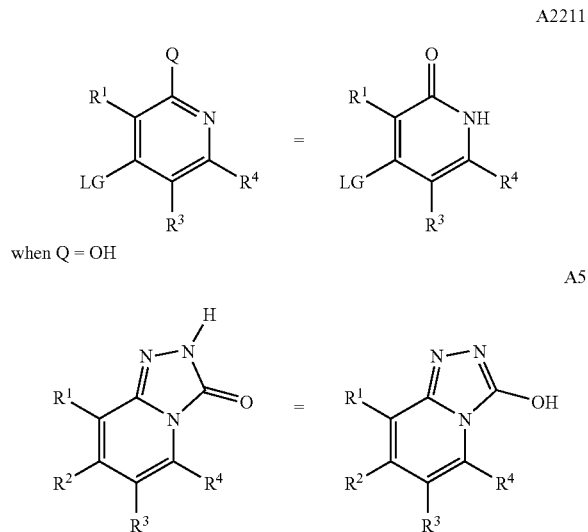

In the retrosynthetic charts and synthetic schemes and descriptions thereof, some intermediates having a pyridine ring without a fused triazole ring have listed among their immediate precursors the expression "acyclic precursors" without a structure. This indicates that the subject intermediate of the chart may be prepared from known or commercially available compounds lacking the pyridine ring by chemistry in which the pyridine ring is formed using known methods such as those described in the following references and references contained therein:

J. E. Toomey and R. Murugan, Progress in Heterocyclic Chemistry, Vol. 6, pp. 206-230, 1994;

J. E. Toomey and R. Murugan, Progress in Heterocyclic Chemistry, Vol. 7, pp. 195-225, 1995;

J. E. Toomey, Jr. and R. Murugan, Progress in Heterocyclic Chemistry, Vol. 8, pp. 209-230, 1996;

D. S. Coffey, et al., Progress in Heterocyclic Chemistry, Vol. 15, pp. 284-305, 2003;

D. S. Coffey, et al., Progress in Heterocyclic Chemistry, Vol. 14, pp. 257-278, 2002;

D. S. Coffey, et al., Progress in Heterocyclic Chemistry, Vol. 13, pp. 238-260, 2001;

R. D. Larsen and I. W. Davies, Progress in Heterocyclic Chemistry, Vol. 11, pp. 230-255, 1999;

R. D. Larsen, Progress in Heterocyclic Chemistry, Vol. 10, pp. 226-250, 1998;

J. G. Keay and J. E. Toomey, Jr., Progress in Heterocyclic Chemistry, Vol. 4, pp. 168-185, 1992;

J. G. Keay and A. R. Sherman, Progress in Heterocyclic Chemistry, Vol. 3, pp. 186-204, 1991;

J. G. Keay and A. R. Sherman, Progress in Heterocyclic Chemistry, Vol. 2, pp. 166-184, 1990;

M. A. Yurovskaya, et al., Chemistry of Heterocyclic Compounds, Vol. 34, pp. 871-899, 1998;

M. A. Yurovskaya, and O. D. Mit'kin, Chemistry of Heterocyclic Compounds, Vol. 35, pp. 383-435, 1999;

K. I. Kobrakov, et al., Chemistry of Heterocyclic Compounds, Vol. 39, pp. 283-307, 2003;

J. M. Bakke, Pure Appl. Chem., Vol. 75, pp. 1403-1415, 2003;

G. Quéguiner, J. Heterocyclic. Chem., Vol. 37, pp. 615-621, 2000;

M. J. Silvester, Aldrichimica Acta, Vol. 24, p. 31, 1991;

G. D. Henry, Tetrahedron, Vol. 60, pp. 6043-6061, 2004;

C. Bobbio and M. Schlosser, J. Org. Chem., Vol. 70, pp. 3039-3045, 2005;

M. Schlosser, et al., Org. Lett., Vol. 7, pp. 127-129, 2005;

M. Schlosser, et al., J. Org. Chem., Vol. 70, pp. 2494-2502, 2005;

F. Marsais, et al., J. Org. Chem., Vol. 57, pp. 565-573, 1992;

M. Mallet, et al., J. Organometallic Chem., Vol. 382, pp. 319-332, 1990;

P. Rocca, et al., J. Org. Chem., Vol. 58, pp. 7832-7838, 1993;

P. Rocca, et al., Tetrahedron, Vol. 49, pp. 49-64, 1993;

F. Cottet and M. Schlosser, Eur. J. Org. Chem., pp. 3793-3798, 2004;

M. A. Walters, et al., Synth. Comm., Vol. 22, pp. 2829-2837, 1992;

V. H. Bönnemann, Angew. Chem., Vol. 90, pp. 517-526, 1978;

WO 2005/037197;

WO 2005/041663;

M. Makosza and K. Sienkiewicz, J. Org. Chem., Vol. 63, pp. 4199-4208, 1998;

V. Canibano, et al., Synthesis, Vol. 14, pp. 2175-2179, 2001;

L. Carles, et al., J. Org. Chem., Vol. 67, pp. 4304-4308, 2002;

K. Yamamoto, et al., J. Org. Chem., Vol. 52, pp. 5239-5243, 1987;

A. W. Erian, Chemical Reviews, Vol. 93, pp. 1991-2005, 1993;

D. L. Comins and S. P. Joseph, Comprehensive Heterocyclic Chemistry II, Vol. 5, pp. 37-90, 1996 (A. McKillop, ed., Pergamon Press);

G. Jones, Comprehensive Heterocyclic Chemistry II, Vol. 5, pp. 167-244, 1996 (A. McKillop, ed., Pergamon Press); and N. Dennis, Comprehensive Heterocyclic Chemistry II, Vol. 5, pp. 91-134, 1996 (A. McKillop, ed., Pergamon Press).

Moreover, these references also describe methods for the manipulation of pyridine compound substituents, as required for many of the transformations represented in the retrosynthetic charts, such as the introduction of Q and LG groups by replacement of hydrogen, the conversion of one type of Q group into another, the conversion of Q groups into LG groups, the conversion of LG groups into R groups, and the conversion of one type of R group into another. Among the known methods for the introduction of Q groups by replacement of hydrogen are for example 1. nitration to introduce a nitro group and 2. deprotonation with a strong base followed by treatment with dimethyl disulfide to introduce a methylthio group or t-butyl hydroperoxide to introduce a hydroxyl group. Among the known methods for the introduction of LG groups by replacement of hydrogen are for example 1. deprotonation with a strong base followed by treatment with a halogen source such as molecular iodine and 2. electrophilic halogenation with molecular bromine. Among the known methods for the conversion of one type of Q group into another are for example 1. reduction of a nitro group to an amino group and 2. demethylation of a methoxy group to produce a hydroxyl group. Among the known methods for the conversion of Q groups into LG groups are for example 1. treatment with phosphorus oxychloride to convert a hydroxyl group into a chloride leaving group; 2. trifluoromethanesulfonylation to convert a hydroxyl group into a trifluoromethanesulfonate group; 3. diazotization to convert an amino group into a dinitrogen (diazonium salt) group; and 4. oxidation to convert a methylthio group into methylsulfonyl group (which can leave as methanesulfinate). Among the known methods for the conversion of LG groups into R groups are for example 1. nucleophilic displacement with alkoxides, aryloxides, and heteroaryloxides to introduce oxygen-linked R groups, with alkylamines, arylamines, and conjugate bases of NH-containing heterocycles to introduce nitrogen-linked R groups, with mercaptan salts to introduce sulfur-linked R groups, and with alkyl and aryl Grignard reagents and other organometallics, as well as cyanide, optionally followed by additional steps described below, to introduce carbon-linked R groups; 2. electron transfer metallation (optionally after deprotonation of any OH or NH groups with a base) followed by trapping of the resulting carbanion with an electrophilic form of R, such as R-LG, to introduce carbon-linked and sulfur-linked R groups; and 3. palladium and other metal catalyzed coupling reactions with organometallics such as $RB(OH)_2$, $RSnBu_3$, or RZnCl, to introduce aryl and heteroaryl R groups, with cyanide, optionally followed by additional steps described below, to introduce cyano, acyl, alkoxycarbonyl, arylcarbamoyl, and related carbon-linked R groups, and with alcohols, phenols and amines, to introduce oxygen-linked and nitrogen-linked R groups.

Furthermore, many of the same methods mentioned and referenced above that may be used to manipulate pyridine ring substituents in intermediates having a pyridine ring without a fused triazole ring may also be used to manipulate substituents in intermediates having a pyridine ring with a fused triazole ring (triazolopyridines).

Additional useful references, with useful references contained therein, that describe the synthesis and reactions of substituted triazolopyridine compounds include:

G. Jones, Advances in Heterocyclic Chemistry, Vol. 83, pp. 1-70.

Additional transformations that are represented in the retrosynthetic charts deserve comment.

Installation of $R^5$ onto the triazolopyridine core, for example in the preparation of "A" from "A5" in Chart 1, may be accomplished with $R^5$-LG by nucleophilic displacement or palladium catalyzed coupling methods, or when $R^5$ is alkyl and the like, it may also be accomplished by Mitsunobu reaction with $R^5$—OH or by opening of epoxide E1, so that $CR^{53}R^{54}CR^{55}R^{56}OH=R^5$. This transformation presents a problem of N-derivatization vs. O-derivatization. Known methods that favor N-derivatization can be employed, for example, nucleophilic displacement reactions using a base with a counterion that coordinates oxygen, such as lithium.

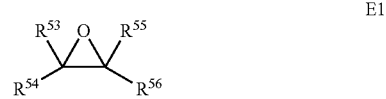

E1

Intermediates such as "A5" (Chart 1), which have a triazolopyridine core but which lack $R^5$, may be prepared from pyridine intermediates such as "A4" ("A5" chart), which lack a fused triazole ring and which have a leaving group substituting the pyridine ring, by displacement of the leaving group with hydrazine, followed by reaction with 1,1'-carbonyldiimidazole, and thermal ring closure. Other examples of LG-CO-LG, such as phosgene, triphosgene, and phenyl chloroformate may be used in place of 1,1'-carbonyldiimidazole. Furthermore, reagents that contain both the hydrazine moiety and the carbonyl moiety ($H_2NNHCO$-LG) may be used to construct the triazole ring in a single operation. Such reagents include semicarbazide ($H_2NNHCONH_2$).

Triazolopyridines bearing an $R^5$ group, such as "A" (Chart 1), may also be prepared from pyridine intermediates such as "A4", which lack a fused triazole ring and which have a leaving group substituting the pyridine ring, by addition of a compound $H_2NNR^5CO$-LG, followed by intramolecular displacement of LG by a pyridine nitrogen to form the triazole ring. In this type of reaction LG may be, for example, an amino group. The compound $H_2NNR^5CO$-LG may be prepared by coupling PG-NHNH$R^5$, wherein PG is a protecting group such as t-butyloxycarbonyl, with LG-CO-LG, followed by deprotection. PG-NHNH$R^5$ may be prepared by protection of $H_2NNR^5$ or by introduction of $R^5$ into PG-NHNH$_2$, for example by reductive alkylation of the primary amino group with $R^{51}COR^{52}$, so that $R^{51}R^{52}CH=R^5$, or nucleophilic displacement or palladium catalyzed coupling with $R^5$-LG.

As an alternative to the aforementioned method of addition of $H_2NNR^5CO$-LG with subsequent triazole ring closure, triazolopyridines bearing an $R^5$ group, may also be prepared from pyridine intermediates which lack a fused triazole ring and which have a leaving group substituting the pyridine ring, by addition of hydrazine, followed by treatment with 1,1'-carbonyldiimidazole, triphosgene, phenyl chloroformate, or other examples of LG-CO-LG, followed by introduction of $R^5$ with $R^5$-LG prior to triazole ring closure. This alternative method is exemplified in Scheme 1.

SCHEME 1

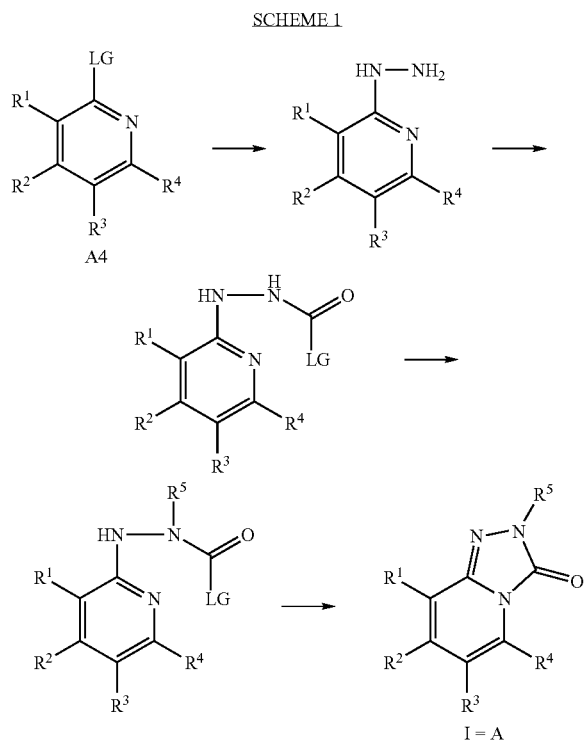

Triazolopyridines bearing an $R^5$ group, such as "A" (Chart 1), may be prepared from pyridine intermediates such as "A6", which have an $R^5$ substituted hydrazine moiety, by treatment with 1,1'-carbonyldiimidazole, phosgene, triphosgene, phenyl chloroformate, or other examples of LG-CO-LG, followed by triazole ring closure.

Pyridine intermediates such as "A6" (Chart 1), which have an $R^5$ substituted hydrazine moiety, may be prepared from pyridine intermediates such as "A4" ("A6" chart), which lack a fused triazole ring and which have a leaving group substituting the pyridine ring, by 1. addition of an $R^5$ substituted hydrazine, $H_2NNHR^5$; 2. addition of hydrazine, followed by reductive alkylation of the primary amino group with $R^{51}COR^{52}$, wherein $R^{51}R^{52}CH=R^5$, or nucleophilic displacement or palladium catalyzed coupling with $R^5$-LG; or 3. addition of trifluoroacetylhydrazine, followed by introduction of $R^5$ onto the trifluoroacetylated nitrogen by nucleophilic displacement with $R^5$-LG or by Mitsunobu reaction with $R^5$—OH, followed by hydrolytic removal of the trifluoroacetyl group.

According to the retrosynthetic charts, conversion of a Q group to an R group is generally a two-step process that involves the intermediacy of an LG group. However, certain oxygen-linked $R^1$, $R^2$, $R^3$, and $R^4$ groups may also be generated from a Q group without the intermediacy of an LG group when the Q group is a hydroxyl group. Generally, the hydroxyl group may be derivatized to produce the desired $R^1$, $R^2$, $R^2$, or $R^4$ group when it acts as the nucleophile in nucleophilic displacement, palladium catalyzed coupling, or Mitsunobu reactions. For example, nucleophilic displacement with benzyl bromide may generate a benzyloxy group as $R^3$ from an intermediate having a hydroxyl group at the position occupied by $R^3$ in the product.

According to the retrosynthetic charts, the introduction of an R group by replacement of hydrogen is generally a two-step process that involves the intermediacy of an LG group. However, certain carbon-linked and sulfur-linked $R^1$, $R^2$, $R^3$, and $R^4$ groups may also be installed by replacement of hydrogen without the intermediacy of an LG group by deprotonation with a strong base followed by trapping of the resulting carbanion with an electrophilic form of R, such as R-LG.

In the above descriptions of synthetic transformations the possible reagent lists are abbreviated, and it is understood that the reagents mentioned are example reagents, not meant to be limiting. Those skilled in the art will recognize that there are many acids (hydrochloric acid, polyphosphoric acid, etc.), many bases (sodium hydride, potassium methoxide, etc.), many oxidants (hydrogen peroxide, 3-chloroperoxybenzoic acid, Dess-Martin periodinane, etc.), many hydrogenation catalysts (palladium, platinum oxide, Raney® Nickel, etc.), and so on that may be employed to synthesize the compounds of the application. In some cases alternative reagents known to those skilled in the art will be superior to those mentioned. Alternative reagents may be found in Reagents For Organic Synthesis (Fieser and Fieser, John Wiley & Sons) and Compendium of Organic Synthetic Methods (John Wiley & Sons). These references will also provide guidance in cases where the description herein designates only a class of reagent rather than a specific reagent (for example oxidant rather than hydrogen peroxide). In some instances the descriptions herein may refer not to specific reagents or reagent classes, but rather to name reactions, for example Curtius rearrangement (a. thionyl chloride b. sodium azide c. alkanol, heat; used for conversion of carboxyl groups to alkoxycarbonylamino groups). Name reactions and their experimental details are well-known to those skilled in the art—see Organic Syntheses Based on Name Reactions and Unnamed Reactions, A. Hassner and C. Stumer, Pergamon Press, 1994.

In general, the interchange of functional groups within the various R groups may be accomplished according to the methods and procedures described in Compendium of Organic Synthetic Methods (John Wiley & Sons), Comprehensive Organic Functional Group Transformations (Editors A. R. Katritzky, O. Meth-Cohn and C. W. Rees, Pergamon Press) and Comprehensive Organic Transformations—A Guide To Functional Group Preparations (R. C. Larock, VCH Publishers, 1989). For example, a compound of Formula I having a double bond in $R^1$ may be reduced by catalytic hydrogenation to produce a compound of Formula I that is saturated in $R^1$. As another example, an intermediate in which $R^2$ is a bromophenyl group may undergo palladium catalyzed coupling with an arylboronic acid to produce an intermediate in which $R^2$ is a biphenyl. As another example, an intermediate in which $R^3$ contains a hydroxyl group may be oxidized to produce an intermediate in which $R^3$ contains an oxo group. As another example, a compound of Formula I in which $R^4$ is an amino group may be alkylated with methyl iodide to produce a compound of Formula I in which $R^4$ is a methylamino group. As another example, a compound of Formula I in which $R^4$ is hydrogen may be deprotonated and alkylated with methyl iodide to produce a compound of Formula I in which $R^4$ is a methyl group. As another example, a compound of Formula I in which $R^2$ is a methylthio group may be oxidized to produce a compound of Formula I in which $R^2$ is a methylsulfonyl group. As another example, a compound of Formula I in which $R^1$ is a methoxy group may be demethylated and carbamoylated to produce a compound of Formula I in which $R^1$ is a carbamoyloxy group. As another example, a compound of Formula I in which $R^2$ is an amino group may be phenylsulfonylated to produce a compound of Formula I in which $R^2$ is a phenylsulfonylamino group. As another example, a compound of Formula I in which $R^1$ is an ethoxycarbonyl group may be hydrolyzed to the corresponding carboxylic acid and made to undergo Curtius degradation to produce a compound of Formula I in which $R^1$ is an amino group. As another example, an intermediate in which $R^2$ is a cyano group may be hydrolyzed to the corresponding carboxylic acid and coupled with aniline to produce an intermediate in which $R^2$ is a phenylcarbamoyl group.

Generally, compounds of Formula I and synthetic intermediates in which an R group contains an aryl moiety substituted by cyano, alkyl, alkenyl, aryl, heteroaryl, alkoxy, aryloxy or any type of amino group may be prepared from the corresponding compounds of Formula I and synthetic intermediates wherein the aryl moiety is substituted by halo or hydroxy, using various palladium catalyzed coupling procedures as described in Aranyos, et al., J. Am. Chem. Soc. 1999, 121, 4369-4378 and Hamann, et al., J. Am. Chem. Soc. 1998, 120, 7369-7370 and references contained therein, and in recent papers authored by Gregory C. Fu, Stephen L. Buchwald, or John F. Hartwig. These procedures are directly applicable when the aryl moiety is substituted by halo. When the aryl moiety is substituted by hydroxy, prior activation by conversion of the hydroxyl group to a trifluoromethylsulfonyloxy group, as described in the aforementioned references, is required.

It is understood that during the course of manipulating any functional group within the various R groups of compounds of Formula I or at any stage of their synthesis, standard protecting groups, as described in Protective Groups in Organic Synthesis ($2^{nd}$ Edition, T. W. Greene and P. G. M. Wuts, John Wiley & Sons, 1991), may be employed to avoid undesired reactions of any other functional group.

The aforementioned retrosynthetic charts follow.

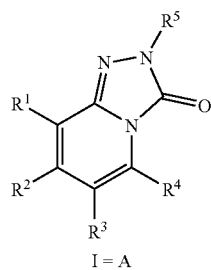

I = A

A CAN BE PREPARED FROM:

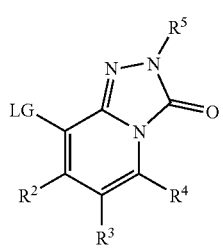

A1

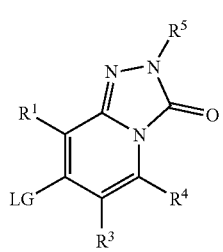

A2

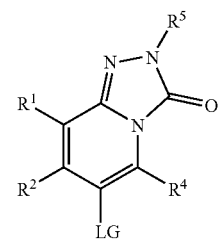

A3

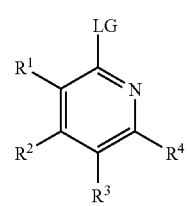

A4

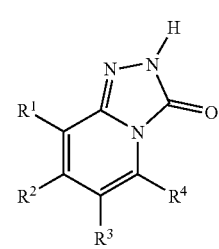

A5

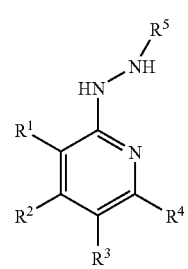

A6

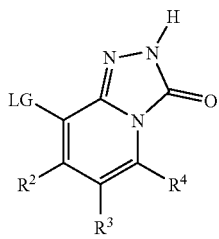

A1 CAN BE PREPARED FROM:

A11

-continued

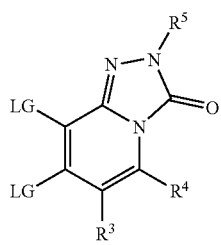
A21

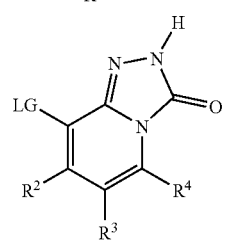

A11 CAN BE PREPARED FROM:

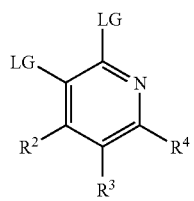

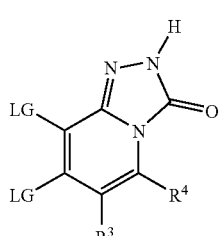
A211

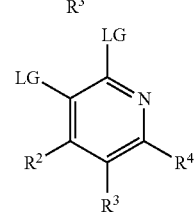

A111 CAN BE PREPARED FROM:

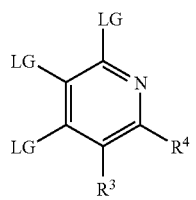

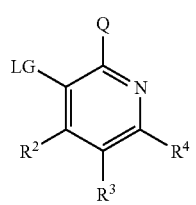

-continued

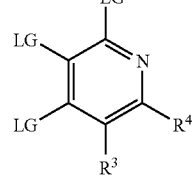

A1111 CAN BE PREPARED FROM:

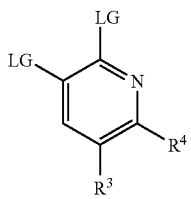
A11111

See also the preparation of 3-bromo-2,4-dichloropyridine in M.A. Walters, et al., Synth. Comm., volume 22, pp. 2829-2837, 1992.

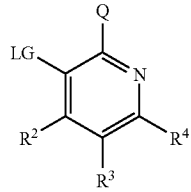

A1112 CAN BE PREPARED FROM:

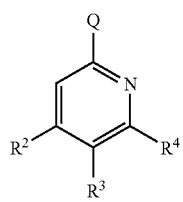
A11121

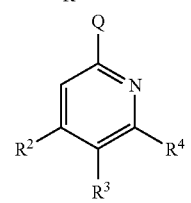

A11121 CAN BE PREPARED FROM:

acyclic precursors for example as 4-phenyl-2-hydroxypyridine is prepared as described in L. Carles, et al., J. Org. Chem., volume 67, pp. 4304-4308, 2002.

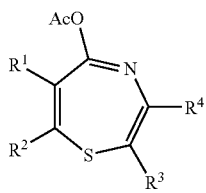

for example as 4,5-diphenyl-2-hydroxypyridine is prepared as described in K. Yamamoto, et al., J. Org. Chem., volume 52, pp. 5239-5243, 1987.

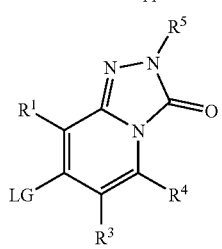

A111
A1111
A1112

-continued
A2 CAN BE PREPARED FROM:
A21
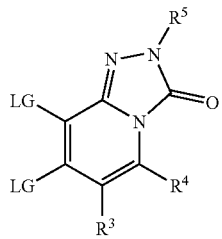
A22
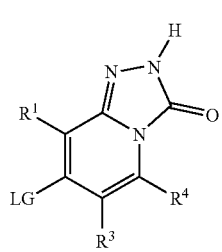
A23
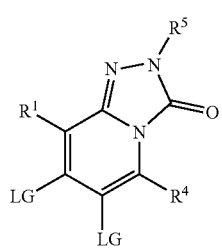
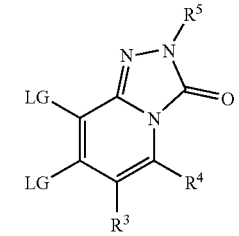
A21 CAN BE PREPARED FROM:
A211
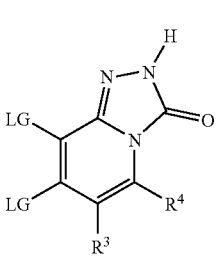
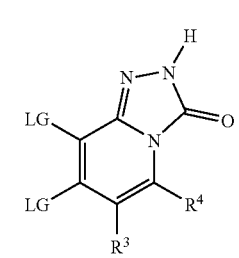
-continued
A211 CAN BE PREPARED FROM:
A1111
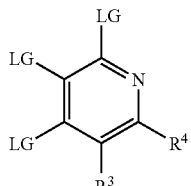
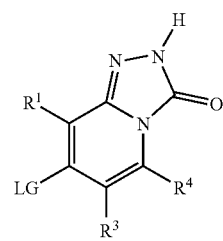
A22 CAN BE PREPARED FROM:
A221
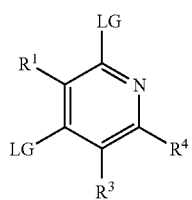
A211
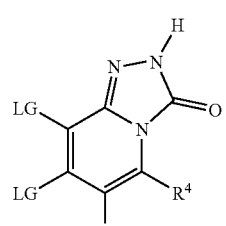
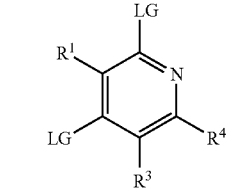
A221 CAN BE PREPARED FROM:
A2211
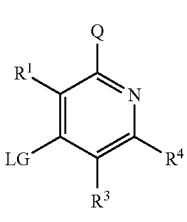
A2311
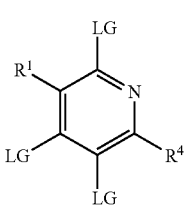

-continued
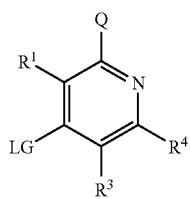
A2211 CAN BE PREPARED FROM:
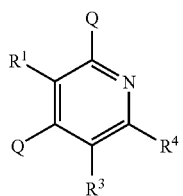
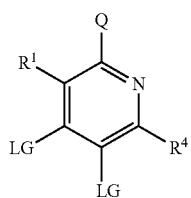
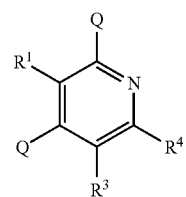
A22111 CAN BE PREPARED FROM:
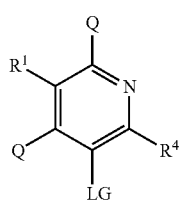
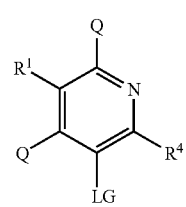
A221111 CAN BE PREPARED FROM:
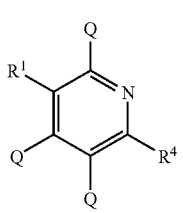
-continued
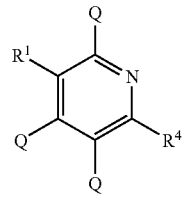
A2211111 CAN BE PREPARED FROM:
A22111
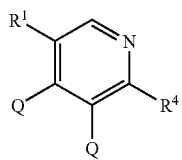
for example as 4-ethoxy-6-hydroxy-3-nitropyridine is prepared from 4-ethoxy-3-nitropyridine as described in M. Makosza and K. Sienkiewicz, J. Org. Chem., volume 63, pp. 4199-4208, 1998.
A23111
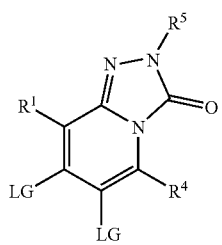
A23 CAN BE PREPARED FROM:
A231
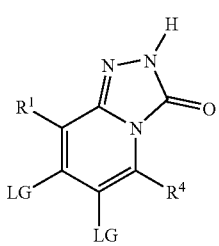
A231 CAN BE PREPARED FROM:
A2311
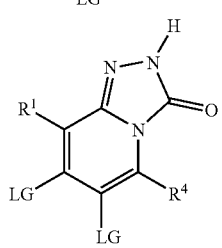
A2211111
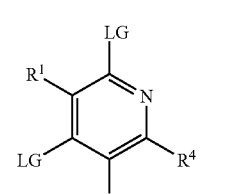
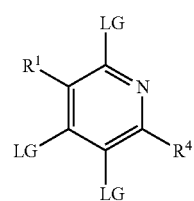

-continued

A2311 CAN BE PREPARED FROM:

A23111

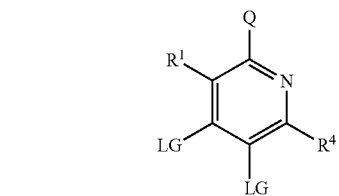

A23112

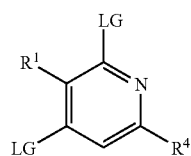

for example as 2,4-difluoro-5-iodopyridine is prepared from 2,4-difluoropyridine as described in M. Schlosser, et al., J. Org. Chem., volume 70, pp. 2494-2502, 2005.

A23113

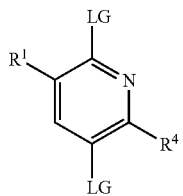

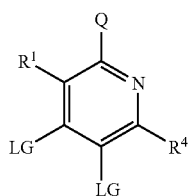

A23111 CAN BE PREPARED FROM:

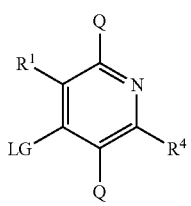

A221111

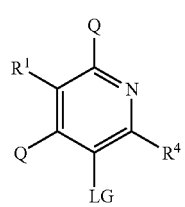

See also the preparation of 3,4-dichloro-2-methoxypyridine in WO 2005/041663.

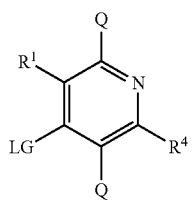

-continued

A231111 CAN BE PREPARED FROM:

A2211111

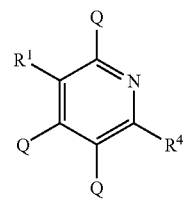

A2311111

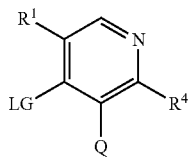

for example as 4-chloro-2-hydroxy-5-nitropyridine is prepared from 4-chloro-3-nitropyridine as described in WO 2005/037197.

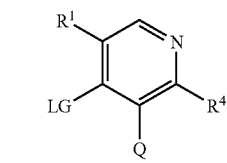

A2311111 CAN BE PREPARED FROM:

A22111111

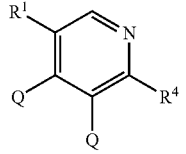

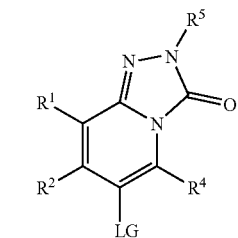

A3 CAN BE PREPARED FROM:

A31

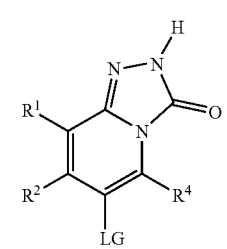

A23

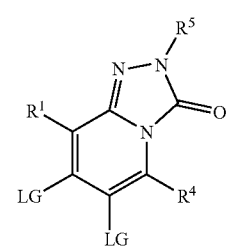

-continued
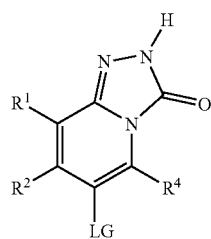
A31 CAN BE PREPARED FROM:
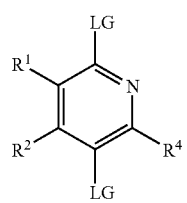
A311 CAN BE PREPARED FROM:
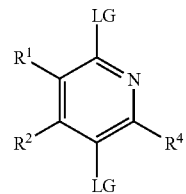
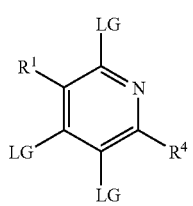
A3111 CAN BE PREPARED FROM:
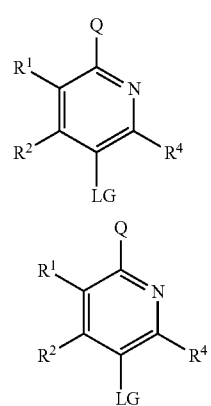
-continued
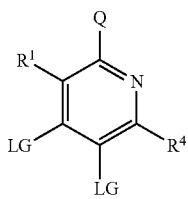
A23111
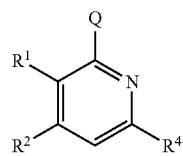
A31111 CAN BE PREPARED FROM:
acyclic precursors
for example as 4-phenyl-2-hydroxypyridine is prepared as described in L. Carles, et al., J. Org. Chem., volume 67, pp. 4304-4308, 2002.
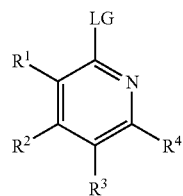
A2311
A4 CAN BE PREPARED FROM:
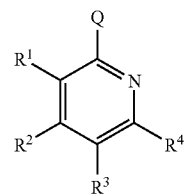
A3111
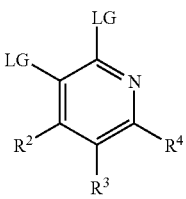
A41
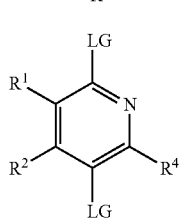
A111
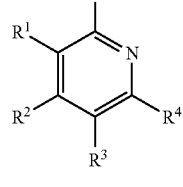
A311
A31111

-continued

A41 CAN BE PREPARED FROM:

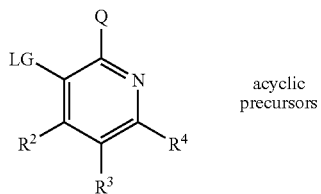

acyclic precursors

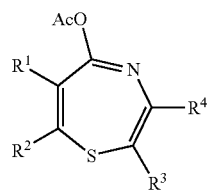

for example as 4,5-diphenyl-2-hydroxypyridine is prepared as described in K. Yamamoto, et al., J. Org. Chem., volume 52, pp. 5239-5243, 1987.

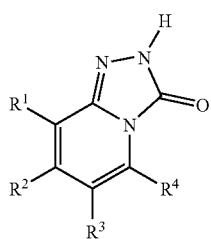
A5

A5 CAN BE PREPARED FROM:

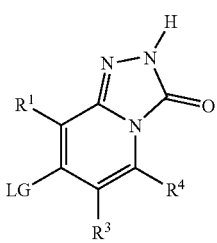
A22

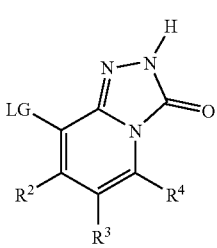
A11

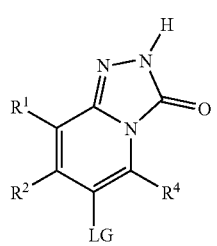
A31

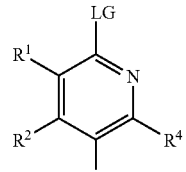
A1112

A4

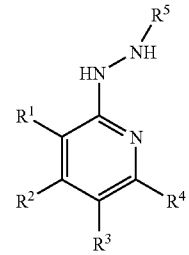

A6 CAN BE PREPARED FROM:

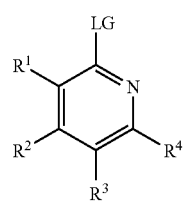
A4

The synthetic schemes below describe, in the forward synthetic direction and in greater detail, some of the more useful synthetic routes to compounds of Formula I.

SCHEME 2

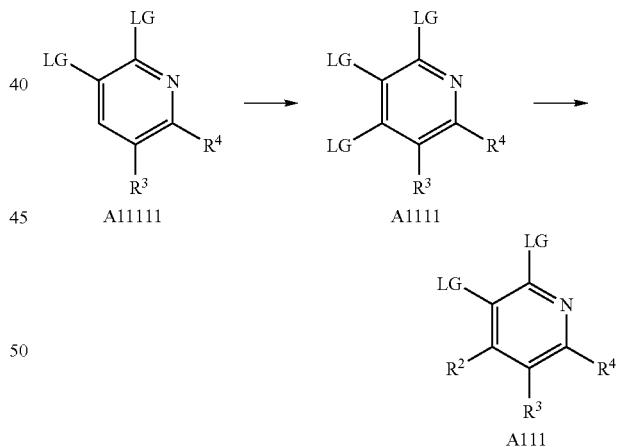

As shown in Scheme 2, a compound of Formula A1111, such as a 2,3-dihalopyridine, may be converted to a compound of Formula A111, such as a 2,3,4-trihalopyridine, for example, by deprotonation with a base, such as lithium diisopropylamide, in a solvent, such as tetrahydrofuran, at a low temperature, such as −78° C., under an inert atmosphere, such as argon, followed by addition of an electrophilic source of halogen, such as molecular iodine or molecular bromine. A compound of Formula A111 may also be prepared as described in M. A. Walters, et al., Synth. Comm., Vol. 22, pp. 2829-2837, 1992, which describes the preparation of 3-bromo-2,4-dichloropyridine.

A compound of Formula A1111, such as a 2,3,4-trihalopyridine, may be converted to a compound of Formula A1111, such as a 4-aryl-2,3-dihalopyridine, for example, by reaction with an $R^2$-containing organometallic reagent, such as an arylboronic acid or the pinacol ester of an arylboronic acid or an aryltrialkylstannane, in a solvent, such as toluene or tetrahydrofuran or n-butanol or 1,4-dioxane or 1,2-dimethoxyethane or a mixture of solvents, such as tetrahydrofuran and methanol, at an elevated temperature, such as 200° C. or 120° C. or 80° C., achieved by either conventional or microwave heating, optionally in a sealed vessel to allow heating above the normal boiling point of the solvent, in the presence of a catalyst, such as a palladium catalyst, such as tetrakis(triphenylphosphine)palladium or (1,1'-bis(diphenylphosphino)ferrocene)-palladium (II) chloride dichloromethane complex or PXPd or a palladium catalyst—ligand combination, such as tris(dibenzylideneacetone)dipalladium with dicyclohexyl(2',6'-dimethoxybiphenyl-2-yl)phosphine, optionally in the presence of a base, such as anhydrous tribasic potassium phosphate or potassium carbonate or aqueous sodium carbonate or potassium carbonate solution, under an inert atmosphere, such as argon.

SCHEME 3

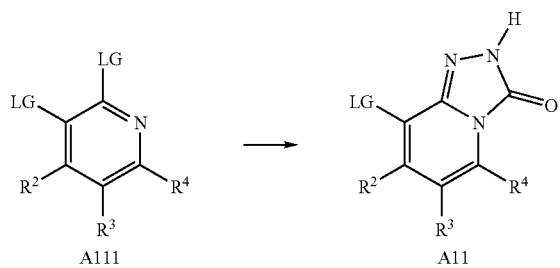

A111 → A11

As shown in Scheme 3, a compound of Formula A111, such as a 4-aryl-2,3-dihalopyridine, may be converted to a compound of Formula A11, such as a 7-aryl-8-halo-[1,2,4]triazolo[4,3-a]pyridin-3(2H)-one, for example, by first nucleophilic displacement at the 2 position with hydrazine in a solvent, such as tetrahydrofuran or 1,4-dioxane or pyridine, at a temperature, such as ambient temperature or 65° C. or 120° C., under an inert atmosphere, such as argon, followed by treatment with a carbonylating agent, such as 1,1'-carbonyldiimidazole or triphosgene, in a solvent, such as tetrahydrofuran, at a temperature, such as ambient temperature or 60° C., under an inert atmosphere, such as argon.

SCHEME 4

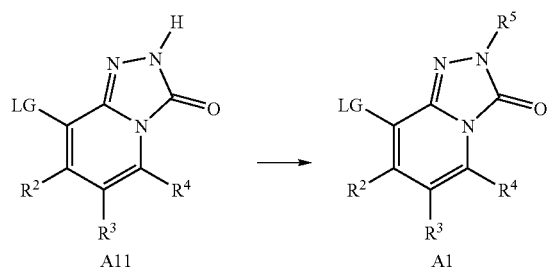

A11 → A1

As shown in Scheme 4, a compound of Formula A11, such as a 7-aryl-8-halo-[1,2,4]triazolo[4,3-a]pyridin-3(2H)-one, may be converted to a compound of Formula A1, such as a 2-substituted 7-aryl-8-halo-[1,2,4]triazolo[4,3-a]pyridin-3(2H)-one, for example, by reaction with an $R^5$-containing electrophile, $R^5$-LG, such as an optionally substituted benzyl halide or an optionally substituted heteroarylmethyl halide or an optionally substituted alkyl halide, in the presence of a base, such as potassium carbonate, in a solvent, such as N,N-dimethylformamide or acetone, at a temperature, such as ambient temperature or 55° C. or 80° C., under an inert atmosphere, such as argon; or by reaction with an $R^5$-containing alcohol, $R^5$—OH, such as an optionally substituted benzyl alcohol or an optionally substituted heteroarylmethyl alcohol or an optionally substituted alcohol, under Mitsunobu reaction conditions.

SCHEME 5

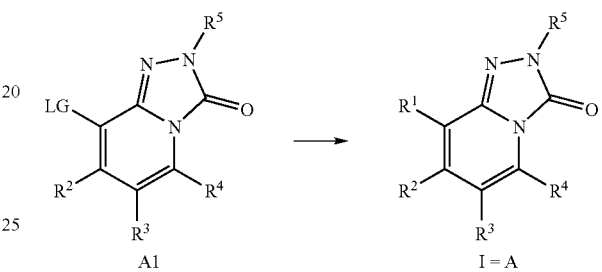

A1 → I = A

As shown in Scheme 5, a compound of Formula A1, such as a 2-substituted 7-aryl-8-halo-[1,2,4]triazolo[4,3-a]pyridin-3(2H)-one, may be converted to a compound of Formula I, such as a 2-substituted 7-aryl-8-heteroaryl-[1,2,4]triazolo[4,3-a]pyridin-3(2H)-one or a 2-substituted 7,8-diaryl-[1,2,4]triazolo[4,3-a]pyridin-3(2H)-one, for example, by reaction with an $R^1$-containing organometallic reagent, such as an arylboronic acid or a heteroarylboronic acid or the pinacol ester of said boronic acids or an aryltrialkylstannane or a heteroaryltrialkylstannane, in a solvent, such as toluene or tetrahydrofuran or n-butanol or 1,4-dioxane or 1,2-dimethoxyethane or a mixture of solvents, such as tetrahydrofuran and methanol, at an elevated temperature, such as 200° C. or 120° C. or 80° C., achieved by either conventional or microwave heating, optionally in a sealed vessel to allow heating above the normal boiling point of the solvent, in the presence of a catalyst, such as a palladium catalyst, such as tetrakis(triphenylphosphine)palladium or (1,1'-bis(diphenylphosphino)ferrocene)-palladium (II) chloride dichloromethane complex or PXPd or a palladium catalyst-ligand combination, such as tris(dibenzylideneacetone)dipalladium with dicyclohexyl(2',6'-dimethoxybiphenyl-2-yl)phosphine, optionally in the presence of a base, such as anhydrous tribasic potassium phosphate or potassium carbonate or aqueous sodium carbonate or potassium carbonate solution, under an inert atmosphere, such as argon. Alternatively, a compound of Formula A1, such as a 2-substituted 7-aryl-8-halo-[1,2,4]triazolo[4,3-a]pyridin-3(2H)-one, may be converted to a compound of Formula I, such as a 2-substituted 7-aryl-8-heteroaryl-[1,2,4]triazolo[4,3-a]pyridin-3(2H)-one or a 2-substituted 7-aryl-8-heteroaryloxy-[1,2,4]triazolo[4,3-a]pyridin-3(2H)-one or a 2-substituted 7-aryl-8-aryloxy-[1,2,4]triazolo[4,3-a]pyridin-3(2H)-one, for example, by reaction with $R^1$—H, where $R^1$—H is a heteroaromatic compound having a hydrogen atom-bearing ring nitrogen, such as imidazole, or a hydroxylated heteroaromatic compound, such as 3-hydroxypyridine, or a hydroxylated aromatic compound, such as phenol, in a solvent, such as 1-methylpyrrolidin-2-one, at a temperature, such as ambient temperature or 135° C., in the presence of a base, such as potassium tertiary butoxide, under an inert atmosphere, such as argon.

SCHEME 6

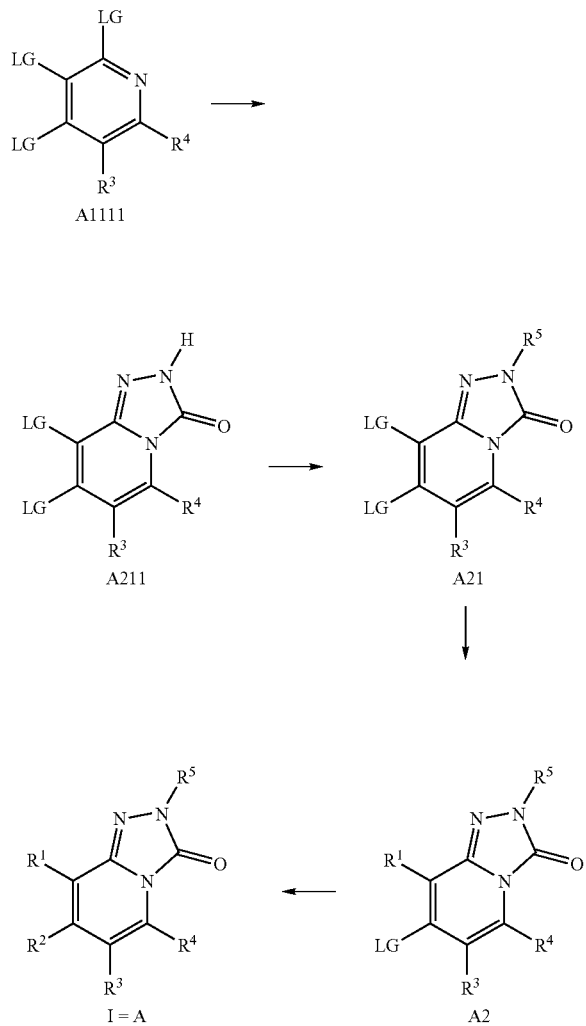

As shown in Scheme 6, a compound of Formula A111, such as a 2,3,4-trihalopyridine, may be converted to a compound of Formula A211, such as a 7,8-dihalo-[1,2,4]triazolo[4,3-a]pyridin-3(2H)-one, for example, by first nucleophilic displacement at the 2 position with hydrazine in a solvent, such as tetrahydrofuran or 1,4-dioxane or pyridine, at a temperature, such as ambient temperature or 65° C. or 120° C., under an inert atmosphere, such as argon, followed by treatment with a carbonylating agent, such as 1,1'-carbonyldiimidazole or triphosgene, in a solvent, such as tetrahydrofuran, at a temperature, such as ambient temperature or 60° C., under an inert atmosphere, such as argon.

A compound of Formula A211, such as a 7,8-dihalo-[1,2,4]triazolo[4,3-a]pyridin-3(2H)-one, may be converted to a compound of Formula A21, such as a 2-substituted 7,8-dihalo-[1,2,4]triazolo[4,3-a]pyridin-3(2H)-one, for example, by reaction with an $R^5$-containing electrophile, $R^5$-LG, such as an optionally substituted benzyl halide or an optionally substituted heteroarylmethyl halide or an optionally substituted alkyl halide, in the presence of a base, such as potassium carbonate, in a solvent, such as N,N-dimethylformamide or acetone, at a temperature, such as ambient temperature or 55° C. or 80° C., under an inert atmosphere, such as argon; or by reaction with an $R^5$-containing alcohol, $R^5$—OH, such as an optionally substituted benzyl alcohol or an optionally substituted heteroarylmethyl alcohol or an optionally substituted alcohol, under Mitsunobu reaction conditions.

A compound of Formula A21, such as a 2-substituted 7,8-dihalo-[1,2,4]triazolo[4,3-a]pyridin-3(2H)-one, may be converted to a compound of Formula A2, such as a 2-substituted 7-halo-8-heteroaryl-[1,2,4]triazolo[4,3-a]pyridin-3(2H)-one or a 2-substituted 8-aryl-7-halo-[1,2,4]triazolo[4,3-a]pyridin-3(2H)-one, for example, by reaction with an $R^1$-containing organometallic reagent, such as an arylboronic acid or a heteroarylboronic acid or the pinacol ester of said boronic acids or an aryltrialkylstannane or a heteroaryltrialkylstannane, in a solvent, such as toluene or tetrahydrofuran or n-butanol or 1,4-dioxane or 1,2-dimethoxyethane or a mixture of solvents, such as tetrahydrofuran and methanol, at an elevated temperature, such as 200° C. or 120° C. or 80° C., achieved by either conventional or microwave heating, optionally in a sealed vessel to allow heating above the normal boiling point of the solvent, in the presence of a catalyst, such as a palladium catalyst, such as tetrakis(triphenylphosphine)palladium or (1,1'-bis(diphenylphosphino)ferrocene)-palladium (II) chloride dichloromethane complex or PXPd or a palladium catalyst-ligand combination, such as tris(dibenzylideneacetone)dipalladium with dicyclohexyl(2',6'-dimethoxybiphenyl-2-yl)phosphine, optionally in the presence of a base, such as anhydrous tribasic potassium phosphate or potassium carbonate or aqueous sodium carbonate or potassium carbonate solution, under an inert atmosphere, such as argon.

A compound of Formula A2, such as a 2-substituted 7-halo-8-heteroaryl-[1,2,4]triazolo[4,3-a]pyridin-3(2H)-one or a 2-substituted 8-aryl-7-halo-[1,2,4]triazolo[4,3-a]pyridin-3(2H)-one, may be converted to a compound of Formula I, such as a 2-substituted 7-aryl-8-heteroaryl-[1,2,4]triazolo[4,3-a]pyridin-3(2H)-one or a 2-substituted 7,8-diaryl-[1,2,4]triazolo[4,3-a]pyridin-3(2H)-one, respectively, for example, by reaction with an $R^2$-containing organometallic reagent, such as an arylboronic acid or the pinacol ester of an arylboronic acid or an aryltrialkylstannane, in a solvent, such as toluene or tetrahydrofuran or n-butanol or 1,4-dioxane or 1,2-dimethoxyethane or a mixture of solvents, such as tetrahydrofuran and methanol, at an elevated temperature, such as 200° C. or 120° C. or 80° C., achieved by either conventional or microwave heating, optionally in a sealed vessel to allow heating above the normal boiling point of the solvent, in the presence of a catalyst, such as a palladium catalyst, such as tetrakis(triphenylphosphine)palladium or (1,1'-bis(diphenylphosphino)ferrocene)-palladium (II) chloride dichloromethane complex or PXPd or a palladium catalyst—ligand combination, such as tris(dibenzylideneacetone)dipalladium with dicyclohexyl(2',6'-dimethoxybiphenyl-2-yl)phosphine, optionally in the presence of a base, such as anhydrous tribasic potassium phosphate or potassium carbonate or aqueous sodium carbonate or potassium carbonate solution, under an inert atmosphere, such as argon.

SCHEME 7

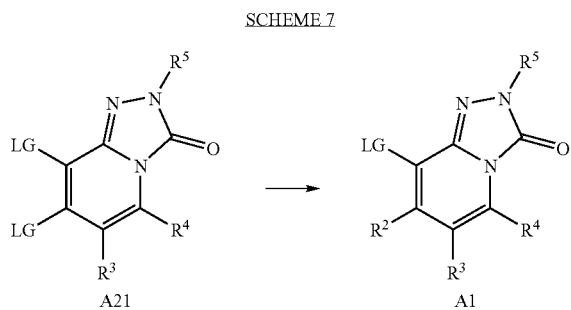

As shown in Scheme 7, a compound of Formula A21, such as a 2-substituted 7,8-dihalo-[1,2,4]triazolo[4,3-a]pyridin-3(2H)-one, may be converted to a compound of Formula A1, such as a 2-substituted 2-substituted 7-aryl-8-halo-[1,2,4]triazolo[4,3-a]pyridin-3(2H)-one, for example, by reaction with an $R^2$-containing organometallic reagent, such as an arylboronic acid or the pinacol ester of an arylboronic acid or an aryltrialkylstannane, in a solvent, such as toluene or tetrahydrofuran or n-butanol or 1,4-dioxane or 1,2-dimethoxyethane or a mixture of solvents, such as tetrahydrofuran and methanol, at an elevated temperature, such as 200° C. or 120° C. or 80° C., achieved by either conventional or microwave heating, optionally in a sealed vessel to allow heating above the normal boiling point of the solvent, in the presence of a catalyst, such as a palladium catalyst, such as tetrakis(triphenylphosphine)palladium or (1,1'-bis(diphenylphosphino)ferrocene)-palladium (II) chloride dichloromethane complex or PXPd or a palladium catalyst—ligand combination, such as tris(dibenzylideneacetone)dipalladium with dicyclohexyl (2',6'-dimethoxybiphenyl-2-yl)phosphine, optionally in the presence of a base, such as anhydrous tribasic potassium phosphate or potassium carbonate or aqueous sodium carbonate or potassium carbonate solution, under an inert atmosphere, such as argon.

SCHEME 8

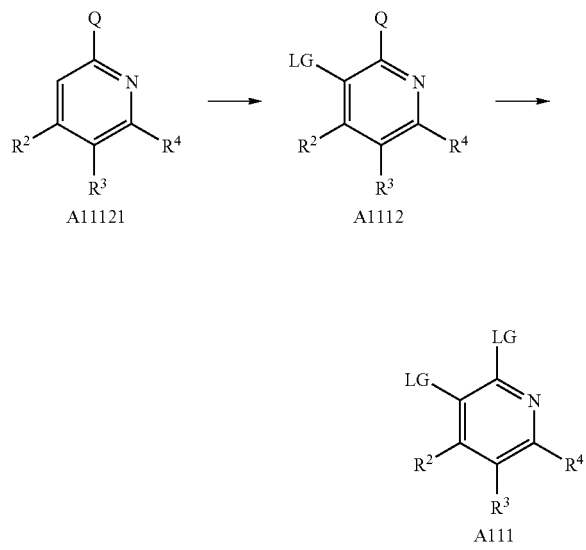

As shown in Scheme 8, a compound of Formula A11121, such as a 4-arylpyridin-2(1H)-one, may be prepared, for example, as described in L. Carles, et al., J. Org. Chem., Vol. 67, pp. 4304-4308, 2002 and may be converted to a compound of Formula A1112, such as a 4-aryl-3-halopyridin-2(1H)-one, for example, by reaction with an electrophilic source of halogen, such as N-bromosuccinimide or molecular bromine or molecular iodine, in a solvent, such as methanol or N,N-dimethylformamide, at a temperature, such as ambient temperature or 40° C., under an inert atmosphere, such as argon.

A compound of Formula A1112, such as a 4-aryl-3-halopyridin-2(1H)-one, may be converted to a compound of Formula A111, such as a 4-aryl-2,3-dihalopyridine, for example, by reaction with a mixed anhydride of a hydrohalic acid, such as phosphorous oxychloride or phosphorus pentachloride or phosphorus oxybromide, optionally in a solvent, such as a chlorinated hydrocarbon, at an elevated temperature, such as 100° C., optionally in the presence of a substoichiometric amount of N,N-dimethylformamide, under an inert atmosphere, such as argon.

SCHEME 9

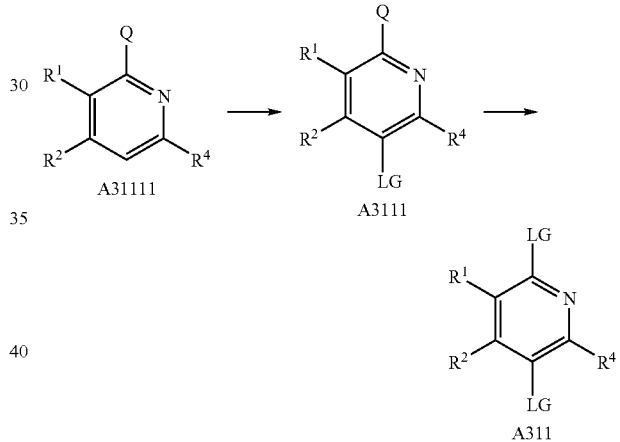

As shown in Scheme 9, a compound of Formula A31111, such as a 4-arylpyridin-2(1H)-one, may be prepared, for example, as described in L. Carles, et al., J. Org. Chem., Vol. 67, pp. 4304-4308, 2002 and may be converted to a compound of Formula A3111, such as a 4-aryl-5-halopyridin-2(1H)-one, for example, by reaction with an electrophilic source of halogen, such as N-bromosuccinimide or molecular bromine or molecular iodine, in a solvent, such as methanol or N,N-dimethylformamide, at a temperature, such as ambient temperature or 40° C., under an inert atmosphere, such as argon.

A compound of Formula A3111, such as a 4-aryl-5-halopyridin-2(1H)-one, may be converted to a compound of Formula A311, such as a 4-aryl-2,5-dihalopyridine, for example, by reaction with a mixed anhydride of a hydrohalic acid, such as phosphorous oxychloride or phosphorus pentachloride or phosphorus oxybromide, optionally in a solvent, such as a chlorinated hydrocarbon, at an elevated temperature, such as 100° C., optionally in the presence of a substoichiometric amount of N,N-dimethylformamide, under an inert atmosphere, such as argon.

SCHEME 10

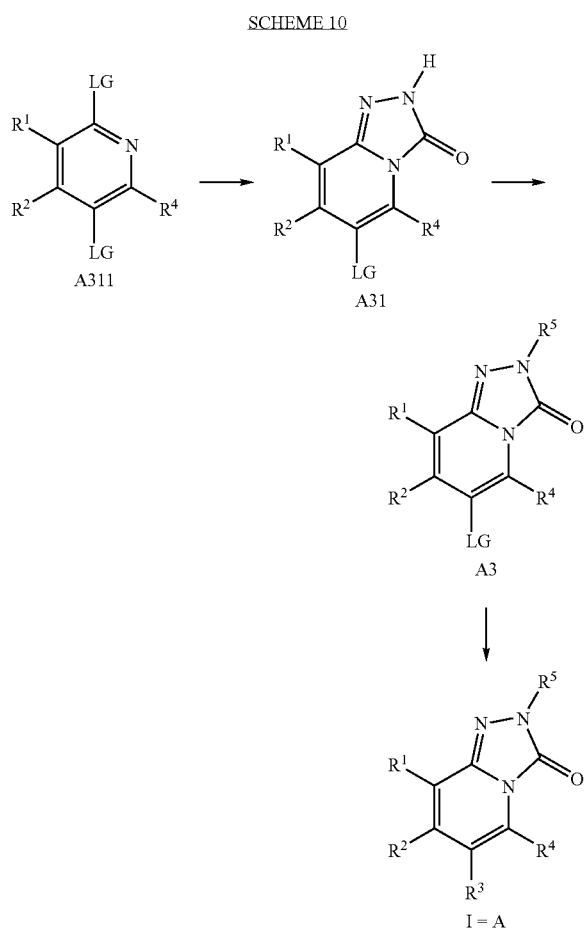

As shown in Scheme 10, a compound of Formula A311, such as a 4-aryl-2,5-dihalopyridine, may be converted to a compound of Formula A31, such as a 7-aryl-6-halo-[1,2,4]triazolo[4,3-a]pyridin-3(2H)-one, for example, by first nucleophilic displacement at the 2 position with hydrazine in a solvent, such as tetrahydrofuran or 1,4-dioxane or pyridine, at a temperature, such as ambient temperature or 65° C. or 120° C., under an inert atmosphere, such as argon, followed by treatment with a carbonylating agent, such as 1,1'-carbonyldiimidazole or triphosgene, in a solvent, such as tetrahydrofuran, at a temperature, such as ambient temperature or 60° C., under an inert atmosphere, such as argon.

A compound of Formula A31, such as a 7-aryl-6-halo-[1,2,4]triazolo[4,3-a]pyridin-3(2H)-one, may be converted to a compound of Formula A3, such as a 2-substituted 7-aryl-6-halo-[1,2,4]triazolo[4,3-a]pyridin-3(2H)-one, for example, by reaction with an $R^5$-containing electrophile, $R^5$-LG, such as an optionally substituted benzyl halide or an optionally substituted heteroarylmethyl halide or an optionally substituted alkyl halide, in the presence of a base, such as potassium carbonate, in a solvent, such as N,N-dimethylformamide or acetone, at a temperature, such as ambient temperature or 55° C. or 80° C., under an inert atmosphere, such as argon; or by reaction with an $R^5$-containing alcohol, $R^5$—OH, such as an optionally substituted benzyl alcohol or an optionally substituted heteroarylmethyl alcohol or an optionally substituted alcohol, under Mitsunobu reaction conditions.

A compound of Formula A3, such as a 2-substituted 7-aryl-6-halo-[1,2,4]triazolo[4,3-a]pyridin-3(2H)-one, may be converted to a compound of Formula I, such as a 2-substituted 7-aryl-6-heteroaryl-[1,2,4]triazolo[4,3-a]pyridin-3(2H)-one or a 2-substituted 6,7-diaryl-[1,2,4]triazolo[4,3-a]pyridin-3(2H)-one, for example, by reaction with an $R^3$-containing organometallic reagent, such as an arylboronic acid or a heteroarylboronic acid or the pinacol ester of said boronic acids or an aryltrialkylstannane or a heteroaryltrialkylstannane, in a solvent, such as toluene or tetrahydrofuran or n-butanol or 1,4-dioxane or 1,2-dimethoxyethane or a mixture of solvents, such as tetrahydrofuran and methanol, at an elevated temperature, such as 200° C. or 120° C. or 80° C., achieved by either conventional or microwave heating, optionally in a sealed vessel to allow heating above the normal boiling point of the solvent, in the presence of a catalyst, such as a palladium catalyst, such as tetrakis(triphenylphosphine)palladium or (1,1'-bis(diphenylphosphino)ferrocene)-palladium (II) chloride dichloromethane complex or PXPd or a palladium catalyst-ligand combination, such as tris(dibenzylideneacetone)dipalladium with dicyclohexyl(2',6'-dimethoxybiphenyl-2-yl)phosphine, optionally in the presence of a base, such as anhydrous tribasic potassium phosphate or potassium carbonate or aqueous sodium carbonate or potassium carbonate solution, under an inert atmosphere, such as argon.

SCHEME 11

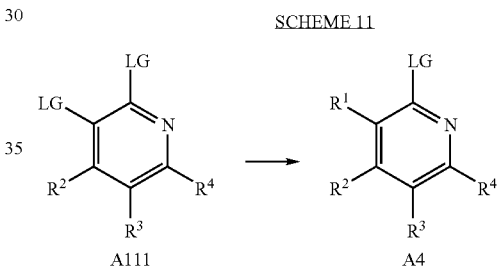

As shown in Scheme 11, a compound of Formula A111, such as a 4-aryl-2,3-dihalopyridine, may be converted to a compound of Formula A4, such as a 3,4-diaryl-2-halopyridine or a 4-aryl-3-heteroaryl-2-halopyridine, for example, by reaction with an $R^1$-containing organometallic reagent, such as an arylboronic acid or a heteroarylboronic acid or the pinacol ester of said boronic acids or an aryltrialkylstannane or a heteroaryltrialkylstannane, in a solvent, such as toluene or tetrahydrofuran or n-butanol or 1,4-dioxane or 1,2-dimethoxyethane or a mixture of solvents, such as tetrahydrofuran and methanol, at an elevated temperature, such as 200° C. or 120° C. or 80° C., achieved by either conventional or microwave heating, optionally in a sealed vessel to allow heating above the normal boiling point of the solvent, in the presence of a catalyst, such as a palladium catalyst, such as tetrakis(triphenylphosphine)palladium or (1,1'-bis(diphenylphosphino)ferrocene)-palladium (II) chloride dichloromethane complex or PXPd or a palladium catalyst-ligand combination, such as tris(dibenzylideneacetone)dipalladium with dicyclohexyl(2',6'-dimethoxybiphenyl-2-yl)phosphine, optionally in the presence of a base, such as anhydrous tribasic potassium phosphate or potassium carbonate or aqueous sodium carbonate or potassium carbonate solution, under an inert atmosphere, such as argon.

SCHEME 12

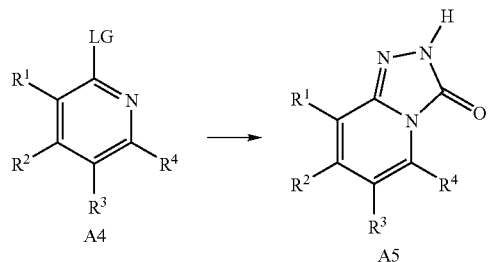

As shown in Scheme 12, a compound of Formula A4, such as a 3,4-diaryl-2-halopyridine or a 4-aryl-3-heteroaryl-2-halopyridine or a 4,5-diaryl-2-halopyridine or a 4-aryl-5-heteroaryl-2-halopyridine, may be converted to a compound of Formula A5, such as a 7,8-diaryl-[1,2,4]triazolo[4,3-a]pyridin-3(2H)-one or a 7-aryl-8-heteroaryl-[1,2,4]triazolo[4,3-a]pyridin-3(2H)-one or a 6,7-diaryl-[1,2,4]triazolo[4,3-a]pyridin-3(2H)-one or a 7-aryl-6-heteroaryl-[1,2,4]triazolo[4,3-a]pyridin-3(2H)-one, respectively, for example, by first nucleophilic displacement at the 2 position with hydrazine in a solvent, such as tetrahydrofuran or 1,4-dioxane or pyridine, at a temperature, such as ambient temperature or 65° C. or 120° C., under an inert atmosphere, such as argon, followed by treatment with a carbonylating agent, such as 1,1'-carbonyldiimidazole or triphosgene, in a solvent, such as tetrahydrofuran, at a temperature, such as ambient temperature or 60° C., under an inert atmosphere, such as argon.

SCHEME 13

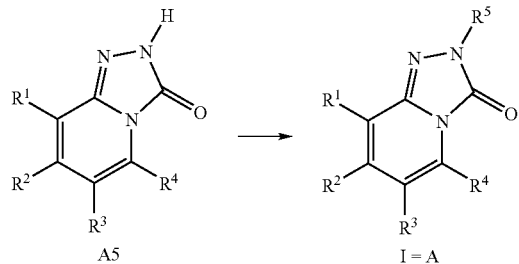

As shown in Scheme 13, a compound of Formula A5, such as a 7,8-diaryl-[1,2,4]triazolo[4,3-a]pyridin-3(2H)-one or a 7-aryl-8-heteroaryl-[1,2,4]triazolo[4,3-a]pyridin-3(2H)-one or a 6,7-diaryl-[1,2,4]triazolo[4,3-a]pyridin-3(2H)-one or a 7-aryl-6-heteroaryl-[1,2,4]triazolo[4,3-a]pyridin-3(2H)-one, may be converted to a compound of Formula I, such as a 2-substituted 7,8-diaryl-[1,2,4]triazolo[4,3-a]pyridin-3(2H)-one or a 2-substituted 7-aryl-8-heteroaryl-[1,2,4]triazolo[4,3-a]pyridin-3(2H)-one or a 2-substituted 6,7-diaryl-[1,2,4]triazolo[4,3-a]pyridin-3(2H)-one or a 2-substituted 7-aryl-6-heteroaryl-[1,2,4]triazolo[4,3-a]pyridin-3(2H)-one, respectively, for example, by reaction with an $R^5$-containing electrophile, $R^5$-LG, such as an optionally substituted benzyl halide or an optionally substituted heteroarylmethyl halide or an optionally substituted alkyl halide, in the presence of a base, such as potassium carbonate, in a solvent, such as N,N-dimethylformamide or acetone, at a temperature, such as ambient temperature or 55° C. or 80° C., under an inert atmosphere, such as argon; or by reaction with an $R^5$-containing alcohol, $R^5$—OH, such as an optionally substituted benzyl alcohol or an optionally substituted heteroarylmethyl alcohol or an optionally substituted alcohol, under Mitsunobu reaction conditions.

SCHEME 14

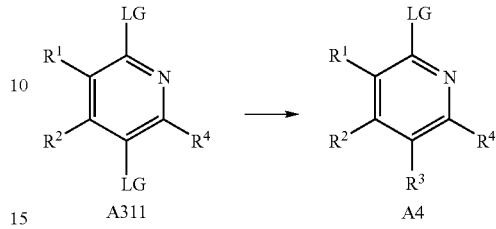

As shown in Scheme 14, a compound of Formula A311, such as a 4-aryl-2,5-dihalopyridine, may be converted to a compound of Formula A4, such as a 4,5-diaryl-2-halopyridine or a 4-aryl-5-heteroaryl-2-halopyridine, for example, by reaction with an $R^3$-containing organometallic reagent, such as an arylboronic acid or a heteroarylboronic acid or the pinacol ester of said boronic acids or an aryltrialkylstannane or a heteroaryltrialkylstannane, in a solvent, such as toluene or tetrahydrofuran or n-butanol or 1,4-dioxane or 1,2-dimethoxyethane or a mixture of solvents, such as tetrahydrofuran and methanol, at an elevated temperature, such as 200° C. or 120° C. or 80° C., achieved by either conventional or microwave heating, optionally in a sealed vessel to allow heating above the normal boiling point of the solvent, in the presence of a catalyst, such as a palladium catalyst, such as tetrakis(triphenylphosphine)palladium or (1,1'-bis(diphenylphosphino)ferrocene)-palladium (II) chloride dichloromethane complex or PXPd or a palladium catalyst—ligand combination, such as tris(dibenzylideneacetone)dipalladium with dicyclohexyl(2',6'-dimethoxybiphenyl-2-yl)phosphine, optionally in the presence of a base, such as anhydrous tribasic potassium phosphate or potassium carbonate or aqueous sodium carbonate or potassium carbonate solution, under an inert atmosphere, such as argon.

SCHEME 15

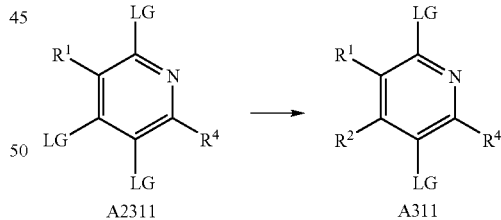

As shown in Scheme 15, a compound of Formula A2311, such as a 2,4,5-trihalopyridine, may be converted to a compound of Formula A311, such as a 4-aryl-2,5-dihalopyridine, for example, by reaction with an $R^2$-containing organometallic reagent, such as an arylboronic acid or the pinacol ester of an arylboronic acid or an aryltrialkylstannane, in a solvent, such as toluene or tetrahydrofuran or n-butanol or 1,4-dioxane or 1,2-dimethoxyethane or a mixture of solvents, such as tetrahydrofuran and methanol, at an elevated temperature, such as 200° C. or 120° C. or 80° C., achieved by either conventional or microwave heating, optionally in a sealed vessel to allow heating above the normal boiling point of the solvent, in the presence of a catalyst, such as a palladium catalyst, such as tetrakis(triphenylphosphine)palladium or (1,1'-bis(diphenylphosphino)ferrocene)-palladium (II) chloride dichloromethane complex or PXPd or a palladium catalyst—ligand combination, such as tris(dibenzylideneacetone)dipalladium with dicyclohexyl(2',6'-dimethoxybiphenyl-2-yl)phosphine, optionally in the presence of a base, such as anhydrous tribasic potassium phosphate or potassium carbonate or aqueous sodium carbonate or potassium carbonate solution, under an inert atmosphere, such as argon.

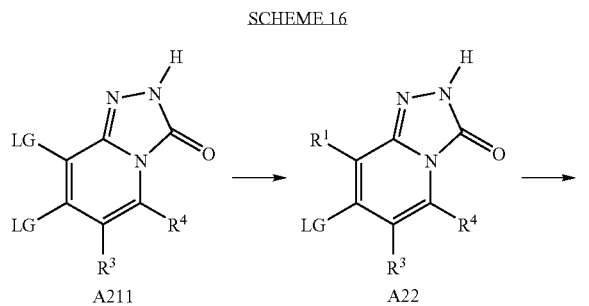

As shown in Scheme 16, a compound of Formula A211, such as a 7,8-dihalo-[1,2,4]triazolo[4,3-a]pyridin-3(2H)-one, may be converted to a compound of Formula A22, such as an 8-aryl-7-halo-[1,2,4]triazolo[4,3-a]pyridin-3(2H)-one or a 7-halo-8-heteroaryl-[1,2,4]triazolo[4,3-a]pyridin-3 (2H)-one, for example, by reaction with an $R^1$-containing organometallic reagent, such as an arylboronic acid or a heteroarylboronic acid or the pinacol ester of said boronic acids or an aryltrialkylstannane or a heteroaryltrialkylstannane, in a solvent, such as toluene or tetrahydrofuran or n-butanol or 1,4-dioxane or 1,2-dimethoxyethane or a mixture of solvents, such as tetrahydrofuran and methanol, at an elevated temperature, such as 200° C. or 120° C. or 80° C., achieved by either conventional or microwave heating, optionally in a sealed vessel to allow heating above the normal boiling point of the solvent, in the presence of a catalyst, such as a palladium catalyst, such as tetrakis(triphenylphosphine)palladium or (1,1'-bis(diphenylphosphino)ferrocene)-palladium (II) chloride dichloromethane complex or PXPd or a palladium catalyst—ligand combination, such as tris(dibenzylideneacetone)dipalladium with dicyclohexyl(2',6'-dimethoxybiphenyl-2-yl)phosphine, optionally in the presence of a base, such as anhydrous tribasic potassium phosphate or potassium carbonate or aqueous sodium carbonate or potassium carbonate solution, under an inert atmosphere, such as argon.

A compound of Formula A22, such as an 8-aryl-7-halo-[1,2,4]triazolo[4,3-a]pyridin-3(2H)-one or a 7-halo-8-heteroaryl-[1,2,4]triazolo[4,3-a]pyridin-3(2H)-one, may be converted to a compound of Formula A5, such as a 7,8-diaryl-[1,2,4]triazolo[4,3-a]pyridin-3(2H)-one or a 7-aryl-8-heteroaryl-[1,2,4]triazolo[4,3-a]pyridin-3(2H)-one, respectively, for example, by reaction with an $R^2$-containing organometallic reagent, such as an arylboronic acid or the pinacol ester of an arylboronic acid or an aryltrialkylstannane, in a solvent, such as toluene or tetrahydrofuran or n-butanol or 1,4-dioxane or 1,2-dimethoxyethane or a mixture of solvents, such as tetrahydrofuran and methanol, at an elevated temperature, such as 200° C. or 120° C. or 80° C., achieved by either conventional or microwave heating, optionally in a sealed vessel to allow heating above the normal boiling point of the solvent, in the presence of a catalyst, such as a palladium catalyst, such as tetrakis(triphenylphosphine)palladium or (1,1'-bis(diphenylphosphino)ferrocene)-palladium (II) chloride dichloromethane complex or PXPd or a palladium catalyst—ligand combination, such as tris(dibenzylideneacetone)dipalladium with dicyclohexyl(2',6'-dimethoxybiphenyl-2-yl)phosphine, optionally in the presence of a base, such as anhydrous tribasic potassium phosphate or potassium carbonate or aqueous sodium carbonate or potassium carbonate solution, under an inert atmosphere, such as argon.

-continued

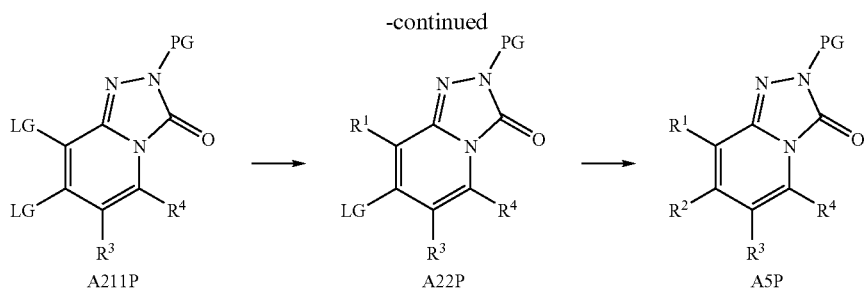

The transformation of A211 to A5 may also be accomplished as shown in Scheme 17, through the intermediacy of N-protected forms of A211, A22, and A5, namely A211P, A22P, and A5P, respectively. These N-protected forms may incorporate standard nitrogen protecting groups known in the art, for example, N-methoxymethyl derivatives. A211 may be converted to A211P, by standard methods for N-protection, for example, by reaction with chloromethyl methyl ether in a solvent, such as N,N-dimethylformamide, at a temperature, such as ambient temperature, in the presence of a base, such as N,N-diisopropylethylamine, under an inert atmosphere, such as argon. A211P may be converted to A5P via A22P by employing the methods described for the transformation of A211 to A5 via A22. Finally, A5P may be converted to A5 by standard methods for N-deprotection, for example, by reaction with trifluoroacetic acid, optionally in a solvent, such as dichloromethane, at a temperature, such as 75° C., under an inert atmosphere, such as argon; and optionally followed by reaction with a base, such as potassium carbonate, in a solvent, such as methanol, at a temperature, such as ambient temperature, under an inert atmosphere, such as argon.

SCHEME 18

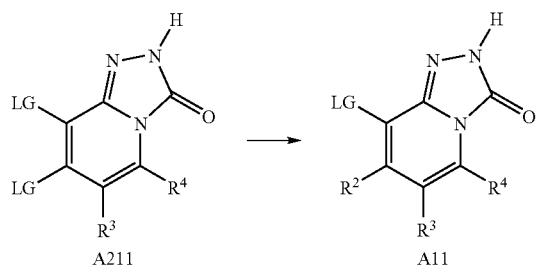

As shown in Scheme 18, a compound of Formula A211, such as a 7,8-dihalo-[1,2,4]triazolo[4,3-a]pyridin-3(2H)-one, may be converted to a compound of Formula A11, such as a 7-aryl-8-halo-[1,2,4]triazolo[4,3-a]pyridin-3(2H)-one, for example, by reaction with an $R^2$-containing organometallic reagent, such as an arylboronic acid or the pinacol ester of an arylboronic acid or an aryltrialkylstannane, in a solvent, such as toluene or tetrahydrofuran or n-butanol or 1,4-dioxane or 1,2-dimethoxyethane or a mixture of solvents, such as tetrahydrofuran and methanol, at an elevated temperature, such as 200° C. or 120° C. or 80° C., achieved by either conventional or microwave heating, optionally in a sealed vessel to allow heating above the normal boiling point of the solvent, in the presence of a catalyst, such as a palladium catalyst, such as tetrakis(triphenylphosphine)palladium or (1,1'-bis(diphenylphosphino)ferrocene)-palladium (II) chloride dichloromethane complex or PXPd or a palladium catalyst—ligand combination, such as tris(dibenzylideneacetone)dipalladium with dicyclohexyl(2',6'-dimethoxybiphenyl-2-yl)phosphine, optionally in the presence of a base, such as anhydrous tribasic potassium phosphate or potassium carbonate or aqueous sodium carbonate or potassium carbonate solution, under an inert atmosphere, such as argon.

SCHEME 19

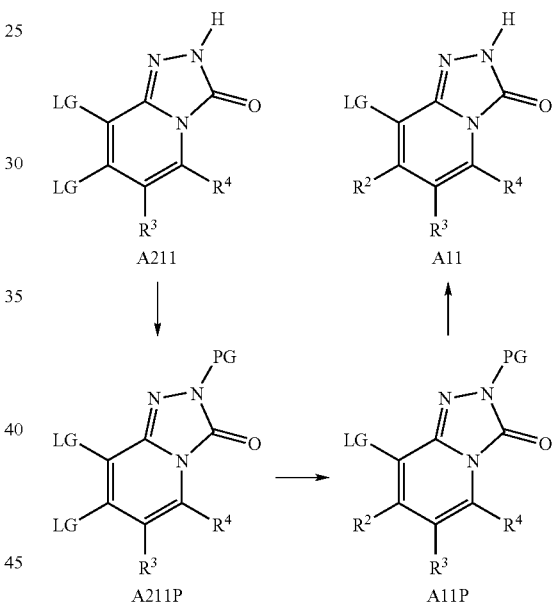

The transformation of A211 to A11 may also be accomplished as shown in Scheme 19, through the intermediacy of N-protected forms of A211 and A11, namely A211P and A11P, respectively. These N-protected forms may incorporate standard nitrogen protecting groups known in the art, for example, N-methoxymethyl derivatives. A211 may be converted to A211P, by standard methods for N-protection, for example, by reaction with chloromethyl methyl ether in a solvent, such as N,N-dimethylformamide, at a temperature, such as ambient temperature, in the presence of a base, such as N,N-diisopropylethylamine, under an inert atmosphere, such as argon. A211P may be converted to A11P by employing the methods described for the transformation of A211 to A11. Finally, A11P may be converted to A11 by standard methods for N-deprotection, for example, by reaction with trifluoroacetic acid, optionally in a solvent, such as dichloromethane, at a temperature, such as 75° C., under an inert atmosphere, such as argon; and optionally followed by reaction with a base, such as potassium carbonate, in a solvent, such as methanol, at a temperature, such as ambient temperature, under an inert atmosphere, such as argon.

SCHEME 20

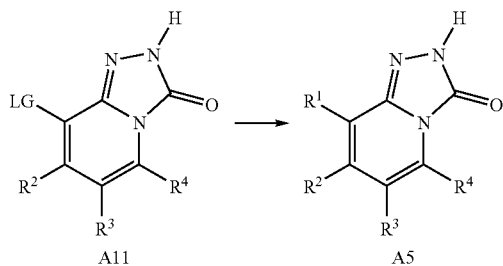

As shown in Scheme 20, a compound of Formula A11, such as a 7-aryl-8-halo-[1,2,4]triazolo[4,3-a]pyridin-3(2H)-one, may be converted to a compound of Formula A5, such as a 7,8-diaryl-[1,2,4]triazolo[4,3-a]pyridin-3(2H)-one or a 7-aryl-8-heteroaryl-[1,2,4]triazolo[4,3-a]pyridin-3(2H)-one, for example, by reaction with an $R^1$-containing organometallic reagent, such as an arylboronic acid or a heteroarylboronic acid or the pinacol ester of said boronic acids or an aryltrialkylstannane or a heteroaryltrialkylstannane, in a solvent, such as toluene or tetrahydrofuran or n-butanol or 1,4-dioxane or 1,2-dimethoxyethane or a mixture of solvents, such as tetrahydrofuran and methanol, at an elevated temperature, such as 200° C. or 120° C. or 80° C., achieved by either conventional or microwave heating, optionally in a sealed vessel to allow heating above the normal boiling point of the solvent, in the presence of a catalyst, such as a palladium catalyst, such as tetrakis(triphenylphosphine)palladium or (1,1'-bis(diphenylphosphino)ferrocene)-palladium (II) chloride dichloromethane complex or PXPd or a palladium catalyst—ligand combination, such as tris(dibenzylideneacetone)dipalladium with dicyclohexyl(2',6'-dimethoxybiphenyl-2-yl)phosphine, optionally in the presence of a base, such as anhydrous tribasic potassium phosphate or potassium carbonate or aqueous sodium carbonate or potassium carbonate solution, under an inert atmosphere, such as argon.

SCHEME 21

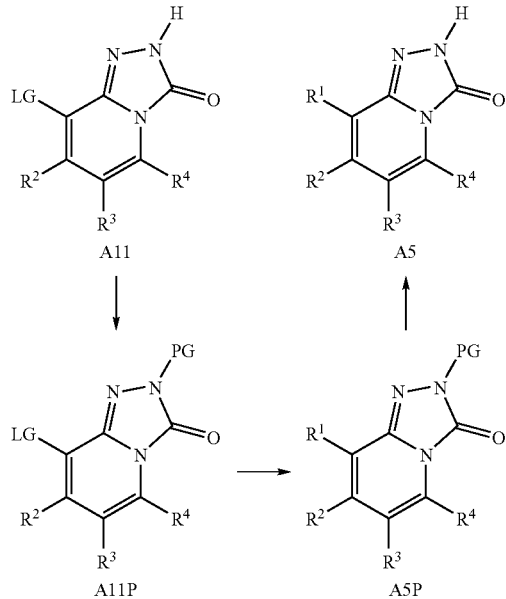

The transformation of A11 to A5 may also be accomplished as shown in Scheme 21, through the intermediacy of N-protected forms of A11 and A5, namely A11P and A5P, respectively. These N-protected forms may incorporate standard nitrogen protecting groups known in the art, for example, N-methoxymethyl derivatives. A11 may be converted to A11P, by standard methods for N-protection, for example, by reaction with chloromethyl methyl ether in a solvent, such as N,N-dimethylformamide, at a temperature, such as ambient temperature, in the presence of a base, such as N,N-diisopropylethylamine, under an inert atmosphere, such as argon. A11P may be converted to A5P by employing the methods described for the transformation of A11 to A5. Finally, A5P may be converted to A5 by standard methods for N-deprotection, for example, by reaction with trifluoroacetic acid, optionally in a solvent, such as dichloromethane, at a temperature, such as 75° C., under an inert atmosphere, such as argon; and optionally followed by reaction with a base, such as potassium carbonate, in a solvent, such as methanol, at a temperature, such as ambient temperature, under an inert atmosphere, such as argon.

In the preceding synthetic schemes, reagents $R^5$-LG and $R^5$—OH were utilized to install the $R^5$ group of compounds of Formula I. The following synthetic schemes focus on some of the more useful synthetic routes to reagents $R^5$-LG, such as substituted benzyl halides and substituted heteroarylmethyl halides, and to the corresponding $R^5$—OH compounds. See, respectively, P3 annd P4 below.

SCHEME 22

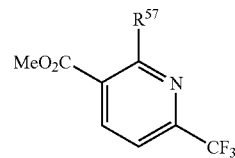

P1

The synthesis of a compound of Formula P1 (Scheme 22), such as methyl 2-cyclopropyl-6-(trifluoromethyl)nicotinate, wherein $R^{57}$ is a group as defined for $R^{11}$, especially an alkyl group that may be optionally substituted with 1 to 3 $R^{12}$, may be accomplished according to E. Okada, et al., Heterocycles, Vol. 46, pp. 129-132, 1997 by reaction of (Z)-4-amino-1,1,1-trifluorobut-3-en-2-one with a methyl 3-($R^{57}$-substituted)-3-oxopropanoate, such as methyl 3-cyclopropyl-3-oxopropanoate, in a solvent, such as toluene, at an elevated temperature, such as 80° C., in the presence of an acid, such as trifluoroacetic acid, under an inert atmosphere, such as argon.

SCHEME 23

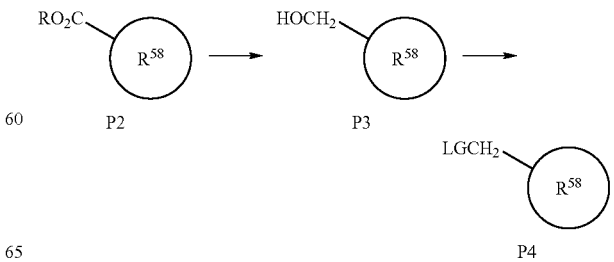

As shown in Scheme 23, a compound of Formula P2, such as P1, a methyl 2-($R^{57}$-substituted)-6-(trifluoromethyl)nicotinate, or another ring-substituted pyridinecarboxylate ester or ring-substituted benzenecarboxylate ester, wherein $R^{58}$ is an aryl or heteroaryl group as defined for $R^{10}$ that may be optionally substituted with 1 to 3 $R^{11}$, may be converted to a compound of Formula P3, such as a ring-substituted pyridinemethanol or ring-substituted benzenemethanol, for example, by reaction with a reducing agent, such as lithium aluminum hydride or sodium borohydride in a solvent, such as diethyl ether or tetrahydrofuran or an alcohol, such as methanol, when the reducing agent is sodium borohydride, at a temperature, such as room temperature or 0° C. or −78° C., the latter especially when the reducing agent is lithium aluminum hydride, under an inert atmosphere, such as argon.

A compound of Formula P3, such as a ring-substituted pyridinemethanol or ring-substituted benzenemethanol, wherein $R^{58}$ is an aryl or heteroaryl group as defined for $R^{10}$ that may be optionally substituted with 1 to 3 $R^{11}$, may be converted to a compound of Formula P4, such as a ring-substituted (halomethyl)pyridine or ring-substituted (halomethyl)benzene, for example, by reaction with a reagent, such as thionyl chloride, optionally in the presence of N,N-dimethylformamide, or 48% aqueous hydrobromic acid or a combination of reagents, such as carbon tetrabromide and triphenylphosphine, optionally in a solvent, such as dichloromethane, at a temperature, such as room temperature or 0° C. or 80° C., under an inert atmosphere, such as argon. Alternatively, a compound of Formula P3, such as a ring-substituted pyridinemethanol or ring-substituted benzenemethanol may be converted to a compound of Formula P4, such as a ring-substituted (methanesulfonyloxymethyl)pyridine or ring-substituted (trifluoromethylsulfonyloxymethyl)benzene, for example, by reaction with a sulfonyl chloride reagent under standard conditions as described in the art.

mosuccinimide or molecular bromine, optionally in the presence of a radical initiator such as benzoyl peroxide, in a solvent, such as carbon tetrachloride, at a temperature, such as room temperature or 80° C., under an inert atmosphere, such as argon.

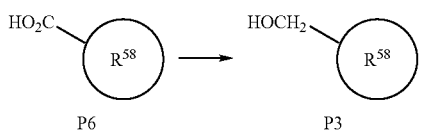

As shown in Scheme 25, a compound of Formula P6, such as a ring-substituted pyridinecarboxylic acid or ring-substituted benzenecarboxylic acid, wherein $R^{58}$ is an aryl or heteroaryl group as defined for $R^{10}$ that may be optionally substituted with 1 to 3 $R^{11}$, may be converted to a compound of Formula P3, such as a ring-substituted pyridinemethanol or ring-substituted benzenemethanol, for example, by reaction with a reducing agent, such as borane, in a solvent, such as tetrahydrofuran, at a temperature, such as room temperature or 0° C. or 70° C., under an inert atmosphere, such as argon.

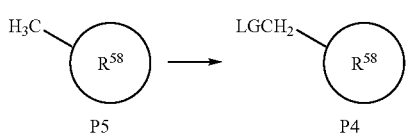

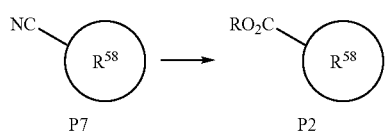

As shown in Scheme 24, a compound of Formula P5, such as a ring-substituted methylpyridine or ring-substituted methylbenzene, wherein $R^{58}$ is an aryl or heteroaryl group as defined for $R^{10}$ that may be optionally substituted with 1 to 3 $R^{11}$, may be converted to a compound of Formula P4, such as a ring-substituted (halomethyl)pyridine or ring-substituted (halomethyl)benzene, for example, by reaction with a radical halogenating reagent, such as N-chlorosuccinimide or N-bro- As shown in Scheme 26, a compound of Formula P7, such as a ring-substituted pyridinenitrile or ring-substituted benzonitrile, wherein $R^{58}$ is an aryl or heteroaryl group as defined for $R^{10}$ that may be optionally substituted with 1 to 3 $R^{11}$, may be converted to a compound of Formula P2, such as a ring-substituted pyridinecarboxylate ester or ring-substituted benzenecarboxylate ester, for example, by reaction with an alcohol, such as methanol or ethanol, and an aqueous mineral acid, such as concentrated aqueous hydrochloric acid, optionally with concentrated sulfuric acid, at a temperature, such as 100° C., under an inert atmosphere, such as argon.

SCHEME 27

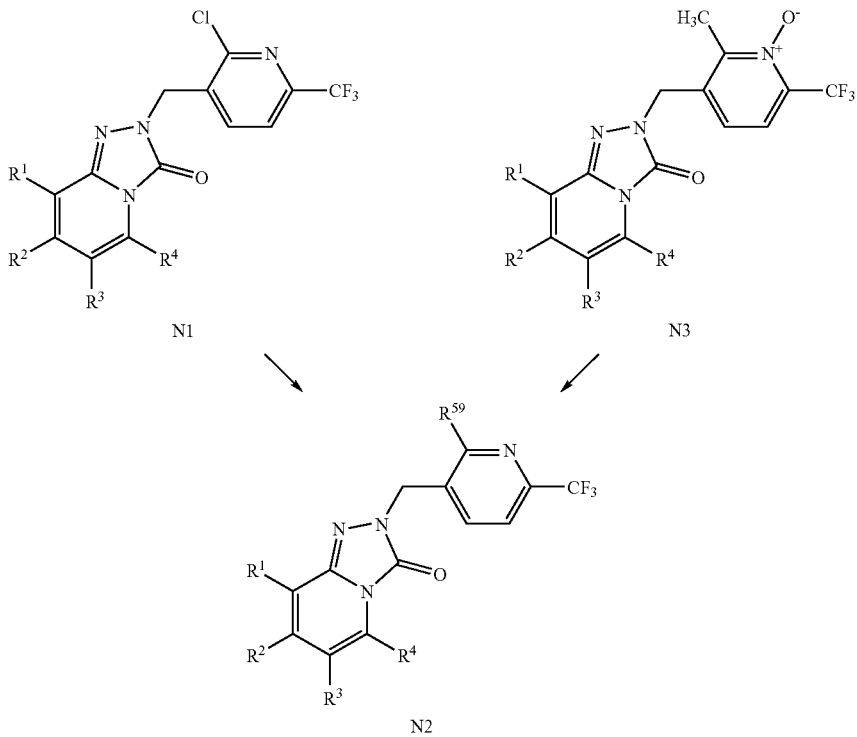

As noted above, the manipulation of functional groups within the various R groups of compounds of Formula I and intermediates leading to compounds of Formula I is possible by methods known in the art. Some of the more useful synthetic routes in which functional groups within the $R^5$ group of compounds of Formula I are manipulated in order to convert one compound of Formula I into another are exemplified in Examples 100-116 below. As shown in Scheme 27, a compound of Formula N1, of which the compound of Example 100 is representative, may be converted to a compound of Formula N2, wherein $R^{59}$ is a group as defined for $R^{11}$ that may be optionally substituted with 1 to 3 $R^{12}$, for example, by chemistry illustrated in Examples 101-108. Additionally, a compound of Formula N3, of which the compound of Example 109 is representative, may be converted to a compound of Formula N2, for example, by chemistry illustrated in Examples 110-116.

EXAMPLES

The following examples serve to better illustrate, but not limit, some of the preferred embodiments of the application.

General

The following methods were used in the working Examples, except where noted otherwise.

Reverse phase preparative HPLC employed a 5 μm octadecyl sulfate (C-18) column eluted with a linear solvent gradient of solvents A and B. In most cases, and unless noted otherwise, solvent A was 10% methanol in water, and solvent B was 90% methanol in water. In some of these cases both solvents A and B contained either 0.1% of trifluoroacetic acid or 10 mM ammonium acetate, as noted (no notation indicates no additive). The solvent gradient employed with methanol-water based solvents began with 20% or more of solvent B and ended with 100% of solvent B. In some cases, as noted, solvent A was 10% acetonitrile in water, and solvent B was 90% acetonitrile in water, each containing 0.1% of trifluoroacetic acid. In these cases, the solvent gradient began with 0% or more of solvent B and ended with 100% of solvent B.

Reverse phase analytical HPLC was performed on Shimadzu LC10AS systems employing a 5 μm C-18 4.6×50 mm column eluted with a linear solvent gradient, starting with 0% of solvent B and finishing with 100% of solvent B over 4 min, with 1 min hold time at 100% B and at a flow rate of 4 mL/min with UV detection at 220 μm. In most cases, and unless noted otherwise, solvent A was 10% methanol in water, and solvent B was 90% methanol in water, each containing 0.2% phosphoric acid. However, as noted, in some cases solvent A was 10% acetonitrile in water, and solvent B was 90% acetonitrile in water, each containing 0.1% of trifluoroacetic acid.

Analytical HPLC/MS was performed, in most cases, on Shimadzu LC10AS systems coupled with Waters ZMD mass spectrometers. The HPLC system employed a Phenomenex Luna or Waters SunFire C-18 4.6×50 mm column eluted with solvent A (0.1% trifluoroacetic acid, 90% water, 10% methanol) and solvent B (0.1% trifluoroacetic acid, 90% methanol, 10% water) through a linear gradient of 0% to 100% solvent B over 4 min, with 1 min hold time at 100% B and at a flow rate of 4 mL/min with UV detection at 220 nm. In some cases, 10 mM ammonium acetate rather than 0.1% trifluoroacetic acid was the solvent additive, as noted (no notation indicates the use of 0.1% trifluoroacetic acid). Diagnostic HPLC/MS m/z values, for instance for [M+H]$^+$, are generally given for only the lowest m/z or main peak in cases where isotope patterns appear. In these cases, it is understood that rest of the isotope pattern peaks are present and confirm the assigned structure.

NMR spectra were obtained with Bruker or Jeol Fourier transform spectrometers operating at frequencies as follows. $^1$H NMR: 400 MHz (Bruker or Jeol) or 500 MHz (Jeol). $^{13}$C NMR: 100 MHz (Bruker or Jeol). $^1$H NMR spectra are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

Example 1

Preparation of 2-(4-(trifluoromethyl)benzyl)-7,8-di-p-tolyl-[1,2,4]triazolo[4,3-a]pyridin-3(2H)-one

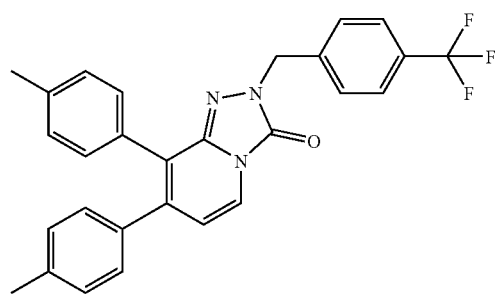

A. Preparation of 2,3-dichloro-4-iodopyridine

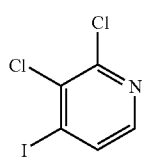

To a stirring solution of 2,3-dichloropyridine (1.47 g, 10 mmol) in 10 mL THF at −78° C. under argon was added 1.0 M lithium diisopropylamide solution in THF (12 mL, 12 mmol) over 2 min. The resulting reaction mixture was stirred at −78° C. for 1 h before a solution of $I_2$ (3.05 g, 12 mmol) in 15 mL THF was added over 5 min. The reaction mixture was allowed to warm up to room temperature over 2 h. Analysis by HPLC/MS indicated that starting material had been consumed. Brine (25 mL) and EtOAc (30 mL) were added to the reaction mixture. The layers were separated. The organic layer was dried ($Na_2SO_4$), filtered, and concentrated under reduced pressure. The crude product was purified by automated silica gel chromatography (eluted with ethyl acetate-hexanes) to obtain 2.3 g of the title compound as a white solid. HPLC/MS: retention time=3.15 min, [M+H]$^+$=273. The regiochemical assignment was based on similar chemistry reported in C. Bobbio and M. Schlosser, J. Org. Chem., Vol. 70, pp. 3039-3045, 2005.

B. Preparation of 2,3-dichloro-4-p-tolylpyridine

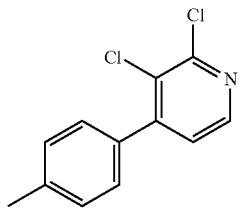

To a solution of 2,3-dichloro-4-iodopyridine (1.92 g, 7.0 mmol) in toluene (20 mL) at room temperature under argon was added 4-methylphenylboronic acid (1.05 g, 7.7 mmol), tetrakis(triphenylphosphine)palladium (0.40 g, 0.35 mmol), and aqueous $Na_2CO_3$ solution (2.0 M, 7 mL, 14 mmol). The resulting suspension was stirred and heated at 100° C. under argon for 5 h. Analysis by HPLC/MS indicated that starting material had been consumed. After the reaction mixture was cooled to room temperature, water (25 mL) and EtOAc (30 mL) were added. The layers were separated. The organic layer was dried ($Na_2SO_4$), filtered, and concentrated under reduced pressure. The crude product was purified by automated silica gel chromatography (eluted with ethyl acetate-hexanes) to obtain 1.64 g of the title compound as a white solid. HPLC/MS: retention time=3.77 min, [M+H]$^+$=238. $^1$H NMR ($CDCl_3$): δ 8.30 (d, J=4.9 Hz, 1H), 7.34-7.29 (m, 4H), 7.20 (d, J=4.9 Hz, 1H), 2.43 (s, 3H).

C. Preparation of 1-(3-chloro-4-p-tolylpyridin-2-yl)hydrazine

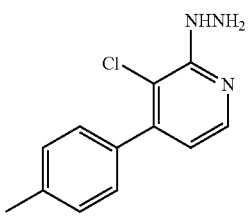

To a stirred solution of 2,3-dichloro-4-p-tolylpyridine (711 mg, 3.0 mmol) in THF (5 mL) at room temperature under argon was added hydrazine (288 mg, 9.0 mmol). The reaction mixture was heated at 60° C. under argon for 5 h. Analysis by HPLC/MS indicated that starting material had been consumed. After cooling the reaction mixture to room temperature, most of the solvent was removed under reduced pressure. Water (25 mL) was added to the residue while stirring. Solid precipitate was collected by filtration and further washed with water (15 mL×2). After drying in a vacuum oven under reduced pressure overnight, 692 mg of nearly pure title compound was obtained as an off-white solid. HPLC/MS: retention time=2.10 min, [M+H]$^+$=234.

D. Preparation of 8-chloro-7-p-tolyl-[1,2,4]triazolo[4,3-a]pyridin-3(2H)-one

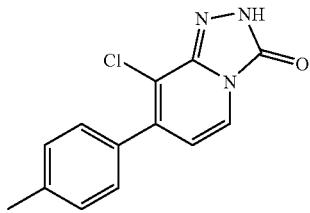

To a stirred solution of triphosgene (2.64 g, 8.9 mmol) in THF (25 mL) at room temperature under argon was added 1-(3-chloro-4-p-tolylpyridin-2-yl)hydrazine (0.692 g, 3.0 mmol). The reaction mixture was stirred at room temperature for 16 h. Analysis by HPLC/MS indicated that starting material had been consumed. Water (25 mL) was added while stirring. The resulting suspension was heated at 100° C. for 40 h. Upon cooling to room temperature, the desired product was filtered and further washed with water (15 mL×2). After drying in a vacuum oven under reduced pressure overnight, 562 mg of the title compound was obtained as a white solid. HPLC/MS: retention time=2.98 min, [M+H]$^+$=260.

E. Preparation of 2-(4-(trifluoromethyl)benzyl)-8-chloro-7-p-tolyl-[1,2,4]triazolo[4,3-a]pyridin-3(2H)-one

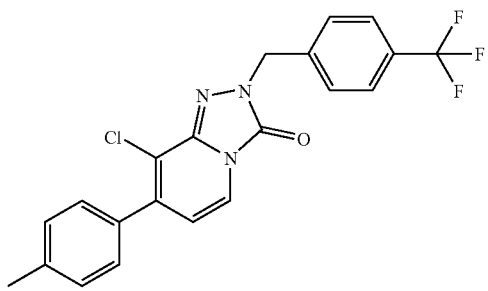

To a stirred solution of 8-chloro-7-p-tolyl-[1,2,4]triazolo[4,3-a]pyridin-3(2H)-one (100 mg, 0.39 mmol) in acetone (10 mL) at room temperature under argon was added 1-(bromomethyl)-4-(trifluoromethyl)benzene (111 mg, 0.46 mmol), followed by K$_2$CO$_3$ (107 mg, 0.77 mmol). The resulting suspension was heated at reflux overnight. Analysis by HPLC/MS indicated that starting material had been consumed. After cooling the reaction mixture to room temperature, most of the solvent was removed under reduced pressure. Water (15 mL) and EtOAc (15 mL) were added. The layers were separated. The organic layer was dried (Na$_2$SO$_4$), filtered, and concentrated under reduced pressure. The crude product was purified by automated silica gel chromatography (eluted with ethyl acetate-hexanes) to obtain 102 mg of the title compound as a white solid. HPLC/MS: retention time=4.03 min, [M+H]$^+$=418. $^1$H NMR (CDCl$_3$): δ 7.77 (d, J=7.0 Hz, 1H), 7.61-7.45 (m, 4H), 7.38 (d, J=8.1 Hz, 2H), 7.27 (d, J=8.1 Hz, 2H), 6.58 (d, J=7.0 Hz, 1H), 5.31 (s, 2H), 2.46 (s, 3H). N-alkylation, rather than O-alkylation, was demonstrated by the presence of a $^{13}$C NMR resonance at 49.6 ppm.

F. Preparation of 2-(4-(trifluoromethyl)benzyl)-7,8-dip-tolyl-[1,2,4]triazolo[4,3-a]pyridin-3(2H)-one

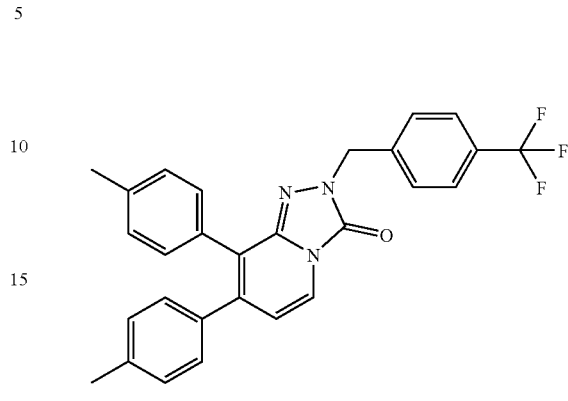

To a stirring solution of 2-(4-(trifluoromethyl)benzyl)-8-chloro-7-p-tolyl-[1,2,4]triazolo[4,3-a]pyridin-3(2H)-one (41.7 mg, 0.10 mmol) in a 1:1 mixture of THF and methanol (4 mL) at room temperature under argon was added 4-methylphenylboronic acid (40.8 g, 0.30 mmol), PXPd (16.2 g, 0.03 mmol), and K$_2$CO$_3$ (41 mg, 0.3 mmol). The resulting suspension was heated at 70° C. under argon for 10 min. Analysis by HPLC/MS indicated that starting material had been consumed. After cooling the reaction mixture to room temperature, water (25 mL) and EtOAc (25 mL) were added. The layers were separated. The organic layer was dried (Na$_2$SO$_4$), filtered, and concentrated under reduced pressure. The crude product was purified by automated silica gel chromatography (eluted with ethyl acetate-hexanes) to obtain 29 mg of the title compound as a white lyophilate. HPLC/MS: retention time=4.36 min, [M+H]$^+$=474. $^1$H NMR (CDCl$_3$): δ 7.78 (d, J=7.5 Hz, 1H), 7.59 (d, J=7.1 Hz, 2H), 7.50 (d, J=7.1 Hz, 2H), 7.18 (d, J=8.0 Hz, 2H), 7.09-7.00 (m, 6H), 6.65 (d, J=7.5 Hz, 1H), 5.22 (s, 2H), 2.32 (s, 3H), 2.31 (s, 3H).

Example 2

Preparation of 8-(4-chlorophenyl)-7-p-tolyl-2-((6-(trifluoromethyl)pyridin-3-yl)methyl)-[1,2,4]triazolo[4,3-a]pyridin-3(2H)-one

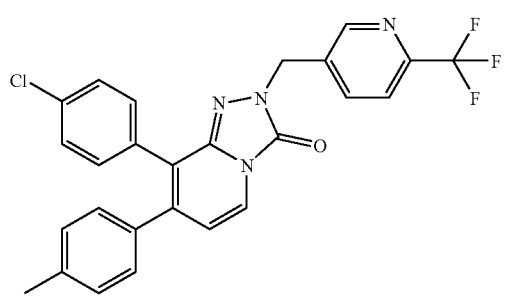

A. Preparation of 8-chloro-7-p-tolyl-2-((6-(trifluoromethyl)pyridin-3-yl)methyl)-[1,2,4]triazolo[4,3-a]pyridin-3(2H)-one

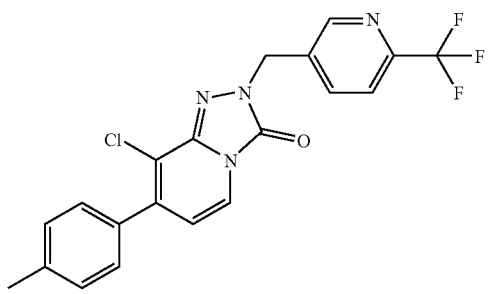

To a stirred solution of 8-chloro-7-p-tolyl-[1,2,4]triazolo[4,3-a]pyridin-3(2H)-one (100 mg, 0.39 mmol) in acetone (10 mL) at room temperature under argon was added 5-(chloromethyl)-2-(trifluoromethyl)pyridine (91 mg, 0.46 mmol), followed by K$_2$CO$_3$ (107 mg, 0.77 mmol). The resulting suspension was heated at reflux overnight. Analysis by HPLC/MS indicated that starting material had been consumed. After cooling the reaction mixture to room temperature, most of the solvent was removed under reduced pressure. Water (15 mL) and EtOAc (15 mL) were added. The layers were separated. The organic layer was dried (Na$_2$SO$_4$), filtered, and concentrated under reduced pressure. The crude product was purified by automated silica gel chromatography (eluted with ethyl acetate-hexanes) to obtain 96 mg of the title compound as an off-white solid. HPLC/MS: retention time=3.71 min, [M+H]$^+$=419.

B. Preparation of 8-(4-chlorophenyl)-7-p-tolyl-2-((6-(trifluoromethyl)pyridin-3-yl)methyl)-[1,2,4]triazolo[4,3-a]pyridin-3(2H)-one

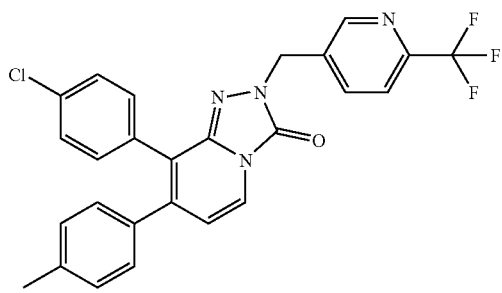

To a stirring solution of 8-chloro-7-p-tolyl-2-((6-(trifluoromethyl)pyridin-3-yl)methyl)-[1,2,4]triazolo[4,3-a]pyridin-3(2H)-one (28 mg, 0.067 mmol) in a 1:1 mixture of THF and methanol (4 mL) at room temperature under argon was added 4-chlorophenylboronic acid (12.5 g, 0.080 mmol), PXPd (11 g, 0.02 mmol), and K$_2$CO$_3$ (18.5 mg, 0.13 mmol). The resulting suspension was heated at 70° C. under argon for 10 min. Analysis by HPLC/MS indicated that starting material had been consumed. After cooling the reaction mixture to room temperature, water (25 mL) and EtOAc (25 mL) were added. The layers were separated. The organic layer was dried (Na$_2$SO$_4$), filtered, and concentrated under reduced pressure. The crude product was purified by preparative reverse phase HPLC (without TFA) to obtain 9 mg of the title compound as a white lyophilate. HPLC/MS: retention time=4.16 min, [M+H]$^+$=495. $^1$H NMR (CDCl$_3$): δ 8.79 (s, 1H), 7.95 (d, J=6.7 Hz, 1H), 7.83 (d, J=6.5 Hz, 1H) 7.69 (d, J=6.7 Hz, 1H), 7.29-7.18 (m, 4H), 7.12 (d, J=6.2 Hz, 2H), 7.00 (d, J=6.2 Hz, 2H), 6.70 (d, J=6.5 Hz, 1H), 5.27 (s, 2H), 2.32 (s, 3H).

Example 3

Preparation of 7,8-bis(4-chlorophenyl)-2-((6-(trifluoromethyl)pyridin-3-yl)methyl)-[1,2,4]triazolo[4,3-a]pyridin-3(2H)-one

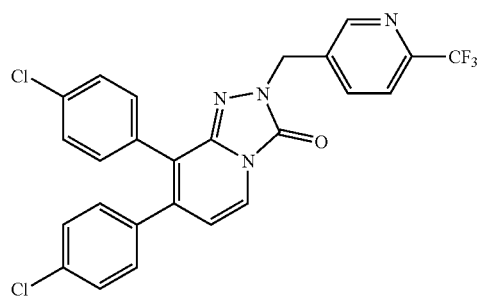

A. Preparation of 1-(3-bromo-4-chloropyridin-2-yl)hydrazine

To stirring anhydrous dioxane (30 mL) at room temperature was added anhydrous hydrazine (3.29 mL, 105 mmol), followed by portion-wise addition of solid 3-bromo-2,4-dichloropyridine (2.39 g, 10.53 mmol, prepared as described in M. A. Walters, et al., Synth. Comm., Vol. 22, pp. 2829-2837, 1992). The resulting turbid solution was stirred in a 65° C. oil bath for 2 h. After cooling to room temperature, the reaction mixture was evaporated to dryness under reduced pressure. The resulting residue was triturated with isopropanol (50 mL), in which it was only partially soluble, and the mixture was filtered, collecting the solid. The filtrate was evaporated, and the resulting solid was triturated once again with isopropanol (25 mL) and filtered, collecting the solid. The two crops of solid were combined and dried in a 50° C. vacuum oven to obtain 1.438 g of an off-white solid, which contained about 70% of the title compound 1-(3-bromo-4-chloropyridin-2-yl)hydrazine and about 30% of its regioisomer (1-(3-bromo-2-chloropyridin-4-yl)hydrazine). HPLC/MS: retention time=1.06 min, [M+H]$^+$=221. Assignment of regioisomers was made based on the fact that the major isomer led to 8-bromo-7-chloro-[1,2,4]triazolo[4,3-a]pyridin-3(2H)-one.

B. Preparation of 8-bromo-7-chloro-[1,2,4]triazolo[4,3-a]pyridin-3(2H)-one

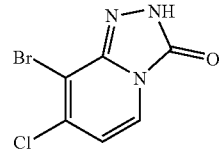

To a stirring solution of triphosgene (5.766 g, 19.43 mmol) in anhydrous THF (50 mL) at room temperature was added 1-(3-bromo-4-chloropyridin-2-yl)hydrazine (1.438 g, 70% pure) portion-wise over 15 min. The resulting suspension was stirred under argon at room temperature overnight, then cooled at 0° C. and quenched carefully by slow addition of water (30 mL). The resulting yellowish suspension was filtered, and the solid collected was washed with water (20 mL×3), then diethyl ether (5 mL), and dried in a 60° C. vacuum oven to obtain 0.525 g of the title compound, 8-bromo-7-chloro-[1,2,4]triazolo[4,3-a]pyridin-3(2H)-one as an off-white solid. HPLC/MS: retention time=1.93 min, [M+H]$^+$=248.

C. Preparation of 8-bromo-7-chloro-2-((6-(trifluoromethyl)pyridin-3-yl)methyl)-[1,2,4]triazolo[4,3-a]pyridin-3(2H)-one

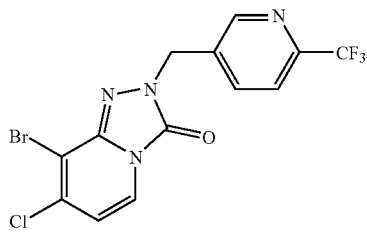

To a solution of 8-bromo-7-chloro-[1,2,4]triazolo[4,3-a]pyridin-3(2H)-one (515 mg, 2.258 mmol) in anhydrous DMF (10 mL) was added 5-(chloromethyl)-2-(trifluoromethyl)pyridine (883 mg, 4.518 mmol), followed by solid potassium carbonate (624 mg, 4.518 mmol). The resulting suspension was stirred under argon at 80° C. for 1.5 h. After cooling to room temperature, the reaction mixture was partitioned between EtOAc and water, and the aqueous layer was extracted with EtOAc twice. The combined EtOAc extracts were washed with water, then saturated aqueous NaCl, dried over Na$_2$SO$_4$, and evaporated under reduced pressure to provide crude product as a brown solid. The crude product was purified by silica gel (40 g) column chromatography eluting with a gradient of EtOAc (0-60%) in hexanes to obtain the title compound as a beige solid (742 mg, 81%). HPLC/MS: retention time=3.17 min, [M+H]$^+$=407. See 7,8-bis(4-chlorophenyl)-2-((6-(trifluoromethyl)pyridin-3-yl)methyl)-[1,2,4]triazolo[4,3-a]pyridin-3(2H)-one for data addressing the question of N vs. O-alkylation.

D. Preparation of 7,8-bis(4-chlorophenyl)-2-((6-(trifluoromethyl)pyridin-3-yl)methyl)-[1,2,4]triazolo[4,3-a]pyridin-3(2H)-one

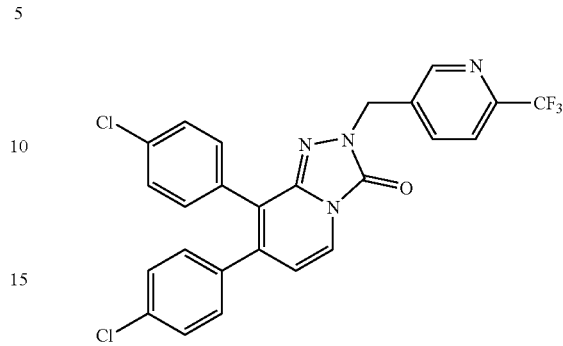

To a suspension of 8-bromo-7-chloro-2-((6-(trifluoromethyl)pyridin-3-yl)methyl)-[1,2,4]triazolo[4,3-a]pyridin-3(2H)-one (273 mg, 0.67 mmol) and 4-chlorophenylboronic acid (210 mg, 1.34 mmol) in toluene (3.5 mL) and 2.0 M aqueous sodium carbonate (0.75 mL) was added (Ph$_3$P)$_4$Pd (116 mg, 0.10 mmol) in one portion, and the resulting yellow mixture was vigorously stirred under argon in a 100° C. oil bath for 1.5 h. HPLC/MS analysis indicated that the majority of the product formed was a 1:1 adduct, 7-chloro-8-(4-chlorophenyl)-2-((6-(trifluoromethyl)pyridin-3-yl)methyl)-[1,2,4]triazolo[4,3-a]pyridin-3(2H)-one. Additional 4-chlorophenylboronic acid (210 mg, 1.34 mmol), toluene (1.5 mL), 2.0 M aqueous sodium carbonate (0.75 mL) and (Ph$_3$P)$_4$Pd (120 mg, 0.104 mmol) were added, and the reaction mixture was stirred at 100° C. under argon for an additional 2.5 h. After cooling to room temperature, the reaction mixture was partitioned between EtOAc and water. The EtOAc phase was washed with water twice, then saturated aqueous NaCl, dried over Na$_2$SO$_4$, and evaporated under reduced pressure to provide crude product as a brown oil. The crude product was purified by silica gel (40 g) column chromatography eluting with a gradient of EtOAc (0-90%) in hexanes to obtain the title compound as a light yellow foam (358 mg, about 90% pure). A fraction, 125 mg, of the title compound was further purified using preparative reverse phase HPLC (Phenomenex Luna 5 μm C-18 21.2×100 mm column eluted with a linear gradient of 70% to 100% B over 8 min (A=0.1% trifluoroacetic acid, 90% water, 10% methanol and B=0.1% trifluoroacetic acid, 90% methanol, 10% water) with flow rate at 20 mL/min and UV detection at 220 nm). The desired fractions were collected, neutralized with saturated aqueous Na$_2$CO$_3$ and concentrated under reduced pressure to remove most of the methanol. The resulting suspension was filtered to collect a yellowish solid, which was washed with water (3×) and dried in a vacuum oven at 50° C. overnight to afford 105 mg of pure title compound, 7,8-bis(4-chlorophenyl)-2-((6-(trifluoromethyl)pyridin-3-yl)methyl)-[1,2,4]triazolo[4,3-a]pyridin-3(2H)-one. HPLC/MS: retention time=4.05 min, [M+H]$^+$=516. $^1$H NMR (CDCl$_3$, 400 MHz): δ 8.78 (s, 1H), 7.91 (dd, J=1.8, 7.9 Hz, 1H), 7.82 (d, J=7.0 Hz, 1H), 7.66 (d, J=7.9 Hz, 1H), 7.28 (d, J=8.4 Hz, 2H), 7.25 (d, J=8.8 Hz, 2H), 7.17 (d, J=8.4 Hz, 2H), 7.04 (d, J=8.8 Hz, 2H), 6.64 (d, J=7.0 Hz, 1H), 5.25 (s, 2H). N-alkylation, rather than O-alkylation, in the previous step was demonstrated by the presence of a $^{13}$C NMR resonance at 47 ppm for 7,8-bis(4-chlorophenyl)-2-((6-(trifluoromethyl)pyridin-3-yl)methyl)-[1,2,4]triazolo[4,3-a]pyridin-3(2H)-one.

Example 4

Preparation of 7-(4-chlorophenyl)-8-(pyridin-4-yl)-2-((6-(trifluoromethyl)pyridin-3-yl)methyl)-[1,2,4]triazolo[4,3-a]pyridin-3(2H)-one

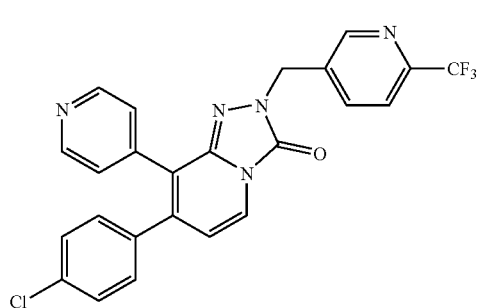

A. Preparation of 7-chloro-8-(pyridin-4-yl)-2-((6-(trifluoromethyl)pyridin-3-yl)methyl)-[1,2,4]triazolo[4,3-a]pyridin-3(2H)-one

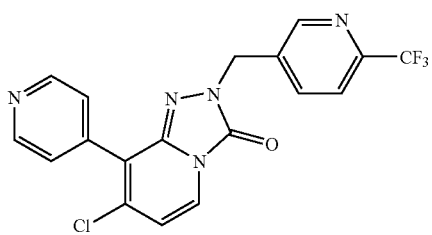

To a suspension of 8-bromo-7-chloro-2-((6-(trifluoromethyl)pyridin-3-yl)methyl)-[1,2,4]triazolo[4,3-a]pyridin-3(2H)-one (389 mg, 0.955 mmol) and 4-(4,4,5,5-tetramethyl-1,3,2-dioxaborolan-2-yl)pyridine (783 mg, 3.823 mmol) in toluene (7 mL) and 2.0 M aqueous sodium carbonate (2.1 mL) was added (Ph$_3$P)$_4$Pd (165 mg, 0.143 mmol) in one portion, and the resulting yellow mixture was vigorously stirred under argon in a 100° C. oil bath for 2.5 h. HPLC/MS indicated that about 20% of the title compound had formed. Additional (Ph$_3$P)$_4$Pd (50 mg, 0.043 mmol) was added, and the reaction mixture was stirred at 100° C. under argon for 3.5 h more. After cooling to room temperature, the reaction mixture was partitioned between EtOAc and water. The EtOAc phase was washed with water, then saturated aqueous NaCl, dried over Na$_2$SO$_4$, and concentrated under reduced pressure to obtain a crude product, which was purified by silica gel (12 g) column chromatography eluting with a gradient of EtOAc (0-100%) in hexanes to obtain the title compound as a yellow foam (169 mg). HPLC/MS: retention time=2.04 min, [M+H]$^+$=406.

B. Preparation of 7-(4-chlorophenyl)-8-(pyridin-4-yl)-2-((6-(trifluoromethyl)pyridin-3-yl)methyl)-[1,2,4]triazolo[4,3-a]pyridin-3(2H)-one

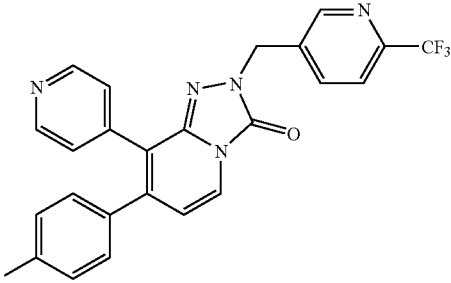

To a suspension of 7-chloro-8-(pyridin-4-yl)-2-((6-(trifluoromethyl)pyridin-3-yl)methyl)-[1,2,4]triazolo[4,3-a]pyridin-3(2H)-one (165 mg, 0.40 mmol), 4-chlorophenylboronic acid (190 mg, 1.20 mmol) in toluene (3.0 mL) and 2.0 M aqueous sodium carbonate (0.66 mL) was added (Ph$_3$P)$_4$Pd (70 mg, 0.06 mmol) in one portion, and the resulting yellow mixture was vigorously stirred under argon in a 100° C. oil bath for 2 h. HPLC/MS analysis indicated that the reaction was complete. After cooling to room temperature, the reaction mixture was partitioned between EtOAc and water. The EtOAc phase was washed with water, then saturated aqueous NaCl twice, dried over Na$_2$SO$_4$, and concentrated under reduced pressure to obtain crude product. The crude product was purified by silica gel (12 g) column chromatography eluting with a gradient of EtOAc (0-100%) in hexanes to provide the title compound as a light yellow foam (160 mg), which was crystallized from hot methanol to afford 60 mg of pure product. The mother liquor was concentrated, and the residue was purified by preparative reverse phase HPLC (Phenomenex Luna 5 μm C-18 21.2×100 mm column eluted with a linear gradient of 40% to 80% B over 8 min (A=0.1% trifluoroacetic acid, 90% water, 10% methanol and B=0.1% trifluoroacetic acid, 90% methanol, 10% water) with flow rate at 20 mL/min and UV detection at 220 nm). The desired fractions were concentrated under reduced pressure. The resulting residue was dissolved in EtOAc, washed with saturated aqueous Na$_2$CO$_3$ once, water twice, then saturated aqueous NaCl, dried over Na$_2$SO$_4$ and evaporated. The residue was dissolved in acetonitrile, frozen and lyophilized to afford an additional 88 mg of pure title compound as a light yellow powder. HPLC/MS: retention time=2.70 min, [M+H]$^+$=482. $^1$H NMR (CDCl$_3$, 400 MHz): δ 8.78 (s, 1H), 8.57 (d, J=6.2 Hz, 2H), 7.91 (dd, J=1.8, 7.9 Hz, 1H), 7.86 (d, J=7.0 Hz, 1H), 7.67 (d, J=7.9 Hz, 1H), 7.26 (d, J=8.4 Hz, 2H), 7.17 (d, J=6.2 Hz, 2H), 7.05 (d, J=8.4 Hz, 2H), 6.65 (d, J=7.5 Hz, 1H), 5.25 (s, 2H).

Example 5

Preparation of 2-((2-methyl-6-(trifluoromethyl)pyridin-3-yl)methyl)-8-(pyridin-4-yl)-7-(4-(trifluoromethyl)phenyl)-[1,2,4]triazolo[4,3-a]pyridin-3(2H)-one

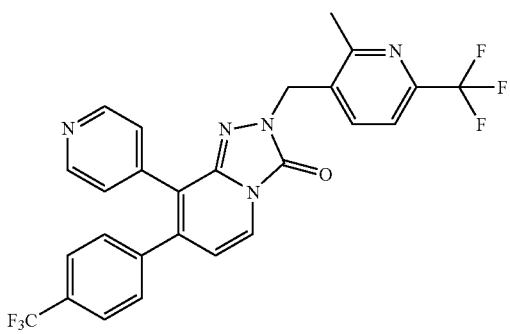

A. Preparation of 8-bromo-7-chloro-2-((2-methyl-6-(trifluoromethyl)pyridin-3-yl)methyl)-[1,2,4]triazolo[4,3-a]pyridin-3(2H)-one

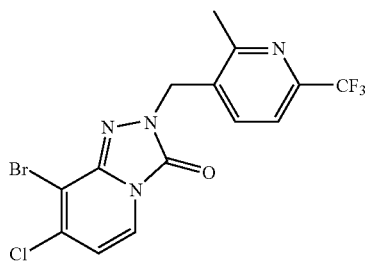

To a solution of 8-bromo-7-chloro-[1,2,4]triazolo[4,3-a]pyridin-3(2H)-one (456 mg, 2.0 mmol) in anhydrous DMF (7 mL) was added 3-(chloromethyl)-2-methyl-6-(trifluoromethyl)pyridine (627 mg, 3.0 mmol), followed by anhydrous potassium carbonate (415 mg, 3.0 mmol). The resulting suspension was stirred under argon at 80° C. for 1.5 h. After cooling to room temperature, the reaction mixture was partitioned between EtOAc and water, and the aqueous layer was extracted with EtOAc (30 mL×2). The combined EtOAc extracts were washed with water, then saturated aqueous NaCl, dried over $Na_2SO_4$, and evaporated under reduced pressure to provide crude product as a brown solid. The crude product was purified using a silica gel cartridge (40 g) eluted with a gradient of EtOAc (0-60%) in hexanes to afford the title compound as an off-white solid (733 mg, 87%). HPLC/MS: retention time=3.36 min, [M+H]$^+$=420.1.

B. Preparation of 7-chloro-2-((2-methyl-6-(trifluoromethyl)pyridin-3-yl)methyl)-8-(pyridin-4-yl)-[1,2,4]triazolo[4,3-a]pyridin-3(2H)-one

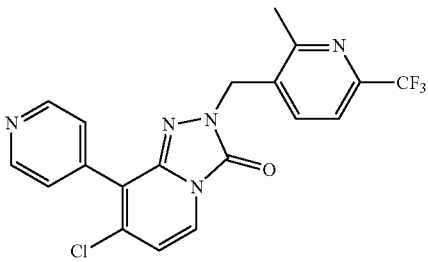

To a suspension of 8-bromo-7-chloro-2-((2-methyl-6-(trifluoromethyl)pyridin-3-yl)methyl)-[1,2,4]triazolo[4,3-a]pyridin-3(2H)-one (506 mg, 1.2 mmol), 4-(4,4,5,5-tetramethyl-1,3,2-dioxaborolan-2-yl)pyridine (984 mg, 4.8 mmol), and 2.0 M aqueous sodium carbonate (2.6 mL) in toluene (10 mL) was added $(Ph_3P)_4Pd$ (208 mg, 0.18 mmol) in one portion, and the resulting yellow mixture was vigorously stirred under argon at 100° C. Analysis by HPLC/MS after 2.5 h indicated about 70% of starting 8-bromo-7-chloro-2-((2-methyl-6-(trifluoromethyl)pyridin-3-yl)methyl)-[1,2,4]triazolo[4,3-a]pyridin-3(2H)-one remained. Additional $(Ph_3P)_4Pd$ (60 mg, 0.05 mmol) was added. After stirring for 3 h more, the same amount of catalyst was again added, and the reaction mixture was stirred at 100° C. under argon for 5 h more. After cooling to room temperature, the reaction mixture was diluted with water and extracted with EtOAc (40 mL×3). The combined EtOAc extracts were washed with water, then saturated aqueous NaCl, dried over $Na_2SO_4$, filtered and concentrated under reduced pressure to afford crude product, which was purified using a silica gel cartridge (80 g) eluted with a gradient of EtOAc (0-100%) in hexanes to afford the title compound as a white foam (320 mg, 62%). HPLC/MS: retention time=2.14 min, [M+H]$^+$=420.1.

C. Preparation of 2-((2-methyl-6-(trifluoromethyl)pyridin-3-yl)methyl)-8-(pyridin-4-yl)-7-(4-(trifluoromethyl)phenyl)-[1,2,4]triazolo[4,3-a]pyridin-3(2H)-one

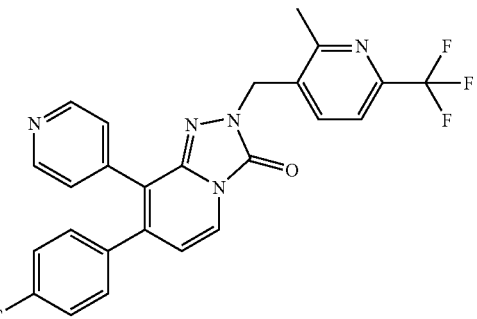

To a suspension of 7-chloro-2-((2-methyl-6-(trifluoromethyl)pyridin-3-yl)methyl)-8-(pyridin-4-yl)-[1,2,4]triazolo[4,3-a]pyridin-3(2H)-one (72 mg, 0.17 mmol), 4-trifluoromethylphenylboronic acid (65 mg, 0.34 mmol), and 2.0 M aqueous sodium carbonate (0.37 mL) in toluene (1.5 mL) was added (Ph₃P)₄Pd (30 mg, 0.025 mmol) in one portion, and the resulting yellow mixture was vigorously stirred under argon at 100° C. for 1.5 h. After cooling to room temperature, the reaction mixture was partitioned between EtOAc and water. The EtOAc layer was washed with water, then saturated aqueous NaCl twice, dried over Na₂SO₄, filtered and concentrated under reduced pressure. The crude product was purified using a silica gel cartridge (12 g) eluted with a gradient of EtOAc (0-80%) in hexanes to afford the desired product, which was contaminated with triphenylphosphine oxide. The product was further purified by preparative reverse phase HPLC (Phenomenex Luna 5 μm C-18 21.2×100 mm column eluted with a linear gradient of 50% to 90% B over 12 min (A=90% water, 10% methanol and B=90% methanol, 10% water) with flow rate at 20 mL/min and UV detection at 220 nm). The desired fractions were concentrated under reduced pressure. The yellow residue was dissolved in acetonitrile, frozen and lyophilized to afford 40 mg of the title compound as a light yellow powder. HPLC/MS: retention time=2.92 min, [M+H]⁺=530.4.

Example 6

Preparation of 4-(2-((2-methyl-6-(trifluoromethyl)pyridin-3-yl)methyl)-3-oxo-8-(pyridin-4-yl)-2,3-dihydro-[1,2,4]triazolo[4,3-a]pyridin-7-yl)benzonitrile

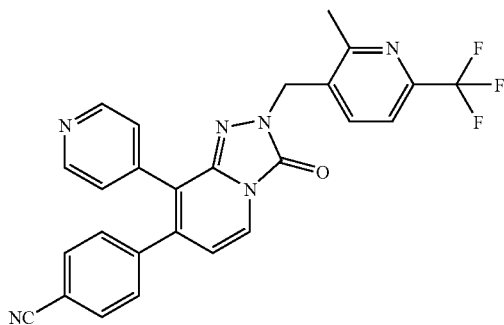

To a suspension of 7-chloro-2-((2-methyl-6-(trifluoromethyl)pyridin-3-yl)methyl)-8-(pyridin-4-yl)-[1,2,4]triazolo[4,3-a]pyridin-3(2H)-one (135 mg, 0.32 mmol), 4-cyanophenylboronic acid (189 mg, 1.29 mmol), and 2.0 M aqueous sodium carbonate (0.70 mL) in toluene (2.5 mL) was added (Ph₃P)₄Pd (55 mg, 0.048 mmol) in one portion, and the resulting yellow mixture was vigorously stirred under argon at 100° C. for 1.5 h. Analysis by HPLC/MS indicated about 30% of the starting 7-chloro-2-((2-methyl-6-(trifluoromethyl)pyridin-3-yl)methyl)-8-(pyridin-4-yl)-[1,2,4]triazolo[4,3-a]pyridin-3(2H)-one remained. Additional catalyst (35 mg, 0.030 mmol) was added. The reaction mixture was stirred at 100° C. for 2 h more. After cooling to room temperature, the reaction mixture was partitioned between EtOAc and water. The EtOAc layer was washed with water, then saturated aqueous NaCl twice, dried over Na₂SO₄, filtered and concentrated under reduced pressure. The crude product was purified using a silica gel cartridge (40 g) eluted with a gradient of EtOAc (0-80%) in hexanes to afford the desired product, which was dissolved in acetonitrile, frozen and lyophilized to afford 80 mg of the title compound as a light yellow powder. HPLC/MS: retention time=2.39 min, [M+H]⁺=487.2.

Example 7

Preparation of 7-(4-fluorophenyl)-2-((2-methyl-6-(trifluoromethyl)pyridin-3-yl)methyl)-8-(pyridin-4-yl)-[1,2,4]triazolo[4,3-a]pyridin-3(2H)-one

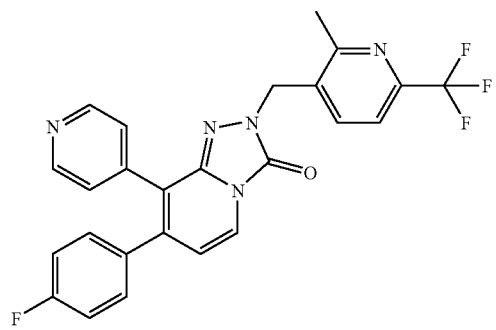

To a suspension of 7-chloro-2-((2-methyl-6-(trifluoromethyl)pyridin-3-yl)methyl)-8-(pyridin-4-yl)-[1,2,4]triazolo[4,3-a]pyridin-3(2H)-one (135 mg, 0.32 mmol), 4-fluorophenylboronic acid (180 mg, 1.29 mmol), and 2.0 M aqueous sodium carbonate (0.70 mL) in toluene (2.5 mL) was added (Ph₃P)₄Pd (55 mg, 0.048 mmol) in one portion, and the resulting yellow mixture was vigorously stirred under argon at 100° C. for 2 h. Analysis by HPLC/MS indicated about 10% of the starting 7-chloro-2-((2-methyl-6-(trifluoromethyl)pyridin-3-yl)methyl)-8-(pyridin-4-yl)-[1,2,4]triazolo[4,3-a]pyridin-3(2H)-one remained. Additional catalyst (15 mg, 0.013 mmol) was added. The reaction mixture was stirred at 100° C. for 1 h more. After cooling to room temperature, the reaction mixture was partitioned between EtOAc and water. The EtOAc layer was washed with water, then saturated aqueous NaCl twice, dried over Na₂SO₄, filtered and concentrated under reduced pressure. The crude product was purified using a silica gel cartridge (12 g) eluted with a gradient of EtOAc (0-80%) in hexanes to afford the desired product, which was contaminated with triphenylphosphine oxide. The product was further purified by preparative reverse phase HPLC (Phenomenex Luna 5 μm C-18 21.2×100 mm column eluted with a linear gradient of 50% to 90% B over 15 min (A=0.1% trifluoroacetic acid, 90% water, 10% methanol and B=0.1% trifluoroacetic acid, 90% methanol, 10% water) with flow rate at 20 mL/min and UV detection at 220 nm). The desired fractions were concentrated under reduced pressure. The residue was dissolved in EtOAc, washed with saturated aqueous NaHCO₃ once, water twice, then saturated aqueous NaCl, dried over Na₂SO₄ and evaporated. The yellow residue was dissolved in acetonitrile, frozen and lyophilized to afford 66 mg of the title compound as a light yellow powder. HPLC/MS: retention time=2.49 min, [M+H]⁺=480.0.

Example 8

Preparation of 7-(4-methoxyphenyl)-2-((2-methyl-6-(trifluoromethyl)pyridin-3-yl)methyl)-8-(pyridin-4-yl)-[1,2,4]triazolo[4,3-a]pyridin-3(2H)-one

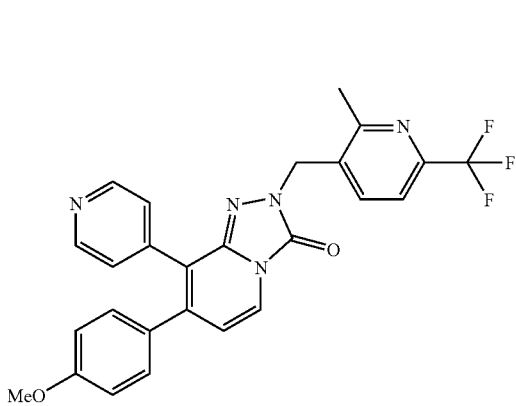

To a suspension of 7-chloro-2-((2-methyl-6-(trifluoromethyl)pyridin-3-yl)methyl)-8-(pyridin-4-yl)-[1,2,4]triazolo[4,3-a]pyridin-3(2H)-one (135 mg, 0.32 mmol), 4-methoxyphenylboronic acid (190 mg, 1.29 mmol), and 2.0 M aqueous sodium carbonate (0.70 mL) in toluene (2.5 mL) was added (Ph$_3$P)$_4$Pd (55 mg, 0.048 mmol) in one portion, and the resulting yellow mixture was vigorously stirred under argon at 100° C. for 1.5 h. Analysis by HPLC/MS indicated the starting 7-chloro-2-((2-methyl-6-(trifluoromethyl)pyridin-3-yl)methyl)-8-(pyridin-4-yl)-[1,2,4]triazolo[4,3-a]pyridin-3(2H)-one had been consumed. After cooling to room temperature, the reaction mixture was partitioned between EtOAc and water. The EtOAc layer was washed with water, then saturated aqueous NaCl twice, dried over Na$_2$SO$_4$, filtered and concentrated under reduced pressure. The crude product was purified using a silica gel cartridge (12 g) eluted with a gradient of EtOAc (0-80%) in hexanes to afford the desired product, which was contaminated with triphenylphosphine oxide. The product was further purified by preparative reverse phase HPLC (Phenomenex Luna 5 μm C-18 21.2×100 mm column eluted with a linear gradient of 50% to 90% B over 15 min (A=0.1% trifluoroacetic acid, 90% water, 10% methanol and B=0.1% trifluoroacetic acid, 90% methanol, 10% water) with flow rate at 20 mL/min and UV detection at 220 nm). The desired fractions were concentrated under reduced pressure. The residue obtained was dissolved in EtOAc, washed with saturated aqueous NaHCO$_3$ once, water twice, then saturated aqueous NaCl, dried over Na$_2$SO$_4$ and evaporated. The yellow residue was dissolved in acetonitrile, frozen and lyophilized to afford 82 mg of the title compound as a light yellow powder. HPLC/MS: retention time=2.56 min, [M+H]$^+$=492.0.

Example 9

Preparation of 4-(2-((2-methyl-6-(trifluoromethyl)pyridin-3-yl)methyl)-3-oxo-8-phenyl-2,3-dihydro-[1,2,4]triazolo[4,3-a]pyridin-7-yl)benzonitrile

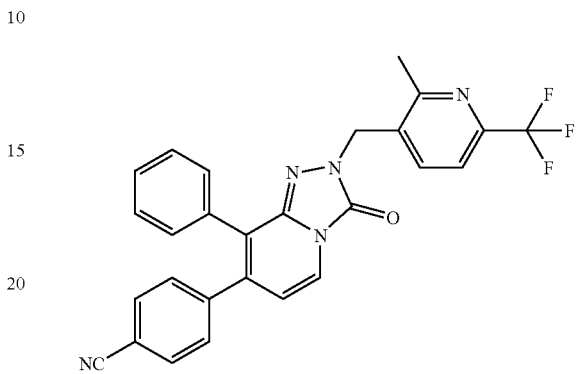

A. Preparation of 4-(3-bromo-2-chloropyridin-4-yl)benzonitrile

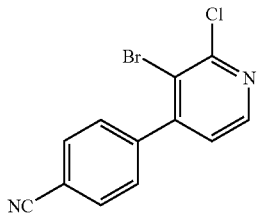

A suspension of impure 3-bromo-2-chloro-4-iodopyridine (2.23 g), 4-cyanophenylboronic acid (1.62 g, 11.0 mmol), 2 M aqueous Na$_2$CO$_3$ solution (6 mL, 12 mmol), and toluene (40 mL) was purged with argon, then (Ph$_3$P)$_4$Pd (1.1 g, 0.95 mmol) was added in one portion. The resulting yellow mixture was vigorously stirred under argon at 100° C. for 4 h. Analysis by HPLC/MS indicated the reaction was not complete, and additional 4-cyanophenylboronic acid (0.82 g, 5.57 mmol), 2 M aqueous Na$_2$CO$_3$ solution (3.5 mL) and (Ph$_3$P)$_4$Pd (850 mg) were added. The reaction mixture was stirred at 100° C. for 12 h more. Additional (Ph$_3$P)$_4$Pd (1.0 g) was added, and the reaction mixture was stirred for another 20 h. After cooling to room temperature, the reaction mixture was diluted with water and extracted with EtOAc (40 mL×3). The combined EtOAc extracts were washed with water, then saturated aqueous NaCl, dried over Na$_2$SO$_4$, filtered and concentrated under reduced pressure. The crude product was purified using a silica gel cartridge (80 g) eluted with a gradient of EtOAc (0-60%) in hexanes to obtain 590 mg (29%) of the title compound as an off-white solid. HPLC/MS: retention time=3.11 min, [M+H]+=292.

B. Preparation of 4-(3-bromo-2-hydrazinylpyridin-4-yl)benzonitrile

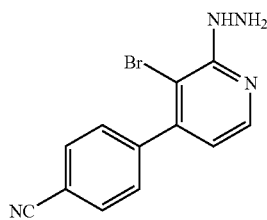

To a suspension of 4-(3-bromo-2-chloropyridin-4-yl)benzonitrile (0.59 g, 2.02 mmol) in dioxane (7 mL) at room temperature was added anhydrous hydrazine (1 mL). The resulting mixture was stirred at 80° C. for 2 h. Analysis by HPLC/MS indicated the reaction was not complete. Additional anhydrous hydrazine (1 mL) was added, and the reaction mixture was stirred at 90° C. for 5 h more. After cooling to room temperature, the reaction mixture was concentrated under reduced pressure. Water was added to the residue, and the resulting suspension was sonicated for 5 min. The resulting slurry was filtered, and the collected solid was washed with water (10 mL×2), then dried in a 45° C. vacuum oven for 16 h to afford 510 mg of the title compound as a beige solid. HPLC/MS: retention time=1.74 min, [M+H]+=289.

C. Preparation of 4-(8-bromo-3-oxo-2,3-dihydro-[1,2,4]triazolo[4,3-a]pyridin-7-yl)benzonitrile

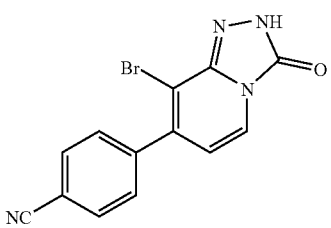

To a solution of triphosgene (1.50 g, 5.20 mmol) in anhydrous THF (10 mL) at 60° C. was added 4-(3-bromo-2-hydrazinylpyridin-4-yl)benzonitrile (500 mg) in small portions over 5 min. The resulting yellow suspension was then refluxed for 2 h. After cooling to room temperature, the reaction mixture was concentrated under reduced pressure to remove most of the THF. Water (5 mL) was added carefully to the remaining solution to destroy the excess triphosgene, then the resulting aqueous suspension was stirred at room temperature for 30 min. The suspension was filtered, and the collected solid was washed with water (10 mL×2), then dried in a 45° C. vacuum oven for 16 h to afford 575 mg of the title compound as a yellow solid. HPLC/MS: retention time=2.44 min, [M+H]+=315.

D. Preparation of 4-(8-bromo-2-((2-methyl-6-(trifluoromethyl)pyridin-3-yl)methyl)-3-oxo-2,3-dihydro-[1,2,4]triazolo[4,3-a]pyridin-7-yl)benzonitrile

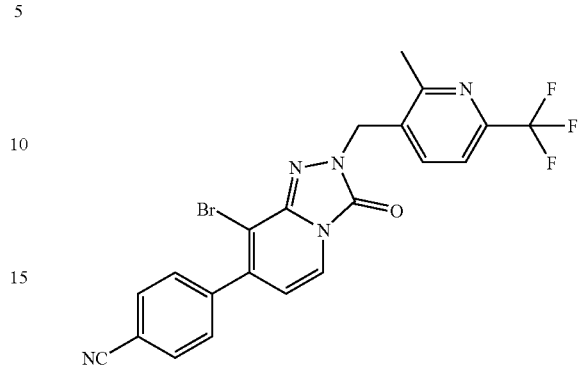

To a solution of 4-(8-bromo-3-oxo-2,3-dihydro-[1,2,4]triazolo[4,3-a]pyridin-7-yl)benzonitrile (510 mg, 1.81 mmol) and 3-(chloromethyl)-2-methyl-6-(trifluoromethyl)pyridine (455 mg, 2.17 mmol) in anhydrous DMF (8 mL) was added anhydrous potassium carbonate (499 mg, 3.62 mmol). The resulting suspension was stirred under argon at 80° C. for 2 h. Analysis by HPLC/MS indicated the reaction was not complete. Additional of 3-(chloromethyl)-2-methyl-6-(trifluoromethyl)pyridine (120 mg, 0.57 mmol) and anhydrous potassium carbonate (200 mg, 2.07 mmol) were added, and the reaction mixture was stirred at 85° C. for 6 h more. After cooling to room temperature, the reaction mixture was partitioned between EtOAc and water, and the aqueous layer was extracted with EtOAc. The combined EtOAc extracts were washed with saturated aqueous NaCl, dried over Na2SO4, and concentrated under reduced pressure to afford a light brown solid. The solid was suspended in EtOAc/hexanes (about 1:1 ratio), then sonicated for 10 min to obtain a fine suspension. After filtration, the collected solid was washed with hexanes and dried in air to afford 500 mg of the title compound as a yellow solid. HPLC/MS: retention time=3.44 min, [M+H]+=489.2.

E. Preparation of 4-(2-((2-methyl-6-(trifluoromethyl)pyridin-3-yl)methyl)-3-oxo-8-phenyl-2,3-dihydro-[1,2,4]triazolo[4,3-a]pyridin-7-yl)benzonitrile

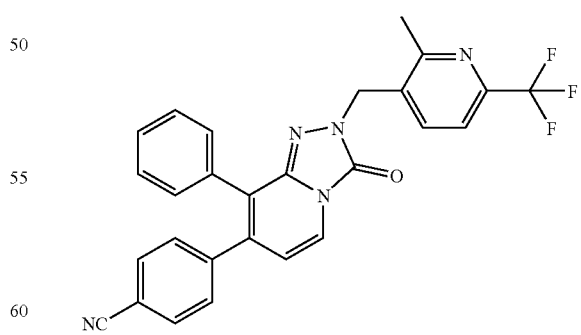

Into a flame-dried reaction vessel under argon was placed 4-(8-bromo-2-((2-methyl-6-(trifluoromethyl)pyridin-3-yl)methyl)-3-oxo-2,3-dihydro-[1,2,4]triazolo[4,3-a]pyridin-7-yl)benzonitrile (49 mg, 0.1 mmol), phenylboronic acid (37 mg, 0.3 mmol), K3PO4 (64 mg, 0.3 mmol), Pd(dppf)

Cl$_2$.CH$_2$Cl$_2$ (8.0 mg, 0.01 mmol) and anhydrous THF (1.5 mL). The suspension was degassed with argon bubbling, and the reaction vessel was sealed and stirred at 90° C. for 4.5 h. Analysis by HPLC/MS indicated the reaction was not complete. Additional palladium catalyst (3 mg) and THF (0.5 mL) was added, and the suspension was degassed again. The reaction mixture was stirred at 90° C. for 16 h more. After cooling to room temperature, the reaction mixture was partitioned between EtOAc and water. The EtOAc layer was washed with water, then saturated aqueous NaCl, dried over Na$_2$SO$_4$, filtered and concentrated under reduced pressure. The crude product was purified using a silica gel cartridge (12 g) eluted with a gradient of EtOAc (0-70%) in hexanes to afford the desired product (90% pure). The product was further purified by preparative reverse phase HPLC (Phenomenex Luna 5 μm C-18 21.2×100 mm column eluted with a linear gradient of 70% to 100% B over 10 min (A=90% water, 10% methanol and B=90% methanol, 10% water) with flow rate at 20 mL/min and UV detection at 220 nm). The desired fractions were concentrated under reduced pressure. The residue obtained was dissolved in acetonitrile, frozen and lyophilized to afford 19.5 mg of the title compound as a light yellow powder. HPLC/MS: retention time=3.69 min, [M+H]$^+$=486.7.

Example 10

Preparation of 4-(8-(4-methoxyphenyl)-2-((2-methyl-6-(trifluoromethyl)pyridin-3-yl)methyl)-3-oxo-2,3-dihydro-[1,2,4]triazolo[4,3-a]pyridin-7-yl)benzonitrile

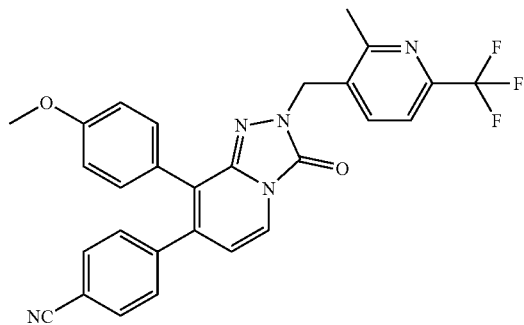

Into a flame-dried reaction vessel under argon was placed 4-(8-bromo-2-((2-methyl-6-(trifluoromethyl)pyridin-3-yl)methyl)-3-oxo-2,3-dihydro-[1,2,4]triazolo[4,3-a]pyridin-7-yl)benzonitrile (49 mg, 0.1 mmol), 4-methoxyphenylboronic acid (46 mg, 0.3 mmol), K$_3$PO$_4$ (64 mg, 0.3 mmol), Pd(dppf) Cl$_2$.CH$_2$Cl$_2$ (17 mg, 0.02 mmol) and anhydrous THF (1.5 mL). The suspension was degassed with argon bubbling, and the reaction vessel was sealed and stirred at 90° C. for 16 h. Analysis by HPLC/MS indicated the reaction was complete. After cooling to room temperature, the reaction mixture was partitioned between EtOAc and water. The EtOAc layer was washed with water, then saturated aqueous NaCl, dried over Na$_2$SO$_4$, filtered and concentrated under reduced pressure. The crude product was purified using a silica gel cartridge (12 g) eluted with a gradient of EtOAc (0-70%) in hexanes to afford the desired product (90% pure). The product was further purified by preparative reverse phase HPLC (Phenomenex Luna 5 μm C-18 21.2×100 mm column eluted with a linear gradient of 70% to 100% B over 10 min (A=90% water, 10% methanol and B=90% methanol, 10% water) with flow rate at 20 mL/min and UV detection at 220 nm). The desired fractions were concentrated under reduced pressure. The residue obtained was dissolved in acetonitrile, frozen and lyophilized to afford 18 mg of the title compound as a light yellow powder. HPLC/MS: retention time=3.71 min, [M+H]$^+$=516.8.

Example 11

Preparation of 7-(4-chlorophenyl)-8-(4-methoxyphenyl)-2-((6-(trifluoromethyl)pyridin-3-yl)methyl)-[1,2,4]triazolo[4,3-a]pyridin-3(2H)-one

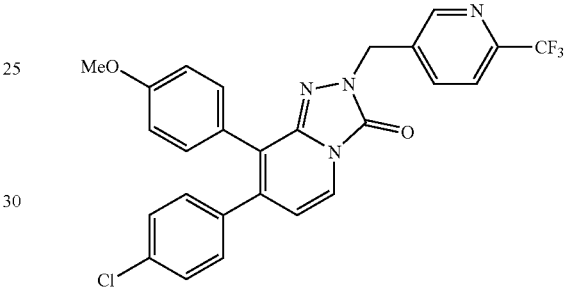

A. Preparation of 3-bromo-2-chloro-4-iodopyridine

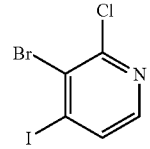

To a solution of 1.8 M lithium diisopropylamide in THF (70 mL, 126 mmol) at −78° C. under argon was added a solution of 2-chloro-3-bromopyridine (25 g, 126 mmol) in THF (100 mL) over 2 h. The resulting reaction mixture was stirred at −78° C. for 1 h before a solution of I$_2$ (32 g, 126 mmol) in 200 mL THF was added over 2 h. The reaction mixture was allowed to stir at −78° C. for 30 min. Brine (150 mL) and then EtOAc (200 mL) were added to the reaction mixture, and the layers were separated. The organic layer was dried (MgSO$_4$), filtered, and concentrated under reduced pressure. The crude product was passed through a bed of silica gel eluting with 2% EtOAc/hexanes to isolate 38.5 g of a regioisomeric mixture of products as a light brown solid. HPLC/MS: retention times=3.073 and 3.151 min, [M+H]$^+$=318.

B. Preparation of 3-bromo-2-chloro-4-(4-chlorophenyl)pyridine

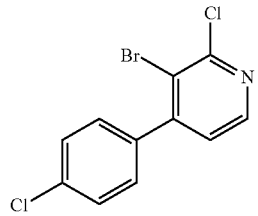

To a solution of crude 3-bromo-2-chloro-4-iodopyridine (10.0 g, 31.41 mmol) in toluene (120 mL) at room temperature under argon was added 4-chlorophenylboronic acid (5.8 g, 37.1 mmol), tetrakis(triphenylphosphine)palladium (2.2 g, 1.9 mmol), and a solution of $Na_2CO_3$ (6.6 g, 62.3 mmol) in water (20 mL). The resulting suspension was stirred and heated at 100° C. under argon for 2.5 h. After the reaction mixture was cooled to room temperature, water (120 mL) and EtOAc (150 mL) were added. The layers were separated. The organic layer was dried ($MgSO_4$), filtered, and concentrated under reduced pressure. The crude product was purified by flash chromatography (silica gel column eluting with 7% ethyl acetate-hexanes) to isolate 3.7 g of the title compound as a white solid. HPLC/MS: retention time=3.78 min, $[M+H]^+=$ 302. $^1$H NMR ($CDCl_3$, 500 MHz): δ 8.35 (d, J=5.0 Hz, 1H), 7.46 (d, J=10.0 Hz, 2H), 7.34 (d, J=10.0 Hz, 2H), 7.14 (d, J=5.0 Hz, 1H).

C. Preparation of 3-bromo-4-(4-chlorophenyl)-2-hydrazinylpyridine

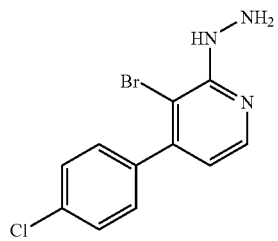

A mixture of 3-bromo-2-chloro-4-(4-chlorophenyl)pyridine (10 g, 33 mmol), pyridine (50 mL) and hydrazine monohydrate (4.8 g, 96 mmol) was heated to 120° C. for 16 h. After cooling to room temperature, water (300 mL) was added, which caused solid desired product to precipitate. This was filtered, washed with water (2×50 mL), and dried to obtain the title compound as a pale yellow solid (6 g), which was used without further purification.

D. Preparation of 8-bromo-7-(4-chlorophenyl)-[1,2,4]triazolo[4,3-a]pyridin-3(2H)-one

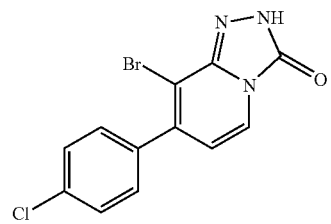

Crude 3-bromo-4-(4-chlorophenyl)-2-hydrazinylpyridine (7 g, 23 mmol) was dissolved in dry THF (100 mL), and the resulting solution was cooled to 0° C. To this was added 1,1'carbonyldiimidazole (18 g, 111 mmol). The reaction mixture was stirred at room temperature for 10 h. The solvent was evaporated under vacuum, and water (10 mL) was added, which caused solid desired product to precipitate. This was filtered, washed with water (2×25 mL), and dried to obtain the title compound as a yellow solid (6.3 g), which was used without further purification.

E. Preparation of 8-bromo-7-(4-chlorophenyl)-2-((6-(trifluoromethyl)pyridin-3-yl)methyl)-[1,2,4]triazolo[4,3-a]pyridin-3(2H)-one

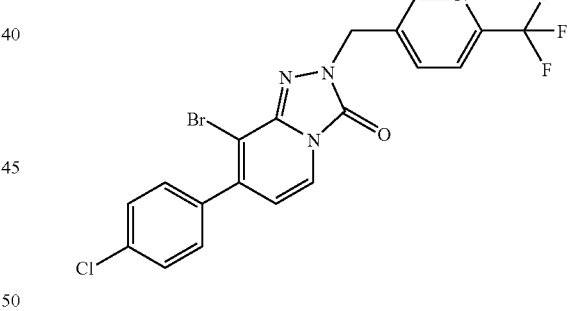

To a stirred mixture of 8-bromo-7-(4-chlorophenyl)-[1,2,4]triazolo[4,3-a]pyridin-3(2H)-one (3.24 g, 10.0 mmol) in DMF (15 mL) at room temperature under argon was added $K_2CO_3$ (2.76 g, 20.0 mmol) and 3-(chloromethyl)-6-(trifluoromethyl)pyridine (2.34 g, 12.0 mmol). After stirring at room temperature for 3 d, HPLC indicated approximately 70% complete reaction. The mixture was then heated to 60° C. for 5 h, after which HPLC indicated complete reaction. The mixture was cooled to room temperature, diluted with water (100 mL), and stirred for 1 h. Solid was collected by filtration and washed with water (10 mL×5), then methanol (5 mL×2), and finally dried under vacuum. The title compound (4.4 g) was obtained as a yellow solid. HPLC/MS: retention time=3.8 min, $[M+H]^+=485$.

F. Preparation of 7-(4-chlorophenyl)-8-(4-methoxyphenyl)-2-((6-(trifluoromethyl)pyridin-3-yl)methyl)-[1,2,4]triazolo[4,3-a]pyridin-3(2H)-one

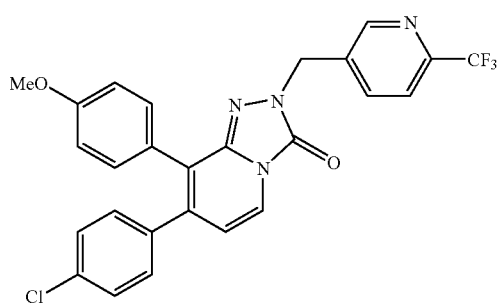

Into a 5 dram vial at room temperature were placed a magnetic stirbar, 8-bromo-7-(4-chlorophenyl)-2-((2-methyl-6-(trifluoromethyl)pyridin-3-yl)methyl)-[1,2,4]triazolo[4,3-a]pyridin-3(2H)-one (100 mg, 0.20 mmol), 4-methoxyphenylboronic acid (94 mg, 0.60 mmol), Pd(dppf)Cl$_2$·CH$_2$Cl$_2$ (17 mg, 0.02 mmol), powdered anhydrous K$_3$PO$_4$ (133 mg, 0.60 mmol), and dry THF (3 mL). The vial was flushed with argon and then capped tightly. The vial was heated to 90° C. for 6 h while stirring. Analysis by HPLC/MS indicated that starting material was absent and one major new product had formed. The reaction mixture was diluted with EtOAc (20 mL) and water (20 mL). The organic layer was separated, and the aqueous layer was extracted with EtOAc. The combined organic extract was dried (Na$_2$SO$_4$), filtered, and concentrated under reduced pressure. The crude product was purified by automated silica gel chromatography (eluted with EtOAc/hexanes) to obtain the title compound (67 mg) as an oil. HPLC/MS: retention time=4.0 min, [M+H]$^+$=511.

Examples 12 to 18

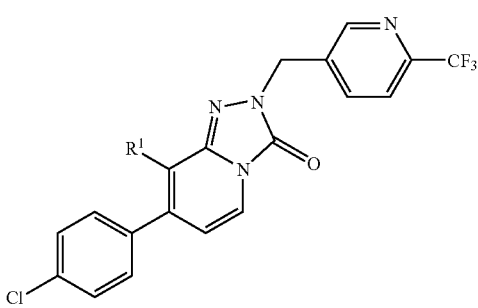

The examples shown in Table 1 below were prepared following the coupling procedure described above for Example 11 and varying the R$^1$ reagent. The following caveats apply: Examples 12-18 were prepared on a 0.50 mmol or 0.25 mmol scale using the same number of equivs as described for Example 11. However, these reactions were run 2-3 times more concentrated in THF. Reaction times were 3-8 h. Work-up was not extractive, but rather consisted of dilution with CH$_2$Cl$_2$, filtration, and filtrate evaporation. Purification by automated silica gel chromatography was sometimes followed by reverse phase preparative HPLC (without TFA).

TABLE 1

| Example | R$^1$ | R$^1$ reagent | HPLC/MS retention time (with TFA) | HPLC/MS [M + H]$^+$ |
|---|---|---|---|---|
| 12 | phenyl | R$^1$B(OH)$_2$ | 3.9 | 481 |
| 13 | 4-methylphenyl | R$^1$B(OH)$_2$ | 4.6 | 495 |
| 14 | 4-hydroxyphenyl | R$^1$B(OCMe$_2$)$_2$ | 3.6 | 497 |
| 15 | 2-methoxypyrimidin-5-yl | R$^1$B(OH)$_2$ | 3.5 | 513 |
| 16 | 4-(methoxymethyl)phenyl | R$^1$B(OH)$_2$ | 3.9 | 525 |
| 17 | 3,5-difluoro-4-(hydroxymethyl)phenyl | R$^1$B(OH)$_2$ | 3.6 | 547 |
| 18 | 4-(cyanomethyl)phenyl | R$^1$B(OCMe$_2$)$_2$ | 3.6 | 520 |

Examples 19 to 24

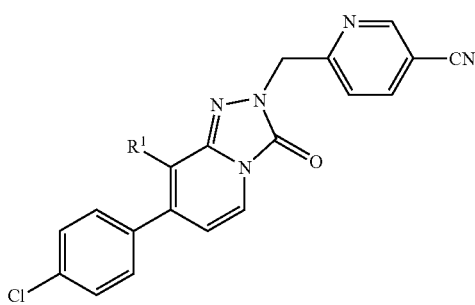

A. Preparation of 6-((8-bromo-7-(4-chlorophenyl)-3-oxo-[1,2,4]triazolo[4,3-a]pyridin-2(3H)-yl)methyl)nicotinonitrile

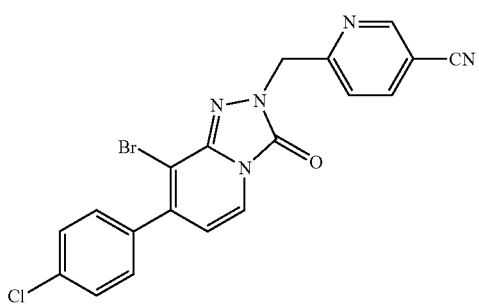

To a stirred mixture of 8-bromo-7-(4-chlorophenyl)-[1,2,4]triazolo[4,3-a]pyridin-3(2H)-one (1.07 g, 3.31 mmol) in DMF (15 mL) at room temperature under argon was added $K_2CO_3$ (0.91 g, 6.62 mmol) and 6-(chloromethyl)nicotinonitrile (0.63 g, 4.14 mmol). The mixture was then heated to 60° C. for 7 h, after which HPLC indicated complete reaction. The mixture was cooled to room temperature, diluted with water (100 mL), and stirred for 30 min. Solid was collected by filtration and washed with water (10 mL×5), then methanol (3 mL×3), and finally dried under vacuum. The title compound (0.98 g) was obtained as a tan solid. HPLC/MS: retention time=3.4 min, $[M+H]^+$=442.

B. Examples 19 to 24

The examples shown in Table 2 below were prepared from 6-((8-bromo-7-(4-chlorophenyl)-3-oxo-[1,2,4]triazolo[4,3-a]pyridin-2(3H)-yl)methyl)nicotinonitrile analogously to the way Example 11 was prepared from 8-bromo-7-(4-chlorophenyl)-2-((2-methyl-6-(trifluoromethyl)pyridin-3-yl)methyl)-[1,2,4]triazolo[4,3-a]pyridin-3(2H)-one and varying the $R^1$ reagent. The following caveats apply: Examples 19-24 were prepared on a 0.10 mmol scale using the same number of equivs as described for Example 11. However, these reactions were run twice as concentrated in THF. Reaction times were 3-4 h and reaction temperatures were 100-120° C. Work-up was not extractive, but rather consisted of dilution with $CH_2Cl_2$, filtration, and filtrate evaporation.

TABLE 2

| Example | $R^1$ | $R^1$ reagent | HPLC/MS retention time (with TFA) | HPLC/MS $[M + H]^+$ |
|---|---|---|---|---|
| 19 | phenyl | $R_1B(OH)_2$ | 3.6 | 438 |
| 20 | 4-methoxyphenyl | $R_1B(OH)_2$ | 3.6 | 468 |
| 21 | 4-methylphenyl | $R_1B(OH)_2$ | 3.8 | 452 |
| 22 | 4-(cyanomethyl)phenyl | $R_1B(OCMe_2)_2$ | 3.2 | 477 |
| 23 | 4-(methoxymethyl)phenyl | $R_1B(OH)_2$ | 3.5 | 482 |
| 24 | 2-methoxypyrimidin-5-yl | $R_1B(OH)_2$ | 3.1 | 470 |

Example 25

Preparation of 4-(8-(4-methoxyphenyl)-3-oxo-2-((6-(trifluoromethyl)pyridin-3-yl)methyl)-2,3-dihydro-[1,2,4]triazolo[4,3-a]pyridin-7-yl)benzonitrile

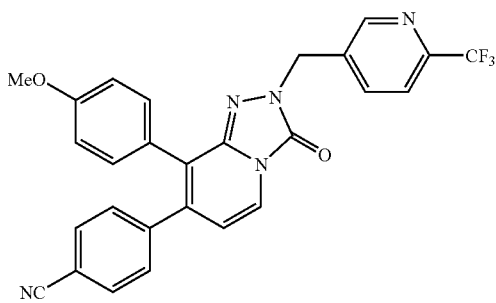

Into a microwave reaction vial were placed 7-(4-chlorophenyl)-8-(4-methoxyphenyl)-2-((6-(trifluoromethyl)pyridin-3-yl)methyl)-[1,2,4]triazolo[4,3-a]pyridin-3(2H)-one (51 mg, 0.10 mmol), CuCN (89.5 mg, 1.0 mmol), and 1-methylpyrrolidin-2-one (1.0 mL, dry). This mixture was heated to 250° C. in a microwave reactor for 8 h. HPLC/MS analysis indicated 55% conversion to desired product. The reaction mixture was cooled to room temperature and poured into 10% aqueous ammonium hydroxide solution. The resulting mixture was stirred at room temperature for 1 h. Solid was filtered off and purified by reverse phase preparative HPLC (without TFA). The title compound (8.6 mg) was obtained as a light yellow solid. HPLC/MS: retention time=3.5 min, [M+H]$^+$= 502.

Examples 26 to 60

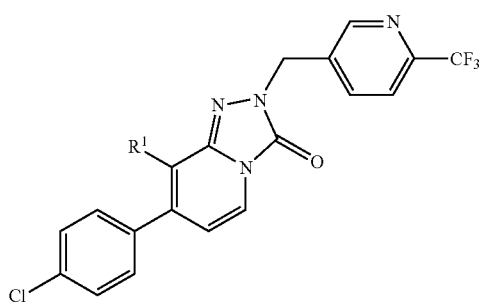

The examples shown in Table 3 below were prepared using the following coupling procedure, carried out on either the 0.10 mmol scale described here or on a 0.07 mmol scale: 8-bromo-7-(4-chlorophenyl)-2-((6-(trifluoromethyl)pyridin-3-yl)methyl)-[1,2,4]triazolo[4,3-a]pyridin-3(2H)-one (48 mg, 0.10 mmol), the requisite boronic acid ($R^1B(OH)_2$) or boronate ester ($R^1B(OCMe_2)_2$) or stannane ($R^1SnBu_3$ or $R^1SnMe_3$) (0.13 mmol), $Pd_2(dba)_3$ (3.5 mg, 0.004 mmol), S-Phos (Aldrich, 2-(2',6'-dimethoxybiphenyl)dicyclohexylphosphine (T. E. Barder, et al., *J. Am. Chem. Soc.* 2005, 127 (13), 4685-4696), 6 mg, 0.015 mmol), $K_3PO_4$ (powdered anhydrous, 42 mg, 0.20 mmol), and n-butanol (dry, Aldrich Sure-Seal, 0.75 mL) were added to a vial with the $K_3PO_4$ and n-butanol added last. The vial was flushed (not bubbled) with argon or nitrogen and sealed before heating to 90-120° C. for 30 min to 2 h, depending inversely on the temperature, with either magnetic stirring or no agitation. After cooling to room temperature, analytical HPLC/MS under acidic (methanol-water-TFA) conditions, and in some cases also under neutral (methanol-water-$NH_4OAc$) conditions, was used to identify any remaining starting material (8-bromo-7-(4-chlorophenyl)-2-((6-(trifluoromethyl)pyridin-3-yl)methyl)-[1,2,4]triazolo[4,3-a]pyridin-3(2H)-one), boronic acid or boronate ester or stannane, S-Phos, S-Phos oxide, dba, desired product, reduction product (Br to H), and bis-reaction product (from reaction at the 4-chlorophenyl group in addition to desired coupling). In cases where significant starting material remained, reactions were pushed closer to completion by further heating after another argon or nitrogen flush subsequent to the introduction of additional reagents. Such additional reagents consisted of $Pd_2(dba)_3$ and optionally S-Phos and/or boronic acid or boronate ester or stannane, as determined by their amounts seen in the analytical HPLC/MS. Once the reaction mixture was judged to be ready for desired product isolation by reverse phase preparative HPLC, methanol (1.5 to 2.0 mL) and then water (0.4 mL) were added while stirring. In cases where TFA would be included in the preparative HPLC solvents, a few drops of TFA were also added to pre-acidify the crude reaction mixture. In either case, the reaction mixture was centrifuged or let stand to allow a clear supernatant to form. The supernatant was then injected onto reverse phase preparative HPLC eluting with methanol-water, which in some cases contained either 0.1% trifluoroacetic acid or 10 mM ammonium acetate. Desired product fractions were evaporated under vacuum to provide the example compounds. In some cases, compounds that were isolated by preparative HPLC with 0.1% trifluoroacetic acid were passed through a basic resin (Polymer Labs PL-HCO$_3$ MP SPE cartridge) in methanol-dichloromethane (1:1) solution to remove any trace or salting TFA, followed by evaporation. Independently, in some cases, additional purification was performed by column chromatography on silica gel eluted with ethyl acetate-hexanes.

TABLE 3

| Example | R$^1$ | R$^1$ reagent | Prep HPLC solvent additive | HPLC/MS retention time (with TFA) | HPLC/MS [M + H]$^+$ |
| --- | --- | --- | --- | --- | --- |
| 26 | phenyl | R$^1$B(OH)$_2$ | TFA | 4.0 | 481 |
| 27 | 4-methylphenyl | R$^1$B(OH)$_2$ | TFA | 4.1 | 495 |
| 28 | 4-methoxyphenyl | R$^1$B(OH)$_2$ | TFA | 4.0 | 511 |
| 29 | 6-cyanopyridin-3-yl | R$^1$B(OCMe$_2$)$_2$ | TFA | 3.5 | 507 |
| 30 | 3,4-difluorophenyl | R$^1$B(OH)$_2$ | NH$_4$OAc | 4.0 | 517 |
| 31 | 6-fluoropyridin-3-yl | R$^1$B(OH)$_2$ | NH$_4$OAc | 3.6 | 500 |
| 32 | 4-(dimethylaminomethyl)phenyl | R$^1$B(OCMe$_2$)$_2$ | NH$_4$OAc | 3.0 | 538 |
| 33 | 3-methylpyridin-4-yl | R$^1$B(OH)$_2$ | NH$_4$OAc | 2.7 | 496 |

TABLE 3-continued

| Example | R¹ | R¹ reagent | Prep HPLC solvent additive | HPLC/MS retention time (with TFA) | HPLC/MS [M + H]⁺ |
|---|---|---|---|---|---|
| 34 | 3-chloropyridin-4-yl | R¹B(OH)₂ | NH₄OAc | 3.6 | 516 |
| 35 | 5-fluoro-6-methoxypyridin-3-yl | R¹B(OH)₂ | NH₄OAc | 3.9 | 530 |
| 36 | 6-ethoxypyridin-3-yl | R¹B(OH)₂ | NH₄OAc | 3.9 | 526 |
| 37 | 6-methoxypyridin-3-yl | R¹B(OH)₂ | NH₄OAc | 3.8 | 512 |
| 38 | pyrazinyl | R¹SnBu₃ | NH₄OAc | 3.3 | 483 |
| 39 | benzopyrazin-6-yl | R¹B(OH)₂ | NH₄OAc | 3.6 | 533 |
| 40 | 2-chlorophenyl | R¹B(OH)₂ | NH₄OAc | 3.9 | 515 |
| 41 | 4-(dimethylaminocarbonyl)phenyl | R¹B(OH)₂ | NH₄OAc | 3.5 | 552 |
| 42 | 4-(methylsulfonylamino)phenyl | R¹B(OH)₂ | NH₄OAc | 3.5 | 574 |
| 43 | 4-cyanophenyl | R¹B(OH)₂ | NH₄OAc | 3.7 | 506 |
| 44 | 3,4-methylenedioxyphenyl | R¹B(OH)₂ | NH₄OAc | 3.9 | 525 |
| 45 | 3-methoxyphenyl | R¹B(OH)₂ | NH₄OAc | 3.9 | 511 |
| 46 | 3-methylphenyl | R¹B(OH)₂ | NH₄OAc | 4.1 | 495 |
| 47 | 2,4-dichlorophenyl | R¹B(OH)₂ | NH₄OAc | 4.1 | 549 |
| 48 | quinolin-5-yl | R¹B(OH)₂ | NH₄OAc | 3.0 | 532 |
| 49 | 4-methylpyridin-3-yl | R¹B(OH)₂ | NH₄OAc | 2.7 | 496 |
| 50 | 6-trifluoromethylpyridin-3-yl | R¹B(OCMe₂)₂ | NH₄OAc | 3.8 | 550 |
| 51 | pyridazin-4-yl | R¹SnBu₃ | NH₄OAc | 3.1 | 483 |
| 52 | 6-methylpyridin-3-yl | R¹B(OH)₂ | NH₄OAc | 2.8 | 496 |
| 53 | 4-(aminomethyl)phenyl | R¹B(OH)₂ | TFA | 3.0 | 510 |
| 54 | pyrimidin-4-yl | R¹SnBu₃ | none | 3.2 | 483 |
| 55 | 4-(hydroxymethyl)phenyl | R¹B(OH)₂ | none | 3.5 | 511 |
| 56 | 4-(ethoxycarbonyl)phenyl | R¹B(OCMe₂)₂ | TFA | 4.1 | 553 |
| 57 | 2-methylpyridin-4-yl | R¹B(OH)₂ | TFA | 2.4 | 496 |
| 58 | 2-fluoropyridin-4-yl | R¹B(OH)₂ | TFA | 3.6 | 500 |
| 59 | pyrimidin-5-yl | R¹B(OH)₂ | none | 3.3 | 483 |
| 60 | 3-(dimethylaminocarbonyl)phenyl | R¹B(OH)₂ | none | 3.5 | 552 |

Examples 61 to 64

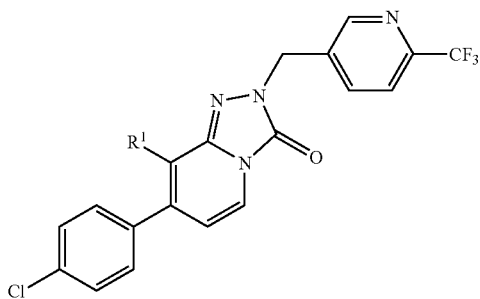

The examples shown in Table 4 below were prepared using the following coupling procedure: 8-bromo-7-(4-chlorophenyl)-2-((6-(trifluoromethyl)pyridine-3-yl)methyl)-[1,2,4]triazolo[4,3-a]pyridine-3(2H)-one (48 mg, 0.10 mmol), the requisite nucleophile source reagent R¹H (0.30 mmol), KOCMe₃ (15 mg, 0.13 mmol), 1-methylpyrrolidin-2-one (dry, Aldrich Sure-Seal, 0.7 mL), and a magnetic stirbar were added to a vial, which was flushed (not bubbled) with argon and sealed before stirring at or above room temperature, as indicated below, for the time indicated below. Next, at room temperature, the reaction mixture was diluted with methanol (2 mL) and then water (1 mL) while stirring. A few drops of TFA were added and the mixture was centrifuged. Supernatant was removed, and the residue was stirred in 1-methylpyrrolidin-2-one (0.5 mL) to which was added methanol (1 mL) and then water (0.5 mL). This mixture was centrifuged and the supernatant was removed and combined with the first supernatant for injection to reverse phase preparative HPLC, which was carried out eluting with methanol-water containing 0.1% trifluoroacetic acid Desired product fractions were evaporated under vacuum to provide the example compounds. In these particular examples, compounds were not passed through a basic resin (Polymer Labs PL-HCO₃ MP SPE cartridge) in methanol-dichloromethane (1:1) solution to remove any trace or salting TFA. In the case of Example 62, two isomeric products were produced. These were separable by column chromatography on silica gel eluting with a stepwise gradient of 0-4% methanol in ethyl acetate. Example 62 (TLC: R_f=0.29, 5% methanol in ethyl acetate) eluted before its isomer (TLC: R_f=0.21, 5% methanol in ethyl acetate).

TABLE 4

| Example | R¹ | Reaction temp and time | HPLC/MS retention time (with TFA) | HPLC/MS [M + H]⁺ |
|---|---|---|---|---|
| 61 | 2-methylimidazol-1-yl | RT, 4 d | 2.8 | 485 |
| 62 | 4-methylimidazol-1-yl | RT, 3 d | 2.9 | 485 |
| 63 | pyridin-3-yloxy | 135° C., 3 h | 3.1 | 498 |
| 64 | 5-chloropyridin-3-yloxy | 135° C., 9 h | 3.8 | 532 |

Example 65

Preparation of 8-(4-acetylphenyl)-7-(4-chlorophenyl)-2-((6-(trifluoromethyl)pyridin-3-yl)methyl)-[1,2,4]triazolo[4,3-a]pyridin-3(2H)-one

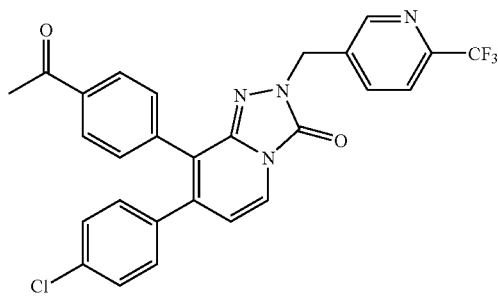

To a stirring solution of 8-bromo-7-(4-chlorophenyl)-2-((6-(trifluoromethyl)pyridin-3-yl)methyl)-[1,2,4]triazolo[4,3-a]pyridin-3(2H)-one (170 mg, 0.35 mmol) in THF (5 mL) at room temperature under argon was added 4-acetylphenylboronic acid (173 mg, 1.05 mmol), Pd(dppf)Cl$_2$.CH$_2$Cl$_2$ (32.2 mg, 0.035 mmol), and K$_3$PO$_4$ (224 mg, 1.05 mmol). The resulting suspension was purged of oxygen by bubbling with argon for 15 min, sealed in a vial under argon, heated at 90° C. for 12 h, and then cooled to room temperature. The reaction mixture was diluted with EtOAc and washed once with brine. The organic layer was dried (MgSO$_4$), filtered, and concentrated under reduced pressure. The crude product was purified by automated silica gel chromatography (eluted with EtOAc/hexanes). Pooling of the desired fractions, washing with saturated aq. NaHCO$_3$ solution to eliminate any possible boronic acid contaminant, drying the organic phase (MgSO$_4$), filtering and evaporation provided the title compound as a yellow solid, after recrystallization from EtOAc/hexanes, to obtain 110 mg, 60%. HPLC/MS: retention time=3.20 min, [M+H]$^+$=523. $^1$H NMR (CDCl$_3$): δ 8.77 (s, 1H), 7.88 (m, 4H), 7.66 (d, J=8.2 Hz, 1H), 7.35 (d, J=8.3 Hz, 2H), 7.23 (d, J=8.3 Hz, 2H), 7.04 (d, J=8.2 Hz, 2H), 6.66 (d, J=7.2 Hz, 2H), 5.25 (s, 2H), 2.60 (s, 3H).

Example 66

Preparation of 7-(4-chlorophenyl)-8-(4-(1-(hydroxyimino)ethyl)phenyl)-2-((6-(trifluoromethyl)pyridin-3-yl)methyl)-[1,2,4]triazolo[4,3-a]pyridin-3(2H)-one

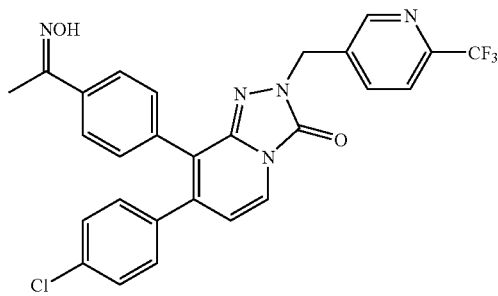

To a stirred solution of 8-(4-acetylphenyl)-7-(4-chlorophenyl)-2-((6-(trifluoromethyl)pyridin-3-yl)methyl)-[1,2,4]triazolo[4,3-a]pyridin-3(2H)-one (43.3 mg, 0.083 mmol) in THF (2 mL) and water (2 mL) at room temperature was added hydroxylamine hydrochloride (11.5 mg, 0.17 mmol). After 108 h, the reaction mixture was diluted with water and extracted twice with EtOAc. The organic extracts are combined, dried (MgSO$_4$), filtered and evaporated. Purification by preparative reverse phase HPLC (methanol-water-trifluoroacetic acid), pooling the fractions, evaporating, redissolving the residuum in dichloromethane, washing with saturated aq. NaHCO$_3$ solution, drying (MgSO$_4$), filtering and evaporating provided the title compound as a yellow solid, 38 mg, 85%. HPLC/MS: retention time=3.38 min, [M+H]$^+$=538. $^1$H NMR (CDCl$_3$): δ 8.79 (d, J=1.8 Hz, 1H), 8.62 (br s, 1H), 7.92 (dd, J=1.8, 8.0 Hz, 1H), 7.84 (d, J=7.0 Hz, 2H), 7.66 (d, J=7.9 Hz, 1H), 7.57 (dd, J=2.2, 6.6 Hz, 2H), 7.23 (m, 5H), 7.06 (d, J=6.6 Hz, 2H), 6.65 (d, J=7.1 Hz, 1H), 5.27 (s, 2H), 2.25 (s, 3H).

Example 67

Preparation of (R,S)-7-(4-chlorophenyl)-8-(4-(1-hydroxyethyl)phenyl)-2-((6-(trifluoromethyl)pyridin-3-yl)methyl)-[1,2,4]triazolo[4,3-a]pyridin-3(2H)-one

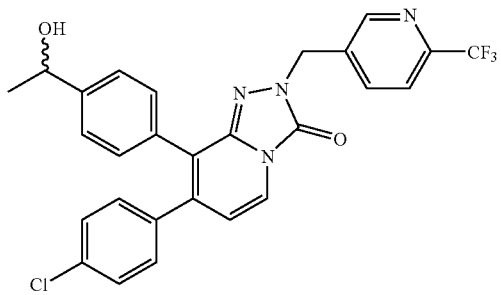

To a stirred slurry of 8-(4-acetylphenyl)-7-(4-chlorophenyl)-2-((6-(trifluoromethyl)pyridin-3-yl)methyl)-[1,2,4]triazolo[4,3-a]pyridin-3(2H)-one (25.0 mg, 0.048 mmol) in MeOH (1 mL) at −5° C. was added sodium borohydride (1.8 mg, 0.05 mmol) in one portion. A solution formed within 5 min. After an additional 10 min, the reaction mixture was diluted with saturated aq. NaHCO$_3$ solution and extracted twice with EtOAc. The organic extracts are combined, dried (MgSO$_4$), filtered and evaporated. Purification by preparative reverse phase HPLC (methanol-water-trifluoroacetic acid), pooling the fractions, evaporating, redissolving the residuum in dichloromethane, washing with saturated aq. NaHCO$_3$ solution, drying (MgSO$_4$), filtering and evaporating provided the title compound as a yellow solid, 15.5 mg, 62%. HPLC/MS: retention time=3.12 min, [M+H]$^+$=507. $^1$H NMR (CDCl$_3$): δ 8.79 (d, J=1.3 Hz, 1H), 7.92 (dd, J=1.3 Hz, 7.9 Hz, 1H), 7.81 (d, J=7.1 Hz, 1H), 7.66 (d, J=8.3 Hz, 1H), 7.31 (d, J=8.3 Hz, 2H), 7.21 (d, J=8.4 Hz, 2H), 7.04 (d, J=8.3 Hz, 2H), 6.64 (d, J=7.1 Hz, 2H), 5.26 (s, 2H), 4.90 (q, J=6.2 Hz, 1H), 1.50 (d, J=6.2 Hz, 3H).

Example 68

Preparation of (R,S)-2-(4-(7-(4-chlorophenyl)-3-oxo-2-((6-(trifluoromethyl)pyridin-3-yl)methyl)-2,3-dihydro-[1,2,4]triazolo[4,3-a]pyridin-8-yl)phenyl)-2-hydroxyacetonitrile

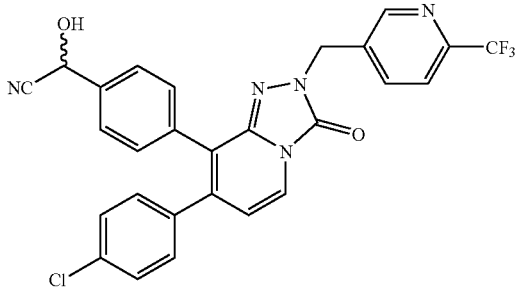

A. Preparation of 4-(7-(4-chlorophenyl)-3-oxo-2-((6-(trifluoromethyl)pyridin-3-yl)methyl)-2,3-dihydro-[1,2,4]triazolo[4,3-a]pyridin-8-yl)benzaldehyde

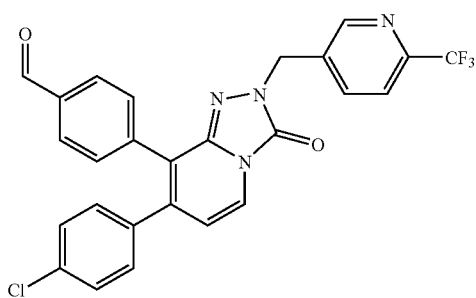

To a stirring solution of 8-bromo-7-(4-chlorophenyl)-2-((6-(trifluoromethyl)pyridin-3-yl)methyl)-[1,2,4]triazolo[4,3-a]pyridin-3(2H)-one (100 mg, 0.21 mmol) in n-butanol (1.6 mL) at room temperature under argon was added 4-formylphenylboronic acid (40.4 mg, 0.27 mmol), $Pd_2(dba)_3$ (7.6 mg, 0.008 mmol), dicyclohexyl(2',6'-dimethoxybiphenyl-2-yl)phosphine (13.6 mg, 0.03 mmol) and $K_3PO_4$ (88.1 mg, 0.41 mmol). The resulting suspension was purged of oxygen by bubbling with argon for 15 min, sealed in a vial under argon, heated at 110° C. for 5 h, and then cooled to room temperature. The reaction mixture was diluted with EtOAc and washed once with water. The organic layer was dried ($MgSO_4$), filtered, and concentrated under reduced pressure. The crude product was purified by automated silica gel chromatography (eluted with EtOAc/hexanes). Pooling of the desired fractions provided the title compound as a yellow solid, 38.8 mg, 36%. HPLC/MS: retention time=2.73 min, $[M+H]^+$=509.

B. Preparation of 2-(4-(7-(4-chlorophenyl)-3-oxo-2-((6-(trifluoromethyl)pyridin-3-yl)methyl)-2,3-dihydro-[1,2,4]triazolo[4,3-a]pyridin-8-yl)phenyl)-2-hydroxyacetonitrile

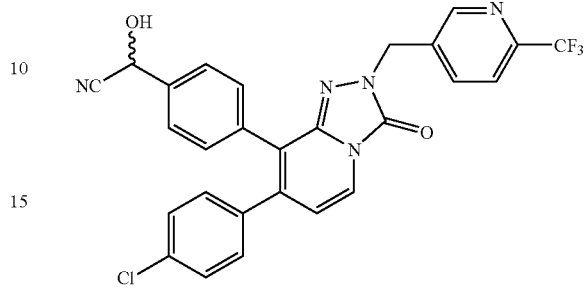

To a stirred solution of 4-(7-(4-chlorophenyl)-3-oxo-2-((6-(trifluoromethyl)pyridin-3-yl)methyl)-2,3-dihydro-[1,2,4]triazolo[4,3-a]pyridin-8-yl)benzaldehyde (38.0 mg, 0.075 mmol) in dichloromethane (1 mL) at room temperature under argon was added cyanotrimethylsilane (9.3 mg, 0.093 mmol) and then $ZnI_2$ (2.4 mg, 0.0075 mmol). After 70 h, the reaction mixture was diluted with water and extracted twice with dichloromethane. The organic extracts were combined, dried ($MgSO_4$), filtered and evaporated. Purification by preparative reverse phase HPLC (methanol-water-trifluoroacetic acid), pooling the fractions, evaporating, redissolving the residuum in dichloromethane, washing with saturated aq. $NaHCO_3$ solution, drying ($MgSO_4$), filtering and evaporating provided the title compound as a light yellow solid, 10.4 mg, 26%. HPLC/MS: retention time=3.56 min, $[M+H]^+$=536. $^1$H NMR ($CDCl_3$): δ 8.71 (d, J=1.7 Hz, 1H), 7.85 (dd, J=1.6 Hz, 7.7 Hz, 1H), 7.61 (d, J=8.3 Hz, 1H), 7.39 (d, J=8.3 Hz, 1H), 7.24 (d, J=6.5 Hz, 1H), 7.17 (d, J=8.3 Hz, 2H), 7.04 (d, J=8.3 Hz, 2H), 6.95 (d, J=6.6 Hz, 2H), 6.60 (d, J=7.2 Hz, 1H), 5.37 (s, 1H), 5.18 (s, 1H), 3.30 (br s, 1H).

Example 69

Preparation of 4-(7-(4-chlorophenyl)-3-oxo-2-((6-(trifluoromethyl)pyridin-3-yl)methyl)-2,3-dihydro-[1,2,4]triazolo[4,3-a]pyridin-8-yl)benzamide

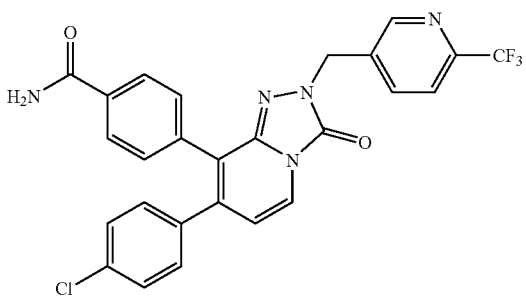

To a stirring solution of 8-bromo-7-(4-chlorophenyl)-2-((6-(trifluoromethyl)pyridin-3-yl)methyl)-[1,2,4]triazolo[4,3-a]pyridin-3(2H)-one (100 mg, 0.21 mmol) in n-butanol (1.6 mL) at room temperature under argon was added 4-carboximidophenylboronic acid (44.5 mg, 0.27 mmol), $Pd_2(dba)_3$ (7.6 mg, 0.008 mmol), dicyclohexyl(2',6'-dimethoxybiphenyl-2-yl)phosphine (13.6 mg, 0.03 mmol) and K₃PO₄ (88.1 mg, 0.41 mmol). The resulting suspension was purged of oxygen by bubbling with argon for 15 min, sealed in a vial under argon, heated at 110° C. for 5 h, and then cooled to room temperature. The reaction mixture was diluted with EtOAc and washed once with water. The organic layer was dried (MgSO₄), filtered, and concentrated under reduced pressure. The crude product was purified by automated silica gel chromatography (eluted with EtOAc/hexanes). Pooling of the desired fractions provided the title compound as a yellow solid, 22.0 mg, 20%. HPLC/MS: retention time=2.82 min, [M+H]⁺=524. ¹H NMR (CDCl₃): δ 8.76 (d, J=1.7 Hz, 1H), 7.91 (dd, J=1.7 Hz, 8.2 Hz, 1H), 7.85 (d, J=7.1 Hz, 1H), 7.75 (d, J=8.3 Hz, 2H), 7.65 (d, J=8.2 Hz, 1H), 7.33 (d, J=8.8 Hz, 2H), 7.22 (d, J=6.6 Hz, 2H), 7.03 (d, J=6.6 Hz, 2H), 6.66 (d, J=6.0 Hz, 1H), 6.12 (br d, 2H), 5.25 (s, 2H).

Example 70

Preparation of 7-(4-chlorophenyl)-8-(2-methoxypyrimidin-5-yl)-2-((2-methyl-6-(trifluoromethyl)pyridin-3-yl)methyl)-[1,2,4]triazolo[4,3-a]pyridin-3(2H)-one

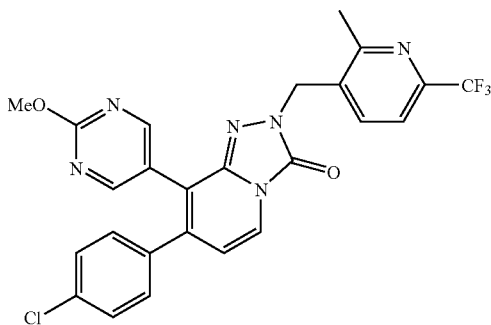

A. Preparation of 8-bromo-7-(4-chlorophenyl)-2-((2-methyl-6-(trifluoromethyl)pyridin-3-yl)methyl)-[1,2,4]triazolo[4,3-a]pyridin-3(2H)-one

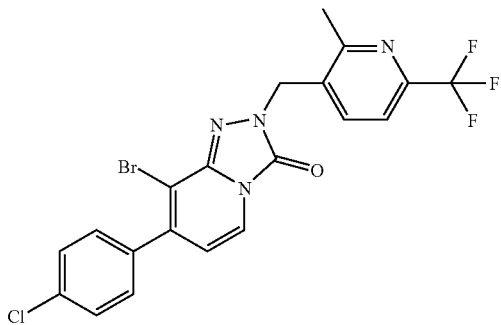

To a stirred solution of 8-bromo-7-(4-chlorophenyl)-[1,2,4]triazolo[4,3-a]pyridin-3(2H)-one (1.00 g, 3.08 mmol) in DMF (12 mL) at room temperature under argon was added 3-(bromomethyl)-2-methyl-6-(trifluoromethyl)pyridine (861 mg, 3.39 mmol), followed by K₂CO₃ (1278 mg, 9.24 mmol). The resulting suspension was warmed to 55° C. for 8 h. After cooling the reaction mixture to room temperature, most of the solvent was removed under reduced pressure. The residue was diluted with water (~20 mL) and shaken vigorously. A solid formed and was filtered, washed with water and air-dried. The crude product was purified by automated silica gel chromatography (eluted with EtOAc/hexanes) to obtain 1.19 g (71% yield) of title compound as a tan amorphous solid. HPLC/MS: retention time=3.90 min, [M+H]⁺=497.

B. Preparation of 7-(4-chlorophenyl)-8-(2-methoxypyrimidin-5-yl)-2-((2-methyl-6-(trifluoromethyl)pyridin-3-yl)methyl)-[1,2,4]triazolo[4,3-a]pyridin-3(2H)-one

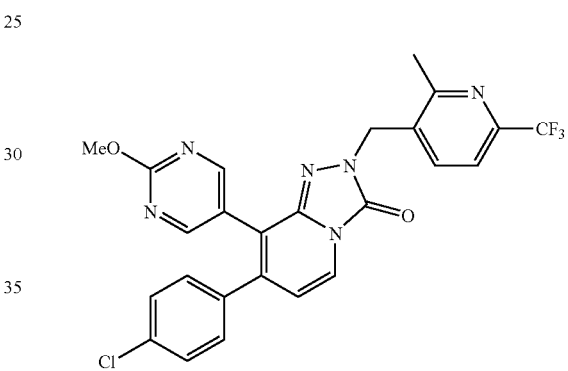

To a stirring solution of 8-bromo-7-(4-chlorophenyl)-2-((2-methyl-6-(trifluoromethyl)pyridin-3-yl)methyl)-[1,2,4]triazolo[4,3-a]pyridin-3(2H)-one (125 mg, 0.25 mmol) in THF (4 mL) at room temperature under argon was added 2-methoxy-4-pyrimidinylboronic acid (116.0 mg, 0.75 mmol), Pd(dppf)Cl₂.CH₂Cl₂ (23 mg, 0.025 mmol), and K₃PO₄ (160 mg, 0.75 mmol). The resulting suspension was purged of oxygen by bubbling with argon for 15 min, sealed in a vial under argon, heated at 90° C. for 12 h, and then cooled to room temperature. Analysis by HPLC/MS indicated that starting material was absent and one major new product had formed. The reaction mixture was diluted with EtOAc and washed once with brine. The organic layer was dried (MgSO₄), filtered, and concentrated under reduced pressure. The crude product was purified by automated silica gel chromatography (eluted with EtOAc/hexanes). Pooling of the desired fractions, washing with saturated aq. NaHCO₃ solution to eliminate any possible boronic acid contaminant, drying the organic phase (MgSO₄), filtering and evaporation provided the title compound as a yellow solid, 147 mg, 80%. HPLC/MS: retention time=3.89 min, [M+H]⁺=527. ¹H NMR (CDCl₃): δ 8.43 (s, 2H), 7.86 (d, J=7.2 Hz, 1H), 7.72 (d, J=7.7 Hz, 1H), 7.50 (d, J=7.7 Hz, 2H), 7.13 (d, J=7.7 Hz, 2H), 6.66 (d, J=7.7 Hz, 1H), 5.25 (s, 2H), 4.01 (s, 3H), 2.76 (s, 3H).

Example 71

Preparation of 7-(4-chlorophenyl)-8-(4-(methoxymethyl)phenyl)-2-((2-methyl-6-(trifluoromethyl)pyridin-3-yl)methyl)-[1,2,4]triazolo[4,3-a]pyridin-3(2H)-one

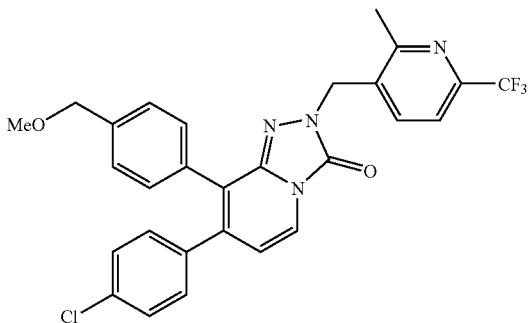

To a stirring solution of 8-bromo-7-(4-chlorophenyl)-2-((2-methyl-6-(trifluoromethyl)pyridin-3-yl)methyl)-[1,2,4]triazolo[4,3-a]pyridin-3(2H)-one (60 mg, 0.12 mmol) in THF (2 mL) at room temperature under argon was added 4-methoxymethylphenylboronic acid (60.0 mg, 0.36 mmol), Pd(dppf)Cl$_2$·CH$_2$Cl$_2$ (11.0 mg, 0.012 mmol), and K$_3$PO$_4$ (77 mg, 0.36 mmol). The resulting suspension was purged of oxygen by bubbling with argon for 15 min, sealed in a vial under argon, heated at 90° C. for 12 h, and then cooled to room temperature. Analysis by HPLC/MS indicated that starting material was absent and one major new product had formed. The reaction mixture was diluted with EtOAc and washed once with brine. The organic layer was dried (MgSO$_4$), filtered, and concentrated under reduced pressure. The crude product was purified by automated silica gel chromatography (eluted with EtOAc/hexanes). Pooling of the desired fractions, washing with saturated aq. NaHCO$_3$ solution to eliminate any possible boronic acid contaminant, drying the organic phase (MgSO$_4$), filtering and evaporation provided the title compound as a yellow solid, 38 mg, 59%. HPLC/MS: retention time=3.94 min, [M+H]$^+$=539. $^1$H NMR (CDCl$_3$): δ 7.82 (d, J=7.7 Hz, 1H), 7.67 (d, J=8.2 Hz, 1H), 7.48 (d, J=7.7 Hz, 1H), 7.25 (m, 5H), 7.05 (d, J=7.7 Hz, 2H), 6.64 (d, J=7.2 Hz, 1H), 5.23 (s, 2H), 4.44 (s, 2H), 3.41 (s, 3H), 2.74 (s, 3H).

Example 72

Preparation of 7-(4-chlorophenyl)-8-(3,5-difluoro-4-(hydroxymethyl)phenyl)-2-((2-methyl-6-(trifluoromethyl)pyridin-3-yl)methyl)-[1,2,4]triazolo[4,3-a]pyridin-3(2H)-one

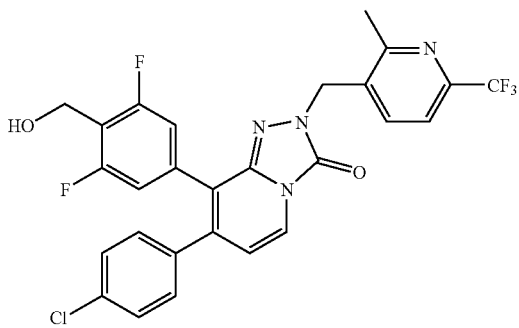

To a stirring solution of 8-bromo-7-(4-chlorophenyl)-2-((2-methyl-6-(trifluoromethyl)pyridin-3-yl)methyl)-[1,2,4]triazolo[4,3-a]pyridin-3(2H)-one (60 mg, 0.12 mmol) in THF (2 mL) at room temperature under argon was added 3,5-difluoro-4-hydroxymethylphenylboronic acid (68.0 mg, 0.36 mmol), Pd(dppf)Cl$_2$·CH$_2$Cl$_2$ (9.8 mg, 0.011 mmol), and K$_3$PO$_4$ (77 mg, 0.36 mmol). The resulting suspension was purged of oxygen by bubbling with argon for 15 min, sealed in a vial under argon, heated at 90° C. for 12 h, and then cooled to room temperature. Analysis by HPLC/MS indicated that starting material was still present and one major new product had formed. The reaction mixture was diluted with EtOAc and washed once with brine. The organic layer was dried (MgSO$_4$), filtered, and concentrated under reduced pressure. The crude product was purified by automated silica gel chromatography (eluted with EtOAc/hexanes). Pooling of the desired fractions, washing with saturated aq. NaHCO$_3$ solution to eliminate any possible boronic acid contaminant, drying the organic phase (MgSO$_4$), filtering and evaporation provided the title compound as a yellow solid, 24 mg, 36%. HPLC/MS: retention time=3.66 min, [M+H]$^+$=561. $^1$H NMR (CDCl$_3$): δ 7.85 (d, J=7.1 Hz, 1H), 7.69 (d, J=8.3 Hz, 1H), 7.49 (d, J=7.7 Hz, 1H), 7.28 (m, 2H), 7.08 (m, 2H), 6.81 (d, J=7.7 Hz, 2H), 6.63 (d, J=7.1 Hz, 1H), 5.23 (s, 2H), 4.75 (d, J=2.8 Hz, 2H), 2.74 (s, 3H), 2.01 (t, J=5.5 Hz).

Example 73

Preparation of 2-(4-(7-(4-chlorophenyl)-2-((2-methyl-6-(trifluoromethyl)pyridin-3-yl)methyl)-3-oxo-2,3-dihydro-[1,2,4]triazolo[4,3-a]pyridin-8-yl)phenyl)acetonitrile

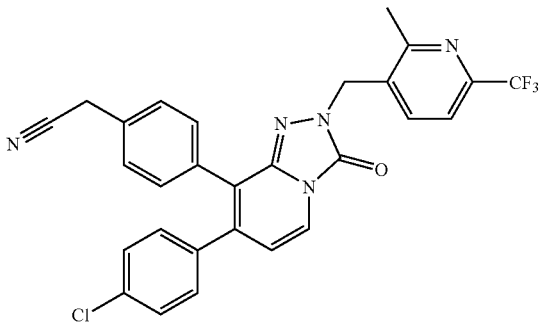

To a stirring solution of 8-bromo-7-(4-chlorophenyl)-2-((2-methyl-6-(trifluoromethyl)pyridin-3-yl)methyl)-[1,2,4]triazolo[4,3-a]pyridin-3(2H)-one (60 mg, 0.12 mmol) in THF (2 mL) at room temperature under argon was added 2-(4-(4,4,5,5-tetramethyl-1,3,2-dioxaborolan-2-yl)phenyl)acetonitrile (87.9 mg, 0.36 mmol), Pd(dppf)Cl$_2$·CH$_2$Cl$_2$ (9.8 mg, 0.011 mmol), and K$_3$PO$_4$ (77 mg, 0.36 mmol). The resulting suspension was purged of oxygen by bubbling with argon for 15 min, sealed in a vial under argon, heated at 90° C. for 48 h, and then cooled to room temperature. Analysis by HPLC/MS indicated that starting material was still present and one major new product had formed. The reaction mixture was diluted with EtOAc and washed once with brine. The organic layer was dried (MgSO$_4$), filtered, and concentrated under reduced pressure. The crude product was purified by automated silica gel chromatography (eluted with EtOAc/hexanes). Pooling of the desired fractions, washing with saturated aq. NaHCO$_3$ solution to eliminate any possible boronic acid contaminant, drying the organic phase (MgSO$_4$), filtering and evaporation provided the title compound as a yellow solid, 38 mg, 59%. HPLC/MS: retention time=3.94 min, [M+H]$^+$=534. $^1$H NMR (CDCl$_3$): δ 7.84 (d, J=7.8 Hz, 1H), 7.66 (d, J=7.9 Hz, 1H), 7.49 (d, J=7.9 Hz, 1H), 7.25 (m, 6H), 7.05 (d, J=8.4 Hz, 2H), 6.66 (d, J=7.1 Hz, 1H), 5.24 (s, 2H), 3.75 (s, 2H), 2.74 (s, 3H).

Example 74

Preparation of 7-(4-chlorophenyl)-8-(4-hydroxyphenyl)-2-((2-methyl-6-(trifluoromethyl)pyridin-3-yl)methy)-[1,2,4]triazolo[4,3-a]pyridin-3(2H)-one

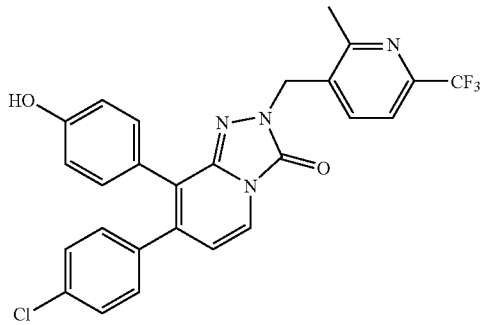

To a stirring solution of 8-bromo-7-(4-chlorophenyl)-2-((2-methyl-6-(trifluoromethyl)pyridin-3-yl)methyl)-[1,2,4]triazolo[4,3-a]pyridin-3(2H)-one (64 mg, 0.13 mmol) in THF (2 mL) at room temperature under argon was added 2-(4-(4,4,5,5-tetramethyl-1,3,2-dioxaborolan-2-yl)phenol (84.9 mg, 0.39 mmol), Pd(dppf)Cl$_2$.CH$_2$Cl$_2$ (10.5 mg, 0.013 mmol), and K$_3$PO$_4$ (82 mg, 0.39 mmol). The resulting suspension was purged of oxygen by bubbling with argon for 15 min, sealed in a vial under argon, heated at 90° C. for 48 h, and then cooled to room temperature. Analysis by HPLC/MS indicated that starting material was still persent and one major new product had formed. The reaction mixture was diluted with EtOAc and washed once with brine. The organic layer was dried (MgSO$_4$), filtered, and concentrated under reduced pressure. The crude product was purified by automated silica gel chromatography (eluted with EtOAc/hexanes). Pooling of the desired fractions, washing with saturated aq. NaHCO$_3$ solution to eliminate any possible boronic acid contaminant, drying the organic phase (MgSO$_4$), filtering and evaporation provided the title compound as a yellow solid, 10 mg, 15%. HPLC/MS: retention time=3.34 min, [M+H]$^+$=511. $^1$H NMR (CDCl$_3$): δ 7.82 (d, J=7.0 Hz, 1H), 7.66 (d, J=7.9 Hz, 1H), 7.47 (d, J=7.9 Hz, 1H), 7.25 (m, 3H), 7.06 (dd, J=2.2, 6.6 Hz, 4H), 6.66 (m, 3H), 5.26 (s, 2H), 4.1 (br s, 1H), 2.73 (s, 3H).

Example 75

7-(4-chlorophenyl)-2-(4-(methylsufonyl)benzyl)-8-(pyridin-4-yl)-[1,2,4]triazolo[4,3-a]pyridin-3(2H)-one

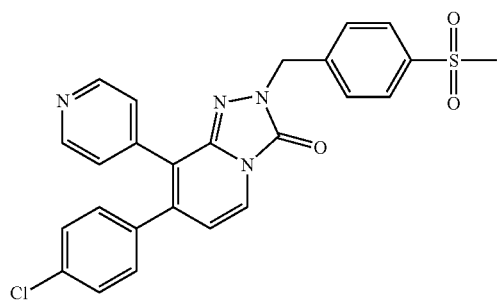

A. Preparation of 2-chloro-4-(4-chlorophenyl)-3,4'-bipyridine

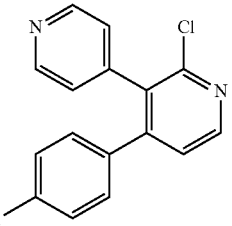

In a pressure tube, to a stirring solution of 3-bromo-2-chloro-4-(4-chlorophenyl)pyridine (1.3 g, 4.49 mmol) in THF (60 mL) at room temperature under argon was added 4-(4,4,5,5-tetramethyl-1,3,2-dioxaborolan-2-yl)pyridine (2.3 g, 11.21 mmol), 1,1'-bis(diphenylphosphino)ferrocene palladium (II) chloride complex with dichloromethane (350 mg, 0.43 mmol), and powdered K$_3$PO$_4$ (1.9 g, 8.96 mmol). The resulting suspension was stirred and heated at 100° C. under argon for 12 h. After the reaction mixture was cooled to room temperature, water (40 mL) and EtOAc (50 mL) were added. The layers were separated. The organic layer was dried (MgSO$_4$), filtered, and concentrated under reduced pressure. The crude product was purified by flash chromatography (silica gel column eluting with 20% ethyl acetate-hexanes) to isolate 850 mg of the title compound as a white solid. HPLC/MS: retention time=2.157 min, [M+H]$^+$=301.

B. Preparation of 4-(4-chlorophenyl)-2-hydrazinyl-3,4'-bipyridine

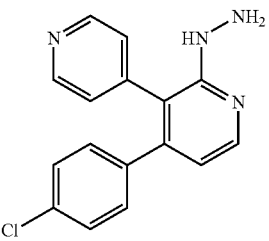

To a stirring solution of 2-chloro-4-(4-chlorophenyl)-3,4'-bipyridine (1.3 g, 4.3 mmol) in pyridine (5 mL) at room temperature under argon was added hydrazine monohydrate (2.5 mL, 51.5 mmol). The reaction mixture was stirred at reflux under argon for 15 h. After cooling the reaction mixture to room temperature, most of the solvent was removed under reduced pressure. Water (25 mL) was added to the residue while stirring and a precipitate formed. The precipitate was collected by filtration and washed with water (15 mL×2). After drying under reduced pressure at elevated temperature, 1.0 g of the title compound was obtained as a yellow solid. HPLC/MS: retention time=1.68 min, [M+H]$^+$=297.

C. Preparation of 7-(4-chlorophenyl)-8-(pyridin-4-yl)-[1,2,4]triazolo[4,3-a]pyridin-3(2H)-one

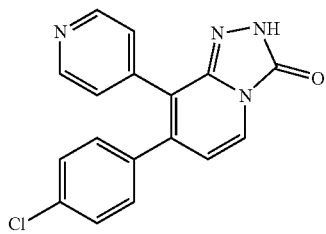

To a stirring solution of 1,1'-carbonyldiimidazole (2.5 g, 15.4 mmol) in THF (15 mL) at room temperature under argon was added 4-(4-chlorophenyl)-2-hydrazinyl-3,4'-bipyridine (0.92 g, 3.1 mmol). The reaction mixture was stirred at room temperature for 45 min. The reaction mixture was then concentrated under vacuum to produce a yellow solid. This solid was stirred in an ice bath and water (25 mL) was added. Solid was collected by filtration and further washed with water (15 mL×2). After drying in an oven at 50° C. under reduced pressure overnight, 960 mg of the title compound was obtained as a yellow solid. HPLC/MS: retention time=1.985 min, [M+H]$^+$=323. $^1$H NMR (DMSO-$d_6$, 500 MHz): δ 12.61 (s, 1H), 8.50 (d, J=6.05 Hz, 2H), 7.94 (d, J=7.15 Hz, 1H), 7.36 (d, J=8.2 Hz, 2H), 7.23 (d, J=6.05 Hz, 2H), 7.18 (d, J=8.2 Hz, 2H), 6.68 (d, J=7.15 Hz, 1H).

D. 7-(4-chlorophenyl)-2-(4-(methylsufonyl)benzyl)-8-(pyridin-4-yl)-[1,2,4]triazolo[4,3-a]pyridin-3(2H)-one

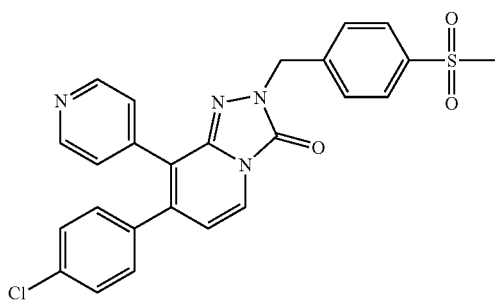

To a stirring solution of 7-(4-chlorophenyl)-8-(pyridin-4-yl)-[1,2,4]triazolo[4,3-a]pyridin-3(2H)-one (16 mg, 0.05 mmol) in DMF (0.25 mL) at room temperature under argon was added K$_2$CO$_3$ (14 mg, 0.1 mmol), followed by 1-(chloromethyl)-4-(methylsulfonyl)benzene (11 mg, 0.0547 mmol). The reaction mixture was stirred at 70° C. for 10 min. After the reaction mixture was cooled to room temperature, water (2 mL) and EtOAc (5 mL) were added. The layers were separated. The organic layer was dried (MgSO$_4$), filtered, and concentrated under reduced pressure to obtain crude product. This was purified by reverse phase preparative HPLC (without TFA) to isolate 14.5 mg of the title compound as a pale yellow solid. HPLC/MS: retention time=2.27 min, [M+H]$^+$=491.

Example 76

7-(4-chlorophenyl)-2-(4-fluorobenzyl)-8-(pyridin-4-yl)-[1,2,4]triazolo[4,3-a]pyridin-3(2H)-one

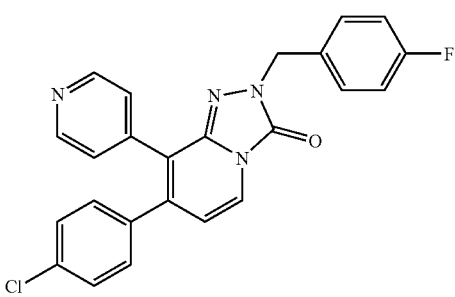

The title compound was prepared by coupling 7-(4-chlorophenyl)-8-(pyridin-4-yl)-[1,2,4]triazolo[4,3-a]pyridin-3(2H)-one with the requisite benzyl halide in a manner analogous to that in which 7-(4-chlorophenyl)-2-(4-(methylsufonyl)benzyl)-8-(pyridin-4-yl)-[1,2,4]triazolo[4,3-a]pyridin-3(2H)-one was prepared. HPLC/MS: retention time=2.825 min, [M+H]$^+$=431.

Example 77

7-(4-chlorophenyl)-2-(4-(ethylsulfonyl)benzyl)-8-(pyridin-4-yl)-[1,2,4]triazolo[4,3-a]pyridin-3(2H)-one

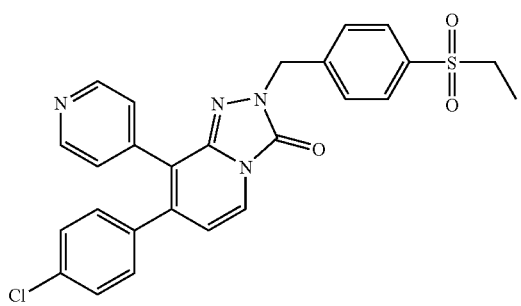

The title compound was prepared by coupling 7-(4-chlorophenyl)-8-(pyridin-4-yl)-[1,2,4]triazolo[4,3-a]pyridin-3(2H)-one with the requisite benzyl halide in a manner analogous to that in which 7-(4-chlorophenyl)-2-(4-(methylsufonyl)benzyl)-8-(pyridin-4-yl)-[1,2,4]triazolo[4,3-a]pyridin-3(2H)-one was prepared. HPLC/MS: retention time=2.428 min, [M+H]$^+$=505.

Example 78

7-(4-chlorophenyl)-2-((5-chloropyridin-2-yl)methyl)-8-(pyridin-4-yl)-[1,2,4]triazolo[4,3-a]pyridin-3(2H)-one

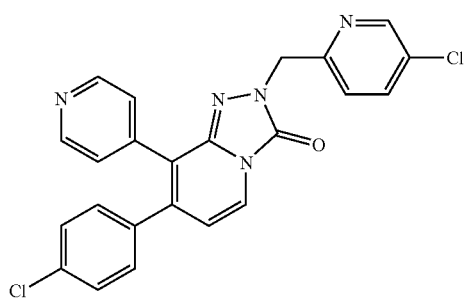

The title compound was prepared by coupling 7-(4-chlorophenyl)-8-(pyridin-4-yl)-[1,2,4]triazolo[4,3-a]pyridin-3(2H)-one with the requisite pyridinylmethyl halide in a manner analogous to that in which 7-(4-chlorophenyl)-2-(4-(methylsufonyl)benzyl)-8-(pyridin-4-yl)-[1,2,4]triazolo[4,3-a]pyridin-3(2H)-one was prepared. HPLC/MS: retention time=2.595 min, [M+H]$^+$=448.

Example 79

7-(4-chlorophenyl)-2-(4-(2-hydroxypropan-2-yl)benzyl)-8-(pyridin-4-yl)-[1,2,4]triazolo[4,3-a]pyridin-3(2H)-one

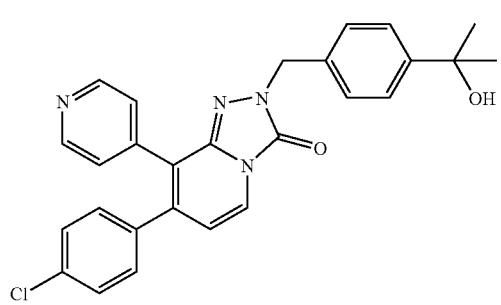

The title compound was prepared by coupling 7-(4-chlorophenyl)-8-(pyridin-4-yl)-[1,2,4]triazolo[4,3-a]pyridin-3(2H)-one with the requisite benzyl halide in a manner analogous to that in which 7-(4-chlorophenyl)-2-(4-(methylsufonyl)benzyl)-8-(pyridin-4-yl)-[1,2,4]triazolo[4,3-a]pyridin-3(2H)-one was prepared. HPLC/MS: retention time=2.658 min, [M+H]$^+$=471.

Example 80

7-(4-chlorophenyl)-8-(pyridin-4-yl)-2-(4-(trifluoromethoxy)benzyl)-[1,2,4]triazolo[4,3-a]pyridin-3(2H)-one

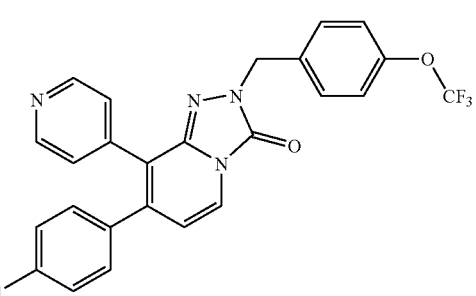

The title compound was prepared by coupling 7-(4-chlorophenyl)-8-(pyridin-4-yl)-[1,2,4]triazolo[4,3-a]pyridin-3(2H)-one with the requisite benzyl halide in a manner analogous to that in which 7-(4-chlorophenyl)-2-(4-(methylsufonyl)benzyl)-8-(pyridin-4-yl)-[1,2,4]triazolo[4,3-a]pyridin-3(2H)-one was prepared. HPLC/MS: retention time=3.135 min, [M+H]$^+$=497.

Example 81

7-(4-chlorophenyl)-2-(4-methoxybenzyl)-8-(pyridin-4-yl)-[1,2,4]triazolo[4,3-a]pyridin-3(2H)-one

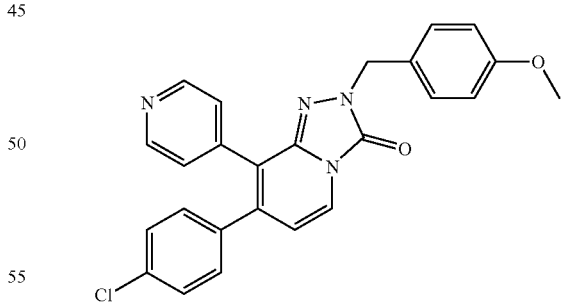

The title compound was prepared by coupling 7-(4-chlorophenyl)-8-(pyridin-4-yl)-[1,2,4]triazolo[4,3-a]pyridin-3(2H)-one with the requisite benzyl halide in a manner analogous to that in which 7-(4-chlorophenyl)-2-(4-(methylsufonyl)benzyl)-8-(pyridin-4-yl)-[1,2,4]triazolo[4,3-a]pyridin-3(2H)-one was prepared. HPLC/MS: retention time=2.213 min, [M+H]$^+$=444.

Example 82

7-(4-chlorophenyl)-2-((2-cyclopropyl-6-(trifluoromethyl)pyridin-3-yl)methyl)-8-(pyridin-4-yl)-[1,2,4]triazolo[4,3-a]pyridin-3(2H)-one

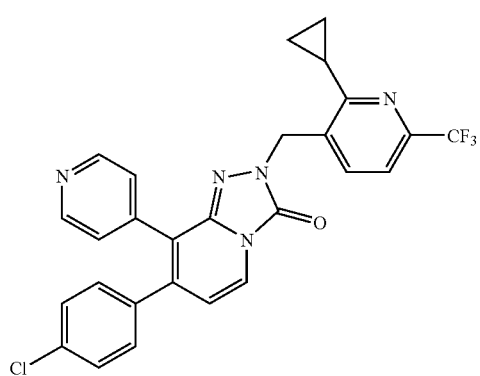

The title compound was prepared by coupling 7-(4-chlorophenyl)-8-(pyridin-4-yl)-[1,2,4]triazolo[4,3-a]pyridin-3(2H)-one with the requisite pyridinylmethyl halide in a manner analogous to that in which 7-(4-chlorophenyl)-2-(4-(methylsufonyl)benzyl)-8-(pyridin-4-yl)-[1,2,4]triazolo[4,3-a]pyridin-3(2H)-one was prepared. HPLC/MS: retention time=3.333 min, [M+H]$^+$=522.

Example 83

Preparation of 7-(4-chlorophenyl)-2-(4-ethoxybenzyl)-8-(pyridin-4-yl)-[1,2,4]triazolo[4,3-a]pyridin-3(2H)-one

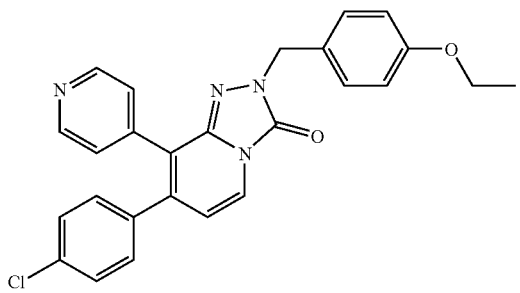

The title compound was prepared by coupling 7-(4-chlorophenyl)-8-(pyridin-4-yl)-[1,2,4]triazolo[4,3-a]pyridin-3(2H)-one with the requisite benzyl halide in a manner analogous to that in which 7-(4-chlorophenyl)-2-(4-(methylsufonyl)benzyl)-8-(pyridin-4-yl)-[1,2,4]triazolo[4,3-a]pyridin-3(2H)-one was prepared. HPLC: retention time=2.27 min. MS: [M+H]$^+$=458.

Example 84

Preparation of 2-((5-chlorobenzo[d]oxazol-2-yl)methyl)-7-(4-chlorophenyl)-8-(pyridin-4-yl)-[1,2,4]triazolo[4,3-a]pyrdin-3(2H)-one

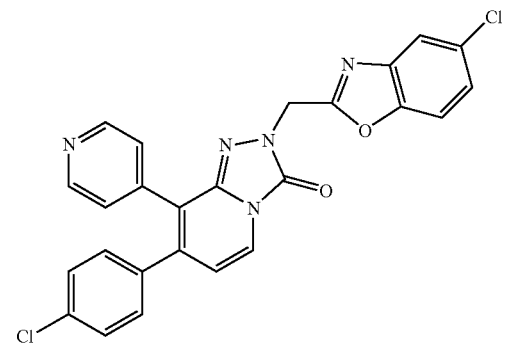

The title compound was prepared by coupling 7-(4-chlorophenyl)-8-(pyridin-4-yl)-[1,2,4]triazolo[4,3-a]pyridin-3(2H)-one with the requisite benzoxazolylmethyl halide in a manner analogous to that in which 7-(4-chlorophenyl)-2-(4-(methylsufonyl)benzyl)-8-(pyridin-4-yl)-[1,2,4]triazolo[4,3-a]pyridin-3(2H)-one was prepared. HPLC: retention time=2.8 min. MS: [M+H]$^+$=488.

Example 85

Preparation of 7-(4-chlorophenyl)-2-(2-(4-fluorophenoxy)ethyl)-8-(pyridin-4-yl)-[1,2,4]triazolo[4,3-a]pyridin-3(2H)-one

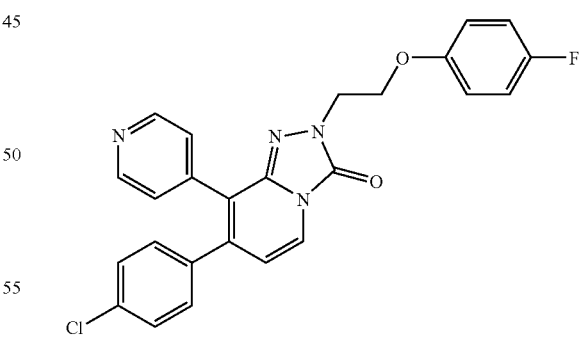

The title compound was prepared by coupling 7-(4-chlorophenyl)-8-(pyridin-4-yl)-[1,2,4]triazolo[4,3-a]pyridin-3(2H)-one with the requisite aryloxyethyl halide in a manner analogous to that in which 7-(4-chlorophenyl)-2-(4-(methylsufonyl)benzyl)-8-(pyridin-4-yl)-[1,2,4]triazolo[4,3-a]pyridin-3(2H)-one was prepared. HPLC: retention time=2.83 min. MS: [M+H]$^+$=461.

Example 86

Preparation of 7-(4-chlorophenyl)-2-(4-(isoxazol-5-yl)benzyl)-8-(pyridin-4-yl)-[1,2,4]triazolo[4,3-a]pyridin-3(2H)-one

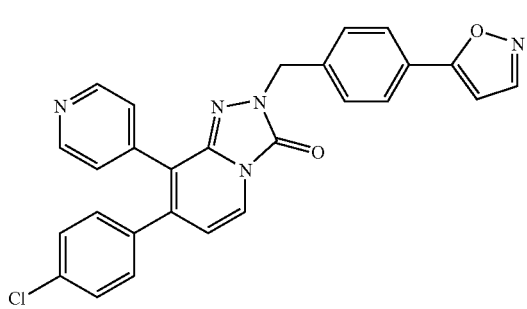

The title compound was prepared by coupling 7-(4-chlorophenyl)-8-(pyridin-4-yl)-[1,2,4]triazolo[4,3-a]pyridin-3(2H)-one with the requisite benzyl halide in a manner analogous to that in which 7-(4-chlorophenyl)-2-(4-(methylsufonyl)benzyl)-8-(pyridin-4-yl)-[1,2,4]triazolo[4,3-a]pyridin-3(2H)-one was prepared. HPLC/MS: retention time=2.77 min, [M+H]$^+$=480.

Example 87

Preparation of 7-(4-chlorophenyl)-2-(4-(isoxazol-3-yl)benzyl)-8-(pyridin-4-yl)-[1,2,4]triazolo[4,3-a]pyridin-3(2H)-one

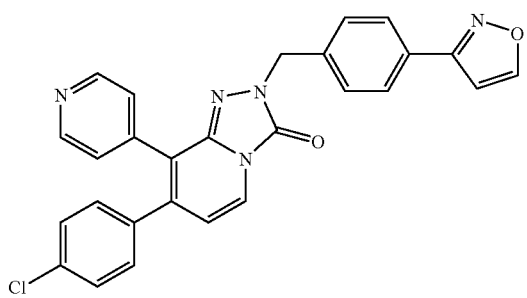

The title compound was prepared by coupling 7-(4-chlorophenyl)-8-(pyridin-4-yl)-[1,2,4]triazolo[4,3-a]pyridin-3(2H)-one with the requisite benzyl halide in a manner analogous to that in which 7-(4-chlorophenyl)-2-(4-(methylsufonyl)benzyl)-8-(pyridin-4-yl)-[1,2,4]triazolo[4,3-a]pyridin-3(2H)-one was prepared. HPLC/MS: retention time=2.67 min, [M+H]$^+$=480.

Example 88

Preparation of 2-(4-(1H-pyrazol-1-yl)benzyl)-7-(4-chlorophenyl)-8-(pyridin-4-yl)-[1,2,4]triazolo[4,3-a]pyridin-3(2H)-one

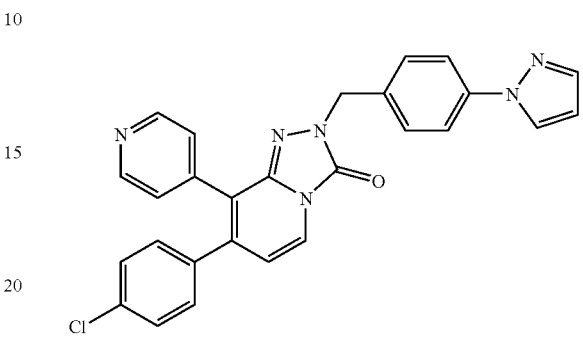

The title compound was prepared by coupling 7-(4-chlorophenyl)-8-(pyridin-4-yl)-[1,2,4]triazolo[4,3-a]pyridin-3(2H)-one with the requisite benzyl halide in a manner analogous to that in which 7-(4-chlorophenyl)-2-(4-(methylsufonyl)benzyl)-8-(pyridin-4-yl)-[1,2,4]triazolo[4,3-a]pyridin-3(2H)-one was prepared. HPLC/MS: retention time=2.72 min, [M+H]$^+$=479.

Example 89

Preparation of 7-(4-chlorophenyl)-8-(pyridin-4-yl)-2-((5-(trifluoromethyl)pyridin-2-yl)methyl)-[1,2,4]triazolo[4,3-a]pyridin-3(2H)-one

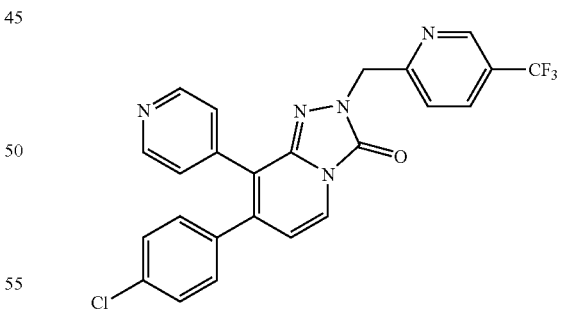

The title compound was prepared by coupling 7-(4-chlorophenyl)-8-(pyridin-4-yl)-[1,2,4]triazolo[4,3-a]pyridin-3(2H)-one with the requisite pyridinylmethyl halide in a manner analogous to that in which 7-(4-chlorophenyl)-2-(4-(methylsufonyl)benzyl)-8-(pyridin-4-yl)-[1,2,4]triazolo[4,3-a]pyridin-3(2H)-one was prepared. HPLC/MS: retention time=2.74 min, [M+H]$^+$=482.

Example 90

Preparation of 6-((7-(4-chlorophenyl)-3-oxo-8-(pyridin-4-yl)-[1,2,4]triazolo[4,3-a]pyridin-2(3H)-yl)methyl)nicotinonitrile

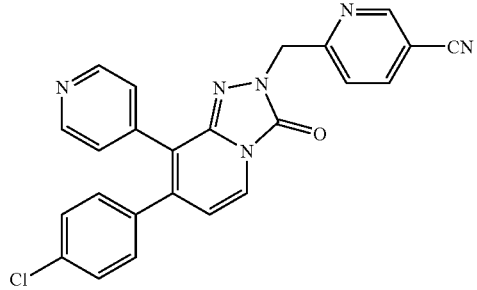

The title compound was prepared by coupling 7-(4-chlorophenyl)-8-(pyridin-4-yl)-[1,2,4]triazolo[4,3-a]pyridin-3(2H)-one with the requisite pyridinylmethyl halide in a manner analogous to that in which 7-(4-chlorophenyl)-2-(4-(methylsufonyl)benzyl)-8-(pyridin-4-yl)-[1,2,4]triazolo[4,3-a]pyridin-3(2H)-one was prepared. HPLC/MS: retention time=2.25 min, [M+H]$^+$=439.

Example 91

Preparation of 7-(4-chlorophenyl)-2-((5-(isoxazol-3-yl)pyridin-2-yl)methyl)-8-(pyridin-4-yl)-[1,2,4]triazolo[4,3-a]pyridin-3(2H)-one

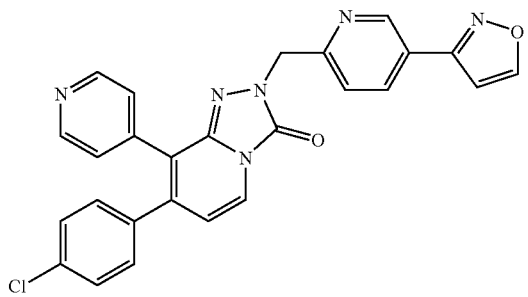

The title compound was prepared by coupling 7-(4-chlorophenyl)-8-(pyridin-4-yl)-[1,2,4]triazolo[4,3-a]pyridin-3(2H)-one with the requisite pyridinylmethyl halide in a manner analogous to that in which 7-(4-chlorophenyl)-2-(4-(methylsufonyl)benzyl)-8-(pyridin-4-yl)-[1,2,4]triazolo[4,3-a]pyridin-3(2H)-one was prepared. HPLC/MS: retention time=2.53 min, [M+H]$^+$=481.

Example 92

Preparation of 7-(4-chlorophenyl)-2-(4-fluoro-2-methoxycarbonyl-benzyl)-8-(pyridin-4-yl)-[1,2,4]triazolo[4,3-a]pyridin-3(2H)-one

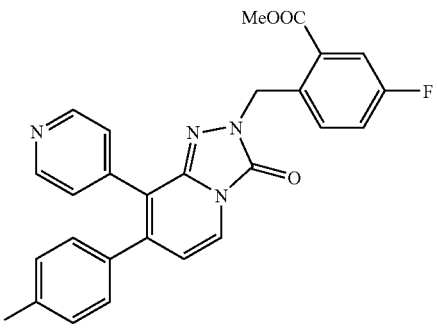

The title compound was prepared by coupling 7-(4-chlorophenyl)-8-(pyridin-4-yl)-[1,2,4]triazolo[4,3-a]pyridin-3(2H)-one with the requisite benzyl halide in a manner analogous to that in which 7-(4-chlorophenyl)-2-(4-(methylsufonyl)benzyl)-8-(pyridin-4-yl)-[1,2,4]triazolo[4,3-a]pyridin-3(2H)-one was prepared. HPLC: retention time=2.97 min. MS: [M+H]$^+$=489.

Example 93

Preparation of 7-(4-chlorophenyl)-2-(4-fluoro-2-carboxyl-benzyl)-8-(pyridin-4-yl)-[1,2,4]triazolo[4,3-a]pyridin-3(2H)-one

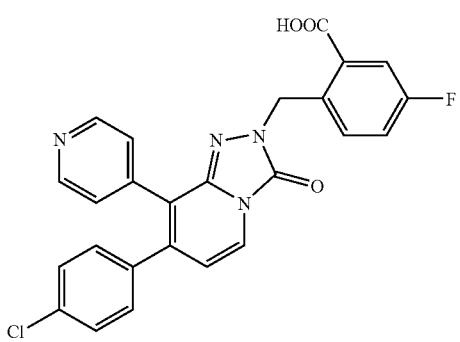

To a solution of 7-(4-chlorophenyl)-2-(4-fluoro-2-methoxycarbonylbenzyl)-8-(pyridin-4-yl)-[1,2,4]triazolo[4,3-a]pyridin-3(2H)-one (40 mg) in 1.5 mL of MeOH at room temperature, 1 N aqueous NaOH solution (0.5 mL) was added and the mixture was stirred for 12 h. The mixture was then concentrated and diluted with 3 mL of water. The resulting solution was then acidified to pH 6 using 10% aqueous sodium bisulfate solution. A light yellow solid precipitated and was filtered, washed with water and dried in vacuo to afford 33 mg of the title compound. HPLC: retention time=2.60 min. MS: [M+H]$^+$=475.

Example 94

Preparation of 2-((5-bromopyridin-2-yl)methyl)-7-(4-chlorophenyl)-8-(pyridin-4-yl)-[1,2,4]triazolo[4,3-a]pyridin-3(2H)-one

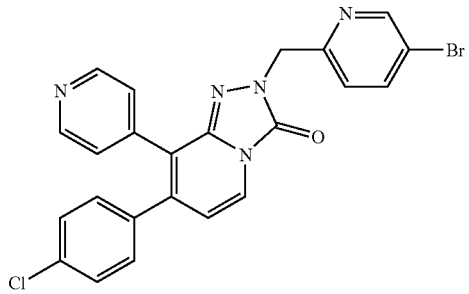

The title compound was prepared by coupling 7-(4-chlorophenyl)-8-(pyridin-4-yl)-[1,2,4]triazolo[4,3-a]pyridin-3(2H)-one with the requisite pyridinylmethyl halide in a manner analogous to that in which 7-(4-chlorophenyl)-2-(4-(methylsufonyl)benzyl)-8-(pyridin-4-yl)-[1,2,4]triazolo[4,3-a]pyridin-3(2H)-one was prepared. HPLC/MS: retention time=2.64 min, [M+H]$^+$=493.

Example 95

Preparation of 2-((5-(1H-pyrazol-1-yl)pyridin-2-yl)methyl)-7-(4-chlorophenyl)-8-(pyridin-4-yl)-[1,2,4]triazolo[4,3-a]pyridin-3(2H)-one

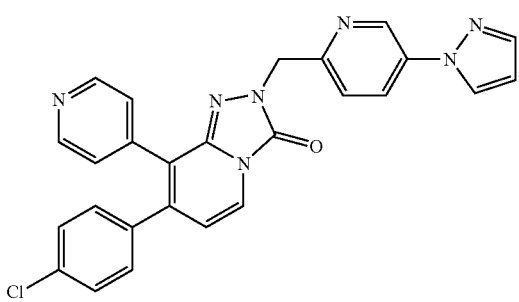

A mixture of 2-((5-bromopyridin-2-yl)methyl)-7-(4-chlorophenyl)-8-(pyridin-4-yl)-[1,2,4]triazolo[4,3-a]pyridin-3(2H)-one (29.6 mg, 0.06 mmol), pyrazole (22.5 mg, 0.33 mmol), copper (I) iodide (8 mg, 0.042 mmol), potassium carbonate (25 mg, 0.18 mmol) and N,N-dimethylethylenediamine (5.3 mg, 0.06 mmol) in 1 mL toluene was heated at 110° C. under argon for 20 h. The reaction mixture was diluted with EtOAc, washed with water, brine, dried (Na$_2$SO$_4$) and concentrated. The crude product was purified by preparative reverse phase HPLC (with TFA) to isolate 1.3 mg of the title compound as a yellow solid. HPLC/MS: retention time=2.44 min, [M+H]$^+$=480.

Example 96

7-(4-chlorophenyl)-2-((2-methyl-6-(trifluoromethyl)pyridin-3-yl)methyl)-8-(pyridin-4-yl)-[1,2,4]triazolo[4,3-a]pyridin-3(2H)-one

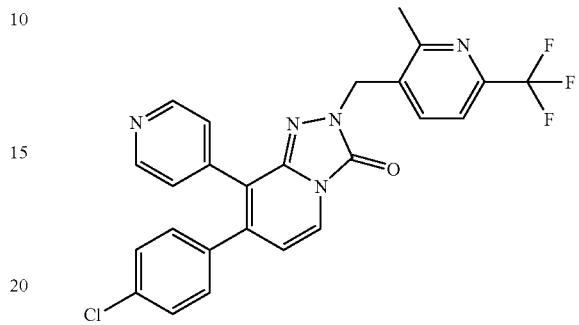

To a solution of 7-(4-chlorophenyl)-8-(pyridin-4-yl)-[1,2,4]triazolo[4,3-a]pyridin-3(2H)-one (162 mg, 0.50 mmol) and 3-(chloromethyl)-2-methyl-6-(trifluoromethyl)pyridine (137 mg, 0.65 mmol) in anhydrous DMF (1.5 mL) at room temperature was added anhydrous K$_2$CO$_3$ (105 mg, 0.75 mmol). The resulting yellow suspension was stirred at 80° C. for 5.5 h. Analysis by HPLC/MS indicated that starting 7-(4-chlorophenyl)-8-(pyridin-4-yl)-[1,2,4]triazolo[4,3-a]pyridin-3(2H)-one had been consumed. After cooling to room temperature, the reaction mixture was diluted with water and extracted with EtOAc (20 mL×3). The combined EtOAc extracts were washed with water, then saturated aqueous NaCl, dried (Na$_2$SO$_4$), filtered, and concentrated under reduced pressure. The crude product was purified using a silica gel cartridge (40 g) eluted with a gradient of ethyl acetate (0-70%) in hexanes to afford 130 mg (53%) of the title compound as a light brown foam. The product was further purified using preparative reverse phase HPLC (Phenomenex Luna 5 μm C-18 21.2×100 mm column eluted with a linear gradient of 50% to 90% B over 10 min (A=0.1% trifluoroacetic acid, 90% water, 10% methanol and B=0.1% trifluoroacetic acid, 90% methanol, 10% water) with flow rate at 20 mL/min and UV detection at 220 nm). The desired fractions were concentrated under reduced pressure. The resulting residue was dissolved in EtOAc, washed with saturated aqueous Na$_2$CO$_3$ once, water twice, then saturated aqueous NaCl, dried over Na$_2$SO$_4$ and evaporated. The residue was dissolved in acetonitrile, frozen and lyophilized to afford the title compound as a light yellow powder. HPLC/MS: retention time=2.80 min, [M+H]$^+$=496.2. $^1$H NMR (CDCl$_3$, 400 MHz): δ 8.56 (d, J=6.2 Hz, 2H), 7.87 (d, J=7.0 Hz, 1H), 7.68 (d, J=7.9 Hz, 1H), 7.49 (d, J=7.9 Hz, 1H), 7.27 (d, J=8.8 Hz, 2H), 7.17 (d, J=6.2 Hz, 2H), 7.05 (d, J=8.8 Hz, 2H), 6.66 (d, J=7.5 Hz, 1H), 5.23 (s, 2H), 2.75 (s, 3H).

Example 97

Preparation of 7-(4-chlorophenyl)-2-((2-ethyl-6-(trifluoromethyl)pyridin-3-yl)methyl)-8-(pyridin-4-yl)-[1,2,4]triazolo[4,3-a]pyridin-3(2H)-one

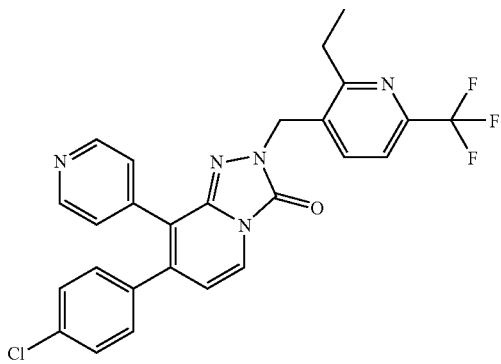

To a solution of 7-(4-chlorophenyl)-8-(pyridin-4-yl)-[1,2,4]triazolo[4,3-a]pyridin-3(2H)-one (65 mg, 0.20 mmol) and 3-(chloromethyl)-2-ethyl-6-(trifluoromethyl)pyridine (60 mg, 0.24 mmol) in anhydrous DMF (1.0 mL) at room temperature was added anhydrous $K_2CO_3$ (66 mg, 0.48 mmol). The resulting suspension was stirred at 80° C. The reaction progressed slowly, and additional 3-(chloromethyl)-2-ethyl-6-(trifluoromethyl)pyridine (60 mg, 0.24 mmol) and $K_2CO_3$ (66 mg, 0.48 mmol) were added after 1.5 h. After stirring for additional 5 h, the same amounts of 3-(chloromethyl)-2-ethyl-6-(trifluoromethyl)pyridine and $K_2CO_3$ were again added. The reaction mixture was stirred at 80° C. for 1 h more before a few drops of diisopropylethylamine were added. The resulting black reaction mixture was stirred at 80° C. overnight. The reaction mixture was cooled to room temperature, then partitioned between EtOAc and water. The EtOAc layer was washed with water twice, then saturated aqueous NaCl, dried ($Na_2SO_4$), filtered and concentrated under reduced pressure. The crude product was purified using a silica gel cartridge (12 g) eluted with a gradient of ethyl acetate (0-70%) in hexanes to afford the title compound (95% pure) as a yellow foam. This was further purified using preparative reverse phase HPLC (Phenomenex Luna 5 μm C-18 21.2×100 mm column eluted with a linear gradient of 50% to 90% B over 10 min (A=0.1% trifluoroacetic acid, 90% water, 10% methanol and B=0.1% trifluoroacetic acid, 90% methanol, 10% water) with flow rate at 20 mL/min and UV detection at 220 nm). The desired fractions were concentrated under reduced pressure. The residue was dissolved in EtOAc, washed with saturated aqueous $Na_2CO_3$ once, water twice, then saturated aqueous NaCl, dried over $Na_2SO_4$ and evaporated. The residue was dissolved in acetonitrile, frozen and lyophilized to afford 35 mg (34%) of the title compound as a light yellow powder. HPLC/MS: retention time=3.07 min, [M+H]$^+$=510.2. $^1$H NMR (CDCl$_3$, 400 MHz): δ 8.55 (dd, J=1.8, 6.2 Hz, 2H), 7.87 (d, J=7.5 Hz, 1H), 7.70 (d, J=7.9 Hz, 1H), 7.47 (d, J=7.9 Hz, 1H), 7.27 (d, J=8.8 Hz, 2H), 7.16 (d, J=1.8, 6.2 Hz, 2H), 7.05 (d, J=8.8 Hz, 2H), 6.66 (d, J=7.5 Hz, 1H), 5.26 (s, 2H), 3.04 (q, J=7.5 Hz, 2H), 1.32 (t, J=7.5 Hz, 3H).

Example 98

Preparation of 7-(4-chlorophenyl)-2-((2-methoxy-6-(trifluoromethyl)pyridin-3-yl)methyl)-8-(pyridin-4-yl)-[1,2,4]triazolo[4,3-a]pyridin-3(2H)-one

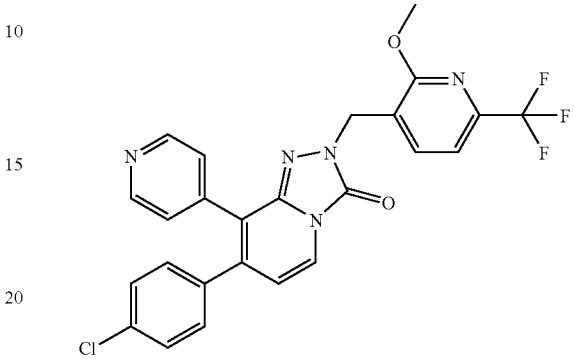

To a solution of 7-(4-chlorophenyl)-8-(pyridin-4-yl)-[1,2,4]triazolo[4,3-a]pyridin-3(2H)-one (161.4 mg, 0.50 mmol) and 3-(chloromethyl)-2-methoxy-6-(trifluoromethyl)pyridine (169 mg, 0.75 mmol) in anhydrous DMF (3.0 mL) at room temperature was added anhydrous $K_2CO_3$ (138 mg, 1.0 mmol). The resulting yellow suspension was stirred at 70° C. for 3 h. Analysis by HPLC/MS indicated that starting 7-(4-chlorophenyl)-8-(pyridin-4-yl)-[1,2,4]triazolo[4,3-a]pyridin-3(2H)-one had been consumed. After cooling to room temperature, the reaction mixture was diluted with water and extracted with EtOAc (20 mL×2). The combined EtOAc extracts were washed with water, then saturated aqueous NaCl, dried ($Na_2SO_4$), filtered, and concentrated under reduced pressure. The crude product was purified using a silica gel cartridge (12 g) eluted with a gradient of ethyl acetate (30-100%) in hexanes to afford 210 mg (82%) of the title compound as a yellow solid. HPLC/MS: retention time=3.11 min, [M+H]$^+$=512.2.

Example 99

Preparation of 7-(4-chlorophenyl)-2-((2-hydroxy-6-(trifluoromethyl)pyridin-3-yl)methyl)-8-(pyridin-4-yl)-[1,2,4]triazolo[4,3-a]pyridin-3(2H)-one

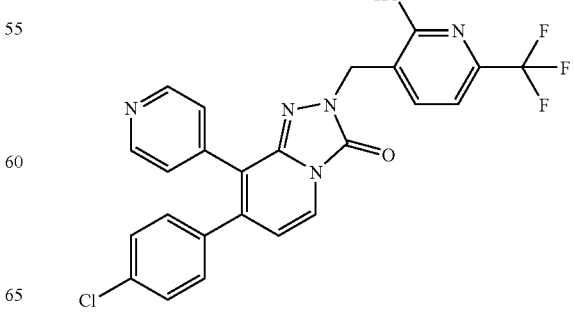

To aqueous HBr solution (48%, 10 mL) was added 7-(4-chlorophenyl)-2-((2-methoxy-6-(trifluoromethyl)pyridin-3-yl)methyl)-8-(pyridin-4-yl)-[1,2,4]triazolo[4,3-a]pyridin-3(2H)-one (210 mg, 0.41 mmol). The resulting solution was stirred at 85° C. for 4 h. After cooling to room temperature, the reaction mixture was concentrated under reduced pressure to remove most of the solvent. The remaining liquid was stirred at 0° C., and neutralized to pH 7-8 by careful addition of 1.0 N aqueous NaOH. Yellow precipitate formed, and this was collected by filtration, washed with water (20 mL×2), and dried in a vacuum oven at 45° C. for 16 h to afford 200 mg (93% pure) of the title compound as a yellow solid. The product was purified by preparative reverse phase HPLC (Phenomenex Luna 5 μm C-18 21.2×100 mm column eluted with a linear gradient of 50% to 90% B over 18 min (A=0.1% trifluoroacetic acid, 90% water, 10% methanol and B=0.1% trifluoroacetic acid, 90% methanol, 10% water) with flow rate at 20 mL/min and UV detection at 220 nm). The desired fractions were concentrated under reduced pressure. The residue was dissolved in EtOAc, washed with saturated aqueous NaHCO$_3$ once, water twice, then saturated aqueous NaCl, dried over Na$_2$SO$_4$ and evaporated. The product was dissolved in acetonitrile, frozen and lyophilized to afford 150 mg (74%) of the title compound as a light yellow powder. HPLC/MS: retention time=2.50 min, [M+H]$^+$=498.2.

Example 100

Preparation of 2-((2-chloro-6-(trifluoromethyl)pyridin-3-yl)methyl)-7-(4-chlorophenyl)-8-(pyridin-4-yl)-[1,2,4]triazolo[4,3-a]pyridin-3(2H)-one

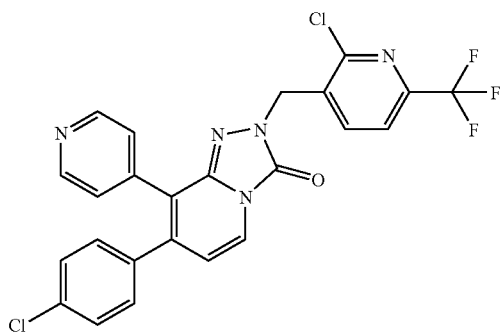

To a solution of 7-(4-chlorophenyl)-8-(pyridin-4-yl)-[1,2,4]triazolo[4,3-a]pyridin-3(2H)-one (200 mg, 0.62 mmol) and 2-chloro-3-(chloromethyl)-6-(trifluoromethyl)pyridine in anhydrous DMF (4.0 mL) at room temperature was added anhydrous K$_2$CO$_3$ (1.8 g, 13 mmol). The resulting yellow suspension was stirred at 70° C. for 3 h. Analysis by HPLC/MS indicated that starting 7-(4-chlorophenyl)-8-(pyridin-4-yl)-[1,2,4]triazolo[4,3-a]pyridin-3(2H)-one had been consumed. After cooling to room temperature, the reaction mixture was diluted with water and extracted with EtOAc (20 mL×2). The combined EtOAc extracts were washed with water, then saturated aqueous NaCl, dried (Na$_2$SO$_4$), filtered, and concentrated under reduced pressure to afford 260 mg (81%) of the title compound as a yellow foam. This product (25 mg) was further purified using preparative reverse phase HPLC (Phenomenex Luna 5 μm C-18 21.2×100 mm column eluted with a linear gradient of 40% to 80% B over 8 min (A=0.1% trifluoroacetic acid, 90% water, 10% methanol and B=0.1% trifluoroacetic acid, 90% methanol, 10% water) with flow rate at 20 mL/min and UV detection at 220 nm). The desired fractions were concentrated under reduced pressure. The residue was dissolved in EtOAc, washed with saturated aqueous NaHCO$_3$ once, water twice, then saturated aqueous NaCl, dried over Na$_2$SO$_4$ and evaporated. The residue was dissolved in acetonitrile, frozen and lyophilized to afford 21 mg of the title compound as a light yellow powder. HPLC/MS: retention time=2.96 min, [M+H]$^+$=516.1.

Example 101

Preparation of 7-(4-chlorophenyl)-2-((2-(methylamino)-6-(trifluoromethyl)pyridin-3-yl)methyl)-8-(pyridin-4-yl)-[1,2,4]triazolo[4,3-a]pyridin-3(2H)-one

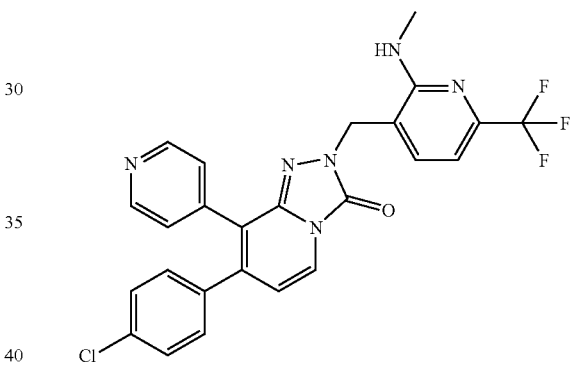

A solution of 2-((2-chloro-6-(trifluoromethyl)pyridin-3-yl)methyl)-7-(4-chlorophenyl)-8-(pyridin-4-yl)-[1,2,4]triazolo[4,3-a]pyridin-3(2H)-one (26 mg, 0.05 mmol) in DMSO (0.5 mL) and 40 wt. % methylamine in water (0.5 mL) was heated in a microwave oven at 200° C. for 30 min. After cooling to room temperature, the reaction mixture was diluted with water and extracted with EtOAc (10 mL×2). The combined EtOAc extracts were concentrated under reduced pressure. The crude product was purified using preparative reverse phase HPLC (Phenomenex Luna 5 μm C-18 21.2×100 mm column eluted with a linear gradient of 50% to 90% B over 8 min (A=0.1% trifluoroacetic acid, 90% water, 10% methanol and B=0.1% trifluoroacetic acid, 90% methanol, 10% water) with flow rate at 20 mL/min and UV detection at 220 nm). The desired fractions were concentrated under reduced pressure. The residue was dissolved in EtOAc, washed with saturated aqueous Na$_2$CO$_3$ once, water twice, then saturated aqueous NaCl, dried over Na$_2$SO$_4$ and evaporated. The residue was dissolved in acetonitrile, frozen and lyophilized to afford 16 mg (63%) of the title compound as a yellow powder. HPLC/MS: retention time=3.28 min, [M+H]$^+$=511.2.

Example 102

Preparation of 7-(4-chlorophenyl)-2-((2-(ethylamino)-6-(trifluoromethyl)pyridin-3-yl)methyl)-8-(pyridin-4-yl)-[1,2,4]triazolo[4,3-a]pyridin-3(2H)-one

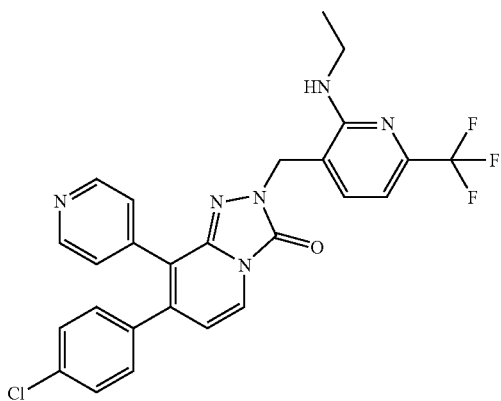

The title compound (14 mg, 54% yield) as a yellow powder was prepared from 2-((2-chloro-6-(trifluoromethyl)pyridin-3-yl)methyl)-7-(4-chlorophenyl)-8-(pyridin-4-yl)-[1,2,4]triazolo[4,3-a]pyridin-3(2H)-one (26 mg, 0.05 mmol), and 2 M ethylamine solution in THF (0.5 mL) according to the procedures described for 7-(4-chlorophenyl)-2-((2-(methylamino)-6-(trifluoromethyl)pyridin-3-yl)methyl)-8-(pyridin-4-yl)-[1,2,4]triazolo[4,3-a]pyridin-3(2H)-one. HPLC/MS: retention time=3.50 min, $[M+H]^+$=525.2.

Example 103

Preparation of 7-(4-chlorophenyl)-2-((2-(dimethylamino)-6-(trifluoromethyl)pyridin-3-yl)methyl)-8-(pyridin-4-yl)-[1,2,4]triazolo[4,3-a]pyridin-3(2H)-one

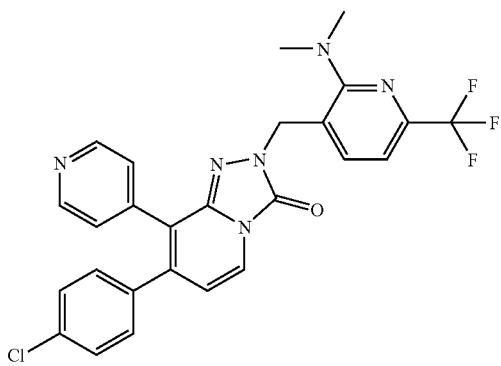

The title compound (12 mg, 46% yield) as a yellow powder was prepared from 2-((2-chloro-6-(trifluoromethyl)pyridin-3-yl)methyl)-7-(4-chlorophenyl)-8-(pyridin-4-yl)-[1,2,4]triazolo[4,3-a]pyridin-3(2H)-one (26 mg, 0.05 mmol) and 40 wt. % dimethylamine in water (0.5 mL) according to the procedures described for 7-(4-chlorophenyl)-2-((2-(methylamino)-6-(trifluoromethyl)pyridin-3-yl)methyl)-8-(pyridin-4-yl)-[1,2,4]triazolo[4,3-a]pyridin-3(2H)-one. HPLC/MS: retention time=3.25 min, $[M+H]^+$=525.2.

Example 104

Preparation of 2-((2-amino-6-(trifluoromethyl)pyridin-3-yl)methyl)-7-(4-chlorophenyl)-8-(pyridin-4-yl)-[1,2,4]triazolo[4,3-a]pyridin-3(2H)-one

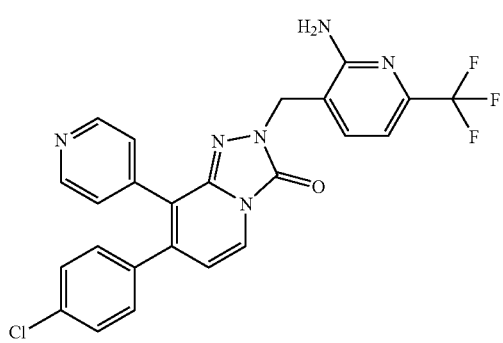

The title compound (6 mg, 33% yield) as a yellow powder was prepared from 2-((2-chloro-6-(trifluoromethyl)pyridin-3-yl)methyl)-7-(4-chlorophenyl)-8-(pyridin-4-yl)-[1,2,4]triazolo[4,3-a]pyridin-3(2H)-one (22 mg, 0.043 mmol), and 28% aqueous ammonium hydroxide solution (0.5 mL) according to the procedures described for 7-(4-chlorophenyl)-2-((2-(methylamino)-6-(trifluoromethyl)pyridin-3-yl)methyl)-8-(pyridin-4-yl)-[1,2,4]triazolo[4,3-a]pyridin-3(2H)-one. HPLC/MS: retention time=2.87 min, $[M+H]^+$=497.2.

Example 105

Preparation of 3-((7-(4-chlorophenyl)-3-oxo-8-(pyridin-4-yl)-[1,2,4]triazolo[4,3-a]pyridin-2(3H)-yl)methyl)-6-(trifluoromethyl)picolinonitrile

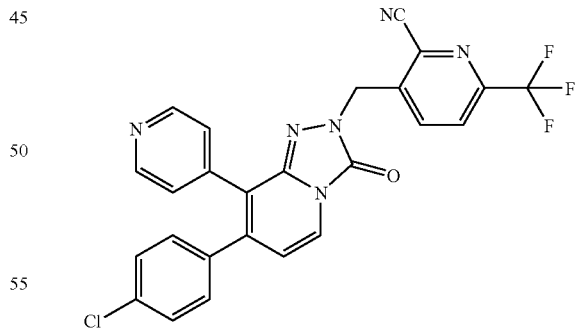

Into a 25 mL flame-dried three necked flask equipped with a condenser under argon was placed 2-((2-chloro-6-(trifluoromethyl)pyridin-3-yl)methyl)-7-(4-chlorophenyl)-8-(pyridin-4-yl)-[1,2,4]triazolo[4,3-a]pyridin-3(2H)-one (250 mg, 0.484 mmol), $Pd(dba)_3$ (44 mg, 0.048 mmol) and dppf (107 mg, 0.194 mmol). The reaction apparatus was purged with argon, and anhydrous DMF (1.5 mL, degassed by bubbling with argon) was added. The resulting suspension was stirred in a pre-heated oil bath at 90° C. To the resulting clear brownish solution, a suspension of zinc cyanide (85.3 mg, 0.73 mmol) in anhydrous DMF (1.5 mL) was added in five portions over 5 min. The reaction mixture was then stirred at 90° C. for 3 h. After cooling to room temperature, the reaction mixture was diluted with water and extracted with EtOAc (30 mL×2). The combined EtOAc extracts were washed with saturated aqueous NaCl, dried over $Na_2SO_4$, filtered and concentrated under reduced pressure. The crude product was purified using a silica gel cartridge (12 g) eluted with a gradient of EtOAc (50-100%) in hexanes to afford 170 mg (69%) of the title compound as a brown foam. A portion of the product was further purified using preparative reverse phase HPLC (Phenomenex Luna 5 μm C-18 21.2×100 mm column eluted with a linear gradient of 50% to 100% B over 20 min (A=0.1% trifluoroacetic acid, 90% water, 10% methanol and B=0.1% trifluoroacetic acid, 90% methanol, 10% water) with flow rate at 20 mL/min and UV detection at 220 nm). The desired fractions were concentrated under reduced pressure. The residue was dissolved in EtOAc, washed with saturated aqueous $NaHCO_3$ once, water twice, then saturated aqueous NaCl, dried over $Na_2SO_4$ and evaporated. The residue was dissolved in acetonitrile, frozen and lyophilized to afford the title compound as a yellow powder. HPLC/MS: retention time=2.82 min, $[M+H]^+=507.1$.

Example 106

Preparation of 2-((2-(aminomethyl)-6-(trifluoromethyl)pyridin-3-yl)methyl)-7-(4-chlorophenyl)-8-(pyridin-4-yl)-[1,2,4]triazolo[4,3-a]pyridin-3(2H)-one

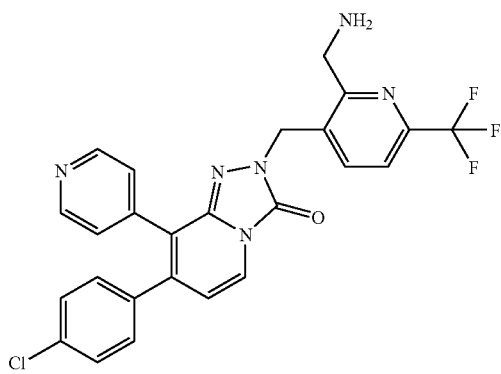

To a solution of 3-((7-(4-chlorophenyl)-3-oxo-8-(pyridin-4-yl)-[1,2,4]triazolo[4,3-a]pyridin-2(3H)-yl)methyl)-6-(trifluoromethyl)picolinonitrile (51 mg, 0.1 mmol) in formic acid (0.8 mL) and water (0.2 mL) was added platinum (IV) oxide (20 mg). The resulting suspension was stirred at 70° C. for 1 h. After cooling to room temperature, the reaction mixture was concentrated under reduced pressure. The residue was dissolved in EtOAc, washed with saturated aqueous $Na_2CO_3$, water, then saturated aqueous NaCl, dried over $Na_2SO_4$ and concentrated under reduced pressure. The crude product was purified using preparative reverse phase HPLC (Phenomenex Luna 5 μm C-18 21.2×100 mm column eluted with a linear gradient of 40% to 80% B over 8 min (A=0.1% trifluoroacetic acid, 90% water, 10% methanol and B=0.1% trifluoroacetic acid, 90% methanol, 10% water) with flow rate at 20 mL/min and UV detection at 220 nm). The desired fractions were concentrated under reduced pressure. The product was dissolved in EtOAc, washed with saturated aqueous $NaHCO_3$ once, water twice, then saturated aqueous NaCl, dried over $Na_2SO_4$ and evaporated. The residue was dissolved in acetonitrile, frozen and lyophilized to afford 7.4 mg of the title compound as a yellow powder. HPLC/MS: retention time=2.26 min, $[M+H]^+=511.0$.

Example 107

Preparation of 2-((2-ethyl-6-(trifluoromethyl)pyridin-3-yl)methyl)-7-(4-ethylphenyl)-8-(pyridin-4-yl)-[1,2,4]triazolo[4,3-a]pyridin-3(2H)-one

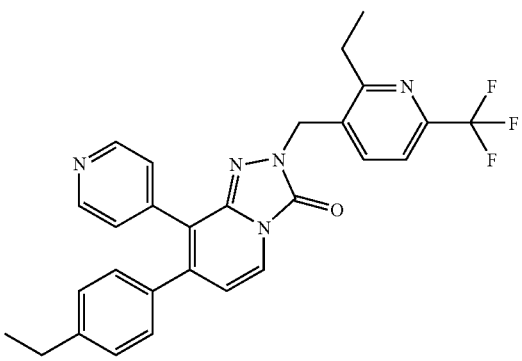

A mixture of 2-((2-chloro-6-(trifluoromethyl)pyridin-3-yl)methyl)-7-(4-chlorophenyl)-8-(pyridin-4-yl)-[1,2,4]triazolo[4,3-a]pyridin-3(2H)-one (22 mg, 0.043 mmol), anhydrous THF (0.5 mL), diethylzinc (1.1 M solution in toluene, 0.059 mL, 0.065 mmol), solid $K_2CO_3$ (18 mg, 0.129 mmol) and $Pd(dppf)Cl_2.CH_2Cl_2$ (7 mg, 0.0086 mmol) in a sealed tube was stirred at 80° C. for 16 h. After cooling to room temperature, the reaction mixture was diluted with EtOAc, washed with water, then saturated aqueous NaCl, dried over $Na_2SO_4$ and concentrated under reduced pressure. Two products were purified using preparative reverse phase HPLC (Phenomenex Luna 5 μm C-18 21.2×100 mm column eluted with a linear gradient of 50% to 80% B over 10 min (A=0.1% trifluoroacetic acid, 90% water, 10% methanol and B=0.1% trifluoroacetic acid, 90% methanol, 10% water) with flow rate at 20 mL/min and UV detection at 220 nm). HPLC fractions were concentrated under reduced pressure. The residue was dissolved in EtOAc, washed with saturated aqueous $NaHCO_3$ once, water twice, then saturated aqueous NaCl, dried over $Na_2SO_4$ and evaporated. The residue was dissolved in acetonitrile, frozen and lyophilized to afford 7-(4-chlorophenyl)-2-((2-ethyl-6-(trifluoromethyl)pyridin-3-yl)methyl)-8-(pyridin-4-yl)-[1,2,4]triazolo[4,3-a]pyridin-3(2H)-one (11 mg) and the title compound (7 mg) as a yellow powder. Title compound: HPLC/MS: retention time=3.20 min, $[M+H]^+=504.3$.

Example 108

Preparation of methyl 3-((7-(4-chlorophenyl)-3-oxo-8-(pyridin-4-yl)-[1,2,4]triazolo[4,3-a]pyridin-2(3H)-yl)methyl)-6-(trifluoromethyl)picolinate

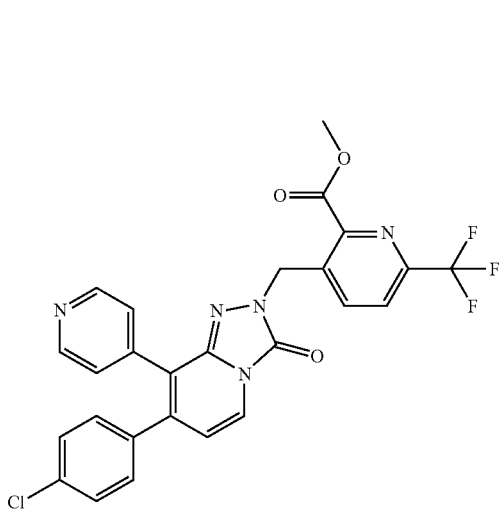

Into a pressure bottle was placed 2-((2-chloro-6-(trifluoromethyl)pyridin-3-yl)methyl)-7-(4-chlorophenyl)-8-(pyridin-4-yl)-[1,2,4]triazolo[4,3-a]pyridin-3(2H)-one (62 mg, 0.12 mmol), Pd(OAc)$_2$ (22 mg, 0.098 mmol), and dppf (40 mg, 0.098 mmol), followed by methanol (1.5 mL), DMSO (3.0 mL) and triethylamine (67 µL, 0.48 mmol). Carbon monoxide gas from a pressure cylinder was bubbled into the reaction bottle to generate a pressure at 25 to 30 psi. The bottle was sealed and heated at 80° C. for 3 h. After cooling to room temperature, the reaction mixture was diluted with EtOAc, washed with water, then saturated aqueous NaCl, dried over Na$_2$SO$_4$ and concentrated under reduced pressure. The crude product was purified using a silica gel cartridge (12 g) eluted with a gradient of ethyl acetate (50-100%) in hexanes to afford the product, which was further purified using preparative reverse phase HPLC (Phenomenex Luna 5 µm C-18 21.2×100 mm column eluted with a linear gradient of 50% to 90% B over 20 min (A=0.1% trifluoroacetic acid, 90% water, 10% methanol and B=0.1% trifluoroacetic acid, 90% methanol, 10% water) with flow rate at 20 mL/min and UV detection at 220 nm). The desired fractions were concentrated under reduced pressure. The residue was dissolved in EtOAc, washed with saturated aqueous NaHCO$_3$ once, water twice, then saturated aqueous NaCl, dried over Na$_2$SO$_4$ and evaporated. The residue was dissolved in acetonitrile, frozen and lyophilized to afford 20 mg of pure title compound as a yellow powder. HPLC/MS: retention time=2.85 min, [M+H]$^+$=540.0.

Example 109

Preparation of 3-((7-(4-chlorophenyl)-3-oxo-8-(pyridin-4-yl)-[1,2,4]triazolo[4,3-a]pyridin-2(3H)-yl)methyl)-2-methyl-6-(trifluoromethyl)pyridine 1-oxide

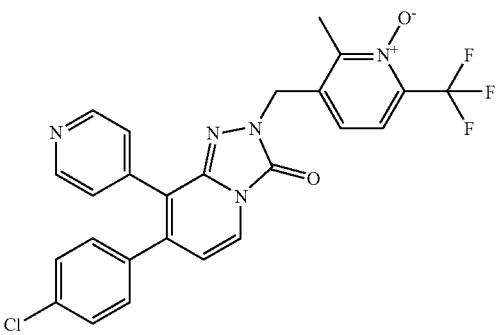

To a suspension of 7-(4-chlorophenyl)-8-(pyridin-4-yl)-[1,2,4]triazolo[4,3-a]pyridin-3(2H)-one (64 mg, 0.2 mmol), 3-(hydroxymethyl)-2-methyl-6-(trifluoromethyl)pyridine 1-oxide (41 mg, 0.2 mmol) and Ph$_3$P (105 mg, 0.4 mmol) in anhydrous THF (3 mL) at room temperature was added dropwise a 40% solution of DEAD in toluene (0.091 mL, 0.4 mmol). The resulting clear, yellowish solution was then stirred at room temperature for 16 h. The reaction mixture was diluted with EtOAc, washed with saturated aqueous NaHCO$_3$, then saturated aqueous NaCl, dried (Na$_2$SO$_4$), filtered, and concentrated under reduced pressure. The crude product was purified using a silica gel cartridge (12 g) eluted with a gradient of ethyl acetate (40-100%) in hexanes to afford 70 mg (69%) of the title compound as a light yellow foam. A portion of the product (10 mg) was further purified using preparative reverse phase HPLC (Phenomenex Luna 5 µm C-18 21.2×100 mm column eluted with a linear gradient of 40% to 80% B over 8 min (A=0.1% trifluoroacetic acid, 90% water, 10% methanol and B=0.1% trifluoroacetic acid, 90% methanol, 10% water) with flow rate at 20 mL/min and UV detection at 220 nm). The desired fractions were concentrated under reduced pressure. The residue was dissolved in EtOAc, washed with saturated aqueous NaHCO$_3$ once, water twice, then saturated aqueous NaCl, dried over Na$_2$SO$_4$ and evaporated. The residue was dissolved in acetonitrile, frozen and lyophilized to afford 7.2 mg of the title compound as a light yellow powder. HPLC/MS: retention time=2.33 min, [M+H]$^+$=512.0.

The title compound was also prepared from 8-bromo-7-(4-chlorophenyl)-[1,2,4]triazolo[4,3-a]pyridin-3(2H)-one by treatment with 3-(bromomethyl)-2-methyl-6-(trifluoromethyl)pyridine 1-oxide and potassium carbonate in N,N-dimethylformamide at 70° C., followed by treatment with 4-(4,4,5,5-tetramethyl-1,3,2-dioxaborolan-2-yl)pyridine and aqueous potassium carbonate solution in toluene under (Ph$_3$P)$_4$Pd catalysis at 100° C.

Example 110

Preparation of (3-((7-(4-chlorophenyl)-3-oxo-8-(pyridin-4-yl)-[1,2,4]triazolo[4,3-a]pyridin-2(3H)-yl)methyl)-6-(trifluoromethyl)pyridin-2-yl)methyl acetate

Example 111

Preparation of 7-(4-chlorophenyl)-2-((2-(hydroxymethyl)-6-(trifluoromethyl)pyridin-3-yl)methyl)-8-(pyridin-4-yl)-[1,2,4]triazolo[4,3-a]pyridin-3(2H)-one

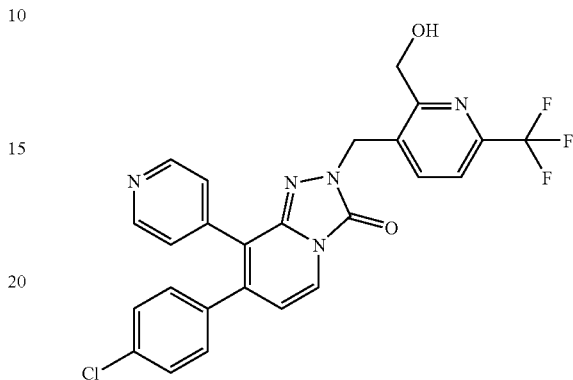

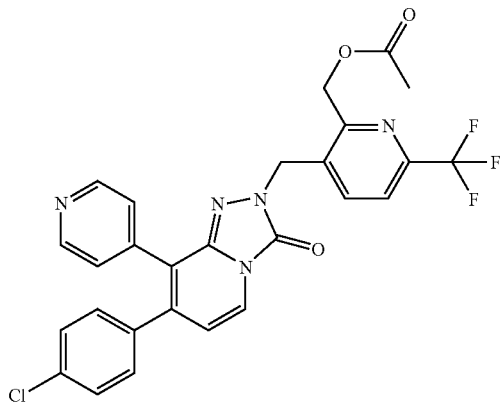

A solution of 3-((7-(4-chlorophenyl)-3-oxo-8-(pyridin-4-yl)-[1,2,4]triazolo[4,3-a]pyridin-2(3H)-yl)methyl)-2-methyl-6-(trifluoromethyl)pyridine 1-oxide (60 mg, 0.12 mmol) in acetic anhydride (2 mL) in a sealed tube was stirred at 130° C. for 6 h. After cooling to room temperature, the reaction mixture was concentrated under reduced pressure. The residue was diluted with EtOAc, washed with saturated aqueous NaHCO$_3$, water, then saturated aqueous NaCl, dried (Na$_2$SO$_4$), filtered, and concentrated under reduced pressure to afford 45 mg of the crude product as a light brown foam. A portion of the product (15 mg) was purified using preparative reverse phase HPLC (Phenomenex Luna 5 μm C-18 21.2×100 mm column eluted with a linear gradient of 50% to 80% B over 8 min (A=0.1% trifluoroacetic acid, 90% water, 10% methanol and B=0.1% trifluoroacetic acid, 90% methanol, 10% water) with flow rate at 20 mL/min and UV detection at 220 nm). The desired fractions were concentrated under reduced pressure. The residue was dissolved in EtOAc, washed with saturated aqueous NaHCO$_3$ once, water twice, then saturated aqueous NaCl, dried over Na$_2$SO$_4$ and evaporated. The residue was dissolved in acetonitrile, frozen and lyophilized to afford 7.5 mg of the title compound as a yellow powder. HPLC/MS: retention time=2.90 min, [M+H]$^+$=554.1.

A solution of (3-((7-(4-chlorophenyl)-3-oxo-8-(pyridin-4-yl)-[1,2,4]triazolo[4,3-a]pyridin-2(3H)-yl)methyl)-6-(trifluoromethyl)pyridin-2-yl)methyl acetate (220 mg, 0.397 mmol) and 1.0 M aqueous K$_2$CO$_3$ solution (3.1 mL, 3.1 mmol) in methanol (7 mL) was stirred at room temperature for 30 min, then concentrated under reduced pressure. The crude product was purified using a silica gel cartridge (12 g) eluted with a gradient of ethyl acetate (50-100%) in hexanes to afford 156 mg (77%) of the title compound as a yellow foam. A portion of the product (110 mg) was further purified using preparative reverse phase HPLC (Phenomenex Luna 5 μm C-18 21.2×100 mm column eluted with a linear gradient of 50% to 100% B over 8 min (A=90% water, 10% methanol and B=90% methanol, 10% water) with flow rate at 20 mL/min and UV detection at 220 nm). The desired fractions were concentrated under reduced pressure. The residue was dissolved in acetonitrile, frozen and lyophilized to afford 97 mg of the title compound as a light yellow powder. HPLC/MS: retention time=2.67 min, [M+H]$^+$=512.0.

The title compound was also prepared as follows: A solution of 3-((7-(4-chlorophenyl)-3-oxo-8-(pyridin-4-yl)-[1,2,4]triazolo[4,3-a]pyridin-2(3H)-yl)methyl)-2-methyl-6-(trifluoromethyl)pyridine 1-oxide (770 mg, 1.50 mmol) in trifluoroacetic anhydride (7 mL) and CH$_2$Cl$_2$ (7 mL) in a sealed tube was stirred at 50° C. for 2 h. After cooling to room temperature, the reaction mixture was concentrated under reduced pressure. The crude product was dissolved in methanol (14 mL), and 1.0 M aqueous K$_2$CO$_3$ solution (7 mL, 7 mmol) was added. The resulting mixture was stirred at room temperature for 30 min, then concentrated under reduced pressure. The residue was diluted with water and extracted with EtOAc (50 mL×2). The combined EtOAc extracts were washed with saturated aqueous NaCl, dried (Na$_2$SO$_4$), filtered, and concentrated under reduced pressure. The product was purified using a silica gel cartridge (80 g) eluted with a gradient of ethyl acetate (50-100%) in hexanes to afford 660 mg (86%, 2 steps) of the title compound as a yellow foam. HPLC/MS: retention time=2.68 min, [M+H]$^+$=512.1.

Example 112

Preparation of 7-(4-chlorophenyl)-2-((2-(methoxymethyl)-6-(trifluoromethyl)pyridin-3-yl)methyl)-8-(pyridin-4-yl)-[1,2,4]triazolo[4,3-a]pyridin-3(2H)-one

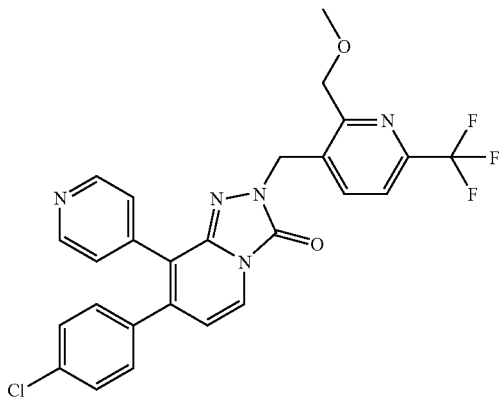

To a solution of 7-(4-chlorophenyl)-2-((2-(hydroxymethyl)-6-(trifluoromethyl)pyridin-3-yl)methyl)-8-(pyridin-4-yl)-[1,2,4]triazolo[4,3-a]pyridin-3(2H)-one (26 mg, 0.05 mmol) in anhydrous DMF (0.5 mL) cooled at 0° C. was added sodium hydride (60% in oil, 4.0 mg, 0.1 mmol). The resulting mixture was stirred at 0° C. for 30 min, then iodomethane (20 μL, 0.25 mmol) was added. The reaction mixture was stirred at 0° C. for 30 min, then quenched by addition of water. The mixture was extracted with EtOAc (10 mL×2), and the combined EtOAc extracts were washed with saturated aqueous NaCl, dried over Na₂SO₄ and concentrated under reduced pressure. The crude product was purified using a silica gel cartridge (4 g) eluted with a gradient of ethyl acetate (50-100%) in hexanes to afford 12 mg of the title compound as a yellow foam. HPLC/MS: retention time=2.93 min, [M+H]⁺=526.1.

Example 113

Preparation of 3-((7-(4-chlorophenyl)-3-oxo-8-(pyridin-4-yl)-[1,2,4]triazolo[4,3-a]pyridin-2(3H)-yl)methyl)-6-(trifluoromethyl)picolinaldehyde

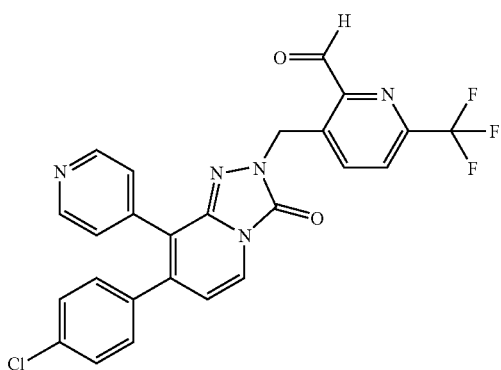

To a stirring solution of oxalyl chloride (12 μL, 0.134 mmol) in CH₂Cl₂ (0.5 mL) cooled at −30° C. under argon was added anhydrous DMSO (19 μL, 0.268 mmol) over 5 min. After stirring at −30° C. for 15 min, the reaction mixture was cooled at −60° C., then a solution of 7-(4-chlorophenyl)-2-((2-(hydroxymethyl)-6-(trifluoromethyl)pyridin-3-yl)methyl)-8-(pyridin-4-yl)-[1,2,4]triazolo[4,3-a]pyridin-3(2H)-one (36 mg, 0.07 mmol) in CH₂Cl₂ (1.0 mL) was added over 5 min. After stirring at −60° C. for 30 min, triethylamine (72 μL, 0.54 mmol) was added, the reaction mixture was stirred at −60° C. for 30 min before warming up to room temperature. The mixture was partitioned between water and CH₂Cl₂. The aqueous layer was extracted with CH₂Cl₂ (10 mL×2), and the combined CH₂Cl₂ layers were washed with saturated aqueous NaCl, dried over Na₂SO₄ and concentrated under reduced pressure. The crude product was purified using a silica gel cartridge (4 g) eluted with a gradient of ethyl acetate (50-100%) in hexanes to afford 25 mg of the title compound as a yellow foam. The product was further purified using preparative reverse phase HPLC (Phenomenex Luna 5 μm C-18 21.2×100 mm column eluted with a linear gradient of 50% to 80% B over 8 min (A=90% water, 10% methanol and B=90% methanol, 10% water) with flow rate at 20 mL/min and UV detection at 220 nm). The desired fractions were concentrated under reduced pressure. The residue was dissolved in acetonitrile, frozen and lyophilized to afford 15 mg of the title compound as a yellow powder. HPLC/MS: retention time=2.76 min, [M+H]⁺=510.6.

The title compound was also prepared as follows: To a stirring solution of 7-(4-chlorophenyl)-2-((2-(hydroxymethyl)-6-(trifluoromethyl)pyridin-3-yl)methyl)-8-(pyridin-4-yl)-[1,2,4]triazolo[4,3-a]pyridin-3(2H)-one (162.4 mg, 0.32 mmol) in CH₂Cl₂ (5 mL) at room temperature was added 1,1,1-tris(acetyloxy)-1,1-dihydro-1,2-benziodoxol-3-(1H)-one (Dess-Martin periodinane, 201 mg, 0.48 mmol) in one portion. The resulting mixture was stirred at room temperature for 10 min, then quenched by addition of water. The aqueous layer was extracted with CH₂Cl₂ (10 mL×2). The combined CH₂Cl₂ layers were washed with saturated aqueous NaCl, dried (Na₂SO₄), filtered, and concentrated under reduced pressure. The product was purified using a silica gel cartridge (12 g) eluted with a gradient of ethyl acetate (30-100%) in hexanes to obtain 160 mg (99%) of the title compound as a yellow foam. HPLC/MS: retention time=2.78 min, [M+H]⁺=510.6.

Example 114

Preparation of 3-((7-(4-chlorophenyl)-3-oxo-8-(pyridin-4-yl)-[1,2,4]triazolo[4,3-a]pyridin-2(3H)-yl)methyl)-6-(trifluoromethyl)picolinic acid

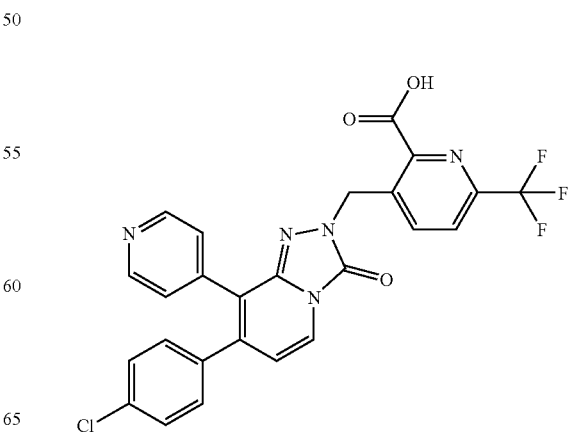

To a stirring solution of 3-((7-(4-chlorophenyl)-3-oxo-8-(pyridin-4-yl)-[1,2,4]triazolo[4,3-a]pyridin-2(3H)-yl)methyl)-6-(trifluoromethyl)picolinaldehyde (150 mg, 0.294 mmol) in CH$_3$CN (10 mL) was added silver nitrate (235 mg, 1.38 mmol), followed by 1.0 M aqueous NaOH solution (2.2 mL, 2.2 mmol). The resulting black mixture was stirred at room temperature for 1 h, then the reaction mixture was adjusted to pH 5 by dropwise addition of 1 N aqueous HCl solution. The resulting mixture was extracted with EtOAc (30 mL×3). The combined EtOAc extracts were washed with saturated aqueous NaCl, dried over Na$_2$SO$_4$ and concentrated under reduced pressure to obtain 150 mg of the title compound as a brownish solid. A portion (10 mg) of the product was purified using preparative reverse phase HPLC (Phenomenex Luna 5 μm C-18 21.2×100 mm column eluted with a linear gradient of 50% to 80% B over 8 min (A=0.1% trifluoroacetic acid, 90% water, 10% methanol and B=0.1% trifluoroacetic acid, 90% methanol, 10% water) with flow rate at 20 mL/min and UV detection at 220 nm). The desired fractions were concentrated under reduced pressure. The residue was partitioned between EtOAc and water, then adjusted to pH 6-7 with saturated aqueous NaHCO$_3$ The EtOAc layer was washed with water, then saturated aqueous NaCl, dried over Na$_2$SO$_4$ and concentrated under reduced pressure. The residue was dissolved in acetonitrile, frozen and lyophilized to afford 8.5 mg of the title compound as a yellow powder. HPLC/MS: retention time=2.58 min, [M+H]$^+$=526.1.

The title compound was also prepared as follows: A solution of methyl 3-((7-(4-chlorophenyl)-3-oxo-8-(pyridin-4-yl)-[1,2,4]triazolo[4,3-a]pyridin-2(3H)-yl)methyl)-6-(trifluoromethyl)picolinate (60 mg, 0.11 mmol) in a mixture of 1 M aqueous NaOH (1 mL) and THF (1 mL) was stirred at room temperature for 4 h. After cooling to 0° C., the reaction mixture was neutralized to pH 6-7 by addition of 1 M aqueous HCl solution, then extracted with EtOAc (30 mL×3). The combined EtOAc extracts were washed with saturated aqueous NaCl, dried (Na$_2$SO$_4$), filtered, and concentrated under reduced pressure to afford the title compound.

Example 115

Preparation of 3-((7-(4-chlorophenyl)-3-oxo-8-(pyridin-4-yl)-[1,2,4]triazolo[4,3-a]pyridin-2(3H)-yl) methyl)-6-(trifluoromethyl)picolinamide

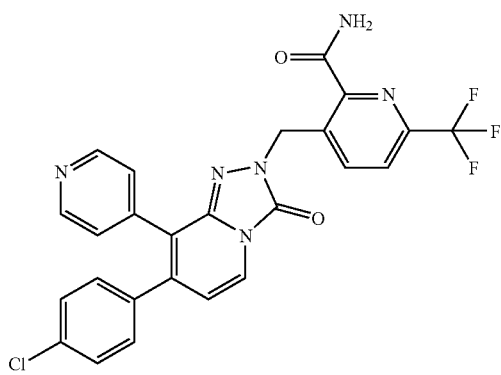

A. Preparation of 3-((7-(4-chlorophenyl)-3-oxo-8-(pyridin-4-yl)-[1,2,4]triazolo[4,3-a]pyridin-2(3H)-yl)methyl)-6-(trifluoromethyl)picolinoyl chloride

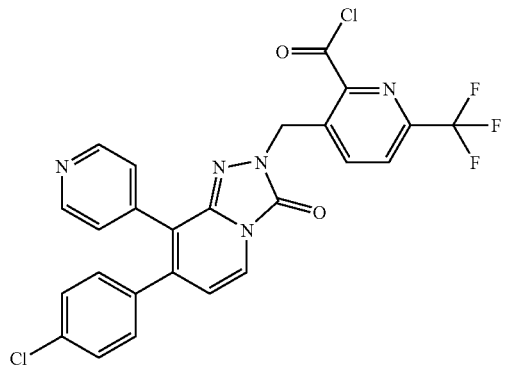

To a stirring solution of 3-((7-(4-chlorophenyl)-3-oxo-8-(pyridin-4-yl)-[1,2,4]triazolo[4,3-a]pyridin-2(3H)-yl)methyl)-6-(trifluoromethyl)picolinic acid (71 mg, 0.133 mmol) in anhydrous ClCH$_2$CH$_2$Cl (1 mL) at room temperature was added dropwise thionyl chloride (2 mL). The mixture was then stirred at 80° C. for 1 h. After cooling to room temperature, the reaction mixture was concentrated under reduced pressure. The residue was evaporated with toluene (5 mL×2), and dried in high vacuum to afford the title compound (72 mg) as a yellow foam, which was used in the next reaction without further purification.

B. Preparation of 3-((7-(4-chlorophenyl)-3-oxo-8-(pyridin-4-yl)-[1,2,4]triazolo[4,3-a]pyridin-2(3H)-yl) methyl)-6-(trifluoromethyl)picolinamide

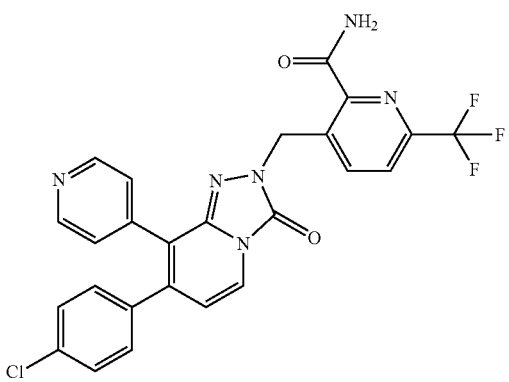

To a stirring solution of 3-((7-(4-chlorophenyl)-3-oxo-8-(pyridin-4-yl)-[1,2,4]triazolo[4,3-a]pyridin-2(3H)-yl)methyl)-6-(trifluoromethyl)picolinoyl chloride (36 mg, 0.066 mmol) in anhydrous THF (1 mL) at room temperature was added 28% aqueous ammonium hydroxide solution (1 mL). The resulting mixture was stirred at room temperature for 10 min. Analysis by HPLC/MS indicated the starting acid chloride had been consumed and the desired product had formed. The reaction mixture was diluted with water and extracted with EtOAc (15 mL×2). The combined EtOAc extracts were washed with saturated aqueous NaCl, dried over Na$_2$SO$_4$ and concentrated under reduced pressure. The residue was purified using preparative reverse phase HPLC (Phenomenex Luna 5 μm C-18 21.2×100 mm column eluted with a linear gradient of 50% to 100% B over 8 min (A=0.1% trifluoroacetic acid, 90% water, 10% methanol and B=0.1% trifluoroacetic acid, 90% methanol, 10% water) with flow rate at 20 mL/min and UV detection at 220 nm). The desired fractions were concentrated under reduced pressure. The residue was dissolved in EtOAc, washed with saturated aqueous NaHCO$_3$ once, water twice, then saturated aqueous NaCl, dried over Na$_2$SO$_4$ and evaporated. The residue was dissolved in acetonitrile, frozen and lyophilized to afford 20 mg (57%) of the title compound as a pale yellow powder. HPLC/MS: retention time=2.75 min, [M+H]$^+$=525.1.

Example 116

Preparation of 3-((7-(4-chlorophenyl)-3-oxo-8-(pyridin-4-yl)-[1,2,4]triazolo[4,3-a]pyridin-2(3H)-yl)methyl)-N-methyl-6-(trifluoromethyl)picolinamide

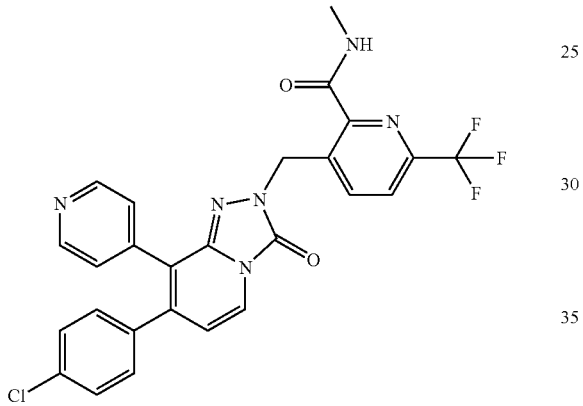

To a stirring solution of 3-((7-(4-chlorophenyl)-3-oxo-8-(pyridin-4-yl)-[1,2,4]triazolo[4,3-a]pyridin-2(3H)-yl)methyl)-6-(trifluoromethyl)picolinoyl chloride (36 mg, 0.066 mmol) in anhydrous THF (1 mL) at 0° C. was added 2 M methylamine solution in THF (0.33 mL, 0.66 mmol), followed by Et$_3$N (0.046 mL, 0.33 mmol). The resulting mixture was stirred at 0° C. for 30 min, then at room temperature for 16 h. Analysis by HPLC/MS indicated the starting acid chloride had been consumed and the desired product had formed. The reaction mixture was diluted with water and extracted with EtOAc (15 mL×2). The combined EtOAc extracts were washed with saturated aqueous NaCl, dried over Na$_2$SO$_4$ and concentrated under reduced pressure. The residue was purified using preparative reverse phase HPLC (Phenomenex Luna 5 μm C-18 21.2×100 mm column eluted with a linear gradient of 50% to 100% B over 8 min (A=0.1% trifluoroacetic acid, 90% water, 10% methanol and B=0.1% trifluoroacetic acid, 90% methanol, 10% water) with flow rate at 20 mL/min and UV detection at 220 nm). The desired fractions were concentrated under reduced pressure. The residue was dissolved in EtOAc, washed with saturated aqueous NaHCO$_3$ once, water twice, then saturated aqueous NaCl, dried over Na$_2$SO$_4$ and evaporated. The residue was dissolved in acetonitrile, frozen and lyophilized to afford 12 mg (34%) of the title compound as a pale yellow powder. HPLC/MS: retention time=2.83 min, [M+H]$^+$=539.2.

Alternate Route to Intermediate of Example 75C

Preparation of 7-(4-chlorophenyl)-8-(pyridin-4-yl)-[1,2,4]triazolo[4,3-a]pyridin-3(2H)-one

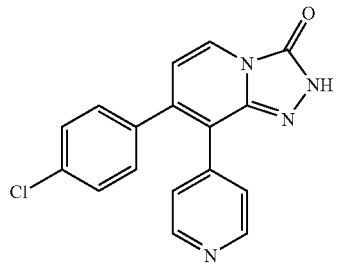

A. Preparation of 4-bromo-2-fluoro-3-iodopyridine

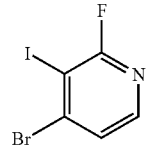

To a flame-dried 3-neck flask under argon were added, LDA (1.8 M solution in THF/heptane/ethylbenzene (Aldrich, 33 mL, 60 mmol) and THF (30 mL), and the resulting solution was cooled to −70° C. in a dry ice/acetone bath. A solution of 3-bromo-2-fluoropyridine (10.0 g, 56 mmol) in THF (20 mL) was added dropwise to the reaction mixture over 1 h. The internal temperature of the reaction was monitored and maintained below −65° C. throughout the addition. The reaction mixture was stirred for an additional 1 h at −70° C. A solution of 12 in THF (50 mL) was added dropwise to the reaction mixture over 1 h, and the internal temperature of the reaction was again maintained below −65° C. throughout the addition. The reaction mixture was stirred for 30 min at −70° C. and quenched by addition of brine (100 mL). The quenched reaction mixture was warmed to room temperature and extracted with Et$_2$O (4×100 mL). The combined organic extracts were washed successively with saturated aqueous NaHCO$_3$ solution, then brine, and dried over MgSO$_4$. The dried solution was filtered through silica gel column (~100 g) to remove polar impurities, and the column was flushed with Et$_2$O/EtOAc (19:1, 200 mL). The combined eluant was concentrated in vacuo and the solid residue was sublimed under high vacuum to obtain the title compound as a yellow solid (16.0 g, 53 mmol). MS: [M+H]$^+$=301.9. $^1$H NMR (400 MHz, CDCl$_3$) δ 7.42 (d, J=4.95 Hz, 1H), 7.98 (d, J=4.95 Hz, 1H). $^{13}$C NMR (101 MHz, CDCl₃) δ 85.47 (d, J=45.78 Hz), 125.72, 143.86, 147.05 (d, J=15.26 Hz), 163.08 (d, J=236.51 Hz).

B. Preparation of 4-bromo-2-hydrazinyl-3-iodopyridine

To a solution of 4-bromo-2-fluoro-3-iodopyridine (29 g, 96 mmol) in THF (300 mL) was added hydrazine (anhydrous, 30 mL, 960 mmol) at 20° C. The reaction mixture was stirred at 20° C. for 2 h. The reaction was monitored by HPLC (acetonitrile-water-TFA) and completed in 2 h. The reaction mixture was concentrated in vacuo to reduce volume by 70% and H₂O (300 mL) was then added. The resulting mixture was filtered and the collected solid (1st crop) was washed with H₂O. The filtrate was concentrated in vacuo to remove most of the THF. Newly formed solid was then filtered. This 2nd crop was washed with H₂O. The two crops were combined and dried under high vacuum to obtain the title compound as an off-white, fluffy solid (28.6 g, 91 mmol). MS: [M+H]⁺=313.9. ¹H NMR (400 MHz, CDCl₃) δ 6.97 (d, J=5.50 Hz, 1H), 7.92 (d, J=4.95 Hz, 1H).

C. Preparation of 7-bromo-8-iodo-[1,2,4]triazolo[4,3-a]pyridin-3(2H)-one

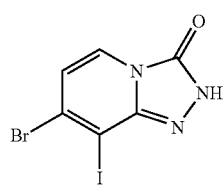

To a solution of triphosgene (91.7 g, 309 mmol) in THF (800 mL) was added 4-bromo-2-hydrazinyl-3-iodopyridine (32.3 g, 103 mmol) in several portions over 1 h at 20° C. The resulting reaction mixture was stirred for an additional 2 h at 20° C. The reaction was monitored by HPLC (acetonitrile-water-TFA) and completed in 2 h. The reaction mixture was cooled in ice bath and quenched by careful addition of H₂O (800 mL). A large amount of solid was precipitated. This was filtered and successively washed with H₂O (2×100 mL) and Et₂O (100 mL). The filtrate was concentrated in vacuo to reduce volume by 50%. Newly formed solid was then filtered. This 2nd crop was also washed with H₂O and Et₂O. The two crops were combined and dried under high vacuum to obtain the title compound as a light beige solid (34 g, 100 mmol). MS: [M+H]⁺=337.9. ¹H NMR (400 MHz, DMSO) δ 6.76 (d, J=7.03 Hz, 1H), 7.78 (d, J=7.47 Hz, 1H), 12.68 (s, 1H).

D. Preparation of 7-bromo-8-iodo-2-(methoxymethyl)-[1,2,4]triazolo[4,3-a]pyridin-3(2H)-one

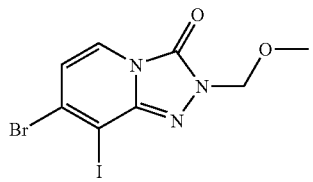

To a solution of 7-bromo-8-iodo-[1,2,4]triazolo[4,3-a]pyridin-3(2H)-one (1.0 g, 2.94 mmol) in DMF (10 mL) and N,N-diisopropylethylamine (2.6 mL, 14.7 mmol) at 20° C. was added chloromethyl methyl ether (473 mg, 5.9 mmol). The resulting reaction mixture was stirred for an additional 3 h at 20° C. and then quenched by addition of H₂O (25 mL). The quenched reaction mixture was extracted with Et₂O/EtOAc (2:1, 3×50 mL). The combined organic extract was washed with saturated aqueous NaHCO₃ solution (30 mL), then brine (30 mL), dried over MgSO₄, filtered and concentrated in vacuo to obtain the title compound as a light yellow solid (1.1 g, 2.86 mmol). MS: [M+H]⁺=384.0. ¹H NMR (400 MHz, CDCl₃) δ 3.46 (s, 3H), 5.34 (s, 2H), 6.68 (d, J=7.15 Hz, 1H), 7.65 (d, J=7.15 Hz, 1H).

E. Preparation of 7-bromo-2-(methoxymethyl)-8-(pyridin-4-yl)-triazolo[4,3-a]pyridin-3(2H)-one

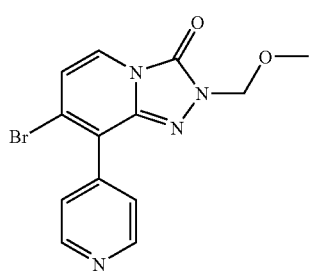

To a degassed mixture of 7-bromo-8-iodo-2-(methoxymethyl)-[1,2,4]triazolo[4,3-a]pyridin-3(2H)-one (711 mg, 1.85 mmol), 4-(4,4,5,5-tetramethyl-1,3,2-dioxaborolan-2-yl)pyridine (615 mg, 3.0 mmol) and K₂CO₃ (640 mg, 15.6 mmol) in 1,4-dioxane (21 mL) and H₂O (7.0 mL) under argon at 20° C. was added Pd(PPh₃)₄ (133 mg, 0.12 mmol). The reaction mixture was refluxed for 40 h under argon and then cooled to 20° C. The reaction was monitored by HPLC (acetonitrile-water-TFA), and >90% of starting material was consumed by 40 h. The reaction mixture was diluted with H₂O (30 mL) and extracted with EtOAc (3×50 mL). The combined organic extract was washed with saturated aqueous NaHCO₃ solution (50 mL), then brine (50 mL), dried over MgSO₄, filtered and concentrated in vacuo to obtain the crude title compound as a yellow solid (620 mg) in 85% purity. The crude product was used without further purification. MS: [M+H]⁺=335.0.

F. Preparation of 7-(4-chlorophenyl)-2-(methoxymethyl)-8-(pyridin-4-yl)-[1,2,4]triazolo[4,3-a]pyridin-3(2H)-one

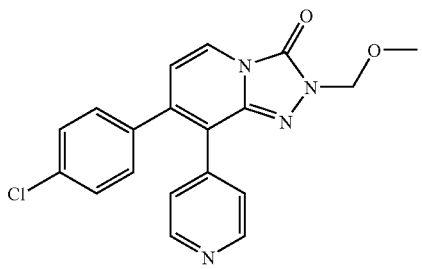

To a degassed mixture of crude 7-bromo-2-(methoxymethyl)-8-(pyridin-4-yl)-[1,2,4]triazolo[4,3-a]pyridin-3(2H)-one (620 mg, 1.85 mmol), 4-chlorophenylboronic acid (850 mg, 5.55 mmol) and $K_2CO_3$ (1.02 g, 7.4 mmol) in 1,4-dioxane (18 mL) and $H_2O$ (6.0 mL) under argon at 20° C. was added Pd(PPh$_3$)$_4$ (107 mg, 0.093 mmol). The reaction mixture was refluxed for 15 h under argon and then cooled to 20° C. The reaction mixture was diluted with $H_2O$ (30 mL) and extracted with EtOAc (3×50 mL). The combined organic extract was washed with saturated aqueous NaHCO$_3$ solution (20 mL), then brine (20 mL), dried over MgSO$_4$, filtered and concentrated in vacuo. The crude product was purified by silica gel column chromatography eluting with a 0-60% gradient of EtOAc in hexanes to obtain the title compound as a yellow solid (510 mg, 1.39 mmol). MS: [M+H]$^+$=367.1. $^1$H NMR (400 MHz, CDCl$_3$) δ 3.46 (s, 3H), 5.32 (s, 2H), 6.62 (d, J=7.1 Hz 1H), 7.01-7.09 (m, 2H), 7.17-7.22 (m, 2H), 7.23-7.29 (m, 2H), 7.85 (d, J=7.1 Hz, 1H), 8.55 (d, J=4.40 Hz, 2H).

G. 7-(4-chlorophenyl)-8-(pyridin-4-yl)-[1,2,4]triazolo[4,3-a]pyridin-3(2H)-one

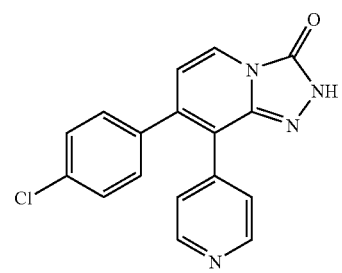

The title compound, a yellow solid (8 mg, 0.025), was prepared from 7-(4-chlorophenyl)-2-(methoxymethyl)-8-(pyridin-4-yl)-[1,2,4]triazolo[4,3-a]pyridin-3(2H)-one (10 mg, 0.027 mmol) by heating in trifluoroacetic acid (0.3 mL) solution at 75° C. for 15 h, followed by evaporation under vacuum and purification by reverse phase preparative HPLC (acetonitrile-water-TFA). MS: [M+H]$^+$=323.1.

Example 117

Preparation of 8-(4-chlorophenyl)-2-((5-(isoxazol-3-yl)pyridin-2-yl)methyl)-7-(pyridin-4-yl)-[1,2,4]triazolo[4,3-a]pyridin-3(2H)-one

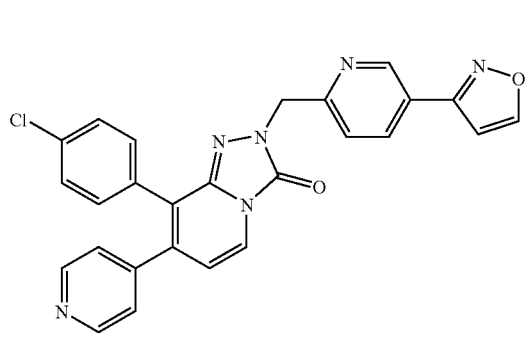

A. Preparation of 7-bromo-8-(4-chlorophenyl)-2-(methoxymethyl)-[1,2,4]triazolo[4,3-a]pyridin-3(2H)-one

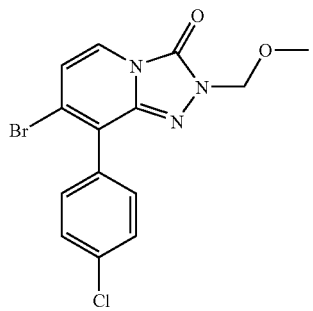

To a degassed mixture of 7-bromo-8-iodo-2-(methoxymethyl)-[1,2,4]triazolo[4,3-a]pyridin-3(2H)-one (3.0 g, 7.8 mmol), 4-chlorophenylboronic acid (1.32 g, 8.6 mmol) and $K_2CO_3$ (2.16 g, 15.6 mmol) in 1,4-dioxane (42 mL) and $H_2O$ (14 mL) under argon at 20° C. was added Pd(PPh$_3$)$_4$ (450 mg, 0.39 mmol). The reaction mixture was refluxed for 40 h under argon and then cooled to 20° C. The reaction mixture was diluted with $H_2O$ (30 mL) and extracted with EtOAc (3×50 mL). The combined organic extract was washed with saturated aqueous NaHCO$_3$ solution (50 mL), then brine (50 mL), dried over MgSO$_4$, filtered and concentrated in vacuo. The residue was successively triturated with hexanes and Et$_2$O and dried under high vacuum to obtain the title compound as a light yellow solid (2.7 g, 7.4 mmol) in 85% purity along with bis-4-chlorophenyl coupled by-product. The crude product was used without further purification. MS: [M+H]$^+$=368.0.

B. Preparation of 8-(4-chlorophenyl)-2-(methoxymethyl)-7-(pyridin-4-yl)-[1,2,4]triazolo[4,3-a]pyridin-3(2H)-one

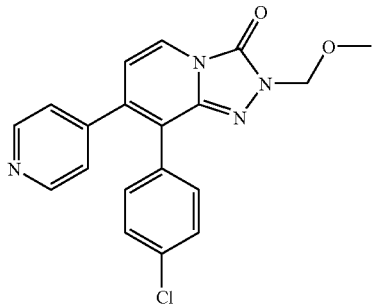

To a degassed mixture of 7-bromo-8-(4-chlorophenyl)-2-(methoxymethyl)-[1,2,4]triazolo[4,3-a]pyridin-3(2H)-one (300 mg, 0.81 mmol), 4-(4,4,5,5-tetramethyl-1,3,2-dioxaborolan-2-yl)pyridine (332 mg, 1.62 mmol) and $K_2CO_3$ (280 mg, 2.0 mmol) in 1,4-dioxane (10 mL) and $H_2O$ (3.0 mL) under argon at 20° C. was added $Pd(PPh_3)_4$ (47 mg, 0.043 mmol). The reaction mixture was refluxed for 15 h under argon and then cooled to 20° C. The reaction mixture was diluted with $H_2O$ (10 mL) and extracted with EtOAc (3×20 mL). The combined organic extract was washed with saturated aqueous $NaHCO_3$ solution (20 mL), then brine (20 mL), dried over $MgSO_4$, filtered and concentrated in vacuo. The crude product was purified by silica gel column chromatography eluting with a 0-60% gradient of EtOAc in hexanes to obtain the title compound as a yellow solid (241 mg, 0.65 mmol). MS: $[M+H]^+=367.2$. $^1$H NMR (400 MHz, $CDCl_3$) δ 3.45 (s, 3H), 5.32 (s, 2H), 6.59 (d, J=7.03 Hz, 1H), 7.04 (d, J=6.15 Hz, 2H), 7.18-7.23 (m, 2H), 7.26-7.30 (m, 2H), 7.85 (d, J=7.47 Hz, 1H), 8.53 (d, J=6.15 Hz, 2H).

C. Preparation of 8-(4-chlorophenyl)-7-(pyridin-4-yl)-[1,2,4]triazolo[4,3-a]pyridin-3(2H)-one

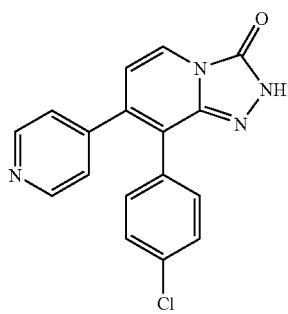

A solution of 8-(4-chlorophenyl)-2-(methoxymethyl)-7-pyridin-4-yl)-[1,2,4]triazolo[4,3-a]pyridin-3(2H)-one (60 mg, 0.16 mmol) in TFA (2.0 mL) was heated at 75° C. for 15 h. The reaction mixture was cooled to 20° C. and concentrated in vacuo. The residue was dissolved in MeOH (2.0 mL) and $K_2CO_3$ (100 mg) was added. The resulting mixture was stirred for 10 min at 20° C. and then filtered. The filtrate was concentrated in vacuo and the residue was re-dissolved in $H_2O$ (3.0 mL). The resulting solution was neutralized to pH 7-8 with 6 N aqueous HCl and extracted with EtOAc. The combined extract was washed with brine, dried over $MgSO_4$, filtered and concentrated in vacuo to obtain the title compound as a yellow solid (43 mg, 0.13 mmol). MS: $[M+H]^+=323.1$. $^1$H NMR (400 MHz, $CDCl_3$) δ 6.61 (d, J=7.15 Hz, 1H), 7.03-7.09 (m, 2H) 7.17-7.23 (m, 2H), 7.26-7.30 (m, 2H), 7.86-7.90 (d, J=7.15 Hz, 1H), 8.50-8.58 (m, 2H) 10.05 (br s, 1H).

Example 118

Preparation of 8-(4-chlorophenyl)-2-((5-(isoxazol-3-yl)pyridin-2-yl)methyl)-7-(pyridin-4-yl)-[1,2,4]triazolo[4,3-a]pyridin-3(2H)-one

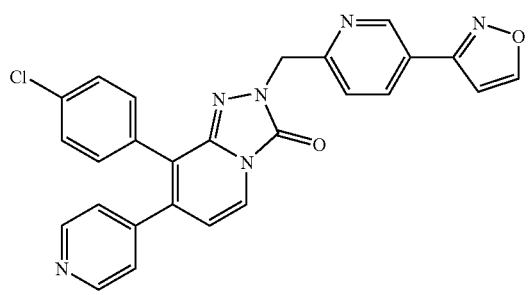

The title compound was prepared by coupling 8-(4-chlorophenyl)-7-(pyridin-4-yl)-[1,2,4]triazolo[4,3-a]pyridin-3(2H)-one with the requisite pyridinylmethyl halide in a manner analogous to that in which 7-(4-chlorophenyl)-2-(4-(methylsufonyl)benzyl)-8-(pyridin-4-yl)-[1,2,4]triazolo[4,3-a]pyridin-3(2H)-one was prepared. HPLC/MS: retention time=2.53 min, $[M+H]^+=480$.

Example 119

Preparation of 7,8-bis(4-chlorophenyl)-2-isobutyl-[1,2,4]triazolo[4,3-a]pyridin-3(2H)-one

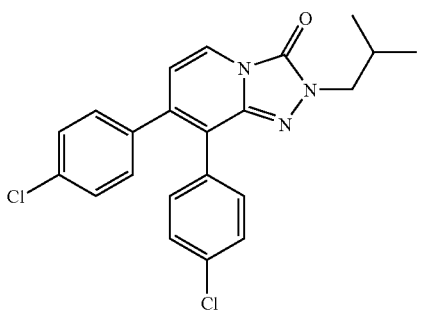

A. Preparation of 7-bromo-8-iodo-2-isobutyl-[1,2,4]triazolo[4,3-a]pyridin-3(2H)-one

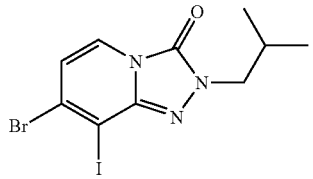

To a stirring solution of 7-bromo-8-iodo-[1,2,4]triazolo[4,3-a]pyridin-3(2H)-one (2.0 g, 5.9 mmol) in 20 mL DMF at 20° C. was added $K_2CO_3$ (1.6 g, 11.8 mmol), followed by addition of 1-iodo-2-methylpropane (2.2 g, 11.8 mmol). The resulting reaction mixture was stirred at 80° C. for 3 h. Analysis by HPLC/MS indicated that starting material had been entirely consumed. The reaction mixture was brought to room temperature, diluted with water, and extracted with diethyl ether and EtOAc. The combined organic extract was washed with saturated aqueous $NaHCO_3$ solution, then brine, then dried ($MgSO_4$), filtered, and concentrated under reduced pressure to obtain the title compound (2.1 g, 5.3 mmol) as a light tan solid. MS: $[M+H]^+$=396. $^1$H NMR ($CDCl_3$): δ 7.65 (d, J=1.9 Hz, 1H), 6.68 (d, J=1.8 Hz, 1H), 3.82 (d, J=1.8, 2H), 2.33-2.30 (m, 1H), 0.96 (d, J=1.7 Hz, 6H).

B. Preparation of 7,8-bis(4-chlorophenyl)-2-isobutyl-[1,2,4]triazolo[4,3-a]pyridin-3(2H)-one

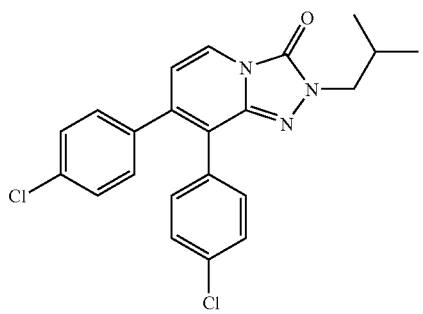

To a stirring, degassed mixture of 7-bromo-8-iodo-2-isobutyl-[1,2,4]triazolo[4,3-a]pyridin-3(2H)-one (50 mg, 0.13 mmol), 4-chlorophenylboronic acid (40 mg, 0.28 mmol), and tetrakis(triphenylphosphine)palladium (7 mg, 0.006 mmol) in dioxane (1.0 mL) at 20° C. was added $K_2CO_3$ (40 mg, 0.25 mmol) in water (0.3 mL). The resulting reaction mixture was heated in a microwave reactor at 200° C. for 10 min under argon. Analysis by HPLC/MS indicated that starting material had been consumed. The reaction mixture was brought to room temperature and was concentrated under reduced pressure. The crude product was purified by reverse phase preparative HPLC (acetonitrile-water-TFA) to isolate the title compound (22 mg, 0.053 mmol) as a light yellow solid. MS: $[M+H]^+$=412.

Example 120

Preparation of 7,8-bis(4-cyanophenyl)-2-isobutyl-[1,2,4]triazolo[4,3-a]pyridin-3(2H)-one

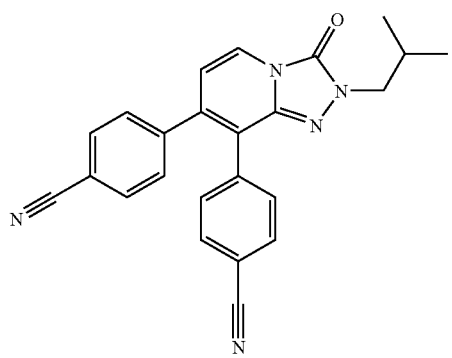

To a stirring, degassed mixture of 7-bromo-8-iodo-2-isobutyl-[1,2,4]triazolo[4,3-a]pyridin-3(2H)-one (50 mg, 0.13 mmol), 4-cyanophenylboronic acid (40 mg, 0.28 mmol), and tetrakis(triphenylphosphine)palladium (7 mg, 0.006 mmol) in dioxane (1.0 mL) at 20° C. was added $K_2CO_3$ (40 mg, 0.25 mmol) in water (0.3 mL). The resulting reaction mixture was heated in a microwave reactor at 200° C. for 10 min under argon. Analysis by HPLC/MS indicated that starting material had been consumed. The reaction mixture was brought to room temperature and was concentrated under reduced pressure. The crude product was purified by reverse phase preparative HPLC (acetonitrile-water-TFA) to isolate the title compound (15 mg, 0.038 mmol) as a yellow solid. MS: $[M+H]^+$=394.

Example 121

Preparation of 7,8-bis(4-trifluoromethylphenyl)-2-isobutyl-[1,2,4]triazolo[4,3-a]pyridin-3(2H)-one

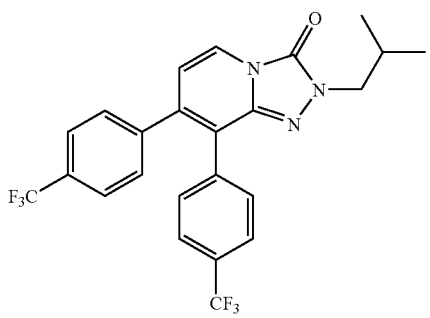

To a stirring, degassed mixture of 7-bromo-8-iodo-2-isobutyl-[1,2,4]triazolo[4,3-a]pyridin-3(2H)-one (50 mg, 0.13 mmol), 4-trifluoromethylphenylboronic acid (40 mg, 0.28 mmol), and tetrakis(triphenylphosphine)palladium (7 mg, 0.006 mmol) in dioxane (1.0 mL) at 20° C. was added $K_2CO_3$ (40 g, 0.25 mmol) in water (0.3 mL). The resulting reaction mixture was heated in a microwave reactor at 200° C. for 12 min under argon. Analysis by HPLC/MS indicated that starting material had been consumed. The reaction mixture was brought to room temperature and was concentrated under reduced pressure. The crude product was purified by reverse phase preparative HPLC (acetonitrile-water-TFA) to isolate the title compound (15 mg, 0.038 mmol) as a yellow solid. MS: [M+H]⁺=394.

Example 122

Preparation of 7,8-bis(4-methylphenyl)-2-isobutyl-[1,2,4]triazolo[4,3-a]pyridin-3(2H)-one

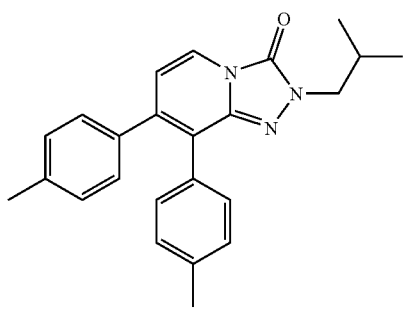

To a stirring, degassed mixture of 7-bromo-8-iodo-2-isobutyl-[1,2,4]triazolo[4,3-a]pyridin-3(2H)-one (50 mg, 0.13 mmol), 4-methylphenylboronic acid (40 mg, 0.28 mmol), and tetrakis(triphenylphosphine)palladium (7 mg, 0.006 mmol) in dioxane (1.0 mL) at 20° C. was added K₂CO₃ (40 mg, 0.25 mmol) in water (0.3 mL). The resulting reaction mixture was heated in a microwave reactor at 200° C. for 7 min under argon. Analysis by HPLC/MS indicated that starting material had been consumed. The reaction mixture was brought to room temperature and was concentrated under reduced pressure. The crude product was purified by reverse phase preparative HPLC (acetonitrile-water-TFA) to isolate the title compound (10 mg, 0.027 mmol) as a pale yellow solid. MS: [M+H]⁺=372.

Example 123

Preparation of 7,8-bis(4-ethoxyphenyl)-2-isobutyl-[1,2,4]triazolo[4,3-a]pyridin-3(2H)-one

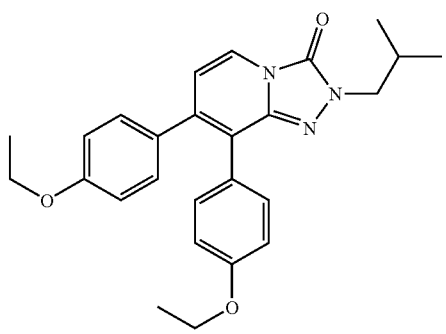

To a stirring, degassed mixture of 7-bromo-8-iodo-2-isobutyl-[1,2,4]triazolo[4,3-a]pyridin-3(2H)-one (50 mg, 0.13 mmol), 4-ethoxyphenylboronic acid (40 mg, 0.28 mmol), and tetrakis(triphenylphosphine)palladium (7 mg, 0.006 mmol) in dioxane (1.0 mL) at 20° C. was added K₂CO₃ (40 mg, 0.25 mmol) in water (0.3 mL). The resulting reaction mixture was heated in a microwave reactor at 200° C. for 10 min under argon. Analysis by HPLC/MS indicated that start-ing material had been consumed. The reaction mixture was brought to room temperature and was concentrated under reduced pressure. The crude product was purified by reverse phase preparative HPLC (acetonitrile-water-TFA) to isolate the title compound (38 mg, 0.088 mmol) as a pale yellow solid. MS: [M+H]⁺=432.

Example 124

Preparation of 7,8-bis(4-methoxyphenyl)-2-isobutyl-[1,2,4]triazolo[4,3-a]pyridin-3(2H)-one

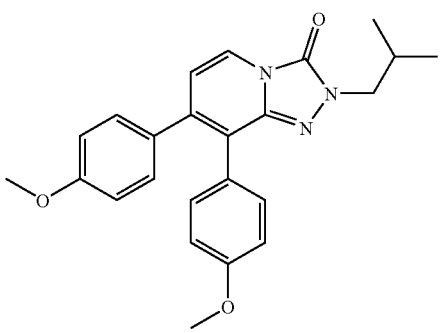

To a stirring, degassed mixture of 7-bromo-8-iodo-2-isobutyl-[1,2,4]triazolo[4,3-a]pyridin-3(2H)-one (50 mg, 0.13 mmol), 4-methoxyphenylboronic acid (40 mg, 0.28 mmol), and tetrakis(triphenylphosphine)palladium (7 mg, 0.006 mmol) in dioxane (1.0 mL) at 20° C. was added K₂CO₃ (40 mg, 0.25 mmol) in water (0.3 mL). The resulting reaction mixture was heated in a microwave reactor at 200° C. for 20 min under argon. Analysis by HPLC/MS indicated that starting material had been consumed. The reaction mixture was brought to room temperature and was concentrated under reduced pressure. The crude product was purified by reverse phase preparative HPLC (acetonitrile-water-TFA) to isolate the title compound (10 mg, 0.025 mmol) as a pale yellow solid. MS: [M+H]⁺=404.

Example 125

Preparation of 7,8-bis(4-fluorophenyl)-2-isobutyl-[1,2,4]triazolo[4,3-a]pyridin-3(2H)-one

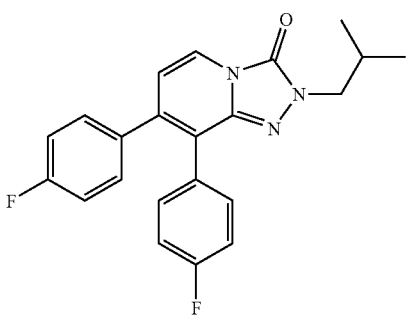

To a stirring, degassed mixture of 7-bromo-8-iodo-2-isobutyl-[1,2,4]triazolo[4,3-a]pyridin-3(2H)-one (50 mg, 0.13 mmol), 4-fluorophenylboronic acid (40 mg, 0.28 mmol), and tetrakis(triphenylphosphine)palladium (7 mg, 0.006 mmol) in dioxane (1.0 mL) at 20° C. was added K₂CO₃ (40 mg, 0.25 mmol) in water (0.3 mL). The resulting reaction mixture was heated in a microwave reactor at 200° C. for 10 min under argon. Analysis by HPLC/MS indicated that starting material had been consumed. The reaction mixture was brought to room temperature and was concentrated under reduced pressure. The crude product was purified by reverse phase preparative HPLC (acetonitrile-water-TFA) to isolate the title compound (33 mg, 0.087) as a pale yellow solid. MS: [M+H]⁺=380.

Example 126

Preparation of 8-(4-chlorophenyl)-7-(2,4-dichlorophenyl)-2-isobutyl-[1,2,4]triazolo[4,3-a]pyridin-3(2H)-one

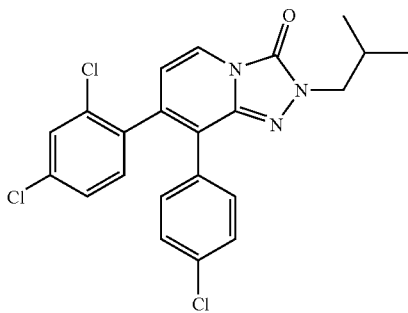

A. Preparation of 7-bromo-8-(4-chlorophenyl)-2-isobutyl-[1,2,4]triazolo[4,3-a]pyridin-3(2H)-one

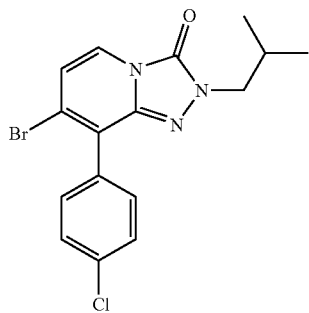

To a stirring, degassed mixture of 7-bromo-8-iodo-2-isobutyl-[1,2,4]triazolo[4,3-a]pyridin-3(2H)-one (100 mg, 0.25 mmol), 4-chlorophenylboronic acid (40 mg, 0.28 mmol), and tetrakis(triphenylphosphine)palladium (15 mg, 0.013 mmol) in dioxane (2.0 mL) at 20° C. was added K₂CO₃ (40 mg, 0.28 mmol) in water (0.6 mL). The resulting reaction mixture was stirred at 100° C. for 15 h under argon. Analysis by HPLC/MS indicated that starting material had been consumed. The reaction mixture was brought to room temperature and was concentrated under reduced pressure. The crude product was purified by reverse phase preparative HPLC (acetonitrile-water-TFA) to isolate the title compound (38 mg, 0.10 mmol) as a yellow solid. MS: [M+H]⁺=380. ¹H NMR (CD₃OD): δ 7.73 (d, J=1.8 Hz, 1H), 7.50 (q, 4H), 6.93 (d, J=1.9, 1H), 3.71 (d, J=1.8, 2H), 2.12 (m, 1H), 0.90 (d, J=1.7, 6H).

B. Preparation of 8-(4-chlorophenyl)-7-(2,4-dichlorophenyl)-2-isobutyl-[1,2,4]triazolo[4,3-a]pyridin-3(2H)-one

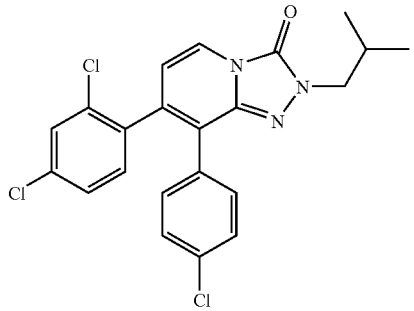

To a stirring, degassed mixture of 7-bromo-8-(4-chlorophenyl)-2-isobutyl-[1,2,4]triazolo[4,3-a]pyridin-3(2H)-one (20 mg, 0.05 mmol), 2,4-dichlorophenylboronic acid (38 mg, 0.20 mmol), and tetrakis(triphenylphosphine)palladium (3 mg, 0.002 mmol) in dioxane (0.4 mL) at 20° C. was added K₂CO₃ (30 mg, 0.2 mmol) in water (0.13 mL). The resulting reaction mixture was heated in a microwave reactor at 200° C. for 10 min under argon. Analysis by HPLC/MS indicated that starting material had been consumed. The reaction mixture was brought to room temperature and was concentrated under reduced pressure. The crude product was purified by reverse phase preparative HPLC (acetonitrile-water-TFA) to isolate the title compound (7 mg, 0.016 mmol) as a yellow oil. MS: [M+H]⁺=446.

Example 127

Preparation of 8-(4-chlorophenyl)-2-isobutyl-7-(4-methoxyphenyl)-[1,2,4]triazolo[4,3-a]pyridin-3(2H)-one

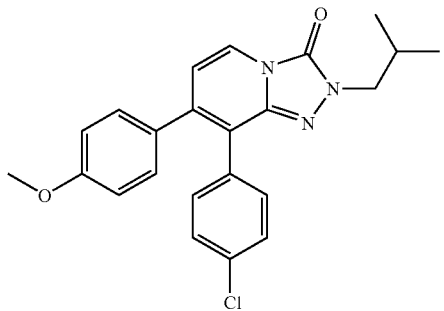

To a stirring, degassed mixture of 7-bromo-8-(4-chlorophenyl)-2-isobutyl-[1,2,4]triazolo[4,3-a]pyridin-3(2H)-one (0.05 g, 0.13 mmol), 4-methoxyphenylboronic acid (0.06 g, 0.39 mmol), and tetrakis(triphenylphosphine)palladium (8 mg, 0.007 mmol) in dioxane (1.0 mL) at 20° C. was added K₂CO₃ (0.04 g, 0.26 mmol) in water (0.34 mL). The resulting reaction mixture was heated in a microwave reactor at 150° C. for 10 min under argon. Analysis by HPLC/MS indicated that starting material had been consumed. The reaction mixture was brought to room temperature and was concentrated under reduced pressure. The crude product was purified by reverse

Example 128

Preparation of 8-(4-chlorophenyl)-2-isobutyl-7-(6-methoxypyridin-3-yl)-[1,2,4]triazolo[4,3-a]pyridin-3(2H)-one

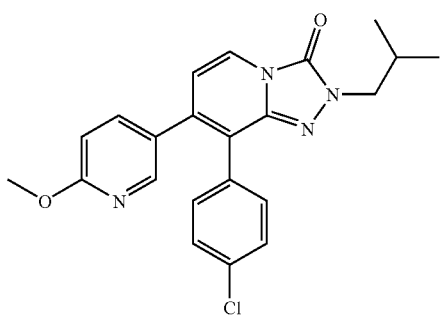

To a stirring, degassed mixture of 7-bromo-8-(4-chlorophenyl)-2-isobutyl-[1,2,4]triazolo[4,3-a]pyridin-3(2H)-one (0.05 g, 0.13 mmol), 2-methoxy-5-(4,4,5,5-tetramethyl-1,3,2-dioxaboralan-2-yl)pyridine (0.09 g, 0.39 mmol), and tetrakis(triphenylphosphine)palladium (8 mg, 0.007 mmol) in dioxane (1.0 mL) at 20° C. was added $K_2CO_3$ (0.04 g, 0.26 mmol) in water (0.34 mL). The resulting reaction mixture was heated in a microwave reactor at 150° C. for 10 min under argon. Analysis by HPLC/MS indicated that starting material had been consumed. The reaction mixture was brought to room temperature and was concentrated under reduced pressure. The crude product was purified by reverse phase preparative HPLC (acetonitrile-water-TFA) to isolate 27 mg of the title compound as a yellow solid. MS: $[M+H]^+=409$.

Example 129

Preparation of 8-(4-chlorophenyl)-7-(3-chloropyridin-4-yl)-2-isobutyl-[1,2,4]triazolo[4,3-a]pyridin-3(2H)-one

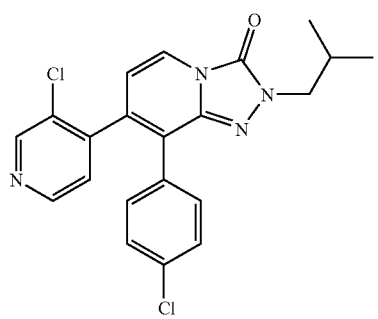

To a stirring, degassed mixture of 7-bromo-8-(4-chlorophenyl)-2-isobutyl-[1,2,4]triazolo[4,3-a]pyridin-3(2H)-one (20 mg, 0.05 mmol), 2-chloro-4-pyridylboronic acid (31 mg, 0.20 mmol), and tetrakis(triphenylphosphine)palladium (3 mg, 0.002 mmol) in dioxane (0.4 mL) at 20° C. was added $K_2CO_3$ (30 mg, 0.2 mmol) in water (0.13 mL). The resulting reaction mixture was heated in a microwave reactor at 200° C. for 10 min under argon. Analysis by HPLC/MS indicated that starting material had been consumed. The reaction mixture was brought to room temperature and was concentrated under reduced pressure. The crude product was purified by reverse phase preparative HPLC (acetonitrile-water-TFA) to isolate the title compound (5 mg, 0.011 mmol) as an off-white solid. MS: $[M+H]^+=446$.

Example 130

Preparation of 2-isobutyl-7-(4-methoxyphenyl)-8-p-tolyl-[1,2,4]triazolo[4,3-a]pyridin-3(2H)-one

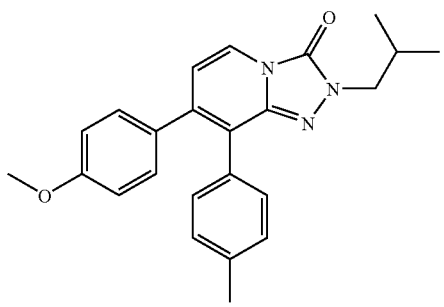

A. Preparation of 7-bromo-2-isobutyl-8-p-tolyl-[1,2,4]triazolo[4,3-a]pyridin-3(2H)-one

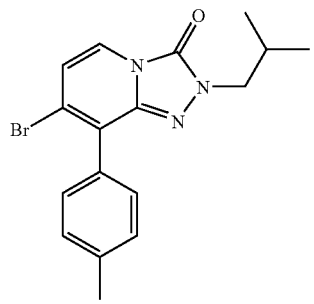

To a stirring, degassed mixture of 7-bromo-8-iodo-2-isobutyl-[1,2,4]triazolo[4,3-a]pyridin-3(2H)-one (0.1 g, 0.25 mmol), 4-methylphenylboronic acid (0.04 g, 0.28 mmol), and tetrakis(triphenylphosphine)palladium (15 mg, 0.013 mmol) in dioxane (2.0 mL) at 20° C. was added $K_2CO_3$ (0.04 g, 0.28 mmol) in water (0.6 mL). The resulting reaction mixture was stirred at 100° C. for 15 h under argon. Analysis by HPLC/MS indicated that starting material had been consumed. The reaction mixture was brought to room temperature and was concentrated under reduced pressure. The crude product was purified by reverse phase preparative HPLC (acetonitrile-water-TFA) to isolate 31 mg of the title compound as a yellow oil. MS: $[M+H]^+=360$.

B. Preparation of 2-isobutyl-7-(4-methoxyphenyl)-8-p-tolyl-[1,2,4]triazolo[4,3-a]pyridin-3(2H)-one

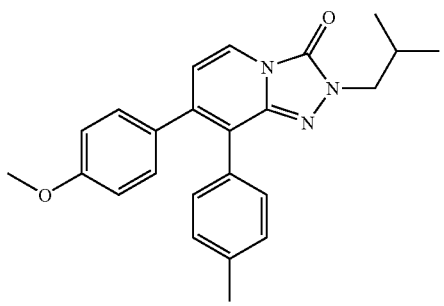

To a stirring, degassed mixture of 7-bromo-2-isobutyl-8-p-tolyl-[1,2,4]triazolo[4,3-a]pyridin-3(2H)-one (0.015 g, 0.04 mmol), 4-methoxyphenylboronic acid (0.026 g, 0.17 mmol), and tetrakis(triphenylphosphine)palladium (2.5 mg, 0.002 mmol) in dioxane (0.3 mL) at 20° C. was added $K_2CO_3$ (0.024 g, 0.17 mmol) in water (0.11 mL). The resulting reaction mixture was heated in a microwave reactor at 150° C. for 10 min under argon. Analysis by HPLC/MS indicated that starting material had been consumed. The reaction mixture was brought to room temperature and was concentrated under reduced pressure. The crude product was purified by reverse phase preparative HPLC (acetonitrile-water-TFA) to isolate 14 mg of the title compound as a yellow solid. MS: [M+H]$^+$=389.

Example 131

Preparation of 2-isobutyl-7-(6-methoxypyridin-3-yl)-8-p-tolyl-[1,2,4]triazolo[4,3-a]pyridin-3(2H)-one

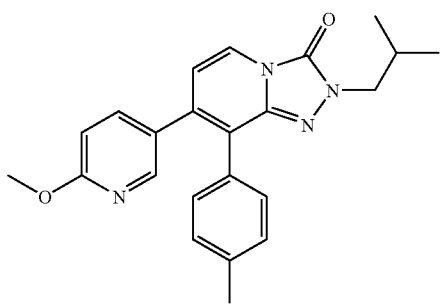

To a stirring, degassed mixture of 7-bromo-2-isobutyl-8-p-tolyl-[1,2,4]triazolo[4,3-a]pyridin-3(2H)-one (0.015 g, 0.04 mmol), 2-methoxy-5-(4,4,5,5-tetramethyl-1,3,2-dioxaborolan-2-yl)pyridine (0.04 g, 0.17 mmol), and tetrakis(triphenylphosphine)palladium (2.5 mg, 0.002 mmol) in dioxane (0.3 mL) at 20° C. was added $K_2CO_3$ (0.024 g, 0.17 mmol) in water (0.11 mL). The resulting reaction mixture was heated in a microwave reactor at 150° C. for 10 min under argon. Analysis by HPLC/MS indicated that starting material had been consumed. The reaction mixture was brought to room temperature and was concentrated under reduced pressure. The crude product was purified by reverse phase preparative HPLC (acetonitrile-water-TFA) to isolate 5 mg of the title compound as a white solid. MS: [M+H]$^+$=388.

Example 132

Preparation of 2-butyl-7,8-bis(4-chlorophenyl)-[1,2,4]triazolo[4,3-a]pyridin-3(2H)-one

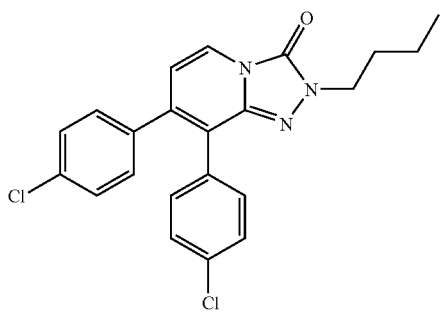

A. Preparation of 7,8-bis(4-chlorophenyl)-[1,2,4]triazolo[4,3-a]pyridin-3(2H)-one

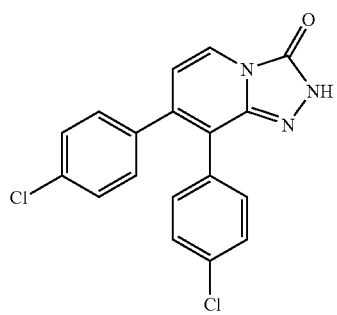

To a stirring mixture of 7-bromo-8-iodo-[1,2,4]triazolo[4,3-a]pyridin-3(2H)-one (1.0 g, 2.9 mmol) in 15 mL dioxane and 5 mL of water at 20° C. was added 4-chlorophenylboronic acid (1.4 g, 8.8 mmol), $K_2CO_3$ (0.8 g, 5.9 mmol), and tetrakis(triphenylphosphine)palladium (0.17 g, 0.15 mmol). The resulting reaction mixture was degassed and then heated in a microwave reactor at 150° C. for 40 min under argon. Analysis by HPLC/MS indicated that starting material had been consumed. The reaction mixture was allowed to cool to room temperature and was concentrated under reduced pressure. The crude product was purified by trituration with methylene chloride to obtain the title compound (0.52 g, 1.5 mmol) as a light yellow solid. MS: [M+H]$^+$=356. $^1$H NMR (CD$_3$OD): δ 7.89 (d, J=1.9 Hz, 1H), 7.37-7.24 (m, 8H), 5.48 (s, 1H).

B. Preparation of 2-butyl-7,8-bis(4-chlorophenyl)-[1,2,4]triazolo[4,3-a]pyridin-3(2H)-one

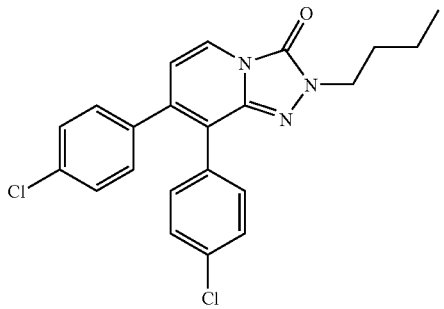

To a stirring mixture of 7,8-bis(4-chlorophenyl)-[1,2,4]triazolo[4,3-a]pyridin-3(2H)-one (50 mg, 0.14 mmol) and K$_2$CO$_3$ (40 mg, 0.28 mmol) in DMF (0.47 mL) at 20° C. was added 4-bromobutane (40 mg, 0.28 mmol). The resulting reaction mixture was heated at 80° C. for 30 min. Analysis by HPLC/MS indicated that starting material had been consumed. The reaction mixture was brought to room temperature, diluted with water, and extracted twice with diethyl ether. The combined organic extract was washed with saturated aqueous NaHCO$_3$ solution, then brine, then dried (MgSO$_4$), filtered, and concentrated under reduced pressure. The crude product was purified by reverse phase preparative HPLC (acetonitrile-water-TFA) to isolate the title compound (18 mg, 0.044 mmol) as a light yellow solid. MS: [M+H]$^+$= 412.

Example 133

Preparation of 4-(7,8-bis(4-chlorophenyl)-3-oxo-[1,2,4]triazolo[4,3-a]pyridin-3(2H)-yl)butanenitrile

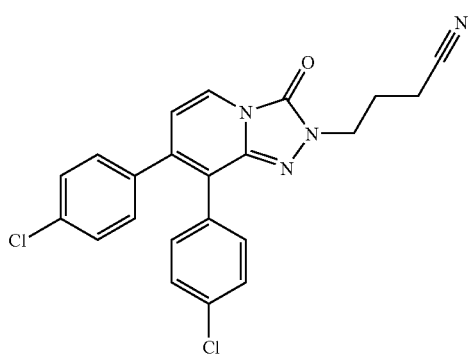

To a stirring mixture of 7,8-bis(4-chlorophenyl)-[1,2,4]triazolo[4,3-a]pyridin-3(2H)-one (50 mg, 0.14 mmol) and K$_2$CO$_3$ (40 mg, 0.28 mmol) in DMF (0.47 mL) at 20° C. was added 4-bromobutanenitrile (40 mg, 0.28 mmol). The resulting reaction mixture was heated at 80° C. for 60 min. Analysis by HPLC/MS indicated that starting material had been consumed. The reaction mixture was brought to room temperature, diluted with water, and extracted twice with diethyl ether. The combined organic extract was washed with saturated aqueous NaHCO$_3$ solution, then brine, then dried (MgSO$_4$), filtered, and concentrated under reduced pressure. The crude product was purified by reverse phase preparative HPLC (acetonitrile-water-TFA) to isolate the title compound (23 mg, 0.054 mmol) as a yellow solid. MS: [M+H]$^+$=423.

Example 134

Preparation of 7,8-bis(4-chlorophenyl)-2-(4,4,4-trifluorobutyl)-[1,2,4]triazolo[4,3-a]pyridin-3(2H)-one

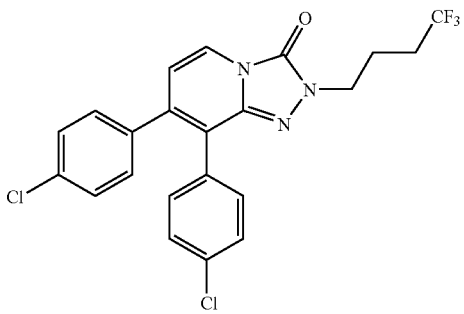

To a stirring mixture of 7,8-bis(4-chlorophenyl)-[1,2,4]triazolo[4,3-a]pyridin-3(2H)-one (50 mg, 0.14 mmol) and K$_2$CO$_3$ (40 mg, 0.28 mmol) in DMF (0.47 mL) at 20° C. was added 4-bromo-1,1,1-trifluorobutane (50 mg, 0.28 mmol). The resulting reaction mixture was heated at 80° C. for 60 min. Analysis by HPLC/MS indicated that starting material had been consumed. The reaction mixture was brought to room temperature, diluted with water, and extracted twice with diethyl ether. The combined organic extract was washed with saturated aqueous NaHCO$_3$ solution, then brine, then dried (MgSO$_4$), filtered, and concentrated under reduced pressure. The crude product was purified by reverse phase preparative HPLC (acetonitrile-water-TFA) to isolate the title compound (18 mg, 0.039 mmol) as a yellow oil. MS: [M+H]$^+$= 466.

Example 135

Preparation of 7,8-bis(4-chlorophenyl)-2-isopentyl-[1,2,4]triazolo[4,3-a]pyridin-3(2H)-one

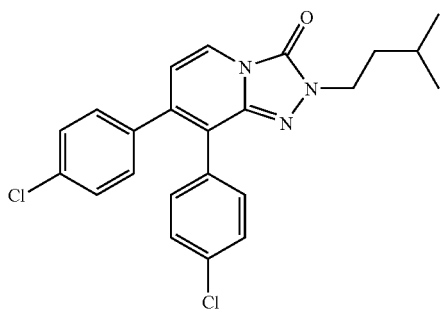

To a stirring mixture of 7,8-bis(4-chlorophenyl)-[1,2,4]triazolo[4,3-a]pyridin-3(2H)-one (50 mg, 0.14 mmol) and K$_2$CO$_3$ (40 mg, 0.28 mmol) in DMF (0.47 mL) at 20° C. was added 1-bromo-3-methylbutane (40 mg, 0.28 mmol). The resulting reaction mixture was heated at 80° C. for 60 min. Analysis by HPLC/MS indicated that starting material had been consumed. The reaction mixture was brought to room temperature, diluted with water, and extracted twice with diethyl ether. The combined organic extract was washed with saturated aqueous NaHCO$_3$ solution, then brine, then dried (MgSO$_4$), filtered, and concentrated under reduced pressure. The crude product was purified by reverse phase preparative HPLC (acetonitrile-water-TFA) to isolate the title compound (27 mg, 0.063 mmol) as a yellow oil. MS: [M+H]$^+$=426.

Example 136

Preparation of 7,8-bis(4-chlorophenyl)-2-(3,3,3-trifluoropropyl)-[1,2,4]triazolo[4,3-a]pyridin-3(2H)-one

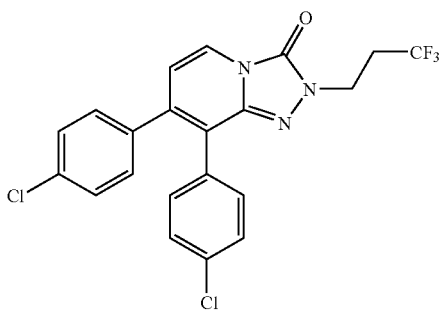

To a stirring mixture of 7,8-bis(4-chlorophenyl)-[1,2,4]triazolo[4,3-a]pyridin-3(2H)-one (50 mg, 0.14 mmol) and K$_2$CO$_3$ (40 mg, 0.28 mmol) in DMF (0.47 mL) at 20° C. was added 3-bromo-1,1,1-trifluoropropane (50 mg, 0.28 mmol). The resulting reaction mixture was heated at 80° C. for 60 min. Analysis by HPLC/MS indicated that starting material had been consumed. The reaction mixture was brought to room temperature, diluted with water, and extracted twice with diethyl ether. The combined organic extract was washed with saturated aqueous NaHCO$_3$ solution, then brine, then dried (MgSO$_4$), filtered, and concentrated under reduced pressure. The crude product was purified by reverse phase preparative HPLC (acetonitrile-water-TFA) to isolate the title compound (37 mg, 0.082 mmol) as a yellow oil. MS: [M+H]$^+$= 452.

Example 137

Preparation of 3-(7,8-bis(4-chlorophenyl)-3-oxo)-[1,2,4]triazolo[4,3-a]pyridin-3(2H)-yl)propanenitrile

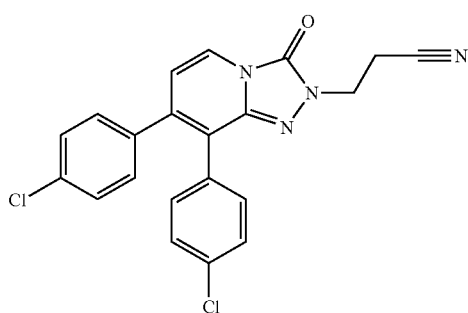

To a stirring mixture of 7,8-bis(4-chlorophenyl)-[1,2,4]triazolo[4,3-a]pyridin-3(2H)-one (50 mg, 0.14 mmol) and K$_2$CO$_3$ (40 mg, 0.28 mmol) in DMF (0.47 mL) at 20° C. was added 3-bromopropanenitrile (40 mg, 0.28 mmol). The resulting reaction mixture was heated at 80° C. for 15 h. Analysis by HPLC/MS at 15 h indicated that starting material had been consumed. The reaction mixture was brought to room temperature, diluted with water, and extracted twice with diethyl ether. The combined organic extract was washed with saturated aqueous NaHCO$_3$ solution, then brine, then dried (MgSO$_4$), filtered, and concentrated under reduced pressure. The crude product was purified by reverse phase preparative HPLC (acetonitrile-water-TFA) to isolate the title compound (23 mg, 0.056 mmol) as a yellow solid. MS: [M+H]$^+$=409.

Example 138

Preparation of 7-(4-chlorophenyl)-5-methyl-2-((2-methyl-6-(trifluoromethyl)pyridin-3-yl)methyl)-8-(pyridin-4-yl)-[1,2,4]triazolo[4,3-a]pyridin-3(2H)-one

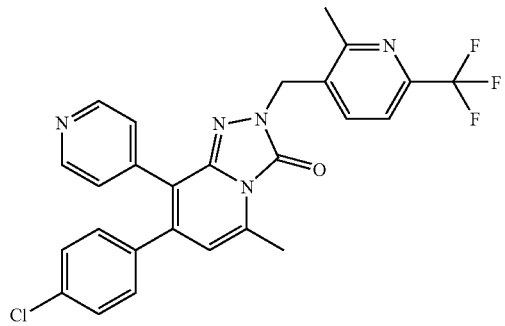

A. Preparation of 4-(4-chlorophenyl)-6-methylpyridin-2(1H)-one

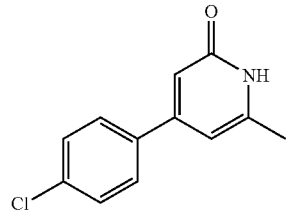

A suspension of (E)-4-(4-chlorophenyl)but-3-en-2-one (5.42 g, 30 mmol, Aldrich Chemical Co.), 1-(2-ethoxy-2-oxoethyl)pyridinium chloride (6.05 g, 30 mmol) (prepared according to the procedure described in WO 94/04502) and ammonium acetate (46.3 g, 0.6 mol) in ethanol (150 mL) was stirred at room temperature for 15 min, then at reflux for 4 h. The reaction mixture was allowed to cool and stand at room temperature overnight. The resulting precipitate was collected by filtration, and the collected solid was washed with ethanol, then water, and dried in a vacuum oven at 45° C. for 16 h to afford 3.1 g (47%) of the title compound as an off-white solid. HPLC/MS: retention time=2.86 min, [M+H]$^+$= 220.3.

B. Preparation of 3-bromo-4-(4-chlorophenyl)-6-methylpyridin-2(1H)-one

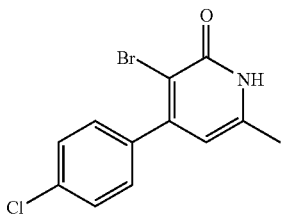

A suspension of 4-(4-chlorophenyl)-6-methylpyridin-2 (1H)-one (0.44 g, 2.0 mmol) in methanol (30 mL) was refluxed until a clear solution formed. The solution was allowed to cool to 40° C., then NBS (285 mg, 1.6 mmol) was added in small portions over 30 min. After completion of the addition, analysis by HPLC/MS indicated about 40% of the starting 4-(4-chlorophenyl)-6-methylpyridin-2(1H)-one remained. Additional NBS (142 mg, 0.8 mmol) was added in portions over 10 min. The reaction mixture was stirred at room temperature for 1 h, then concentrated under reduced pressure. The residue was triturated with a mixture of water (50 mL) and EtOAc (50 mL), and filtered to obtain a solid product which contained mainly the regioisomeric bromide, 5-bromo-4-(4-chlorophenyl)-6-methylpyridin-2(1H)-one. The filtrate was extracted with EtOAc (30 mL×3). The combined extracts were washed with aqueous saturated NaCl solution, dried (Na$_2$SO$_4$), filtered, and concentrated under reduced pressure. The residue was purified using a silica gel cartridge (80 g) eluted with a gradient of EtOAc (30-100%) in hexanes to afford 280 mg (47%) of the title product as a white solid. HPLC/MS: retention time=3.15 min, [M+H]$^+$=298.0.

C. Preparation of 3-bromo-2-chloro-4-(4-chlorophenyl)-6-methylpyridine

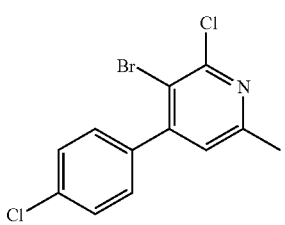

To a suspension of 3-bromo-4-(4-chlorophenyl)-6-methylpyridin-2(1H)-one (280 mg, 0.94 mmol) in phosphorus oxychloride (5 mL) was added anhydrous DMF (a few drops). The mixture was stirred at 100° C. for 7 h. After cooling to room temperature, the reaction mixture was concentrated under reduced pressure to remove most of the phosphorus oxychloride. The remaining liquid was cooled at 0° C. and carefully quenched by addition of water. The resulting mixture was then adjusted to pH 7-8 by addition of saturated aqueous NaHCO$_3$. The mixture was then extracted with EtOAc (30 mL×3). The combined EtOAc extracts were washed with saturated aqueous NaCl, dried over Na$_2$SO$_4$, filtered and concentrated under reduced pressure. The residue was purified using a silica gel cartridge (12 g) eluted with a gradient of EtOAc (0-70%) in hexanes to obtain 180 mg (60%) of the title compound as a white solid. HPLC/MS: retention time=3.95 min, [M+H]$^+$=316.0.

D. Preparation of 3-bromo-4-(4-chlorophenyl)-2-hydrazinyl-6-methylpyridine

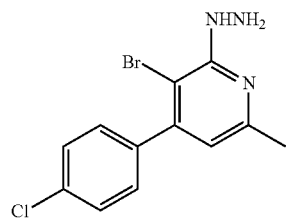

To a suspension of 3-bromo-2-chloro-4-(4-chlorophenyl)-6-methylpyridine (0.18 g, 0.56 mmol) in dioxane (4 mL) at room temperature was added anhydrous hydrazine (0.4 mL). The resulting mixture was stirred at 65° C. for 1 h. Analysis by HPLC/MS indicated the reaction was not complete. Additional anhydrous hydrazine (0.3 mL) was added, and the reaction mixture was stirred at 65° C. for 4 h more. After cooling to room temperature, the reaction mixture was concentrated under reduced pressure. To the residue was added water, and the resulting suspension was sonicated for 5 min. The resulting slurry was filtered, and the collected solid was washed with water (10 mL×2), then dried in a 45° C. vacuum oven for 16 h to afford 160 mg (90%) of the title compound as a white solid. HPLC/MS: retention time=2.53 min, [M+H]$^+$=312.1.

E. Preparation of 8-bromo-7-(4-chlorophenyl)-5-methyl-[1,2,4]triazolo[4,3-a]pyridin-3(2H)-one

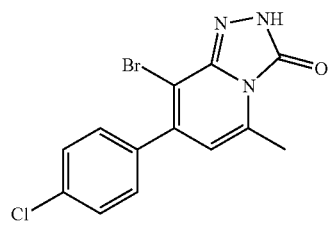

To a solution of triphosgene (225 mg, 0.75 mmol) in anhydrous THF (2.5 mL) at 60° C. was added 3-bromo-4-(4-chlorophenyl)-2-hydrazinyl-6-methylpyridine (80 mg, 0.256 mmol) in small portions over 5 min. The resulting suspension was refluxed for 30 min. After cooling to room temperature, the reaction mixture was concentrated under reduced pressure to remove most of the THF. Water (5 mL) was added carefully to the remaining solution to destroy the excess triphosgene. The resulting aqueous suspension was stirred at room temperature for 30 min, then filtered. The collected solid was washed with water (5 mL×2), the hexanes, and dried in a 45° C. vacuum oven for 3 h to afford 70 mg (84%) of the title compound as a yellow solid. HPLC/MS: retention time=3.38 min, [M+H]$^+$=338.0.

F. Preparation of 8-bromo-7-(4-chlorophenyl)-5-methyl-2-((2-methyl-6-(trifluoromethyl)pyridin-3-yl)methyl)-[1,2,4]triazolo[4,3-a]pyridin-3(2H)-one

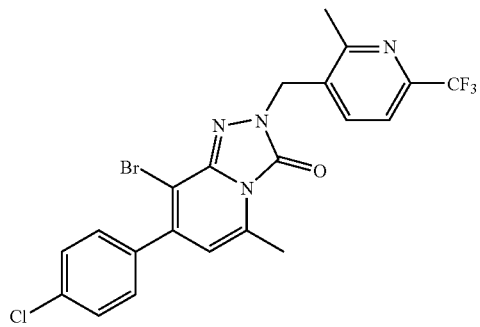

To a solution of 8-bromo-7-(4-chlorophenyl)-5-methyl-[1,2,4]triazolo[4,3-a]pyridin-3(2H)-one (42 mg, 0.124 mmol), and 3-(chloromethyl)-2-methyl-6-(trifluoromethyl)pyridine (39 mg, 0.186 mmol) in anhydrous DMF (0.5 mL) was added anhydrous potassium carbonate (34.6 mg, 0.25 mmol). The resulting suspension was stirred under argon at 80° C. for 1 h. After cooling to room temperature, the reaction mixture was diluted with water (10 mL). The resulting precipitate was filtered, washed with water, and dried in a vacuum oven at 60° C. for 16 h to afford 56 mg (89%) of the title compound as an off-white solid. HPLC/MS: retention time=4.15 min, [M+H]$^+$=512.2.

G. Preparation of 7-(4-chlorophenyl)-5-methyl-2-((2-methyl-6-(trifluoromethyl)pyridin-3-yl)methyl)-8-(pyridin-4-yl)-[1,2,4]triazolo[4,3-a]pyridin-3(2H)-one

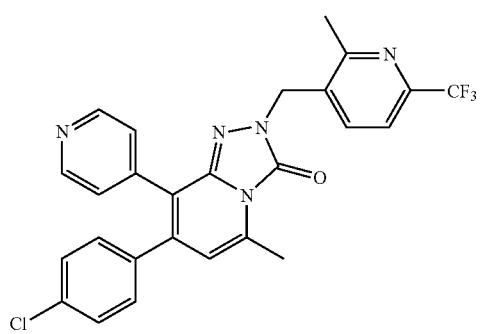

To a suspension of 8-bromo-7-(4-chlorophenyl)-5-methyl-2-((2-methyl-6-(trifluoromethyl)pyridin-3-yl)methyl)-[1,2,4]triazolo[4,3-a]pyridin-3(2H)-one (53 mg, 0.103 mmol), 4-(4,4,5,5-tetramethyl-1,3,2-dioxaborolan-2-yl)pyridine (84 mg, 0.414 mmol), and 2.0 M aqueous sodium carbonate (1 mL, 2 mmol) in toluene (2 mL) was added (Ph$_3$P)$_4$Pd (36 mg, 0.03 mmol), and the resulting yellow mixture was vigorously stirred under argon at 100° C. for 16 h. After cooling to room temperature, the reaction mixture was diluted with water and extracted with EtOAc (20 mL×3). The combined EtOAc extracts were washed with water, then saturated aqueous NaCl, dried over Na$_2$SO$_4$, filtered and concentrated under reduced pressure. The crude product was purified using a silica gel cartridge (12 g) eluted with a gradient of EtOAc (30-70%) in hexanes to obtain 85 mg of the desired product, which was contaminated with triphenylphosphine oxide. The product was further purified using preparative reverse phase HPLC (Phenomenex Luna 5 μm C-18 21.2×100 mm column eluted with a linear gradient of 50% to 90% B over 10 min (A=90% water, 10% methanol and B=90% methanol, 10% water) with flow rate at 20 mL/min and UV detection at 220 nm). The desired fractions were concentrated under reduced pressure. The residue was dissolved in acetonitrile, frozen and lyophilized to afford 32 mg (62%) of the title compound as a light yellow powder. HPLC/MS: retention time=3.00 min, [M+H]$^+$=510.4.

Example 139

Preparation of 7-(4-chlorophenyl)-5-methyl-8-(pyridin-4-yl)-2-((6-(trifluoromethyl)pyridin-3-yl)methyl)-[1,2,4]triazolo[4,3-a]pyridin-3(2H)-one

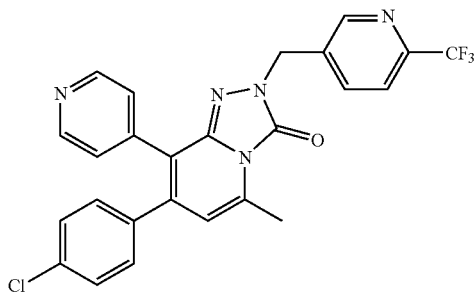

A. Preparation of 8-bromo-7-(4-chlorophenyl)-5-methyl-2-((6-(trifluoromethyl)pyridin-3-yl)methyl)-[1,2,4]triazolo[4,3-a]pyridin-3(2H)-one

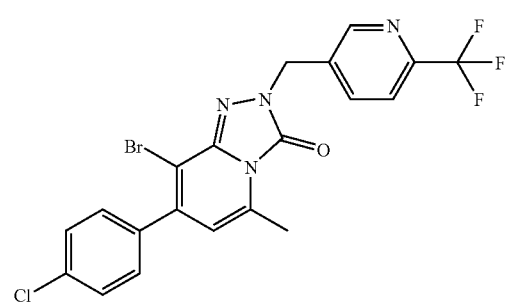

The title compound (27 mg, 74%) was prepared from 8-bromo-7-(4-chlorophenyl)-5-methyl-[1,2,4]triazolo[4,3-a]pyridin-3(2H)-one (25 mg, 0.074 mmol) and 5-(chloromethyl)-2-(trifluoromethyl)pyridine (21.7 mg, 0.11 mmol) by procedures analogous to those used for the preparation of 8-bromo-7-(4-chlorophenyl)-5-methyl-2-((2-methyl-6-(trifluoromethyl)pyridin-3-yl)methyl)-[1,2,4]triazolo[4,3-a]pyridin-3(2H)-one. HPLC/MS: retention time=4.03 min, [M+H]$^+$=498.1.

B. Preparation of 7-(4-chlorophenyl)-5-methyl-8-(pyridin-4-yl)-2-((6-(trifluoromethyl)pyridin-3-yl)methyl)-[1,2,4]triazolo[4,3-a]pyridin-3(2H)-one

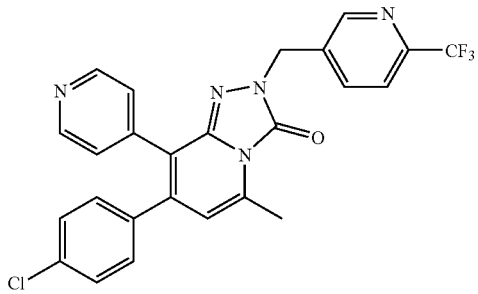

The title compound (20 mg, 81%) as a light yellow powder was prepared from 8-bromo-7-(4-chlorophenyl)-5-methyl-2-((6-(trifluoromethyl)pyridin-3-yl)methyl)-[1,2,4]triazolo[4,3-a]pyridin-3(2H)-one (25 mg, 0.05 mmol) by procedures analogous to those used for the preparation of 7-(4-chlorophenyl)-5-methyl-2-((2-methyl-6-(trifluoromethyl)pyridin-3-yl)methyl)-8-(pyridin-4-yl)-[1,2,4]triazolo[4,3-a]pyridin-3(2H)-one. HPLC/MS: retention time=2.92 min, [M+H]$^+$=496.3.

Example 140

Preparation of 6-((7-(4-chlorophenyl)-5-methyl-3-oxo-8-(pyridin-4-yl)-[1,2,4]triazolo[4,3-a]pyridine-2(3H)-yl)methyl)nicotinonitrile

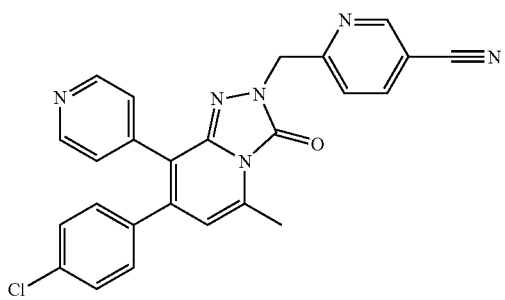

A. Preparation of 6-((8-bromo-7-(4-chlorophenyl)-5-methyl-3-oxo-[1,2,4]triazolo[4,3-a]pyridine-2(3H)-yl)methyl)nicotinonitrile

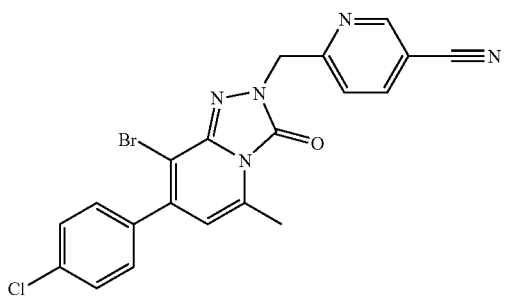

To a stirring solution of 8-bromo-7-(4-chlorophenyl)-5-methyl-[1,2,4]triazolo[4,3-a]pyridin-3(2H)-one (40 mg, 0.11 mmol) in DMF (0.25 mL) at room temperature under argon was added K$_2$CO$_3$ (50 mg, 0.36 mmol), followed by 6-(chloromethyl)nicotinonitrile (20 mg, 0.13 mmol). The reaction mixture was stirred at 70° C. for 1 h. The reaction mixture was cooled to room temperature, water (2 mL) and EtOAc (5 mL) were added. The layers were separated. The organic layer was dried (MgSO$_4$), filtered, and concentrated under reduced pressure to obtain 55 mg of the title compound as a yellow solid. HPLC/MS: retention time=3.55 min, [M+H]$^+$=454.

B. Preparation of 6-((7-(4-chlorophenyl)-5-methyl-3-oxo-8-(pyridin-4-yl)-[1,2,4]triazolo[4,3-a]pyridine-2(3H)-yl)methyl)nicotinonitrile

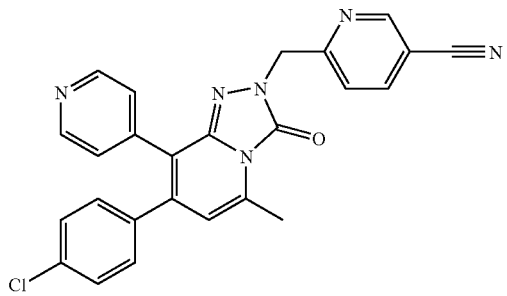

In a pressure tube, to a stirring solution of 6-((8-bromo-7-(4-chlorophenyl)-5-methyl-3-oxo-[1,2,4]triazolo[4,3-a]pyridine-2(3H)-yl)methyl)nicotinonitrile (54 mg, 0.11 mmol) in THF (2 mL) at room temperature under argon was added 4-(4,4,5,5-tetramethyl-1,3,2-dioxaborolan-2-yl)pyridine (45 mg, 0.22 mmol), 1,1'-bis(diphenylphosphino)ferrocene palladium (II) chloride complex with dichloromethane (9 mg, 0.011 mmol) and powdered K$_3$PO$_4$ (60 mg, 0.28 mmol). The resulting suspension was stirred and heated at 100° C. under argon for 7 h. The reaction mixture was filtered through filter paper and the filtrate was concentrated under vacuum to a dark brown solid. The crude product thus obtained was purified by reverse phase preparative HPLC (without TFA) to obtain 31 mg of the title compound as a yellow solid. HPLC/MS: retention time=2.482 min, [M+H]$^+$=453.

Example 141

Preparation of 7-(4-chlorophenyl)-5-methyl-6-phenyl-2-((6-(trifluoromethyl)pyridin-3-yl)methyl)-[1,2,4]triazolo[4,3-a]pyridin-3(2H)-one

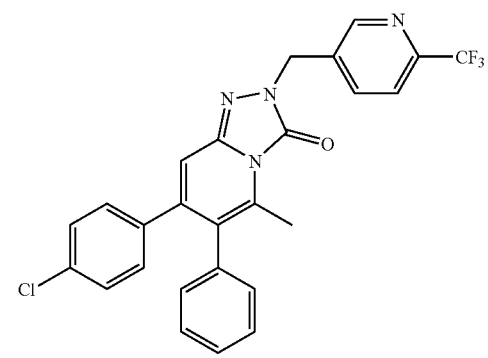

A. Preparation of 5-bromo-4-(4-chlorophenyl)-6-methylpyridin-2(1H)-one

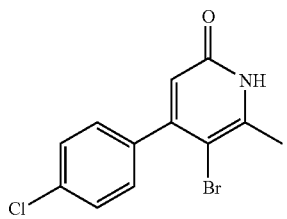

To a solution of 4-(4-chlorophenyl)-6-methylpyridin-2(1H)-one (1.1 g, 5.0 mmol) in DMF (20 mL) was added NBS (1.07 g, 6.0 mmol) in small portions over 15 min. The reaction mixture was stirred at room temperature for 20 min. Analysis by HPLC/MS indicated the starting 4-(4-chlorophenyl)-6-methylpyridin-2(1H)-one was consumed, and about 17% (based on the UV absorption) of the desired product had formed. The reaction mixture was partitioned between water (50 mL) and EtOAc (50 mL). The resulting suspension was filtered, and the collected solid was washed with water, the dried in a vacuum oven at 50° C. for 16 h to afford 250 mg (17%) of the title compound as an off-white solid. HPLC/MS: retention time=3.35 min, [M+H]$^+$=298.2.

B. Preparation of 3-bromo-6-chloro-4-(4-chlorophenyl)-2-methylpyridine

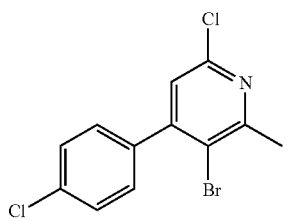

To a suspension of 5-bromo-4-(4-chlorophenyl)-6-methylpyridin-2(1H)-one (300 mg, 1.0 mmol) in phosphorus oxychloride (5 mL) was added anhydrous DMF (0.015 mL). The mixture was stirred at 100° C. for 20 h. Analysis by HPLC/MS indicated about 27% of the starting 5-bromo-4-(4-chlorophenyl)-6-methylpyridin-2(1H)-one remained. Additional phosphorus oxychloride (1 mL) was added, followed by anhydrous DMF (0.1 mL). The reaction mixture was stirred at 100° C. for 24 h more. After cooling to room temperature, the reaction mixture was concentrated under reduced pressure to remove most of the phosphorus oxychloride. The residue was dissolved in EtOAc, washed with saturated aqueous NaHCO$_3$, then saturated aqueous NaCl, dried over Na$_2$SO$_4$, filtered and concentrated under reduced pressure. The crude product was purified using a silica gel cartridge (12 g) eluted with a gradient of EtOAc (20-40%) in hexanes to obtain 220 mg (70%) of the title compound as a white solid. HPLC/MS: retention time=4.07 min, [M+H]$^+$=316.2.

C. Preparation of 3-bromo-4-(4-chlorophenyl)-6-hydrazinyl-2-methylpyridine

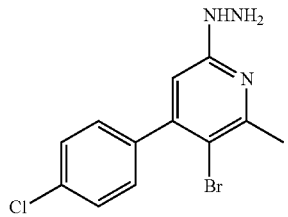

The title compound (200 mg, 92% yield) as a white solid was prepared from 3-bromo-6-chloro-4-(4-chlorophenyl)-2-methylpyridine (220 mg, 0.7 mmol) by procedures analogous to those used for the preparation of 3-bromo-4-(4-chlorophenyl)-2-hydrazinyl-6-methylpyridine. HPLC/MS: retention time=2.87 min, [M+H]$^+$=312.2.

D. Preparation of 6-bromo-7-(4-chlorophenyl)-5-methyl-[1,2,4]triazolo[4,3-a]pyridin-3(2H)-one

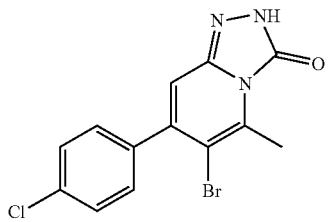

The title compound (125 mg, 96% yield) as a pale yellow solid was prepared from 3-bromo-4-(4-chlorophenyl)-6-hydrazinyl-2-methylpyridine (120 mg, 0.384 mmol) by procedures analogous to those used for the preparation of 8-bromo-7-(4-chlorophenyl)-5-methyl-[1,2,4]triazolo[4,3-a]pyridin-3(2H)-one. HPLC/MS: retention time=3.65 min, [M+H]$^+$=338.2.

E. Preparation of 6-bromo-7-(4-chlorophenyl)-5-methyl-2-((6-(trifluoromethyl)pyridin-3-yl)methyl)-[1,2,4]triazolo[4,3-a]pyridin-3(2H)-one

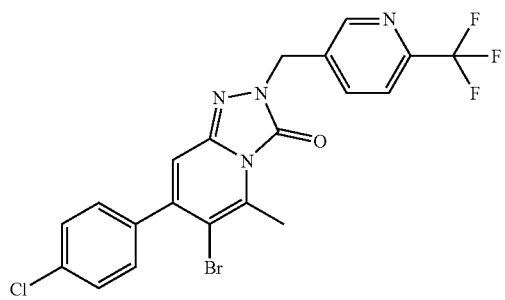

The title compound (120 mg, 66% yield) as an off-white solid was prepared from 6-bromo-7-(4-chlorophenyl)-5-methyl-[1,2,4]triazolo[4,3-a]pyridin-3(2H)-one (125 mg, 0.369 mmol) by procedures analogous to those used for the preparation of 8-bromo-7-(4-chlorophenyl)-5-methyl-2-((6-(trifluoromethyl)pyridin-3-yl)methyl)-[1,2,4]triazolo[4,3-a]pyridin-3(2H)-one. HPLC/MS: retention time=4.10 min, [M+H]⁺=497.2.

F. Preparation of 7-(4-chlorophenyl)-5-methyl-6-phenyl-2-((6-(trifluoromethyl)pyridin-3-yl)methyl)-[1,2,4]triazolo[4,3-a]pyridin-3(2H)-one

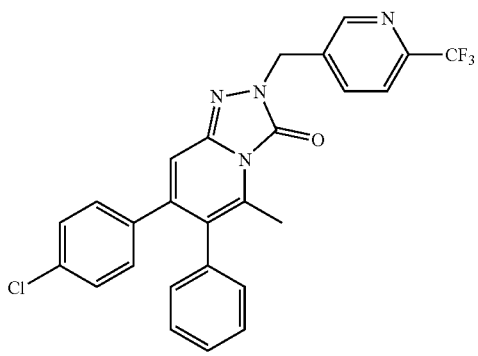

The title compound (17 mg, 68%) as a light yellow powder was prepared from 6-bromo-7-(4-chlorophenyl)-5-methyl-2-((6-(trifluoromethyl)pyridin-3-yl)methyl)-[1,2,4]triazolo[4,3-a]pyridin-3(2H)-one (25 mg, 0.05 mmol) and phenylboronic acid (25 mg, 0.2 mmol) by procedures analogous to those used for the preparation of 4-(2-((2-methyl-6-(trifluoromethyl)pyridin-3-yl)methyl)-3-oxo-8-phenyl-2,3-dihydro-[1,2,4]triazolo[4,3-a]pyridin-7-yl)benzonitrile. HPLC/MS: retention time=4.14 min, [M+H]⁺=495.3.

Example 142

Preparation of 7-(4-chlorophenyl)-5-methyl-6-(pyridin-4-yl)-2-((6-(trifluoromethyl)pyridin-3-yl)methyl)-[1,2,4]triazolo[4,3-a]pyridin-3(2H)-one

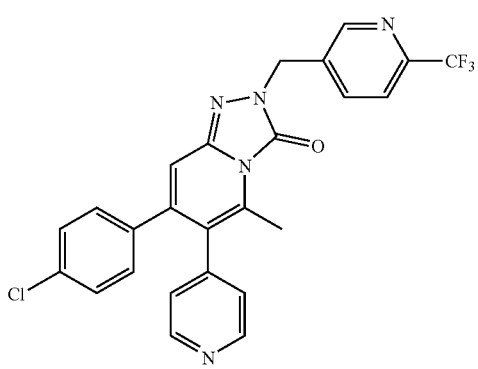

The title compound (16 mg, 64%) as a light yellow powder was prepared from 6-bromo-7-(4-chlorophenyl)-5-methyl-2-((6-(trifluoromethyl)pyridin-3-yl)methyl)-[1,2,4]triazolo[4,3-a]pyridin-3(2H)-one (25 mg, 0.05 mmol) and 4-(4,4,5,5-tetramethyl-1,3,2-dioxaborolan-2-yl)pyridine (42.5 mg, 0.2 mmol) by procedures analogous to those used for the preparation of 4-(2-((2-methyl-6-(trifluoromethyl)pyridin-3-yl)methyl)-3-oxo-8-phenyl-2,3-dihydro-[1,2,4]triazolo[4,3-a]pyridin-7-yl)benzonitrile. HPLC/MS: retention time=2.87 min, [M+H]⁺=496.4.

Example 143

Preparation of 6-(2-chlorophenyl)-7-(4-chlorophenyl)-5-methyl-2-((6-(trifluoromethyl)pyridin-3-yl)methyl)-[1,2,4]triazolo[4,3-a]pyridin-3(2H)-one

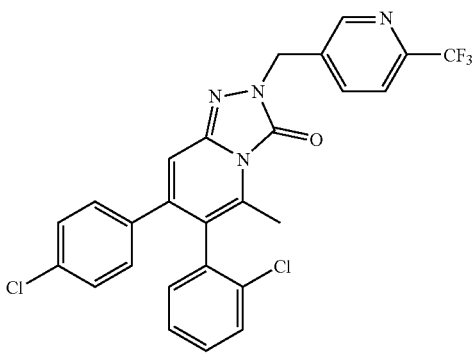

Into a flame-dried 25 mL round bottom flask was placed 6-bromo-7-(4-chlorophenyl)-5-methyl-2-((6-(trifluoromethyl)pyridin-3-yl)methyl)-[1,2,4]triazolo[4,3-a]pyridin-3(2H)-one (25 mg, 0.05 mmol), 2-chlorophenylboronic acid (16 mg, 0.1 mmol), K₃PO₄ (43 mg, 0.2 mmol), Pd(dba)₃ (4.6 mg, 0.005 mmol), and S-Phos (dicyclohexyl(2',6'-dimethoxybiphenyl-2-yl)phosphine, 4.2 mg, 0.01 mmol). The reaction flask was purged with argon three times before toluene (1 mL) was added. The reaction mixture was stirred at 95° C. for 16 h. Analysis by HPLC/MS indicated the starting 6-bromo-7-(4-chlorophenyl)-5-methyl-2-((6-(trifluoromethyl)pyridin-3-yl)methyl)-[1,2,4]triazolo[4,3-a]pyridin-3(2H)-one had been consumed. After cooling to room temperature, the reaction mixture was partitioned between EtOAc and water. The aqueous layer was extracted with EtOAc (15 mL×2). The combined EtOAc extracts were washed with saturated aqueous NaCl, dried over Na₂SO₄, filtered and concentrated under reduced pressure. The crude product was purified using a silica gel cartridge (4 g) eluted with a gradient of EtOAc (30-70%) in hexanes to afford the desired product (86% pure). The product was further purified by preparative reverse phase HPLC (Phenomenex Luna 5 μm C-18 21.2×100 mm column eluted with a linear gradient of 70% to 100% B over 10 min (A=90% water, 10% methanol and B=90% methanol, 10% water) with flow rate at 20 mL/min and UV detection at 220 nm). The desired fractions were concentrated under reduced pressure. The residue obtained was dissolved in acetonitrile, frozen and lyophilized to afford 10 mg (40%) of the title compound as a light yellow powder. HPLC/MS: retention time=4.13 min, [M+H]⁺=529.3.

Example 144

Preparation of 6-(2-chlorophenyl)-7-(4-chlorophenyl)-2-((2-methyl-6-(trifluoromethyl)pyridin-3-yl)methyl)-[1,2,4]triazolo[4,3-a]pyridin-3(2H)-one

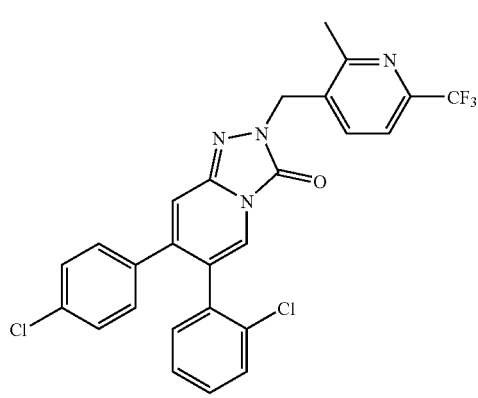

A. Preparation of 5-chloro-4-(4-chlorophenyl)-2-fluoropyridine

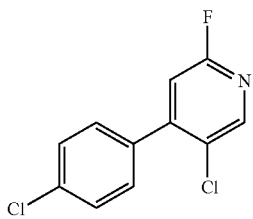

A suspension of 5-chloro-2-fluoro-4-iodopyridine (2.57 g, 10 mmol), 4-chlorophenylboronic acid (1.72 g, 11 mmol) and (Ph₃P)₄Pd (462 mg, 0.4 mmol) in a mixture of 2.0 M aqueous sodium carbonate (6 mL) and toluene (10 mL) was heated at 140° C. in a microwave oven for 30 min. Analysis by HPLC/MS indicated that the reaction was not complete. Additonal 4-chlorophenylboronic acid (0.156 g, 1 mmol) was added, followed by (Ph₃P)₄Pd (116 mg, 0.1 mmol). The reaction mixture was again heated at 140° C. in a microwave oven for 30 min. After cooling to room temperature, the reaction mixture was diluted with water and extracted with EtOAc (50 mL×3). The combined EtOAc extracts were washed with saturated aqueous NaCl, dried over Na₂SO₄, filtered and concentrated under reduced pressure. The crude product was purified using a silica gel cartridge (120 g) eluted with a gradient of EtOAc (0-50%) in hexanes to afford 2.6 g of the product (~60% pure) as an off-white solid. This was crystallized in EtOAc-hexanes to obtain the pure title compound (0.9 g) as a white solid. HPLC/MS: retention time=3.80 min, [M+H]⁺=242.0.

B. Preparation of 5-(2-chlorophenyl)-4-(4-chlorophenyl)-2-fluoropyridine

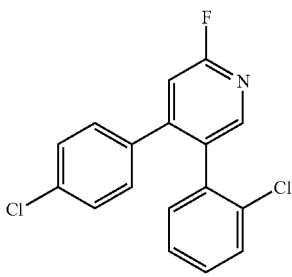

The title compound (0.33 g, 35% yield) as a white foam was prepared from 5-chloro-4-(4-chlorophenyl)-2-fluoropyridine (0.71 g, 2.93 mmol) and 2-chlorophenylboronic acid (0.55 g, 3.52 mmol) in a manner analogous to that in which 6-(2-chlorophenyl)-7-(4-chlorophenyl)-5-methyl-2-((6-(trifluoromethyl)pyridin-3-yl)methyl)-[1,2,4]triazolo[4,3-a]pyridin-3(2H)-one was prepared. HPLC/MS: retention time=4.03 min, [M+H]⁺=318.1.

C. Preparation of 5-(2-chlorophenyl)-4-(4-chlorophenyl)-2-hydrazinylpyridine

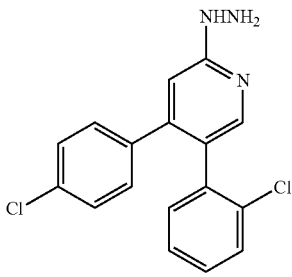

To a suspension of 5-(2-chlorophenyl)-4-(4-chlorophenyl)-2-fluoropyridine (0.32 g, 1 mmol) in pyridine (4 mL) at room temperature was added anhydrous hydrazine (1 mL). The resulting mixture was stirred at 90° C. for 1 hour. Analysis by HPLC/MS indicated the reaction was complete. After cooling to room temperature, the reaction mixture was concentrated under reduced pressure. To the residue was added water, and the resulting suspension was extracted with EtOAc (50 mL×3). The combined EtOAc extracts were washed with saturated aqueous NaCl, dried over Na₂SO₄, filtered and concentrated under reduced pressure to yield 0.28 g of the title compound (85%) as a white foam. HPLC/MS: retention time=3.03 min, [M+H]⁺=330.1.

D. Preparation of 6-(2-chlorophenyl)-7-(4-chlorophenyl)-[1,2,4]triazolo[4,3-a]pyridin-3(2H)-one

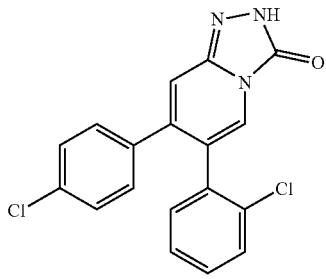

The title compound (190 mg, 88% yield) as a yellow foam was prepared from 5-(2-chlorophenyl)-4-(4-chlorophenyl)-2-hydrazinylpyridine (200 mg, 0.61 mmol) in a manner analogous to that in which 8-bromo-7-(4-chlorophenyl)-5-methyl-[1,2,4]triazolo[4,3-a]pyridin-3(2H)-one was prepared. HPLC/MS: retention time=3.83 min, [M+H]$^+$=356.1.

E. Preparation of 6-(2-chlorophenyl)-7-(4-chlorophenyl)-2-((2-methyl-6-(trifluoromethyl)pyridin-3-yl)methyl)-[1,2,4]triazolo[4,3-a]pyridin-3(2H)-one

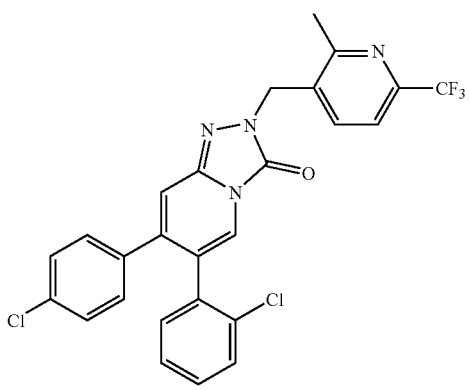

The title compound (25 mg, 47% yield) as an off-white solid was prepared from 6-(2-chlorophenyl)-7-(4-chlorophenyl)-[1,2,4]triazolo[4,3-a]pyridin-3(2H)-one (36 mg, 0.1 mmol) and 3-(chloromethyl)-2-methyl-6-(trifluoromethyl) pyridine (31 mg, 0.15 mmol) in a manner analogous to that in which 8-bromo-7-(4-chlorophenyl)-5-methyl-2-((2-methyl-6-(trifluoromethyl)pyridin-3-yl)methyl)-[1,2,4]triazolo[4,3-a]pyridin-3(2H)-one was prepared. HPLC/MS: retention time=4.30 min, [M+H]$^+$=529.1.

The following are preparations of reagents R$^5$-LG and R$^5$—OH used in the preparations of the working Examples above.

Preparation of Reagent 3-(chloromethyl)-2-methyl-6-(trifluoromethyl)pyridine

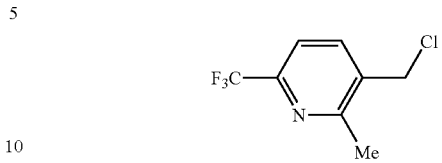

A. Preparation of (Z)-4-amino-1,1,1-trifluorobut-3-en-2-one

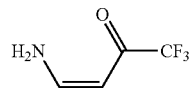

M. Hojo, et al., Tetrahedron Lett., Vol. 30, pp. 6173-6176, 1989 and M. Buback, et al., Chem. Ber., Vol. 122, pp. 1179-1186, 1989 provide procedures for this exact transformation. To a solution of 4-ethoxy-1,1,1-trifluorobut-3-en-2-one (technical grade, 50 g, 0.3 mol) in 300 mL of acetonitrile stirring at room temperature under argon was added concentrated aqueous ammonium hydroxide solution (28% ammonia in water, 21.6 g, 0.36 mol) over 2 min. The resulting mixture was stirred at room temperature under argon for 14 h. Solvent was removed under reduced pressure to afford 40.1 g of compound the title compound as a yellow oil at about 85-90% purity according to $^1$H NMR. This (Z)-4-amino-1,1,1-trifluorobut-3-en-2-one was used in the next step as is, although it is possible to purify it by distillation (see reference).

B. Preparation of methyl 2-methyl-6-(trifluoromethyl)nicotinate

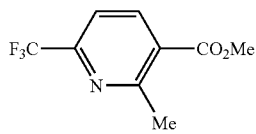

E. Okada, et al., Heterocycles, Vol. 46, pp. 129-132, 1997 provides a procedure for this exact transformation. A solution of crude (Z)-4-amino-1,1,1-trifluorobut-3-en-2-one (20.7 g, 85-90% purity, about 18.2 g net, 0.13 mol), methyl acetoacetate (20.9 g, 0.18 mol), and TFA (20.6 g, 0.18 mol) in 150 mL toluene under argon was heated at 80° C. for 16 h. HPLC/MS analysis indicated that the reaction was complete. Solvent was evaporated under vacuum. The resulting residue was dissolved in 200 mL EtOAc and washed with 10% aqueous sodium carbonate solution (100 mL), then brine (100 mL). The organic phase was dried over anhydrous sodium sulfate and filtered. The filtrate was concentrated under vacuum to obtain 33.7 g of brown oil, which was purified by silica gel column chromatography eluting with (hexanes-EtOAc, 3:1)

C. Preparation of (2-methyl-6-(trifluoromethyl)pyridin-3-yl)methanol

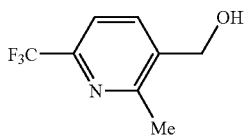

To the solution of methyl 2-methyl-6-(trifluoromethyl) nicotinate (8.8 g, 40 mmol) in 40 mL dry THF at 0° C. under argon was added 1.0 M lithium aluminum hydride in THF solution (40 mL, 40 mmol) drop-wise over 15 min. The reaction mixture was allowed to warm to room temperature over 1 h. HPLC/MS analysis indicated that the reaction was complete. Rochelle's salt, 10% aqueous solution (20 mL) was carefully added to the stirring reaction mixture over a period of 10 min. After 1 h of subsequent stirring, 50 mL EtOAc and water were added. The layers were separated. The organic phase was dried over anhydrous sodium sulfate and filtered. The filtrate was concentrated to obtain 7.5 g of the title compound as a colorless oil, which was greater than 98% pure. HPLC/MS: retention time=2.1 min, [M+H]$^+$=192.

D. Preparation of 3-(chloromethyl)-2-methyl-6-(trifluoromethyl)pyridine

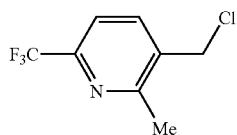

To a solution of (2-methyl-6-(trifluoromethyl)pyridin-3-yl)methanol (14.5 g, 71 mmol) in 100 mL CH$_2$Cl$_2$ at room temperature under argon was added SOCl$_2$ (16.8 g, 142 mmol), followed by about 1.5 mL DMF, which was added to re-dissolve the rapidly formed, precipitating hydrochloride salt of the starting material. The resulting reaction mixture was stirred for 16 h. HPLC/MS analysis indicated that the reaction was complete. Solvent was evaporated under vacuum. The resulting residue was dissolved in 200 mL Et$_2$O, and the resulting solution was washed with 10% aqueous sodium carbonate solution (100 mL), then brine (100 mL). The organic phase was dried over anhydrous sodium sulfate and filtered. The filtrate was concentrated under vacuum to obtain 13.7 g of the title compound as a tan oil, which was greater than 98% pure. HPLC/MS: retention time=2.9 min, [M+H]$^+$=210.

Preparation of Reagent 3-(bromomethyl)-2-methyl-6-(trifluoromethyl)pyridine

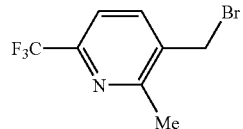

A mixture of (2-methyl-6-(trifluoromethyl)pyridin-3-yl)methanol (1.677 g, 8.77 mmol, 76% pure) in 48% aq. HBr (10 mL) was heated to reflux (oil bath temperature, 135° C.) for 24 h. The volatile components of the resulting biphasic mixture were distilled under vacuum to remove most of the hydrogen bromide (sodium hydroxide trap). The residue was partitioned between 2:1 EtOAc/THF and water (at pH 3) and the organic phase was dried (MgSO$_4$), filtered and evaporated. The solid residue was re-evaporated after addition of dichloromethane/hexanes to obtain the title compound as a tan solid, 1.19 g, 71% yield (based on the purity of the starting material). HPLC/MS: retention time=2.15 min, [M+H]$^+$=254.

Preparation of Reagent 3-(chloromethyl)-2-ethyl-6-(trifluoromethyl)pyridine

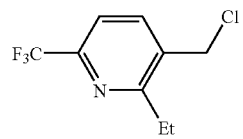

The title compound was prepared from (Z)-4-amino-1,1,1-trifluorobut-3-en-2-one and methyl 3-oxopentanoate analogously to the way 3-(chloromethyl)-2-methyl-6-(trifluoromethyl)pyridine was prepared from (Z)-4-amino-1,1,1-trifluorobut-3-en-2-one and methyl acetoacetate in three steps: 1. TFA-mediated cyclocondensation to methyl 2-ethyl-6-(trifluoromethyl)nicotinate (HPLC/MS: retention time=3.2 min, [M+H]$^+$=234); 2. reduction with lithium aluminum hydride to (2-ethyl-6-(trifluoromethyl)pyridin-3-yl)methanol (HPLC/MS: retention time=2.4 min, [M+H]$^+$=206); and 3. reaction with SOCl$_2$ to afford the title compound (HPLC/MS: retention time=3.3 min, [M+H]$^+$=224).

Preparation of Reagent 3-(chloromethyl)-2-cyclopropyl-6-(trifluoromethyl)pyridine

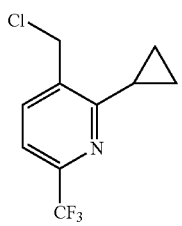

A. Preparation of methyl 2-cyclopropyl-6-(trifluoromethyl)nicotinate

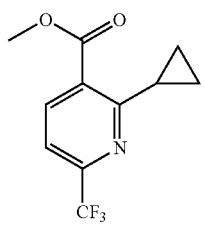

To a stirring solution of (Z)-4-amino-1,1,1-trifluorobut-3-en-2-one (3 g, 21.58 mmol) and methyl 3-cyclopropyl-3-oxopropanoate (3.7 g, 26.03 mmol) in toluene (20 mL) at room temperature under argon was added TFA (2.96 g, 25.92 mmol). The reaction mixture was stirred at reflux for 10 h. The reaction mixture was then cooled to room temperature and concentrated under vacuum to obtain a gum. EtOAc (50 mL) and 15% aqueous sodium carbonate solution (50 mL) were added, and the resulting mixture was stirred at room temperature for 10 min. The organic layer was separated, washed with brine, dried (MgSO$_4$), filtered and concentrated to obtain crude product as a yellow oil. This crude product was purified by automated silica gel chromatography (eluted with ethyl acetate-hexanes) to isolate 1 g of the title compound as a pale yellow oil. HPLC/MS: retention time=3.618 min, [M+H]$^+$=246.

B. Preparation of (2-cyclopropyl-6-(trifluoromethyl)pyridin-3-yl)methanol

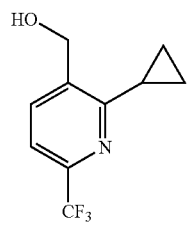

To a solution of methyl 2-cyclopropyl-6-(trifluoromethyl) nicotinate (1 g, 4.08 mmol) in THF (6 mL) at 0° C. under argon was added 1.0 M lithium aluminum hydride in THF solution (6 mL, 6.0 mmol). The reaction mixture was stirred at 0° C. for 15 min. EtOAc (20 mL) was added to the reaction mixture, which was then stirred at room temperature for 30 min. A 10% aqueous potassium sodium tartrate solution (20 mL) was added to the reaction mixture and stirring was continued for another 30 min. The organic layer was separated, washed with brine, dried (MgSO$_4$), filtered and concentrated to obtain 890 mg of the title compound as a pale yellow oil. HPLC/MS: retention time=3.055 min, [M+H]$^+$=218.

C. Preparation of 3-(chloromethyl)-2-cyclopropyl-6-(trifluoromethyl)pyridine

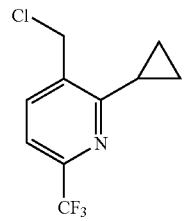

To a stirring solution of (2-cyclopropyl-6-(trifluoromethyl)pyridin-3-yl)methanol (890 mg, 4.1 mmol) in dichloromethane (10 mL) at room temperature under argon was added thionyl chloride (730 mg, 6.1 mmol) followed by 3 drops of DMF. The reaction mixture was stirred at room temperature for 15 h. The reaction mixture was then concentrated under vacuum to obtain a light brown oil. This oil was diluted with EtOAc (20 mL) and washed with 10% aqueous Na$_2$CO$_3$ solution (20 mL). The organic layer was separated, washed with brine, dried (MgSO$_4$), filtered and concentrated to obtain 900 mg of the title compound as a light brown oil. HPLC/MS: retention time=3.66 min, [M+H]$^+$=236.

Preparation of Reagent 3-(chloromethyl)-2-methoxy-6-(trifluoromethyl)pyridine

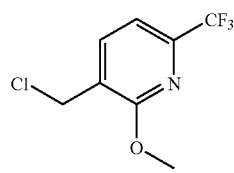

A. Preparation of methyl 2-methoxy-6-(trifluoromethyl)nicotinate

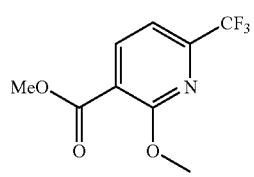

To a stirring solution of 2-hydroxy-6-(trifluoromethyl) nicotinic acid (2.07 g, 10 mmol) in anhydrous DMF (15 mL) at room temperature was added iodomethane (3.1 mL, 50 mmol), followed by anhydrous K$_2$CO$_3$ (4.15 g, 30 mmol). The resulting suspension was stirred at 70° C. for 2 h. Analysis by HPLC/MS indicated the starting acid had been consumed. After cooling to room temperature, the reaction mixture was diluted with water and extracted with EtOAc (50 mL×3). The combined EtOAc extracts were washed with saturated aqueous NaCl, dried (Na$_2$SO$_4$), filtered, and concentrated under reduced pressure. The crude product was purified using a silica gel cartridge (40 g) eluted with a gradient of ethyl acetate (0-100%) in hexanes to afford 950 mg (40%) of the title compound. HPLC/MS: retention time=3.17 min, [M+H]⁺=236.3.

B. Preparation of 2-methoxy-6-(trifluoromethyl)pyridin-3-yl)methanol

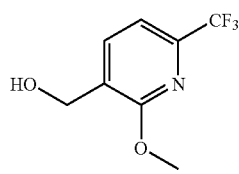

To a stirring solution of methyl 2-methoxy-6-(trifluoromethyl)nicotinate (950 mg, 4.04 mmol) in anhydrous THF (5 mL) cooled at 0° C. was slowly added 1.0 M LAH solution in toluene (4.9 mL, 4.90 mmol) over 5 min. The reaction mixture was stirred at room temperature for 16 h, then quenched carefully by addition of water (1 mL), followed by 10% aqueous KOH (1 mL) and water (1 mL). The resulting mixture was stirred at room temperature for 30 min. The obtained white gummy residue was triturated with ether (40 mL), then the ether layer was decanted. Trituration with ether was repeated three more times. The combined ether extracts were concentrated under reduced pressure. The crude product was purified using a silica gel cartridge (40 g) eluted with a gradient of ether (0-10%) in dichloromethane to afford 800 mg (96%) of the title compound as a colorless oil. HPLC/MS: retention time=2.84 min, [M+H]⁺=208.3.

C. Preparation of 3-(chloromethyl)-2-methoxy-6-(trifluoromethyl)pyridine

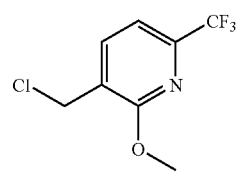

To a stirring solution of 2-methoxy-6-(trifluoromethyl)pyridin-3-yl)methanol (414 mg, 2.0 mmol) in anhydrous CH₂Cl₂ (5 mL) at room temperature was added dropwise thionyl chloride (0.44 mL, 6.0 mmol). The resulting mixture was stirred at room temperature for 30 min. Additional thionyl chloride (0.22 mL, 3.0 mmol) was added, then the reaction mixture was stirred at 40° C. for 6 h. After cooling to room temperature, the reaction mixture was concentrated under reduced pressure. The residue was dissolved in CH₂Cl₂ (50 mL), washed with saturated aqueous NaHCO₃, then saturated aqueous NaCl, dried (Na₂SO₄), filtered and concentrated under reduced pressure. The crude product was purified using a silica gel cartridge (40 g) eluted with dichloromethane to afford 360 mg (80%) of the title compound as a colorless oil. HPLC/MS: retention time=3.58 min, [M+H]⁺=226.3.

Preparation of Reagent 2-chloro-3-(chloromethyl)-6-(trifluoromethyl)pyridine

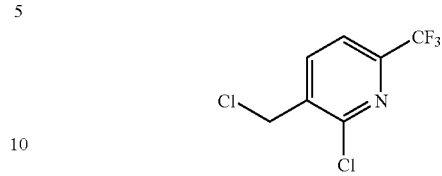

A. Preparation of 2-chloro-6-(trifluoromethyl)pyridin-3-yl)methanol

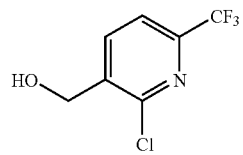

To a stirring solution of 2-chloro-6-(trifluoromethyl)nicotinic acid (790 mg, 3.5 mmol) in anhydrous THF (5 mL) at room temperature was added 1.0 M borane solution in THF (5.25 mL, 5.25 mmol) over 5 min. The resulting mixture was stirred at room temperature for 16 h. Analysis by HPLC/MS indicated that starting acid had been consumed. The reaction mixture was carefully quenched by slow addition of methanol (1 mL). The resulting mixture was stirred at room temperature for 30 min, then diluted with water and extracted with ether (50 mL×2). The combined ether extracts were washed with saturated aqueous NaCl, dried (Na₂SO₄), filtered and concentrated under reduced pressure. The crude product was purified using a silica gel cartridge (40 g) eluted with a gradient of EtOAc (0-70%) in hexanes to afford 700 mg (96%) of the title compound as a colorless oil. HPLC/MS: retention time=2.31 min, [M+H]⁺=212.0.

B. Preparation of 2-chloro-3-(chloromethyl)-6-(trifluoromethyl)pyridine

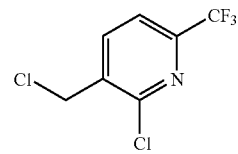

To a stirring solution of 2-chloro-6-(trifluoromethyl)pyridin-3-yl)methanol (0.71 g, 3.36 mmol) in anhydrous CH₂Cl₂ (5 mL) at room temperature was added dropwise thionyl chloride (0.74 mL, 10.08 mmol). The mixture was stirred at room temperature for 16 h. Analysis by HPLC/MS indicated that the reaction was not complete. The reaction mixture was concentrated under reduced pressure. To the residue was added fresh thionyl chloride (5 mL of 2 M SOCl₂ in CH₂Cl₂). The reaction mixture was stirred at room temperature for 2 days, then concentrated under reduced pressure to afford the crude product as a colorless oil, which was used for the next reaction without further purification.

Preparation of Reagent 3-(hydroxymethyl)-2-methyl-6-(trifluoromethyl)pyridine 1-oxide

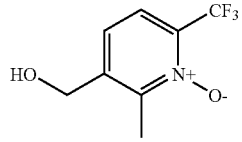

To a stirring solution of (2-methyl-6-(trifluoromethyl)pyridin-3-yl)methanol (2.70 g, 14.1 mmol) in acetonitrile (20 mL) at room temperature was added dropwise a solution of 3-chloroperoxybenzoic acid (77% pure, 3.8 g, 16.9 mmol) in acetonitrile. The reaction mixture was stirred at room temperature for 16 h before concentration under reduced pressure. The residue was diluted with EtOAc, and the EtOAc solution was washed with 5% aqueous $Na_2S_2O_3$, water, then saturated aqueous NaCl, dried over $Na_2SO_4$ and concentrated under reduced pressure. The crude product was purified using a silica gel cartridge (40 g) eluted with a gradient of EtOAc (30-100%) in hexanes to afford 730 mg (25%) of the title compound as a white solid. HPLC/MS: retention time=0.92 min, $[M+H]^+=208.0$. In addition, (2-methyl-6-(trifluoromethyl)pyridin-3-yl)methanol (1.90 g) was recovered.

Preparation of Reagent 3-(bromomethyl)-2-methyl-6-(trifluoromethyl)pyridine 1-oxide

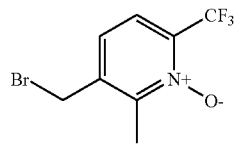

To a stirring solution of 3-(hydroxymethyl)-2-methyl-6-(trifluoromethyl)pyridine 1-oxide (207 mg, 1.0 mmol) and carbon tetrabromide (400 mg, 1.2 mmol) in $CH_2Cl_2$ (5 mL) at 0° C. was added $Ph_3P$ (393 mg, 1.5 mmol) in small portions over 5 min. The reaction mixture was then stirred at 0° C. for 30 min. Analysis by HPLC/MS indicated the reaction was complete. The reaction mixture was directly loaded onto a silica gel cartridge (40 g) and eluted with a gradient of EtOAc (0-100%) in hexanes to afford 202 mg (75%) of the title compound as a white solid. HPLC/MS: retention time=2.10 min, $[M+H]^+=269.9$.

Preparation of Reagent 3-(6-(chloromethyl)pyridin-3-yl)isoxazole

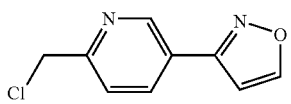

A. Preparation of (6-methylpyridin-3-yl)methanol

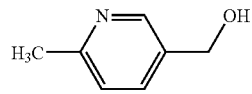

To a solution of lithium aluminum hydride (1 M in diethyl ether, 80 mL, 80 mmol) in 20 mL THF at −78° C. under argon, a solution of methyl 6-methylnicotinate (6.05 g, 40 mmol) in 60 mL diethyl ether was added over 1 h. The resulting reaction mixture was stirred at −78° C. for 1 h before 12 mL EtOAc was added over 10 min. The reaction mixture was allowed to warm up to 0° C. and 12 mL water was added drop-wise over 10 min. The resulting mixture was stirred for 30 min, then filtered through Celite. The filtrate was dried ($Na_2SO_4$), filtered and concentrated to obtain 3.07 g (62%) of the title compound as an off-white solid. HPLC: retention time=0.19 min.

B. Preparation of 6-methylnicotinaldehyde

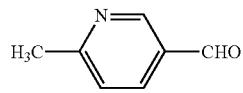

To a solution of oxalyl chloride (2 M in dichloromethane, 9.34 mL, 18.68 mmol) in 30 mL dichloromethane at −60° C. under argon, dimethyl sulfoxide (3.1 g, 2.81 mL, 39.63 mmol) was added over 20 min. The mixture was stirred at −60° C. for 20 min before a solution of (6-methylpyridin-3-yl)methanol in 8 mL dichloromethane was added over 20 min. The reaction mixture was stirred for 20 min, and then triethylamine (8.02 g, 11.05 mL, 79.25 mmol) was added over 10 min. The reaction mixture was allowed to warm up to room temperature and 48 mL water was added. The mixture was extracted with dichloromethane and the combined extracts were dried ($Na_2SO_4$), filtered and concentrated. The crude product was purified by automated silica gel chromatography (eluted with ethyl acetate-hexanes) to isolate 1.67 g (85%) of the title compound as a light brown oil. HPLC: retention time=0.19 min.

C. Preparation of 6-methylnicotinaldehyde oxime

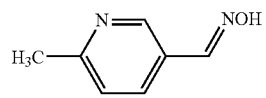

To a solution of 6-methylnicotinaldehyde (1.67 g, 13.79 mmol) in 27.6 mL MeOH, hydroxylamine (50% weight in water, 0.87 mL, 14.2 mmol) was added. The reaction mixture was stirred at room temperature for 2 h and then at 40° C. for an additional 2 h. The reaction mixture was concentrated to obtain 1.76 g (94%) of the title compound as a light brown solid. HPLC: retention time=0.20 min.

D. Preparation of N-hydroxy-6-methylnicotinimidoyl chloride

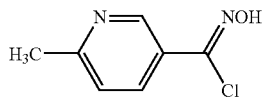

To a stirring mixture of 6-methylnicotinaldehyde oxime (500 mg, 3.67 mmol) in 4 mL DMF at room temperature, was added N-chlorosuccinimide (490 mg, 3.67 mmol) in roughly one tenth portions over 5 min. Additional N-chlorosuccinimide (175 mg, 1.31 mmol) was added after about 4 h. After a total of 6 h, the reaction mixture was diluted with EtOAc, washed with water, brine, dried ($Na_2SO_4$) and filtered. The filtrate was passed through a short silica gel column eluted with EtOAc. The eluant was concentrated under vacuum to provide the title compound as a light brown solid. All of this was used in the next step without further purification. HPLC: retention time=0.44 min.

E. Preparation of 3-(6-methylpyridin-3-yl)isoxazole

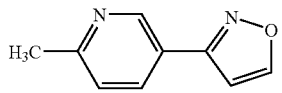

To crude N-hydroxy-6-methylnicotinimidoyl chloride in 10 mL toluene was added vinyl bromide (1 M in THF, 11 mL, 11.0 mmol), followed by bis(tributyltin)oxide (2.12 g, 1.87 mL, 3.67 mmol). The reaction mixture was stirred at room temperature for 5 h and then concentrated. The crude product was purified by automated silica gel chromatography (eluted with ethyl acetate-hexanes) to isolate 155 mg (26%, for two steps) of the title compound as a white solid. HPLC/MS: retention time=0.39 min, $[M+H]^+=161$.

F. Preparation of 3-(6-(chloromethyl)pyridin-3-yl)isoxazole

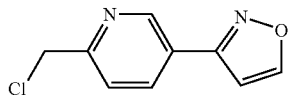

To a stirring mixture of 3-(6-methylpyridin-3-yl)isoxazole (76 mg, 0.474 mmol) and 6 mL carbon tetrachloride, was added N-chlorosuccinimide (69.7 mg, 0.52 mmol), followed by 3 mg benzoyl peroxide. The reaction mixture was refluxed. Additional N-chlorosuccinimide (40 mg, 0.30 mmol) was added in two portions after stirring 2 h and 4 h. After refluxing for a total of 13 h the reaction mixture was diluted with EtOAc, then washed sequentially with 1 N aq. NaOH solution, water and brine. The organic phase was dried ($Na_2SO_4$), filtered and concentrated under reduced pressure. The crude product was purified by automated silica gel chromatography (eluted with ethyl acetate-hexanes) to isolate 31 mg (34%) of the title compound as a white solid. HPLC/MS: retention time=1.77 min, $[M+H]^+=195$.

Preparation of Reagent 2-(4-(bromomethyl)phenyl)propan-2-ol

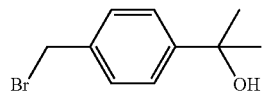

To a stirring solution of 2-p-tolylpropan-2-ol (500 mg, 3.3 mmol) in carbon tetrachloride at room temperature under argon was added N-bromosuccinimide (590 mg, 3.3 mmol), followed by benzoyl peroxide (16 mg, 0.06 mmol). The reaction mixture was stirred at reflux for 4 h. The reaction mixture was concentrated under reduced pressure to obtain a colorless gum. EtOAc (20 mL) and water (20 mL) were added and the layers were separated. The organic layer was dried ($MgSO_4$), filtered and concentrated under vacuum to obtain crude product, which was purified by flash chromatography (silica gel column eluted with 30% EtOAc/hexanes) to isolate 620 mg of the title compound as a colorless gum. HPLC/MS: retention time=2.908 min, $[M+H-H_2O]^+=211$.

Preparation of Reagent 5-chloro-2-(chloromethyl)pyridine

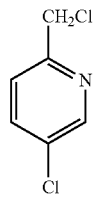

A. Preparation of methyl 5-chloropicolinate

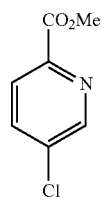

A mixture of 5-chloropicolinonitrile (4 g, 28.87 mmol), concentrated aq. HCl (10 mL) and concentrated $H_2SO_4$ (5 mL) in methanol (30 mL) was stirred at reflux for 35 h under argon. The reaction mixture was concentrated and then carefully diluted with water (50 mL). The pH was adjusted to 6-7 with 20% aqueous NaOH solution. The product was extracted with EtOAc (3×20 mL). The combined organic phase was washed with brine, dried ($MgSO_4$), filtered and concentrated under vacuum to obtain 4.9 g of the title compound as a white solid. HPLC/MS: retention time=1.977 min, [M+H]$^+$=172.

B. Preparation of (5-chloropyridin-2-yl)methanol

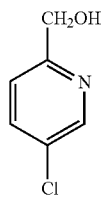

To a stirring solution of methyl 5-chloropicolinate (1 g, 5.8 mmol) in methanol at room temperature under argon was added sodium borohydride (440 mg, 11.57 mmol). The reaction mixture was allowed to stir at room temperature for 1 h. The reaction mixture was concentrated under vacuum to obtain a gum. Water (15 mL) and EtOAc (30 mL) were added and the layers were separated. The organic layer was washed with brine, dried (MgSO$_4$), filtered, and concentrated under reduced pressure to obtain 840 mg of the title compound as colorless gum. HPLC/MS: retention time=0.755 min, [M+H]$^+$=144.

C. Preparation of 5-chloro-2-(chloromethyl)pyridine

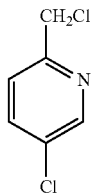

To a stirring solution of (5-chloropyridin-2-yl)methanol (840 mg, 5.8 mmol) in dichloromethane (10 mL) at 0° C. under argon was added thionyl chloride (0.64 mL, 8.77 mmol), followed by 4 drops of DMF (white precipitate formed). The reaction mixture was allowed to stir at room temperature for 1 h. The reaction mixture was concentrated to a white solid. The solid thus obtained was cooled in an ice bath before EtOAc (20 mL) and water (20 mL) and then 10% aqueous Na$_2$CO$_3$ solution (20 mL) were added. The organic layer was separated, washed with brine, dried (MgSO$_4$), filtered and concentrated to obtain 840 mg of the title compound as a light brown gum. HPLC/MS: retention time=2.392 min, [M+H]$^+$=162.

Preparation of Reagent
1-(chloromethyl)-4-(ethylsulfonyl)benzene

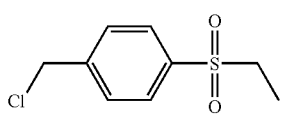

A. Preparation of 4-(ethylsulfonyl)benzoic acid

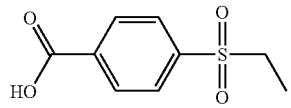

To a stirring solution of 4-(ethylthio)benzoic acid (1 g, 5.5 mmol) in methanol (30 mL) at 0° C. under argon was added a solution of potassium peroxymonosulfate (6.8 g, 11 mmol) in water (30 mL). The resulted suspension was stirred at room temperature for 15 h. Methanol was evaporated under vacuum, the reaction mixture was diluted with water (30 mL), and the product was extracted with EtOAc (2×30 mL). The combined organic phase was washed with brine, dried (MgSO$_4$), filtered and concentrated under reduced pressure to obtain 910 mg of title compound as a white solid. HPLC/MS: retention time=1.695 min, [M+H]$^+$=215.

B. Preparation of (4-(ethylsulfonyl)phenyl)methanol

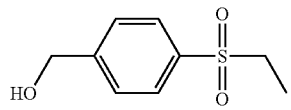

To a stirring solution of 4-(ethylsulfonyl)benzoic acid (500 mg, 2.33 mmol) in THF (5 mL) at 0° C. under argon was added 1 M borane in THF solution (3.5 mL, 3.5 mmol). The reaction mixture was stirred at 70° C. for 20 min. The reaction mixture was then cooled to room temperature, and the THF was removed under reduced pressure. The residue thus obtained was diluted with methanol (5 mL) and stirred for 5 min. Methanol was then removed under reduced pressure. This process was repeated two more times to ensure complete methanolysis of any borane complex. After residual solvent removal under vacuum, 420 mg of the title compound was obtained as a colorless gum. HPLC/MS: retention time=1.373 min, [M+H]$^+$=201.

C. Preparation of
1-(chloromethyl)-4-(ethylsulfonyl)benzene

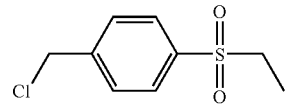

A mixture of (4-(ethylsulfonyl)phenyl)methanol (200 mg, 1 mmol) and thionyl chloride (3 mL) was stirred at reflux for 4 h. The solvent was removed under reduced pressure to obtain a gum. Dichloromethane (10 mL) was added, and the mixture was stirred for 5 min and then concentrated under vacuum. This process was repeated two more times to ensure complete removal of thionyl chloride. After residual solvent removal under vacuum, 205 mg of the title compound was obtained as a white solid. HPLC/MS: retention time=2.308 min, [M+H]$^+$=219.

The contemplated examples of compounds of Formula I shown in Table 5 prepared by the methods outlined above.

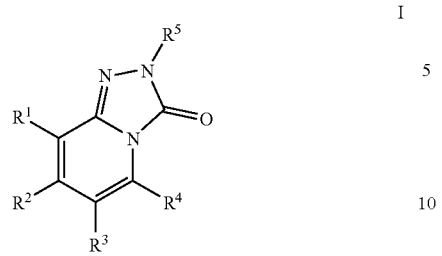

I

TABLE 5

| Example | $R^1$ | $R^2$ | $R^3$ | $R^4$ | $R^5$ |
|---|---|---|---|---|---|
| 145 | pyridin-4-yl | 4-chlorophenyl | H | H | cyclohexylmethyl |
| 146 | pyridin-4-yl | 4-chlorophenyl | H | methyl | 4-trifluoromethyl-benzyl |
| 147 | pyridin-4-yl | 4-chlorophenyl | cyano | H | 6-trifluoromethyl-pyridin-3-ylmethyl |
| 148 | pyridin-4-yl | 4-chlorophenyl | methyl | H | 6-trifluoromethyl-pyridin-3-ylmethyl |
| 149 | pyridin-4-yl | 4-chlorophenyl | methoxy | H | 6-trifluoromethyl-pyridin-3-ylmethyl |
| 150 | pyridin-4-yl | 4-chlorophenyl | H | methoxy | 6-trifluoromethyl-pyridin-3-ylmethyl |
| 151 | 4-chlorophenyl | pyridin-4-yl | H | benzyl | methyl |
| 152 | 4-chlorophenyl | 4-cyanophenyl | H | 6-trifluoromethyl-pyridin-3-ylmethyl | ethyl |
| 153 | 4-chlorophenyl | 4-cyanophenyl | H | 2-($H_2O_3POCH_2$)-6-trifluoromethyl-pyridin-3-ylmethyl | ethyl |
| 154 | 4-chlorophenyl | 4-chlorophenyl | H | phenoxy | methyl |
| 155 | 4-chlorophenyl | pyridin-4-yl | H | phenylamino | methyl |
| 156 | imidazol-1-yl | 2-chlorophenyl | H | H | 4-trifluoromethyl-benzyl |
| 157 | H | 4-chlorophenyl | 2-chlorophenyl | H | 4-trifluoromethyl-benzyl |
| 158 | H | 4-chlorophenyl | 2-chlorophenyl | H | 6-trifluoromethyl-pyridin-3-ylmethyl |
| 159 | H | 4-chlorophenyl | 2-chlorophenyl | H | cyclohexylmethyl |
| 160 | H | 4-chlorophenyl | 2-chlorophenyl | H | 5-trifluoromethyl-pyridin-2-ylmethyl |
| 161 | H | 4-chlorophenyl | 2-chlorophenyl | H | 5-chloro-pyridin-2-ylmethyl |
| 162 | H | 4-chlorophenyl | 2-chlorophenyl | H | 5-cyano-pyridin-2-ylmethyl |
| 163 | H | 4-chlorophenyl | 2-chlorophenyl | H | 2-(hydroxymethyl)-6-trifluoromethyl-pyridin-3-ylmethyl |
| 164 | H | 4-chlorophenyl | 2-chlorophenyl | H | 2-($H_2O_3POCH_2$)-6-trifluoromethyl-pyridin-3-ylmethyl |
| 165 | cyano | 4-chlorophenyl | 2-chlorophenyl | H | 6-trifluoromethyl-pyridin-3-ylmethyl |
| 166 | methyl | 4-chlorophenyl | 2-chlorophenyl | H | 6-trifluoromethyl-pyridin-3-ylmethyl |
| 167 | methoxy | 4-chlorophenyl | 2-chlorophenyl | H | 6-trifluoromethyl-pyridin-3-ylmethyl |
| 168 | pyridin-4-yl | 4-chlorophenyl | methyl | H | 2-(hydroxymethyl)-6-trifluoromethyl-pyridin-3-ylmethyl |
| 169 | pyridin-4-yl | 4-chlorophenyl | H | H | 2-($H_2O_3POCH_2$)-6-trifluoromethyl-pyridin-3-ylmethyl |
| 170 | pyridin-4-yl | 4-chlorophenyl | H | methyl | 2-(hydroxymethyl)-6-trifluoromethyl-pyridin-3-ylmethyl |
| 171 | pyridin-4-yl | 4-chlorophenyl | H | methyl | 2-($H_2O_3POCH_2$)-6-trifluoromethyl-pyridin-3-ylmethyl |

Biological Evaluation

Cannabinoid Receptor Binding Assay

Radioligand binding studies were conducted in membranes prepared from Chinese Hamster Ovary (CHO) cells that over-express recombinant human CB-1 (CHO-CB-1 cells). Total assay volume for the binding studies was 100 μL. 5 μg of membranes were brought up to a final volume of 95 μl with Binding Buffer (25 mM HEPES, 150 mM NaCl, 2.5 mM $CaCl_2$, 1 mM $MgCl_2$, 0.25% BSA). The diluted membranes were preincubated with a compound or DMSO vehicle. The binding reaction was initiated by the addition of 2 nM final $^3$H-CP-55,940 (120 Ci/mmol) and proceeded for 2.5 h at room temperature. The binding reaction was terminated by transferring the reaction to GF/B 96 well plates (presoaked with 0.3% polyethylenimine) using a Packard Cell Harvester. The filter was washed with 0.25×PBS, 30 μL MicroScint was added per well, and the bound radiolabel was quantitated by scintillation counting on a Packard TopCount Scintillation Counter. The CB-2 radioligand binding assay was conducted identically except that the membranes from CHO-CB-2 cells were used.

For a compound to be considered a CB-1 antagonist, the compound must process a CB-1 receptor binding affinity Ki less than 13000 nM. As determined by the assay described above, the CB-1 receptor binding $K_i$ values of the working Examples fall within the range of 0.01 nM to 10000 nM.

Cannabinoid Receptor Functional Activity Assay

Functional CB-1 inverse agonist activity of test compounds was determined in CHO-CB-1 cells using a cAMP accumulation assay. CHO-CB-1 cells were grown in 96 well plates to near confluence. On the day of the functional assay, growth medium was aspirated and 100 of Assay Buffer (PBS plus 25 mM HEPES/0.1 mM 3-isobutyl-1-methylxanthine/ 0.1% BSA) was added. Compounds were added to the Assay buffer diluted 1:100 from 100% DMSO and allowed to pre-incubate for 10 minutes prior to addition of 5 uM forskolin. The mixture was allowed to proceed for 15 minutes at room temperature and was terminated by the addition of 0.1 N HCl. The total intracellular cAMP concentration was quantitated using the Amersham cAMP SPA kit.

Utilities and Combinations

Utilities

The compounds of the present application are cannabinoid receptor modulators, and include compounds which are, for example, selective agonists, partial agonists, inverse agonists, antagonists or partial antagonists of the cannabinoid receptor. Accordingly, the compounds of the present application may be useful for the treatment or prevention of diseases and disorders associated with G-protein coupled cannabinoid receptor activity. Preferably, compounds of the present application possess activity as antagonists or inverse agonists of the CB-1 receptor, and may be used in the treatment of diseases or disorders associated with the activity of the CB-1 receptor.

Accordingly, the compounds of the present application can be administered to mammals, preferably humans, for the treatment of a variety of conditions and disorders, including, but not limited to metabolic and eating disorders as well as conditions associated with metabolic disorders, (e.g., obesity, diabetes, arteriosclerosis, hypertension, polycystic ovary disease, cardiovascular disease, osteoarthritis, dermatological disorders, hypertension, insulin resistance, hypercholesterolemia, hypertriglyceridemia, cholelithiasis and sleep disorders, hyperlipidemic conditions, bulimia nervosa and compulsive eating disorders) or psychiatric disorders, such as substance abuse, depression, anxiety, mania and schizophrenia. These compounds could also be used for the improvement of cognitive function (e.g., the treatment of dementia, including Alzheimer's disease, short term memory loss and attention deficit disorders); neurodegenerative disorders (e.g., Parkinson's Disease, cerebral apoplexy and craniocerebral trauma) and hypotension (e.g., hemorrhagic and endotoxin-induced hypotension). These compounds could also be used for treatment of catabolism in connection with pulmonary dysfunction and ventilator dependency; treatment of cardiac dysfunction (e.g., associated with valvular disease, myocardial infarction, cardiac hypertrophy or congestive heart failure); and improvement of the overall pulmonary function; transplant rejection; rheumatoid arthritis; multiple sclerosis; inflammatory bowel disease; lupus; graft vs. host disease; T-cell mediated hypersensitivity disease; psoriasis; asthma; Hashimoto's thyroiditis; Guillain-Barre syndrome; cancer; contact dermatitis; allergic rhinitis; and ischemic or reperfusion injury.

Compounds useful in the treatment of appetitive or motivational disorders regulate desires to consume sugars, carbohydrates, alcohol or drugs and more generally to regulate the consumption of ingredients with hedonic value. In the present description and in the claims, appetitive disorders are understood as meaning: disorders associated with a substance and especially abuse of a substance and/or dependency on a substance, disorders of eating behaviors, especially those liable to cause excess weight, irrespective of its origin, for example: bulimia nervosa, craving for sugars. The present application therefore further relates to the use of a CB-1 receptor antagonist or inverse agonist for the treatment of bulimia and obesity, including obesity associated with type II diabetes (non-insulin-dependent diabetes), or more generally any disease resulting in the patient becoming overweight. Obesity, as described herein, is defined by a body mass index ($kg/m^2$) of at least 26. It may be due to any cause, whether genetic or environmental, including overeating and bulemia, polycycstic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure. As used with reference to the utilities described herein, the term "treating" or "treatment" encompasses prevention, partial alleviation, or cure of the disease or disorder. Further, treatment of obesity is expected to prevent progression of medical covariants of obesity, such as arteriosclerosis, Type II diabetes, polycystic ovary disease, cardiovascular disease, osteoarthritis, dermatological disorders, hypertension, insulin resistance, hypercholesterolemia, hypertriglyceridemia, cholelithiasis and sleep disorders.

Compounds in the present application may also be useful in treating substance abuse disorders, including substance dependence or abuse without physiological dependence. Substances of abuse include alcohol, amphetamines (or amphetamine-like substances), caffeine, cannabis, cocaine, hallucinogens, inhalants, nicotine, opioids, phencyclidine (or phencyclidine-like compounds), sedative-hypnotics or benzodiazepines, and other (or unknown) substances and combinations of the above. The terms "substance abuse disorders" also includes drug or alcohol withdrawal syndromes and substance-induced anxiety or mood disorder with onset during withdrawal.

Compounds in the present application may be useful in treating memory impairment and cognitive disorders. The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. Dementias are diseases that include memory loss and additional intellectual impairment separate from memory. Cannabinoid receptor modulators may also be useful in treating cognitive impairments related to attentional deficits, such as attention deficit disorder.

Compounds in the present application may also be useful in treating diseases associated with dysfunction of brain dopaminergic systems, such as Parkinson's Disease and substance abuse disorders. Parkinsons's Disease is a neurodenerative movement disorder characterized by bradykinesia and tremor.

As modulators of the cannabinoid receptor, the compounds of the present application are further useful for the treatment and prevention of respiratory diseases and disorders. Respiratory diseases for which cannabinoid receptor modulators are useful include, but are not limited to, chronic pulmonary obstructive disorder, emphysema, asthma, and bronchitis. In addition, cannabinoid receptor modulators block the activation of lung epithelial cells by moeties such as allergic agents, inflammatory cytokines or smoke, thereby limiting release of mucin, cytokines, and chemokines, or selectively inhibiting lung epithelial cell activation.

Moreover, the compounds employed in the present application may stimulate inhibitory pathways in cells, particularly in leukocytes, lung epithelial cells, or both, and are thus useful in treating such diseases. "Leukocyte activation" is defined herein as any or all of cell proliferation, cytokine production, adhesion protein expression, and production of inflammatory mediators. "Epithelial cell activation" is defined herein as the production of any or all of mucins, cytokines, chemokines, and adhesion protein expression.

Use of the compounds of the present application for treating leukocyte activation-associated disorders is exemplified by, but is not limited to, treating a range of disorders such as: transplant (such as organ transplant, acute transplant, xenotransplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis; serum sickness; uticaria; allergic diseases such as respiratory allergies (asthma, hayfever, allergic rhinitis) or skin allergies; scleracierma; mycosis fungoides; acute inflammatory and respiratory responses (such as acute respiratory distress syndrome and ishchemia/reperfusion injury); dermatomyositis; alopecia greata; chronic actinic dermatitis; eczema; Behcet's disease; Pustulosis palmoplanteris; Pyoderma gangrenum; Sezary's syndrome; atopic dermatitis; systemic schlerosis; and morphea. The term "leukocyte activation-associated" or "leukocyte-activation mediated" disease as used herein includes each of the above referenced diseases or disorders. In a particular embodiment, the compounds of the present application are useful for treating the aforementioned exemplary disorders irrespective of their etiology. The combined activity of the present compounds towards monocytes, macrophages, T-cells, etc. may be useful in treating any of the above-mentioned disorders.

Cannabinoid receptors are important in the regulation of Fc gamma receptor responses of monocytes and macrophages. Compounds of the present application inhibit the Fc gamma dependent production of TNF alpha in human monocytes/macrophages. The ability to inhibit Fc gamma receptor dependent monocyte and macrophage responses results in additional anti-inflammatory activity for the present compounds. This activity is especially of value, for example, in treating inflammatory diseases such as arthritis or inflammatory bowel disease. In particular, the present compounds are useful for treating autoimmune glomerulonephritis and other instances of glomerulonephritis induced by deposition of immune complexes in the kidney that trigger Fc gamma receptor responses leading to kidney damage.

Cannabinoid receptors are expressed on lung epithelial cells. These cells are responsible for the secretion of mucins and inflammatory cytokines/chemokines in the lung and are thus intricately involved in the generation and progression of respiratory diseases. Cannabinoid receptor modulators regulate both the spontaneous and the stimulated production of both mucins and cytokines. Thus, such compounds are useful in treating respiratory and pulmonary diseases including, COPD, ARDS, and bronchitis.

Further, cannabinoid receptors may be expressed on gut epithelial cells and hence regulate cytokine and mucin production and may be of clinical use in treating inflammatory diseases related to the gut. Cannabinoid receptors are also expressed on lymphocytes, a subset of leukocytes. Thus, cannabinoid receptor modulators will inhibit B and T-cell activation, proliferation and differentiation. Thus, such compounds will be useful in treating autoimmune diseases that involve either antibody or cell mediated responses such as multiple sclerosis and lupus.

In addition, cannabinoid receptors regulate the Fc epsilon receptor and chemokine induced degranulation of mast cells and basophils. These play important roles in asthma, allergic rhinitis, and other allergic disease. Fc epsilon receptors are stimulated by IgE-antigen complexes. Compounds of the present application inhibit the Fc epsilon induced degranulation responses, including the basophil cell line, RBL. The ability to inhibit Fc epsilon receptor dependent mast cell and basophil responses results in additional anti-inflammatory and anti-allergic activity for the present compounds. In particular, the present compounds are useful for treating asthma, allergic rhinitis, and other instances of allergic disease.

Combinations

The present application includes within its scope pharmaceutical compositions comprising, as an active ingredient, a therapeutically effective amount of at least one of the compounds of Formula I, alone or in combination with a pharmaceutical carrier or diluent. Optionally, compounds of the present application can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

Such other therapeutic agent(s) may be administered prior to, simultaneously with, or following the administration of the cannabinoid receptor modulators in accordance with the application.

Examples of suitable anti-obesity agents for use in combination with the compounds of the present application include melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonsist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inihibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and WO 00/039077 (KaroBio), a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, or cannabinoid-1 receptor antagonists, such as SR-141716 (Sanofi) or SLV-319 (Solvay).

Examples of suitable anti-diabetic agents for use in combination with the compounds of the present application include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors, SGLT2 inhibitors, glycogen phosphorylase inhibitors, and/or meglitinides, as well as insulin, and/or glucagon-like peptide-1 (GLP-1), GLP-1 agonist, and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present application will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present application may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594,016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of the present application may be employed with a PPARα/γ dual agonist such as MK-767/KRP-297 (Merck/Kyorin; as described in, K. Yajima, et. al., *Am. J. Physiol. Endocrinol. Metab.,* 284: E966-E971 (2003)), AZ-242 (tesaglitazar; Astra-Zeneca; as described in B. Ljung, et. al., *J. Lipid Res.,* 43, 1855-1863 (2002)); muraglitazar; or the compounds described in U.S. Pat. No. 6,414,002.

The compounds of the present application may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller, et al., *J. Med. Chem.*, 31, 1869-1871 (1998) including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., *Current Pharmaceutical Design*, 2, 1-40 (1996).

In addition, other squalene synthetase inhibitors suitable for use herein include the terpenoid pyrophosphates disclosed by P. Ortiz de Montellano, et al., *J. Med. Chem.*, 20, 243-249 (1977), the farnesyl diphosphate analog A and presqualene pyrophosphate (PSQ-PP) analogs as disclosed by Corey and Volante, *J. Am. Chem. Soc.*, 98, 1291-1293 (1976), phosphinylphosphonates reported by McClard, R. W. et al., *J. Am. Chem. Soc.*, 109, 5544 (1987) and cyclopropanes reported by Capson, T. L., PhD dissertation, June, 1987, Dept. Med. Chem. U of Utah, Abstract, Table of Contents, pp 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (SECHOLEX, POLICEXIDE) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, *Drugs of the Future*, 24, 9-15 (1999), (Avasimibe); "The ACAT inhibitor, C1-1011 is effective in the prevention and regression of aortic fatty streak area in hamsters", Nicolosi et al., *Atherosclerosis* (Shannon, Irel), 137 (1), 77-85 (1998); "The pharmacological profile of FCE 27677: a novel ACAT inhibitor with potent hypolipidemic activity mediated by selective suppression of the hepatic secretion of ApoB100-containing lipoprotein", Ghiselli, Giancarlo, *Cardiovasc. Drug Rev.*, 16 (1), 16-30 (1998); "RP 73163: a bioavailable alkylsulfinyl-diphenylimidazole ACAT inhibitor", Smith, C., et al., *Bioorg. Med. Chem. Lett*, 6 (1), 47-50 (1996); "ACAT inhibitors: physiologic mechanisms for hypolipidemic and anti-atherosclerotic activities in experimental animals", Krause et al., Editor(s): Ruffolo, Robert R., Jr.; Hollinger, Mannfred A., *Inflammation: Mediators Pathways*, 173-98 (1995), Publisher: CRC, Boca Raton, Fla.; "ACAT inhibitors: potential anti-atherosclerotic agents", Sliskovic et al., *Curr. Med. Chem.*, 1 (3), 204-25 (1994); "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", Stout et al., *Chemtracts: Org. Chem.*, 8 (6), 359-62 (1995), or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in *Atherosclerosis* 115, 45-63 (1995) and *J. Med. Chem.* 41, 973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal $Na^+$/bile acid cotransporter inhibitor such as disclosed in Drugs of the Future, 24, 425-430 (1999). The ATP citrate lyase inhibitor which may be employed in the combination of the application may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin and rosuvastatin, as well as niacin and/or cholestagel.

The compounds of the present application may be employed in combination with anti-hypertensive agents. Examples of suitable anti-hypertensive agents for use in combination with the compounds of the present application include beta adrenergic blockers, calcium channel blockers (L-type and/or T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Cannbinoid receptor modulators could be useful in treating other diseases associated with obesity, including sleep disorders. Therefore, the compounds described in the present application could be used in combination with therapeutics for treating sleep disorders. Examples of suitable therapies for treatment of sleeping disorders for use in combination with the compounds of the present application include melatonin analogs, melatonin receptor antagonists, ML 1 B agonists, GABA receptor modulators; NMDA receptor modulators, histamine-3 (H3) receptor modulators, dopamine agonists and orexin receptor modulators.

Cannabinoid receptor modulators may reduce or ameliorate substance abuse or addictive disorders. Therefore, combination of cannabinoid receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

Cannabinoid receptor modulators may reduce anxiety or depression; therefore, the compounds described in this application may be used in combination with anti-anxiety agents or antidepressants. Examples of suitable anti-anxiety agents for use in combination with the compounds of the present application include benzodiazepines (e.g., diazepam, lorazepam, oxazepam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present application include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpah-adrenoreceptor antagonists, and atypical antidepressants (bupropion, lithium, nefazodone, trazodone and viloxazine).

The combination of a conventional antipsychotic drug with a CB-1 receptor antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present application include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), dipheyylbutylpiperidine (pimozide) and indolone (molindolone) classes of antipsychotic agents. Other antipsychotic agents with potential therapeutic value in combination with the compounds in the present application include loxapine, sulpiride and risperidone.

Combination of the compounds in the present application with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, schizoaffective disorder, delusional disorder, brief psychotic disorder and psychotic disorder not specified. Examples of suitable antipsychotic drugs for combination with the compounds in the present application include the antipsychotics mentioned above, as well as dopamine receptor antagonists, muscarinic receptor agonists, 5HT2A receptor antagonists and 5HT2A/dopamine receptor antagonists or partial agonists (e.g., olanzepine, aripiprazole, risperidone, ziprasidone).

The compounds described in the present application could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and nootropic agents (e.g., piracetam, levetiracetam). Examples of suitable therapies for treatment of Alzheimer's disease and cognitive disorders for use in combination with the compounds of the present application include donepezil, tacrine, revastigraine, 5HT6, gamma secretase inhibitors, beta secretase inhibitors, SK channel blockers, Maxi-K blockers, and KCNQs blockers.

The compounds described in the present application could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transportor modulators, such as ropinirole, or pramipexole or neurotrophic factors such as glial derived neurotrophic factor (GDNF).

The compounds described in the present application could be used in combination with suitable anti-inflammatory agents. Examples of suitable anti-inflammatory agents for use in combination with the compounds of the present application include prednisone, dexamethasone, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, tumor necrosis factor (TNF) antagonists (e.g., infliximab, OR1384, including TNF-alpha inhibitors, such as tenidap, anti-TNF antibodies or soluble TNF receptor such as etanercept (Enbrel®), rapamycin (sirolimus or Rapamune) and leflunomide (Arava)), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelnorm® and Maxi-K® openers such as those disclosed in U.S. Pat. No. 6,184, 231 B1).

Exemplary of such other therapeutic agents which may be used in combination with cannabinoid receptor modulators include the following: cyclosporins (e.g., cyclosporin A), anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i.e., CD154), fusion proteins constructed from CD40 and gp39 (CD40I g and CD8gp39), inhibitors, such as nuclear translocation inhibitors, of NF-kappa B function, such as deoxyspergualin (DSG), gold compounds, antiproliferative agents such as methotrexate, FK506 (tacrolimus, Prograf), mycophenolate mofetil, cytotoxic drugs such as azathiprine and cyclophosphamide, anticytokines such as antiIL-4 or IL-4 receptor fusion proteins and PDE 4 inhibitors such as Ariflo, and the PTK inhibitors disclosed in the following U.S. patent applications, incorporated herein by reference in their entirety: Ser. No. 09/097,338, filed Jun. 15, 1998; Ser. No. 09/094,797, filed Jun. 15, 1998; Ser. No. 09/173,413, filed Oct. 15, 1998; and Ser. No. 09/262,525, filed Mar. 4, 1999. See also the following documents and references cited therein and incorporated herein by reference: Hollenbaugh, D., et al., "Cleavable CD40I g Fusion Proteins and the Binding to Sgp39", *J. Immunol. Methods* (Netherlands), 188 (1), pp. 1-7 (Dec. 15, 1995); Hollenbaugh, D., et al., "The Human T Cell Antigen Gp39, A Member of the TNF Gene Family, Is a Ligand for the CD40 Receptor: Expression of a Soluble Form of Gp39 with B Cell Co-Stimulatory Activity", *EMBO J* (England), 11 (12), pp. 4313-4321 (December 1992); and Moreland, L. W. et al., "Treatment of Rheumatoid Arthritis with a Recombinant Human Tumor Necrosis Factor Receptor (P75)-Fc Fusion Protein," *New England J. of Medicine*, 337 (3), pp. 141-147 (1997).

The above other therapeutic agents, when employed in combination with the compounds of the present application, may be used, for example, in those amounts indicated in the Physicians' Desk Reference (PDR) or as otherwise determined by one of ordinary skill in the art.

The compounds of Formula I of the application can be administered orally or parenterally, such as subcutaneously or intravenously, as well as by nasal application, rectally or sublingually to various mammalian species known to be subject to such maladies, e.g., humans, in an effective amount up to 1 gram, preferably up to 200 mg, more preferably to 50 mg in a regimen of single, two or four divided daily doses.

The compounds of the Formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of Formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

It should be understood that while this application has been described herein in terms of specific embodiments set forth in detail, such embodiments are presented by way of illustration of the general principles of the application, and the application is not necessarily limited thereto. Certain modifications and variations in any given material, process step or chemical formula will be readily apparent to those skilled in the art without departing from the true spirit and scope of the present application, and all such modifications and variations should be considered within the scope of the claims that follow.

What is claimed is:

1. A compound according to Formula I

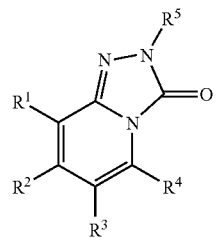

or a pharmaceutically acceptable salt or a stereoisomer thereof wherein $R^1$ is selected from the group consisting of hydrogen, cyano, halogen, phenyl, pyridyl, pyrazinyl, pyridazinyl, pyrimidinyl, imidazolyl, quinolinyl, methylendioxyphenyl, benzopyrazinyl, alkyl, -and $OR^6$, any of which may be optionally substituted with 1 to 3 $R^{11}$;

$R^2$ is selected from the group consisting of phenyl and pyridyl, either of which may be optionally substituted with 1 to 3 $R^{11}$;

$R^3$ is selected from the group consisting of hydrogen, halogen, cyano, alkyl, alkoxy, phenyl and pyridyl, where the phenyl and pyridyl may be optionally substituted with 1 to 3 $R^{11}$;

$R^4$ is selected from the group consisting of hydrogen, alkyl, methoxy, phenoxy and phenylamino, $R^5$ is alkyl which may be optionally substituted with 1 to 3 $R^{10}$, provided that $R^5$ as substituted is not optionally substituted 2-[4-(indol-3-yl)piperidin-1-yl]ethyl, 2-[4-(indol-3-yl)-3,6-dihydro-2H-pyridin-1-yl]ethyl, 3-[4-(indol-3-yl)piperidin-1-yl]propyl, 3-[4-(indol-3-yl)-3,6-dihydro-2H-pyridin-1-yl]propyl, 4-[4-(indol-3-yl)piperidin-1-yl]butyl, or 4-[4-(indol-3-yl)-3,6-dihydro-2H-pyridin-1-yl]butyl;

$R^6$ is selected from the group consisting of H, alkyl, phenyl and pyridyl;

$R^7$, $R^8$, and $R^9$ are each independently selected from the group consisting of hydrogen, alkyl, alkenyl, and alkynyl;

$R^{10}$ in each instance is independently selected from the group consisting of phenyl, pyridyl, pyridine-N-oxide, benzoxazolyl, and $OR^6$, any of which may be optionally substituted with 1 to 3 $R^{11}$;

$R^{11}$ in each instance is independently selected from the group consisting of phenyl, isoxazolyl, pyrazolyl, alkyl, $OR^6$, $NR^7SO_2R^6$, $SO_2R^6$, $COR^7$, $CO_2R^6$, $CONR^7R^8$, halogen, cyano, hydroxyl, any of which, except for halogen and cyano, may be optionally substituted with 1 to 3 $R^{12}$; and $R^{12}$ in each instance is independently selected from the group consisting of alkyl, alkenyl, alkynyl, heterocyclyl, $OR^6$, $OCOR^7$, $OCONR^7R^8$, $OSO_2NR^7R^8$, $NR^7R^8$, $NR^7COR^8$, $NR^7CO_2R^6$, $NR^7CONR^8R^9$, $NR^7SO_2R^6$, $NR^7SO_3R^6$, $NR^7SO_2NR^8R^9$, $SR^6$, $SO_2R^6$, $SO_2NR^7R^8$, $COR^7$, $CO_2R^6$, $CONR^7R^8$, halogen, cyano, hydroxyl, carboxyl, and the divalent groups oxo (=O) and oximato (=NOR$^7$);

provided that $R_1$ and $R_3$ are not both H.

2. The compound according to claim 1, wherein $R^2$ is phenyl which may be optionally substituted with 1 to 3 $R^{11}$.

3. The compound according to claim 1, wherein $R^3$ is selected from the group consisting of H, phenyl and pyridyl wherein the phenyl and pyridyl may each be optionally substituted with 1 to 3 $R^{11}$.

4. The compound according to claim 1, wherein $R^5$ is alkyl substituted with phenyl or pyridyl either of which may be optionally substituted with 1 to 3 $R^{10}$.

5. The compound according to claim 1, wherein:

$R^1$ is selected from the group consisting of phenyl and pyridyl, either of which may be optionally substituted with 1 to 3 $R^{11}$;

$R^2$ is phenyl which may be optionally substituted with 1 to 3 $R^{11}$;

$R^3$ is selected from the group consisting of hydrogen and alkyl;

$R^4$ is seleded from the group consisting of hydrogen and alkyl; and $R^5$ Is alkyl substituted with phenyl or pyridyl, either of which may be optionally substituted with 1 to 3 $R^{10}$.

6. The compound according to claim 1, wherein:

$R^1$ is hydrogen;

$R^2$ is phenyl which may be optionally substituted with 1 to 3 $R^{11}$;

$R^3$ is selected from the group consisting of phenyl and pyridyl either of with may be optionally substituted with 1 to 3 $R^{11}$.

7. A compound selected from the group consisting of a) a compound of any of the following formulas:

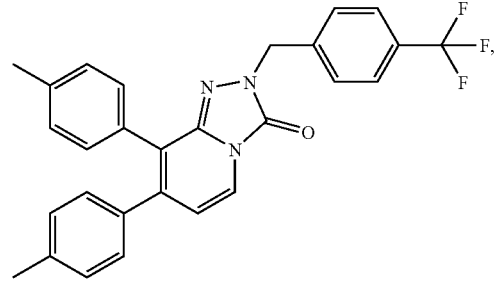

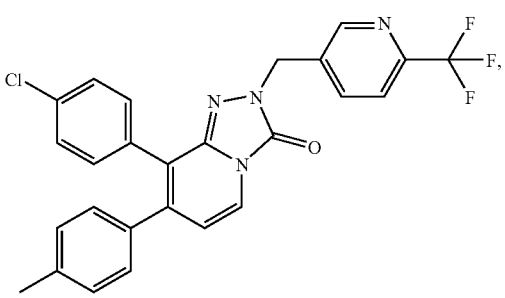

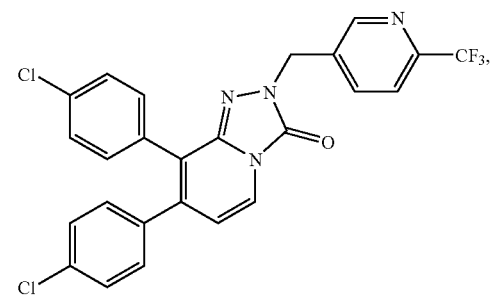

181
-continued
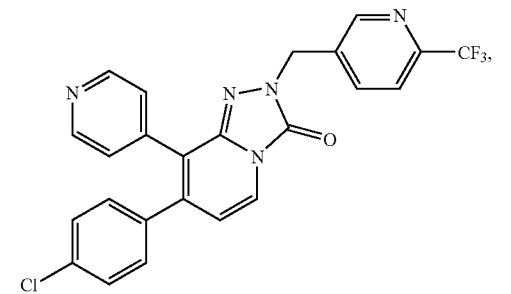
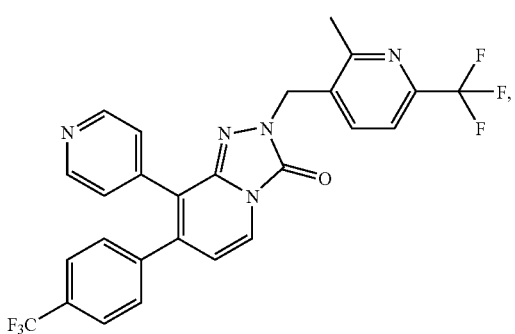
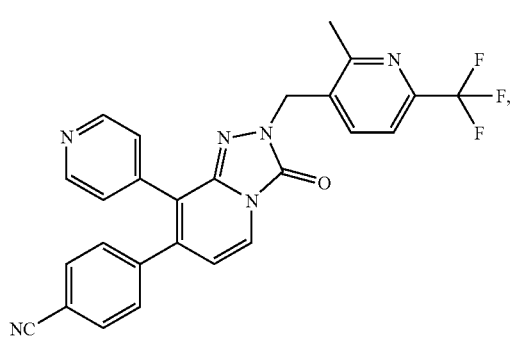
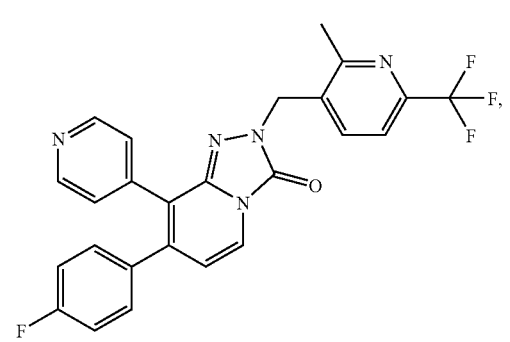
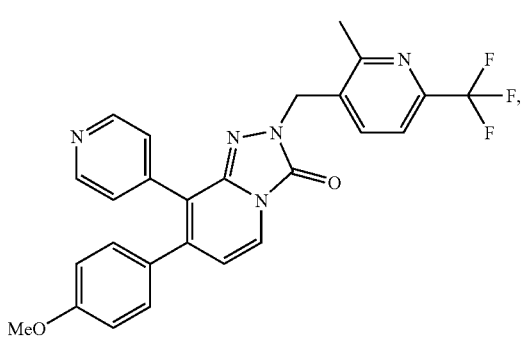
182
-continued
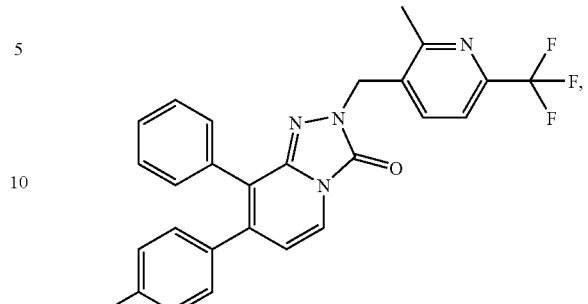
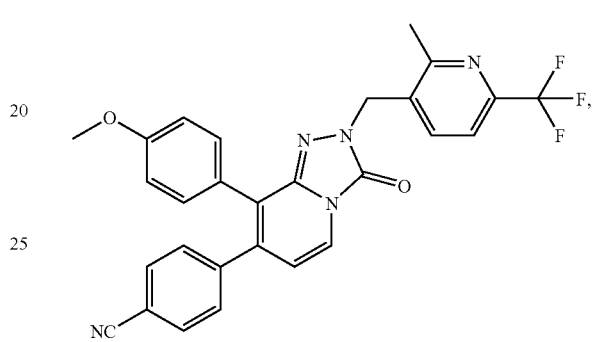
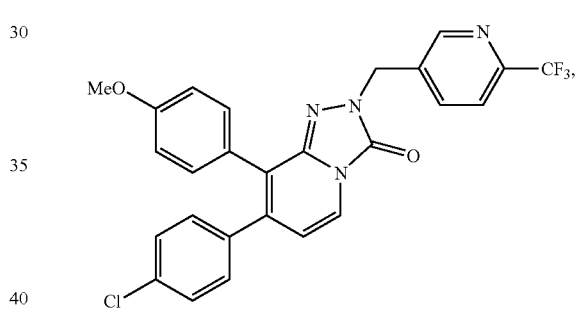
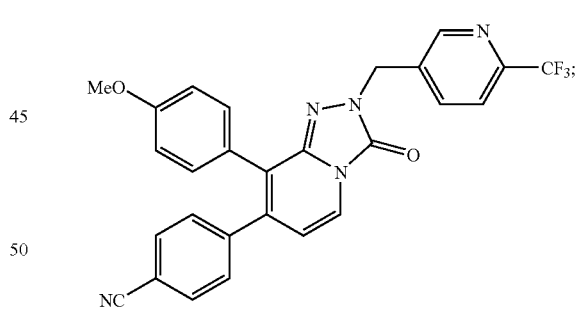
b) a compounds of formula:
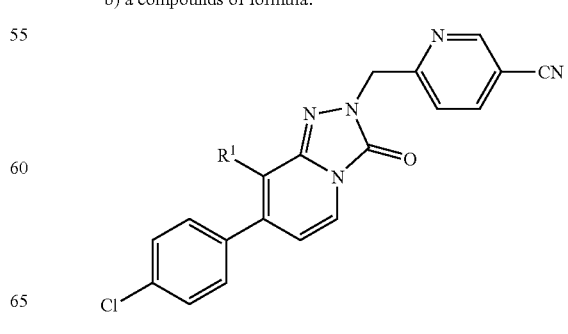

wherein R¹ is selected from the group consisting of phenyl
4-methoxyphenyl
4-methylphenyl
4-(cyanomethyl)phenyl
4-(methoxymethyl)phenyl and
2-methoxypyrimidin-5-yl;

c) a compound of formula:

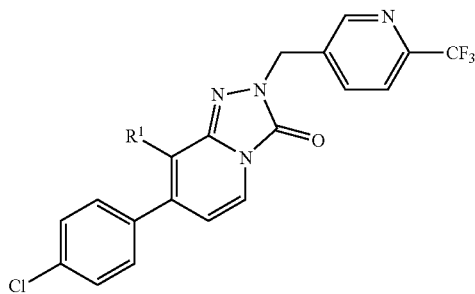

wherein R¹ is selected from the group consisting of 2-methylimidazol-1-yl
4-methylimidazol-1-yl
pyridin-3-yloxy and
5-chloropyridin-3-yloxy;

d) a compounds of formula:

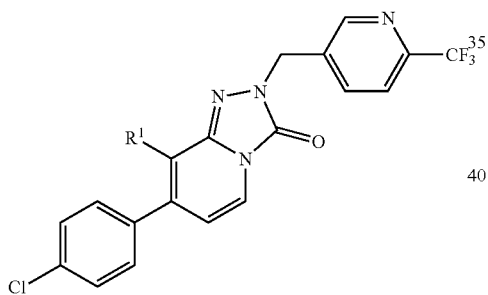

wherein R¹ is selected from the group consisting of phenyl
4-methylphenyl
4-methoxyphenyl
4-hydroxyphenyl
2-methoxypyrimidin-5-yl
4-(methoxymethyl)phenyl
3,5-difluoro-4-(hydroxymethyl)phenyl
4-(cyanomethyl)phenyl
6-cyanopyridin-3-yl
3,4-difluorophenyl
6-fluoropyridin-3-yl
4-(dimethylaminomethyl)phenyl
3-methylpyridin-4-yl
3-chloropyridin-4-yl
5-fluoro-6-methoxypyridin-3-yl
6-ethoxypyridin-3-yl
6-methoxypyridin-3-yl
pyrazinyl
benzopyrazin-6-yl
2-chlorophenyl
4-(dimethylaminocarbonyl)phenyl
4-(methylsulfonylamino)phenyl
4-cyanophenyl
3,4-methylenedioxyphenyl
3-methoxyphenyl
3-methylphenyl
2,4-dichlorophenyl
quinolin-5-yl
4-methylpyridin-3-yl
6-trifluoromethylpyridin-3-yl
pyridazin-4-yl
6-methylpyridin-3-yl
4-(aminomethyl)phenyl
pyrimidin-4-yl
4-(hydroxymethyl)phenyl
4-(ethoxycarbonyl)phenyl
2-methylpyridin-4-yl
2-fluoropyridin-4-yl
pyrimidin-5-yl and
3-(dimethylaminocarbonyl)phenyl;

e) a compound of any of the following formulas:

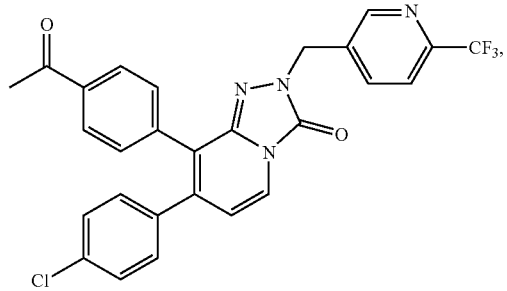

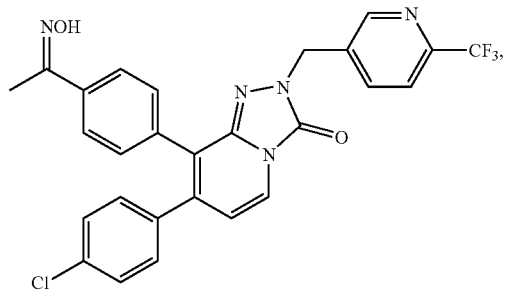

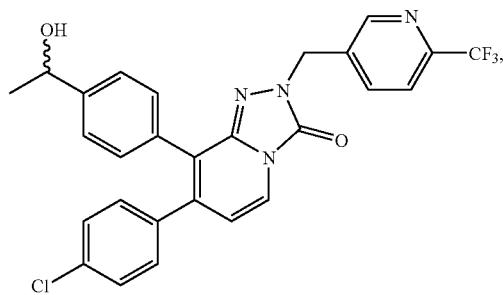

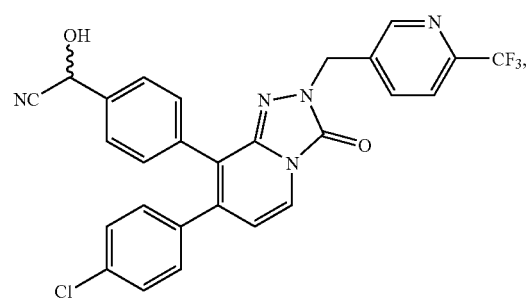

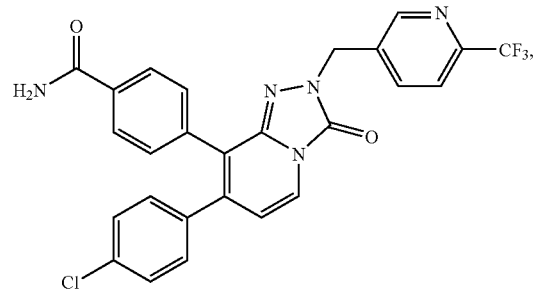
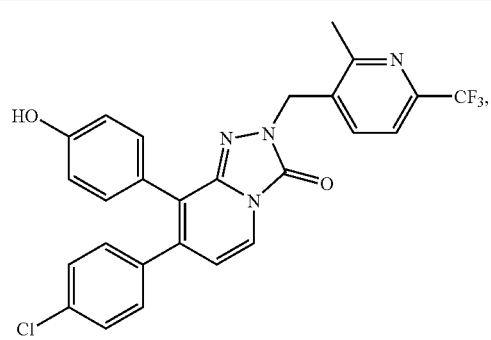
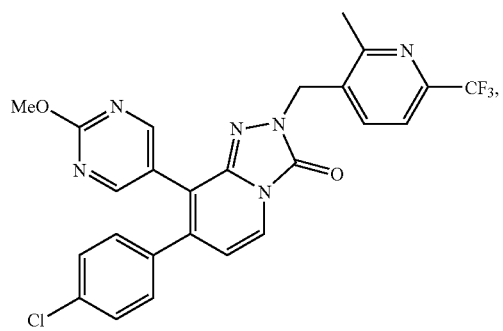
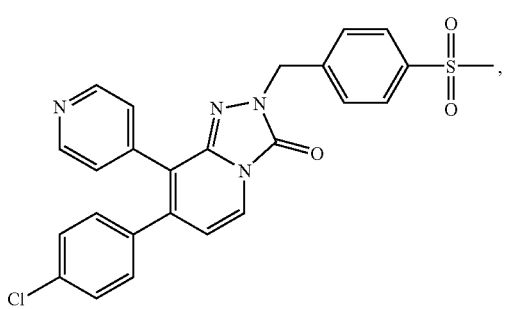
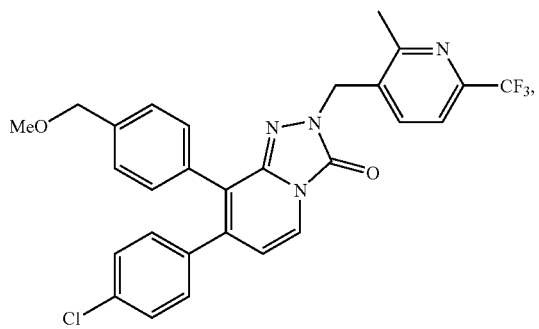
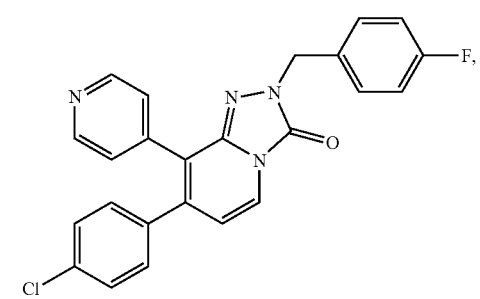
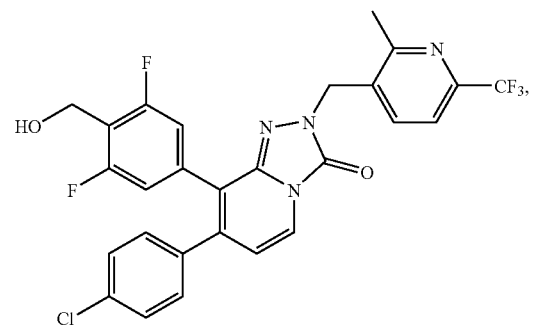
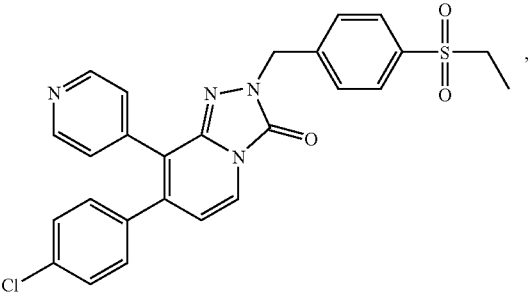
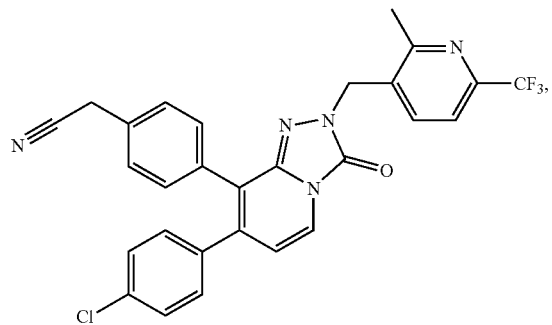
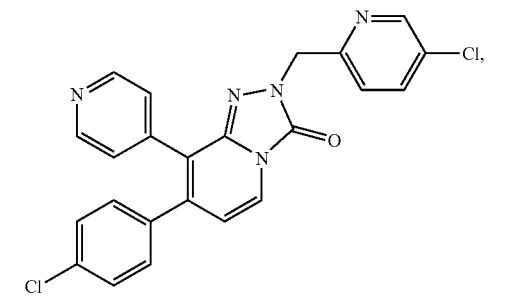

187
-continued
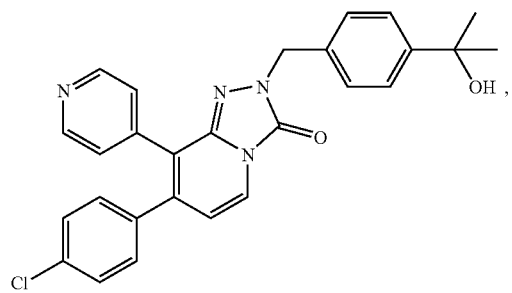
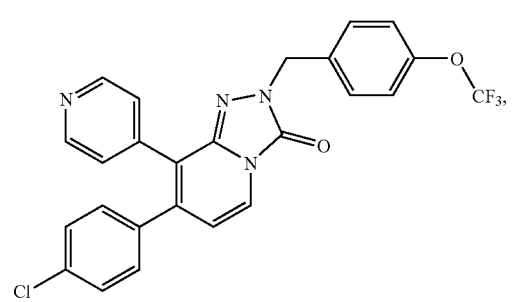
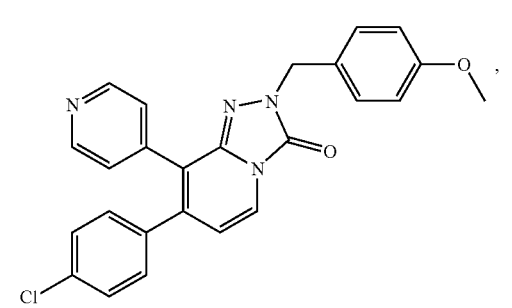
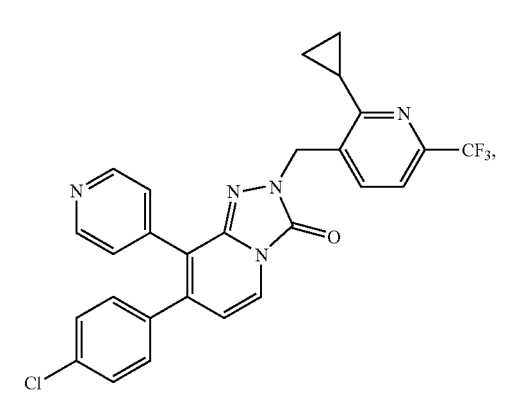
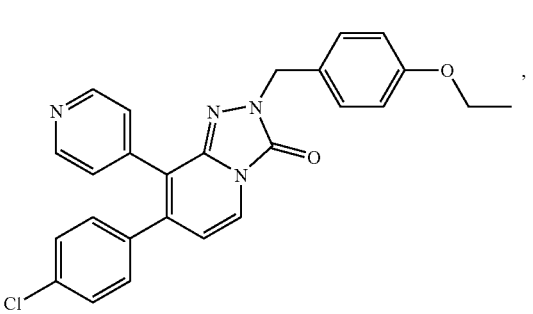
188
-continued
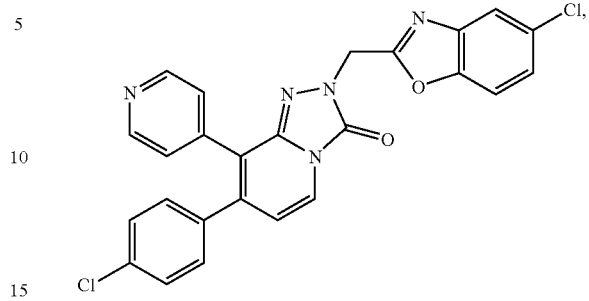
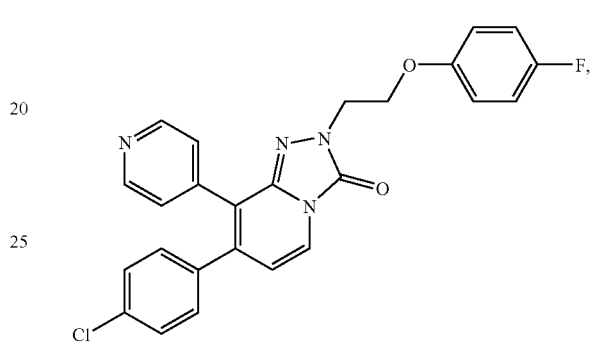
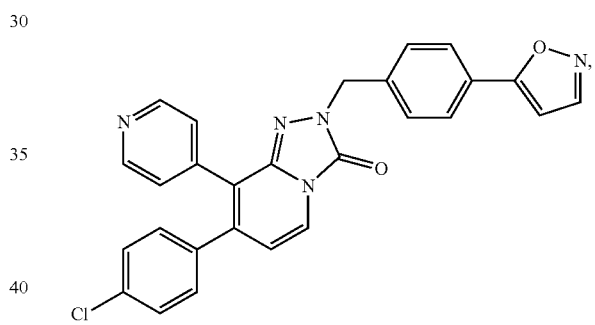
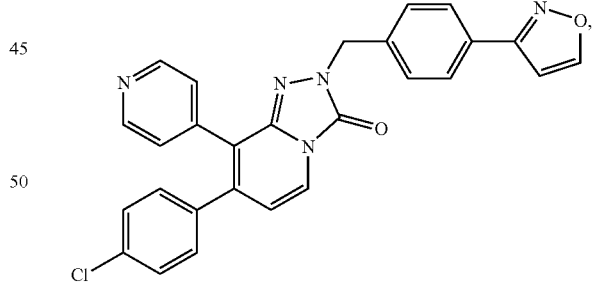
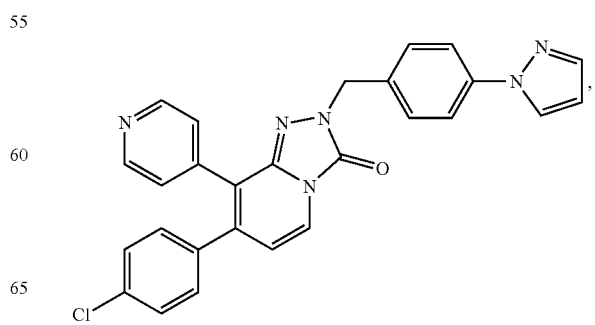

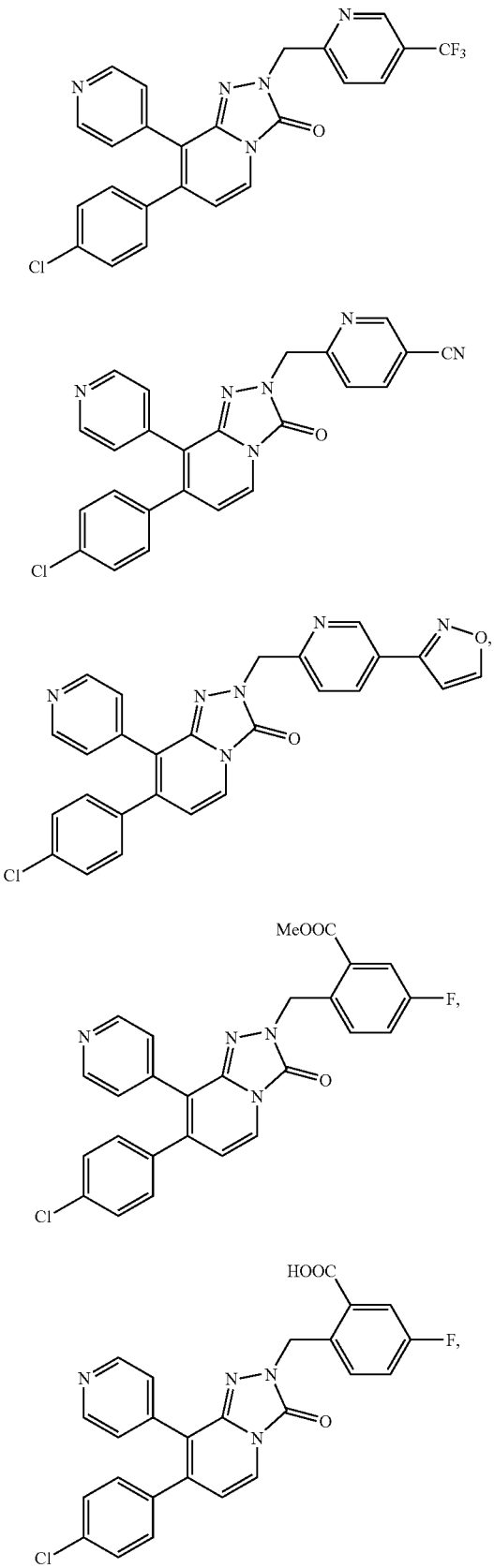
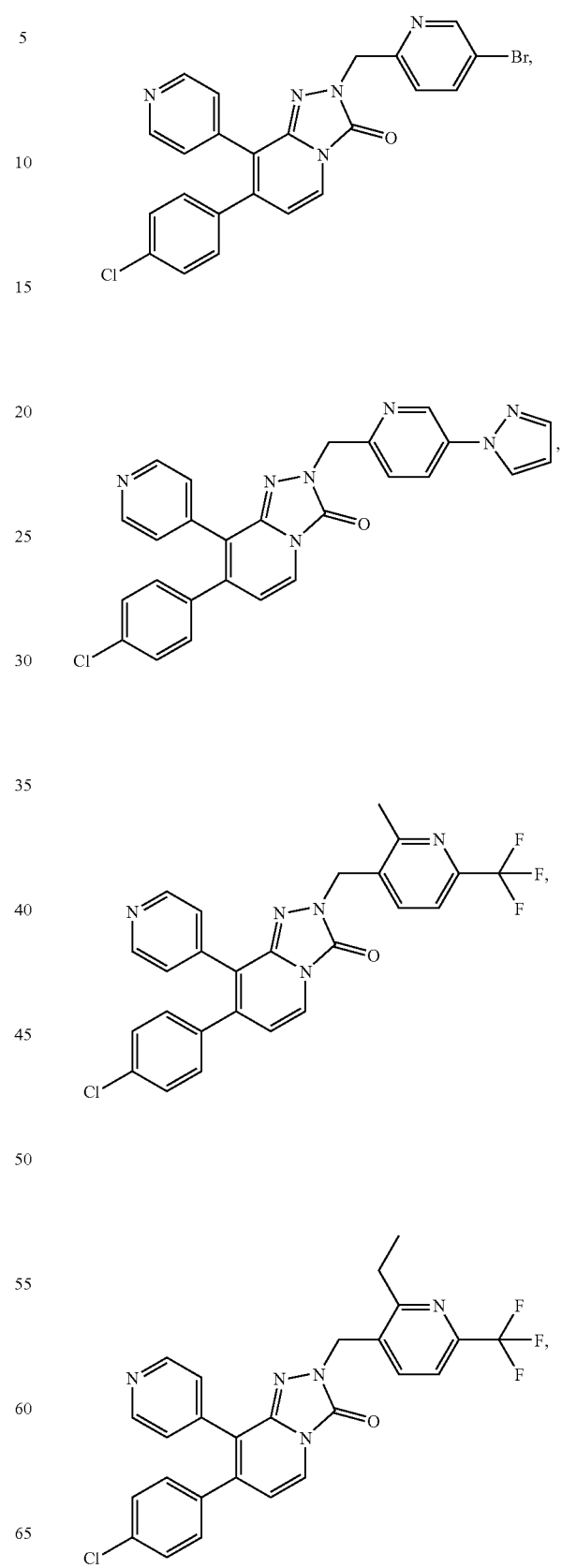

| 191 | 192 |
|---|---|
| 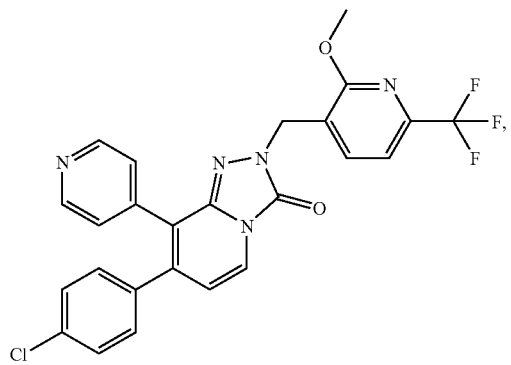 | 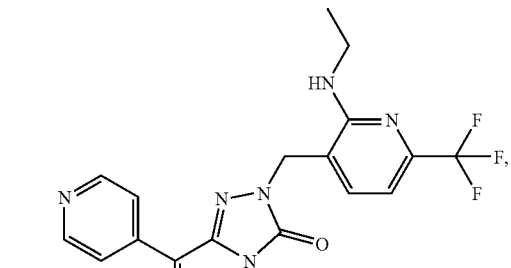 |
| 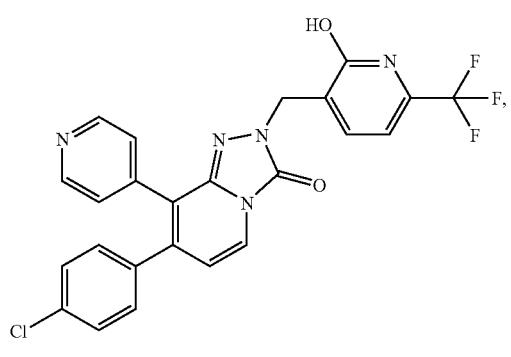 | 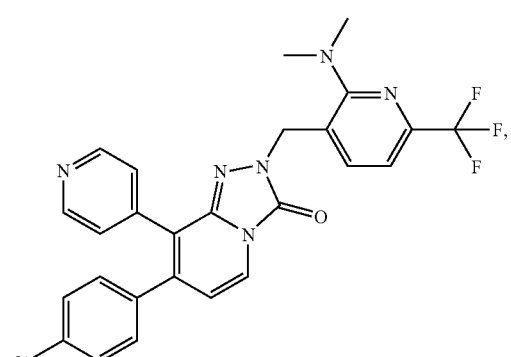 |
| 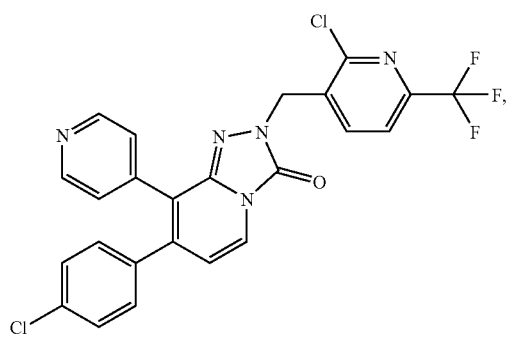 | 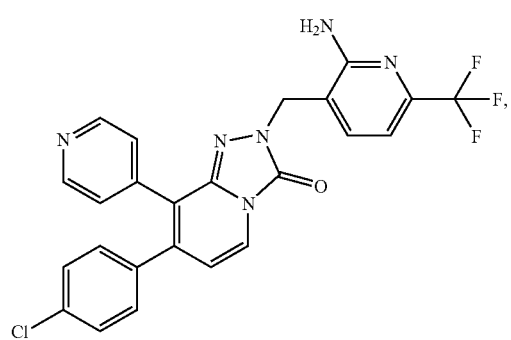 |
| 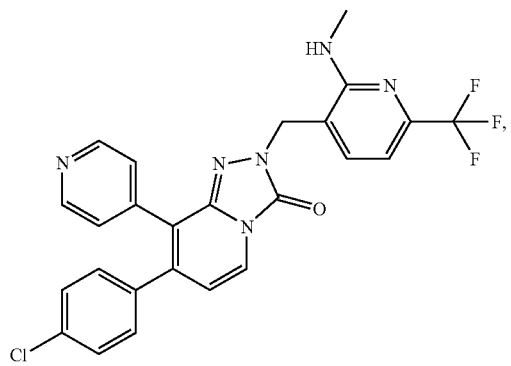 | 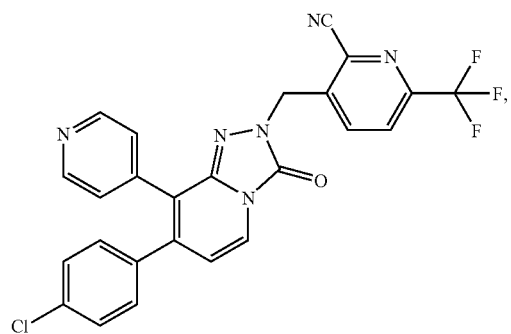 |

193
-continued
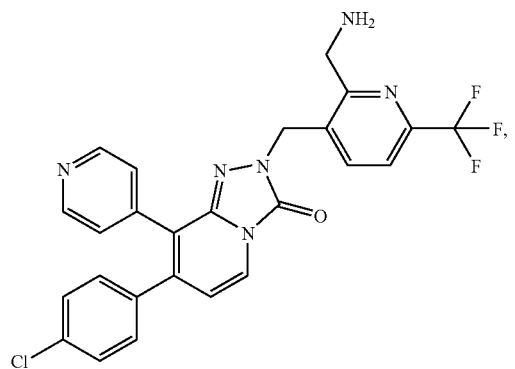
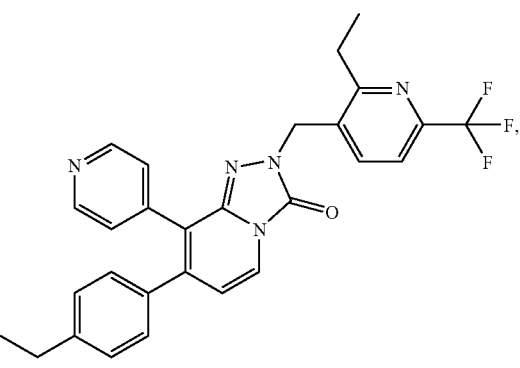
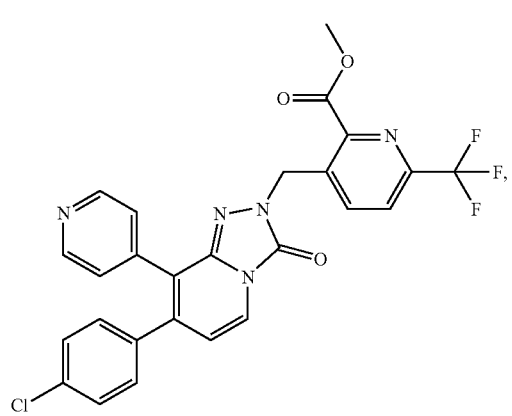
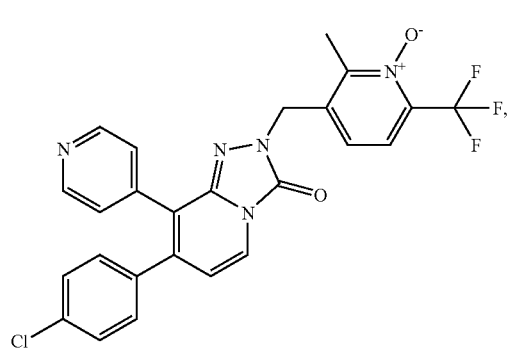
194
-continued
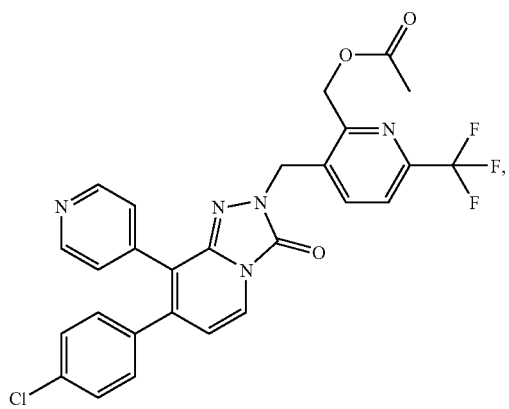
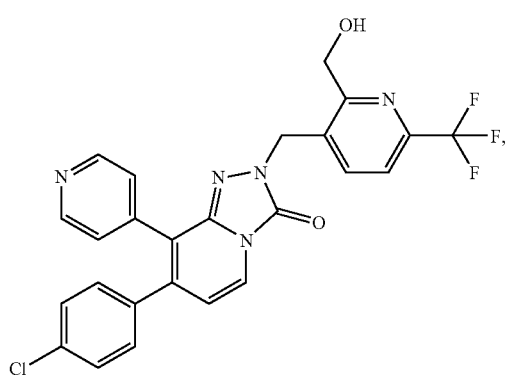
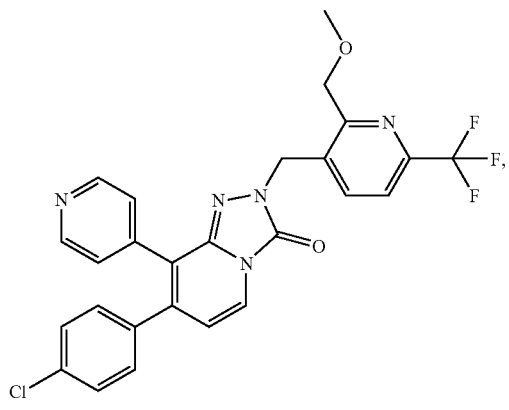
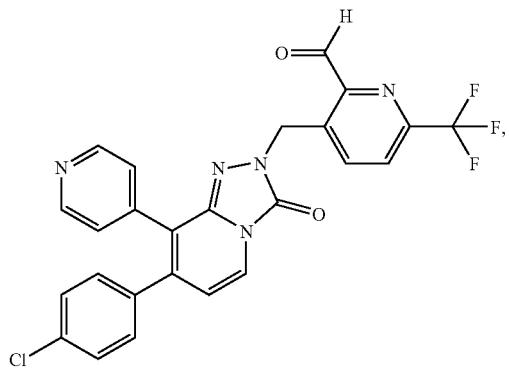

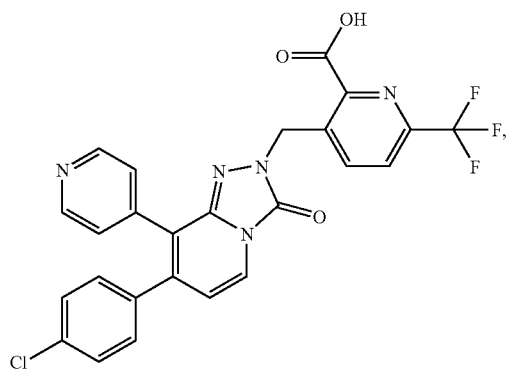
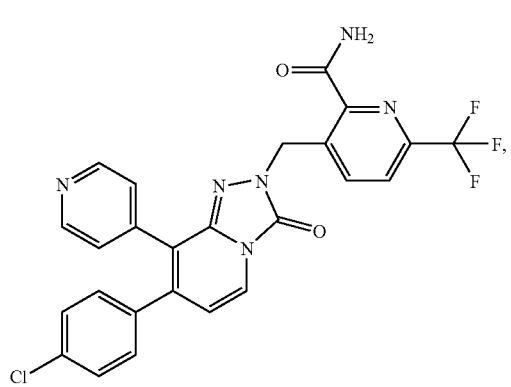
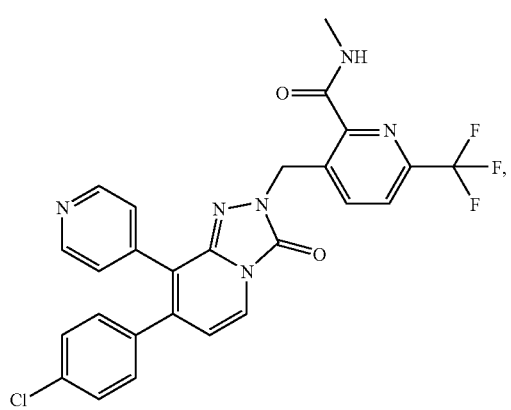
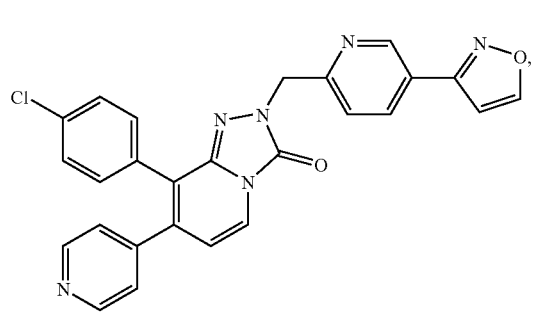
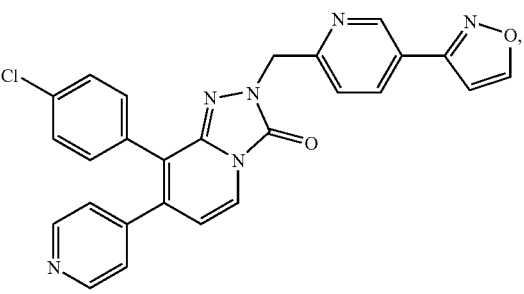
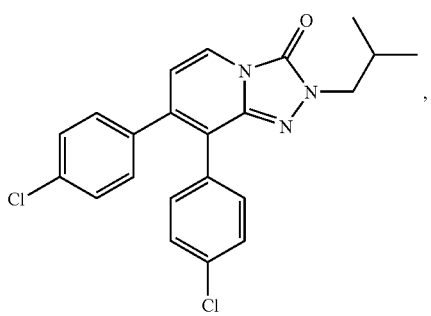
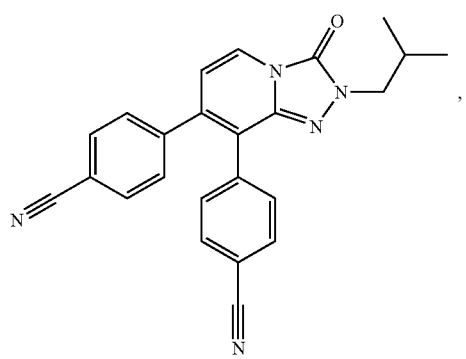
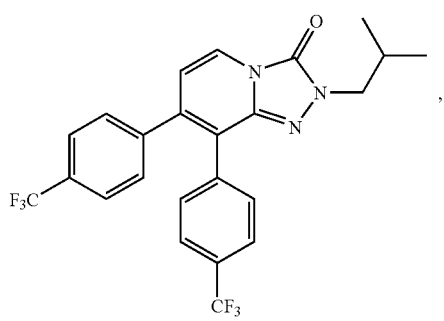
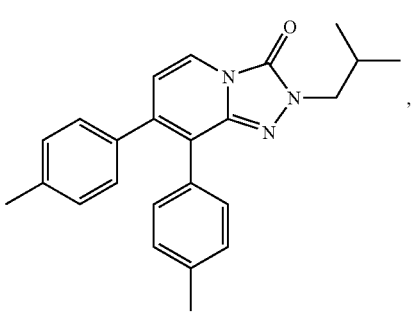

| 197 | 198 |
|---|---|
| -continued | -continued |
| 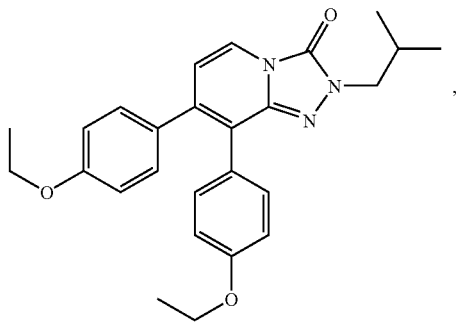, | 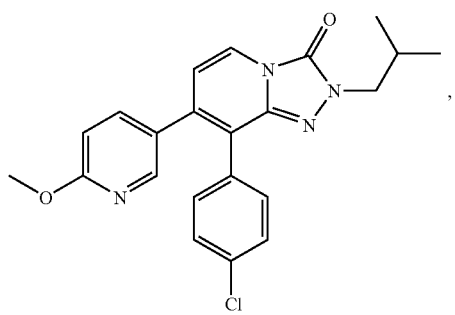, |
| 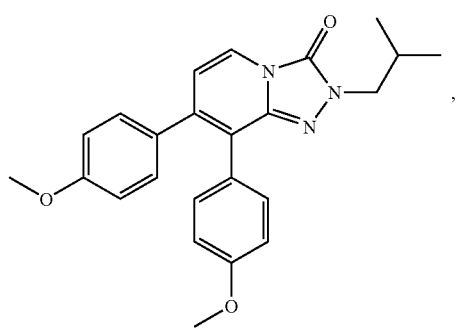, | 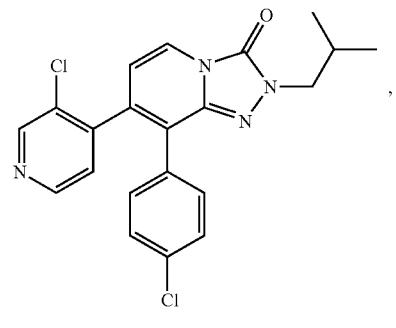, |
| 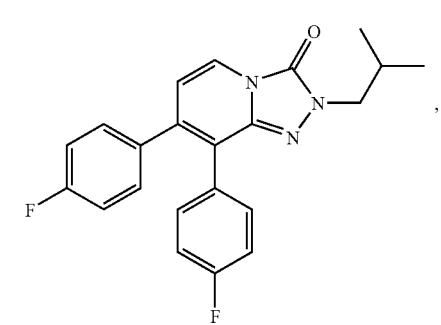, | 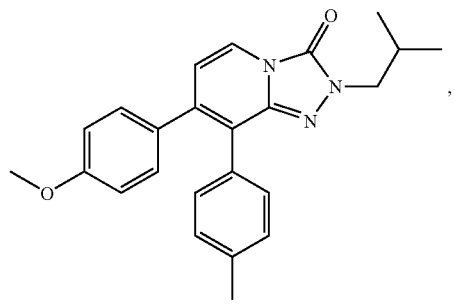, |
| 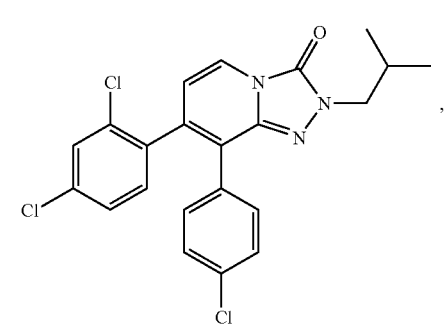, | 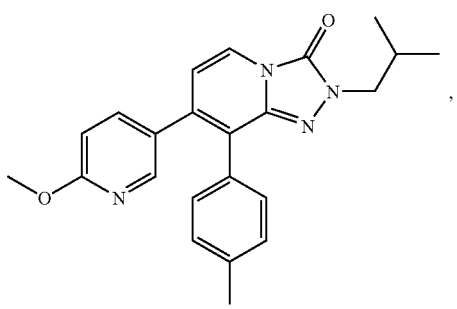, |
| 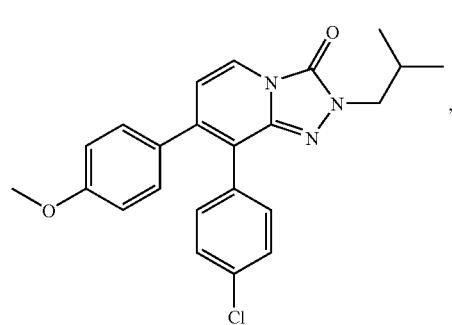, | 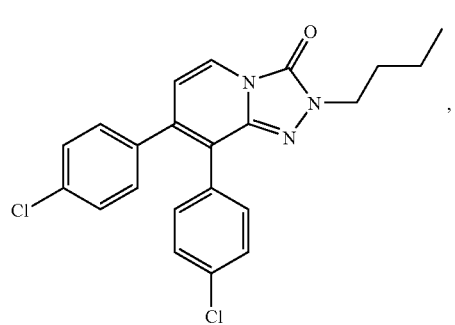, |

| 199 | 200 |
|---|---|
| -continued | -continued |
| 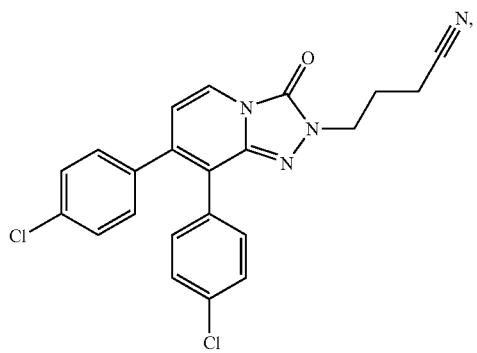 | 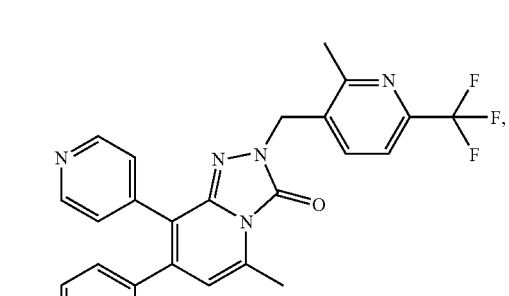 |
| 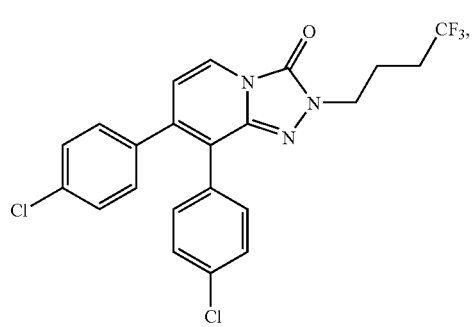 | 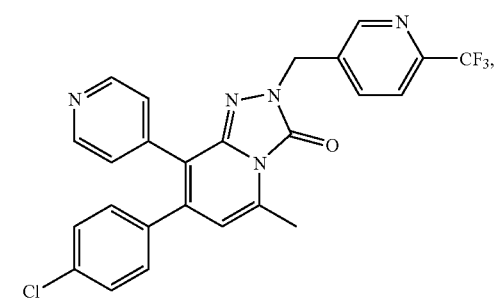 |
| 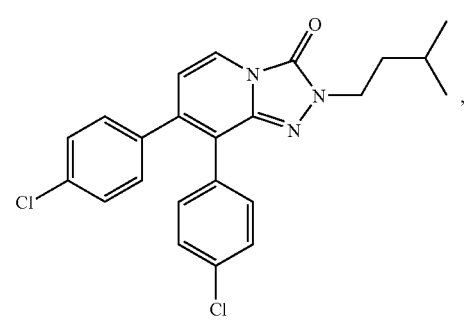 | 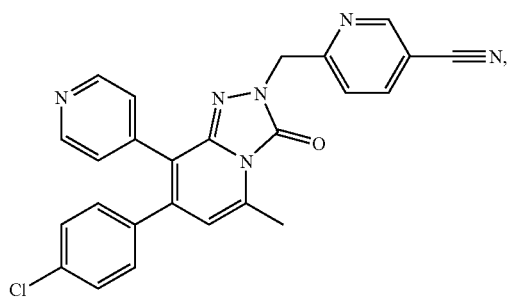 |
| 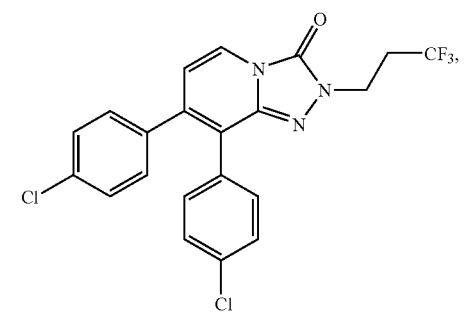 | 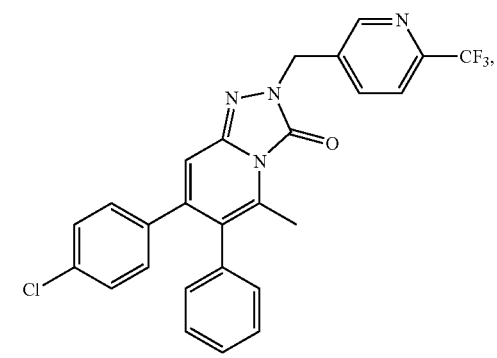 |
| 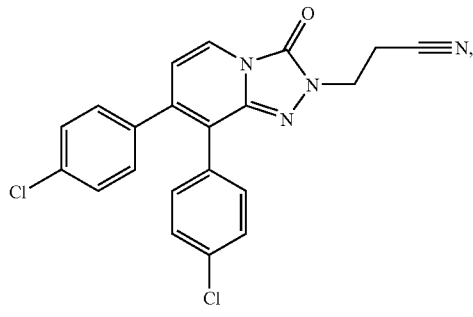 | |

-continued
201
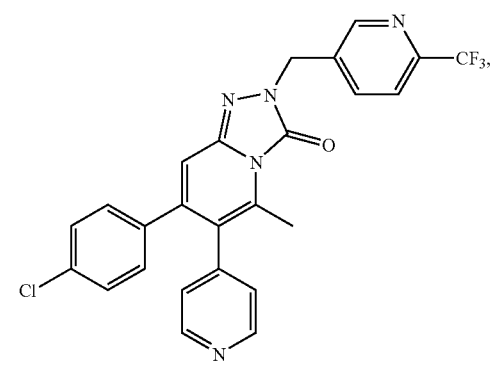
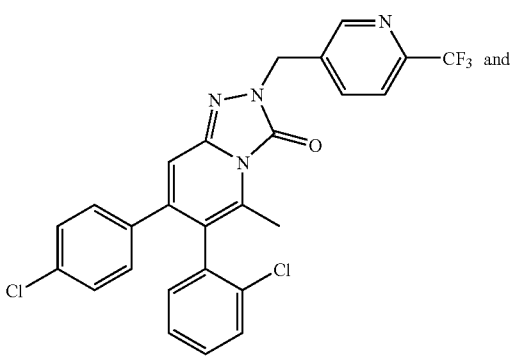
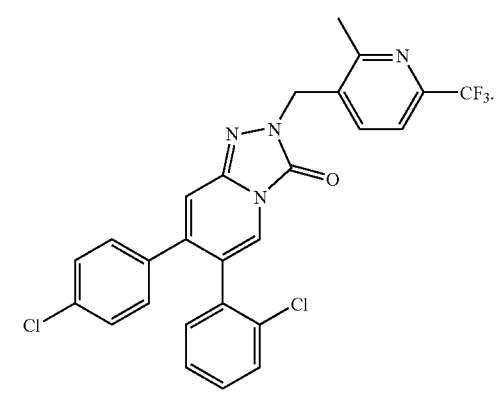
8. A compound s-selected from the group consisting of
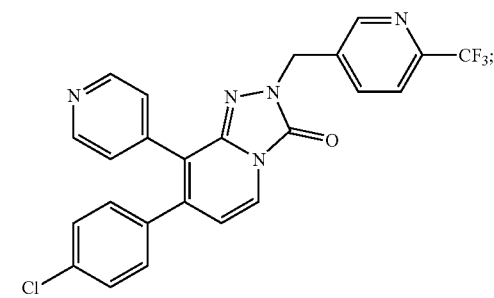
202
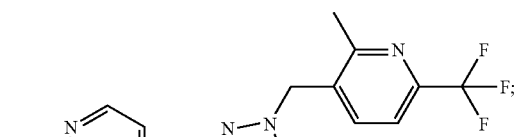
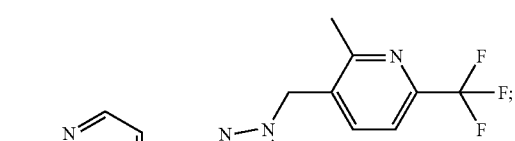
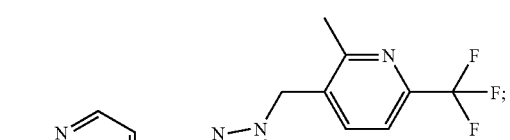
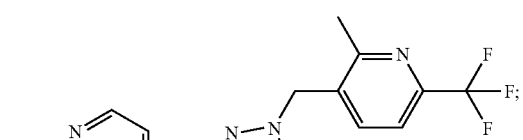
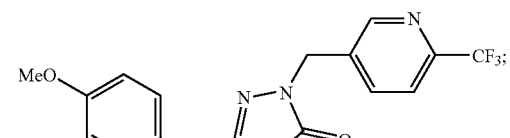

| 203 | 204 |
|---|---|
| 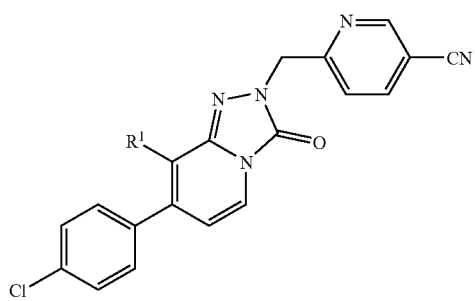 | 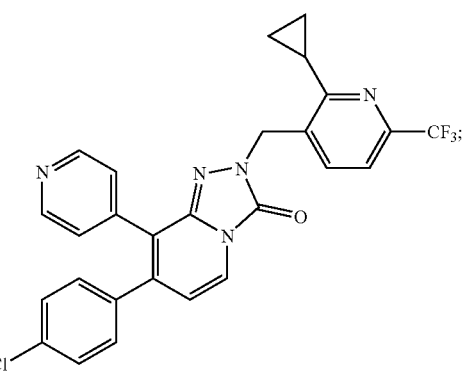 |
| R¹ — 4-methoxyphenyl 4-(cyanomethyl)phenyl | |
| 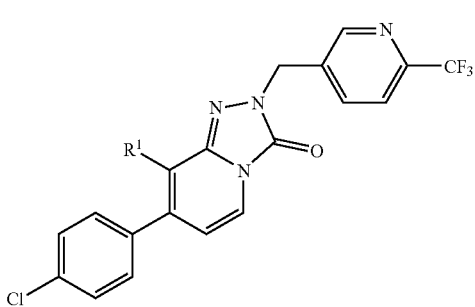 | 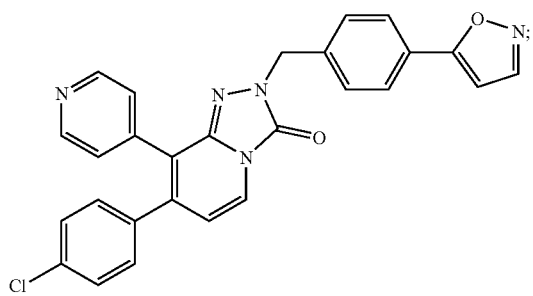 |
| R¹ — phenyl 4-methylphenyl 4-methoxyphenyl 4-hydroxyphenyl 4-(hydroxymethyl)phenyl 2-methylpyridin-4-yl | 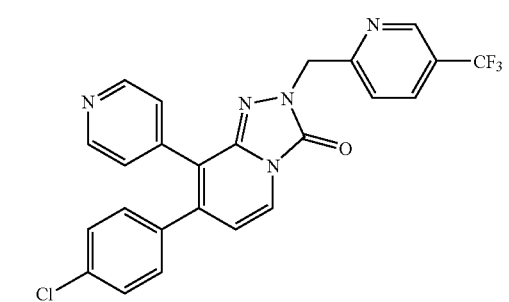 |
| 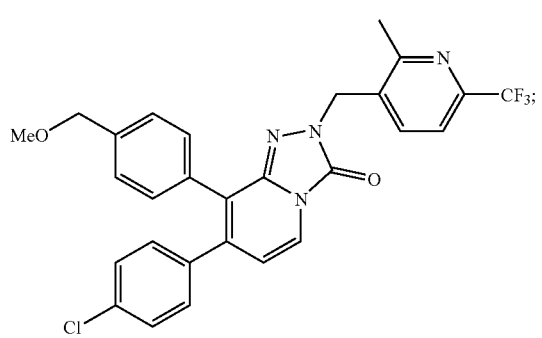 | 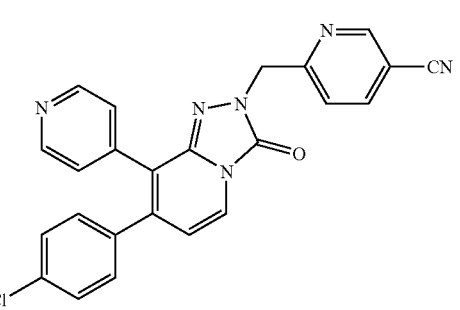 |
| 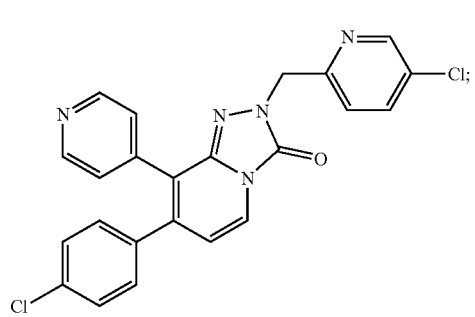 | 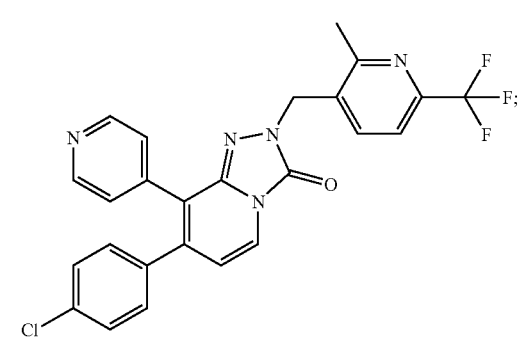 |

205
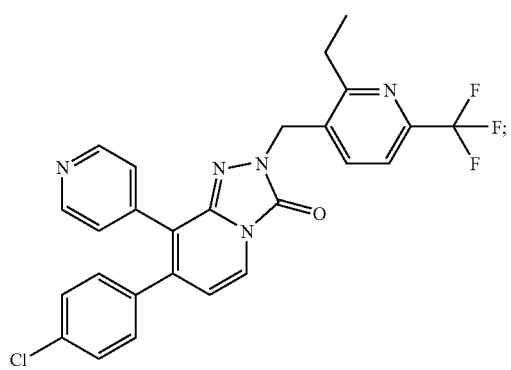
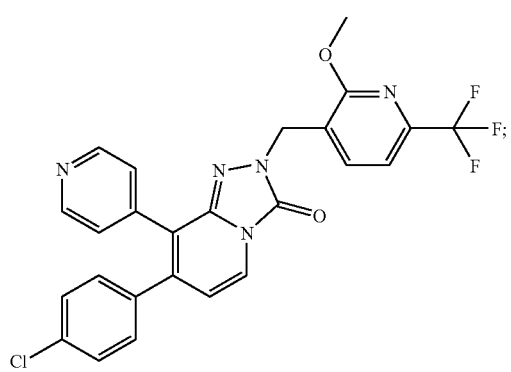
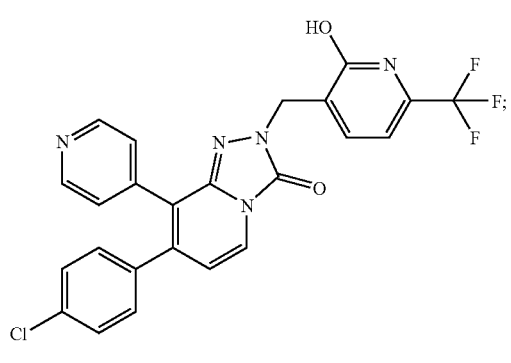
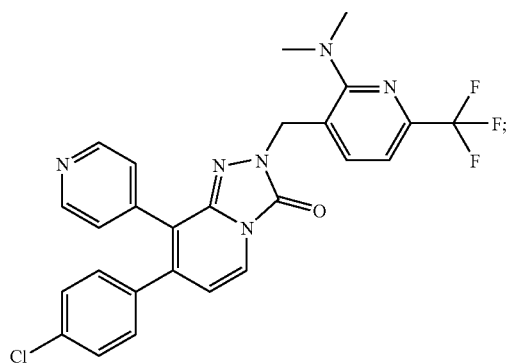
206
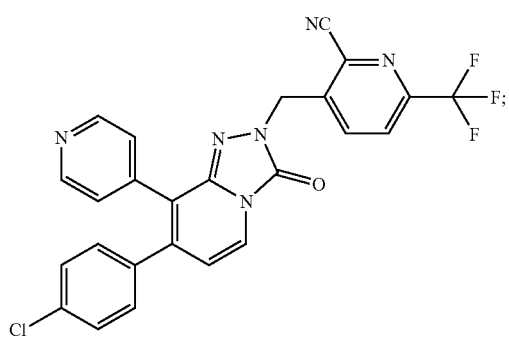
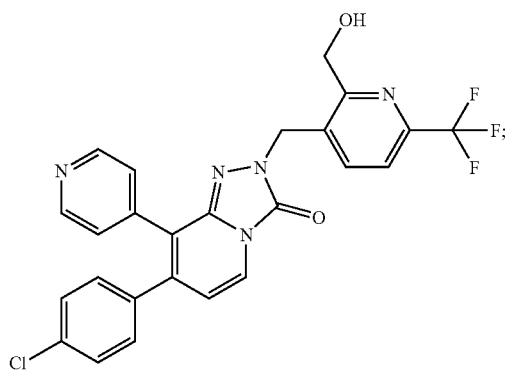
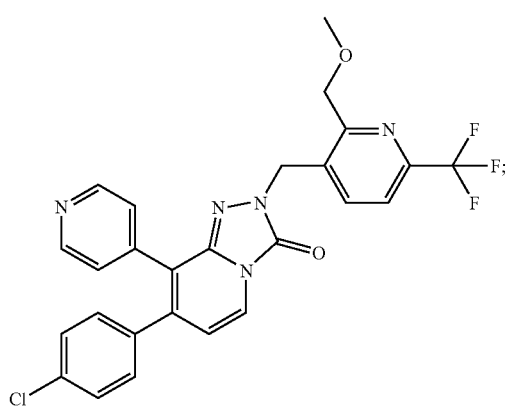
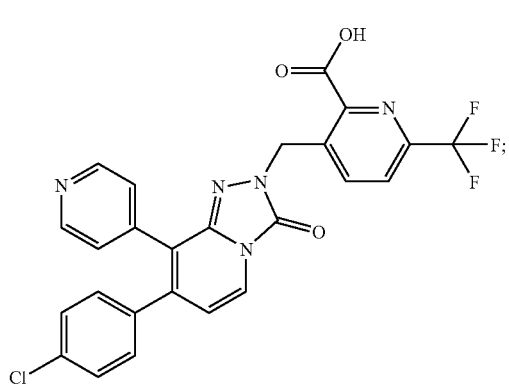

207

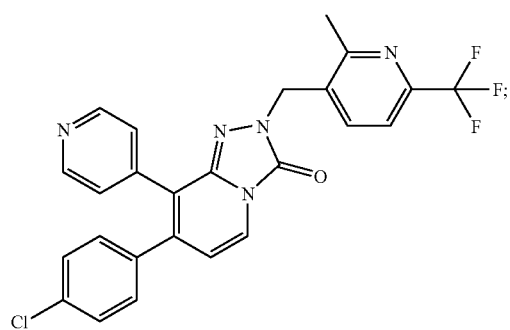

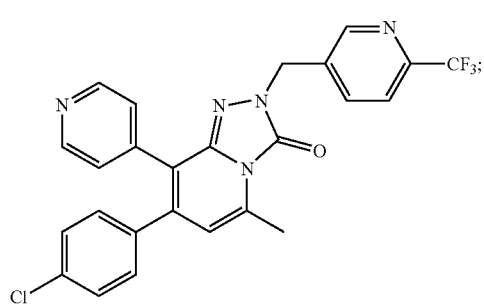

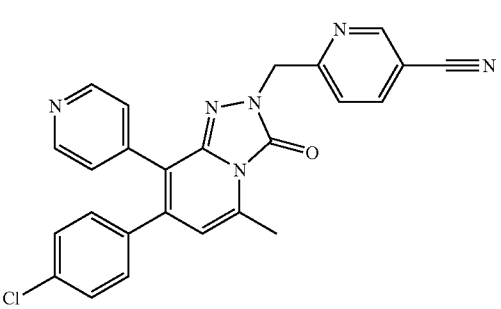

and

208

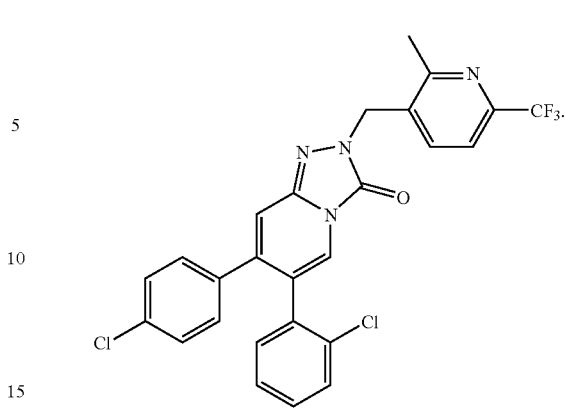

9. A pharmaceutical composition comprising at least one compound according to claim 1 in an amount therapeutically effective for treating obesity and at least one pharmaceutically acceptable carrier or diluent.

10. The pharmaceutical composition according to claim 9, further comprising at least one additional therapeutic agent selected from anti-obesity agents; anti-diabetic agents, appetite suppressants; cholesterol/lipid-lowering agents, HDL-raising agents, anti-hypertensive agents; and cardiac glycosides.

11. A method for treating obesity, comprising administering to a mammal in need of thereof a therapeutically effective amount of at least one cannabinoid receptor I antagonist according to claim 1.

12. A pharmaceutical composition comprising at least one compound according to claim 7 in an amount therapeutically effective for treating obesity and at least one pharmaceutically acceptable carrier or diluent.

13. A pharmaceutical composition comprising at least one compound according to claim 8 in an amount therapeutically effective for treating obesity and at least one pharmaceutically acceptable carrier or diluent.

* * * * *